(12) United States Patent
Cheney et al.

(10) Patent No.: US 12,042,386 B2
(45) Date of Patent: Jul. 23, 2024

(54) SHAPE MEMORY IMPLANTS AND METHODS AND APPARATUS FOR THE LOADING AND IMPLANTING THEREOF

(71) Applicant: DEPUY SYNTHES PRODUCTS, INC., Raynham, MA (US)

(72) Inventors: Daniel F. Cheney, Downingtown, PA (US); Joseph P. Ritz, Castroville, TX (US)

(73) Assignee: DePuy Synthes Products, Inc., Raynham, MA (US)

( * ) Notice: Subject to any disclaimer, the term of this patent is extended or adjusted under 35 U.S.C. 154(b) by 385 days.

(21) Appl. No.: 16/775,577

(22) Filed: Jan. 29, 2020

(65) Prior Publication Data

US 2021/0228364 A1    Jul. 29, 2021

(51) Int. Cl.
*A61F 2/30* (2006.01)
*A61B 17/064* (2006.01)

(52) U.S. Cl.
CPC ...... *A61F 2/30734* (2013.01); *A61B 17/0642* (2013.01); *A61F 2002/30092* (2013.01); *A61F 2002/30535* (2013.01); *A61F 2002/30736* (2013.01); *A61F 2002/30878* (2013.01)

(58) Field of Classification Search
CPC ........ A61F 2/30734; A61F 2002/30092; A61F 2002/30535; A61F 2002/30736; A61F 2002/30878; A61B 17/0642; A61B 17/1775; A61B 17/17; A61B 17/0684;
(Continued)

(56) References Cited

U.S. PATENT DOCUMENTS

| | | |
|---|---|---|
| 1,106,241 A | 8/1914 | Richardson |
| 2,544,492 A | 3/1947 | Downing |
| 3,939,828 A | 2/1976 | Mohr et al. |

(Continued)

FOREIGN PATENT DOCUMENTS

| | | |
|---|---|---|
| EP | 0682920 B1 | 2/1995 |
| EP | 0857462 A1 | 1/1998 |

(Continued)

OTHER PUBLICATIONS

4-Fusion Shape Memory Implant Training Slide Images, Memometal, Inc., 2008.

(Continued)

*Primary Examiner* — Yashita Sharma
(74) *Attorney, Agent, or Firm* — Christopher L. Makay

(57) ABSTRACT

An orthopedic fixation system includes an implant and an implant insertion device. The implant transitions between a natural shape and an insertion shape and includes a bridge and first and second anchoring members extending from the bridge. The first and second anchoring members each include a segment extending exterior to the bridge to provide an engagement point. The implant insertion device moves between loaded and unloaded positions. The implant insertion device in its loaded position by-passes the bridge and engages the segment of the first anchoring member at its engagement point and the segment of the second anchoring member at its engagement point such that the implant insertion device constrains the implant in its insertion shape. The implant insertion device in its unloaded position releases the implant.

61 Claims, 96 Drawing Sheets

(58) Field of Classification Search
CPC .. A61B 2017/00867; A61B 2017/0641; A61B 17/10; A61B 2017/0645
See application file for complete search history.

(56) References Cited

U.S. PATENT DOCUMENTS

| | | | |
|---|---|---|---|
| 3,960,147 | A | 6/1976 | Murray |
| 4,269,180 | A | 5/1981 | Dall et al. |
| 4,438,769 | A | 3/1984 | Pratt et al. |
| 4,485,816 | A | 12/1984 | Krumme |
| 4,526,174 | A | 7/1985 | Froehlich |
| 4,570,623 | A | 2/1986 | Ellison et al. |
| 4,592,346 | A | 6/1986 | Jurgutis |
| 4,608,972 | A | 9/1986 | Small |
| 4,665,906 | A | 5/1987 | Jervis |
| 4,713,077 | A | 12/1987 | Small |
| 4,869,243 | A | 9/1989 | Huene |
| 5,067,957 | A | 11/1991 | Jervis |
| 5,112,336 | A | 5/1992 | Krevolin et al. |
| 5,163,557 | A | 11/1992 | Sokolowski |
| 5,171,252 | A | 12/1992 | Friedland |
| 5,246,443 | A | 9/1993 | Mai |
| 5,357,732 | A | 10/1994 | Markle et al. |
| 5,425,489 | A | 6/1995 | Shichman et al. |
| 5,474,557 | A | 12/1995 | Mai |
| 5,478,354 | A | 12/1995 | Tovey et al. |
| 5,769,856 | A | 6/1998 | Dong et al. |
| 5,779,707 | A | 7/1998 | Bertholet et al. |
| 5,785,713 | A | 7/1998 | Jobe |
| 5,976,159 | A | 11/1999 | Bolduc et al. |
| 6,001,110 | A | 12/1999 | Adams |
| 6,187,009 | B1 | 2/2001 | Herzog et al. |
| 6,268,589 | B1 | 7/2001 | Flot |
| 6,323,461 | B2 | 11/2001 | Flot |
| 6,412,639 | B1 | 7/2002 | Hickey |
| 6,607,542 | B1 | 8/2003 | Wild |
| 6,685,708 | B2 | 2/2004 | Monassevitch et al. |
| 6,783,531 | B2 | 8/2004 | Allen |
| 6,827,723 | B2 | 12/2004 | Carson |
| 7,240,677 | B2 | 7/2007 | Fox |
| 7,344,539 | B2 | 3/2008 | Serhan et al. |
| 7,428,807 | B2 | 9/2008 | Vander Bush et al. |
| 7,556,647 | B2 | 7/2009 | Drews et al. |
| 7,678,115 | B2 | 3/2010 | D'Alessio et al. |
| 7,867,265 | B2 | 1/2011 | Beutter |
| 8,057,490 | B2 | 11/2011 | Harris |
| 8,114,138 | B2 | 2/2012 | Nehls |
| 8,118,952 | B2 | 2/2012 | Gall et al. |
| 8,137,351 | B2 | 3/2012 | Prandi |
| 8,191,220 | B2 | 6/2012 | Magnuson et al. |
| 8,211,109 | B2 | 7/2012 | Groiso |
| D669,984 | S | 10/2012 | Cheney et al. |
| D669,985 | S | 10/2012 | Cheney et al. |
| D676,962 | S | 2/2013 | Cheney et al. |
| 8,584,853 | B2 | 11/2013 | Knight et al. |
| 8,596,514 | B2 | 12/2013 | Miller et al. |
| 9,585,656 | B2 | 3/2017 | Taber et al. |
| 9,855,036 | B2 | 1/2018 | Palmer et al. |
| 9,931,115 | B2 | 4/2018 | Morgan et al. |
| 10,080,599 | B2 | 9/2018 | Caldarella et al. |
| 2004/0097970 | A1 | 5/2004 | Hughett |
| 2005/0033430 | A1 | 2/2005 | Powers et al. |
| 2005/0043757 | A1 | 2/2005 | Arad et al. |
| 2005/0080454 | A1 | 4/2005 | Drews et al. |
| 2005/0009660 | A1 | 5/2005 | Allen |
| 2005/0107807 | A1 | 5/2005 | Nakao |
| 2005/0113832 | A1 | 5/2005 | Molz et al. |
| 2005/0143749 | A1 | 6/2005 | Zalenski et al. |
| 2006/0106388 | A1 | 5/2006 | Lococo |
| 2006/0229627 | A1 | 10/2006 | Hunt et al. |
| 2007/0118141 | A1 | 5/2007 | Marchyn et al. |
| 2007/0118224 | A1 | 5/2007 | Shah et al. |
| 2008/0065153 | A1 | 3/2008 | Allard et al. |
| 2008/0110957 | A1 | 5/2008 | McBride et al. |
| 2008/0319443 | A1 | 12/2008 | Focht et al. |
| 2009/0062800 | A1 | 3/2009 | Shano |
| 2009/0062806 | A1 | 3/2009 | Scott et al. |
| 2009/0216285 | A1 | 8/2009 | Ek et al. |
| 2009/0272786 | A1 | 11/2009 | Zeiner et al. |
| 2010/0133316 | A1 | 6/2010 | Lizee et al. |
| 2010/0191258 | A1 | 7/2010 | Harris et al. |
| 2010/0217270 | A1 | 8/2010 | Polinski et al. |
| 2011/0093018 | A1 | 4/2011 | Prasad et al. |
| 2011/0186456 | A1 | 8/2011 | Bertazzoni et al. |
| 2011/0270327 | A1 | 11/2011 | Blakemore et al. |
| 2012/0024937 | A1 | 2/2012 | Allen |
| 2012/0085809 | A1 | 4/2012 | Milo |
| 2012/0209305 | A1 | 8/2012 | Deodhar et al. |
| 2012/0209401 | A1 | 8/2012 | Euteneuer et al. |
| 2012/0228355 | A1 | 9/2012 | Combrowski et al. |
| 2012/0259419 | A1 | 10/2012 | Brown et al. |
| 2013/0026206 | A1 | 1/2013 | Fox |
| 2013/0026207 | A1 | 1/2013 | Fox |
| 2013/0030437 | A1 | 1/2013 | Fox |
| 2013/0030438 | A1* | 1/2013 | Fox ............... A61B 17/064 29/452 |
| 2013/0184476 | A1 | 7/2013 | Mclff et al. |
| 2013/0231667 | A1 | 9/2013 | Taylor et al. |
| 2014/0018809 | A1 | 1/2014 | Allen |
| 2014/0097228 | A1 | 4/2014 | Solana |
| 2014/0175157 | A1 | 6/2014 | Vold et al. |
| 2014/0276830 | A1 | 9/2014 | Cheney |
| 2014/0277516 | A1 | 9/2014 | Miller et al. |
| 2015/0230843 | A1 | 8/2015 | Palmer et al. |
| 2015/0257801 | A1 | 9/2015 | Palmer |
| 2016/0015384 | A1 | 1/2016 | Roedl et al. |
| 2016/0066907 | A1 | 3/2016 | Cheney et al. |
| 2016/0074037 | A1 | 3/2016 | Cheney et al. |
| 2016/0235460 | A1 | 8/2016 | Wahl |
| 2017/0000482 | A1 | 1/2017 | Averous et al. |
| 2017/0065275 | A1 | 3/2017 | Cheney |
| 2017/0252036 | A1 | 9/2017 | Palmer et al. |
| 2017/0281157 | A1 | 10/2017 | Hartdegen et al. |
| 2019/0117219 | A1* | 4/2019 | Ritz ............... A61B 17/10 |
| 2019/0192140 | A1 | 6/2019 | Ducharme et al. |

FOREIGN PATENT DOCUMENTS

| | | |
|---|---|---|
| EP | 0826340 A2 | 3/1998 |
| EP | 1870042 A1 | 12/2007 |
| EP | 3187134 A1 | 7/2017 |
| EP | 3260053 B1 | 2/2019 |
| FR | 2874166 A1 | 2/2006 |
| WO | 1992017122 A2 | 10/1992 |
| WO | 2008129061 A1 | 10/2008 |
| WO | 2013055824 A1 | 4/2013 |
| WO | 2015131106 A1 | 9/2015 |
| WO | 2015179652 A1 | 11/2015 |
| WO | 2016007624 A1 | 1/2016 |

OTHER PUBLICATIONS

4-Fusion Shape Memory Implant Brochure, Memometal, Inc., Jun. 23, 2009.
MemoGraph Brochure, M.B.A. (Memory Biological Application), Parc Club de Nancy de Brabois, Batiment B11, 4 allee Vincennes, 54500 Vandceurve, France, 1999.
OSStaple Brochure Including pictures of staple loaded in shipping block, BioMedical Enterprises, Inc., 14875 Omicron Drive, Suite 205, San Antonio, TX 78245, 2010.
E. A. Van Amerongen et al., "Four-Corner Arthrodesis Using the Quad Memory Staple," Journal of Hand Surgery (European vol. 2008) (Jan. 7, 2009).
U. Rethnam et al., "Mechanical Characteristics of Three Staples Commonly Used in Foot Surgery," Journal of Foot and Ankle Research (Feb. 25, 2009) available at http://www.jfootankleres.com/content/2/1/5.
T. F. Smith, "The Bone Staple: Tried and True Superhero of Bone Fixation," Educational Materials Update Chapter 41 (2010) available at www.podiatryinstitute.com/pdfs/Update 2010/2010 41.pdf.
Elevest Procedure Kit, Instructions for Use by CooperSurgical ( © 2007).

(56) References Cited

OTHER PUBLICATIONS

Agee WristJack, Surgeon's Manual by Hand BioMechanics Labs, Inc. ( © 1990-2002).

Development of a Nickel-Titanium Shape Memory Alloy Bone Repair Staple and Other In-Vivo Orthopaedic and Cardio-Vascular Devices, A.W. Anson, D.H.R. Jenkins, and S. Andrews, Proceedings of the Technology Transfer Workshop, Held at ESA/ESTEC Noordwijk, The Netherlands, May 1994 (ESA SP-364, Aug. 1994).

Superelastic Fixation System Brochure, Memometal Inc., USA, Aug. 12, 2009.

Shape Memory Staple System for Arthrodesis and Skeletal Fixation of the Hand Brochure, Core Essence Orhtopaedics, Inc., 2009.

ENTact™ Septal Stapler, Product brochure by ENTrigue Surgical, Inc. ( © 2009).

R. M. Sloan et al., "Orthopedic Fixation Devices," Radiographics at 823 (Sep. 1991).

J. Arthur, "Improving Operating Efficiency in Five Days," Lean Six Sigma for Hospitals, McGraw-Hill (2011).

K. Yamauchi et al. (ed.), "Shape Memory and Superelastic Alloys: Applications and Technologies" (2011).

BioResearch Innovations (BRI), "Memodyn Compression Staple," FDA 510(K) disclosure (Jan. 2004).

G. C. Taylor et al., "Complications of Internal Fixation," Podiatry Institute Educational Materials Update Chapter 79 (1992).

Wright Medical Technology, Inc., "Charlotte Compression Staple as described by Robert Anderson, MD; Bruce Cohen, MD; and W. Hodges Davis, MD" (2007).

A. A. Weinbroum et al., "Efficiency of the Operating Room Suite," American Journal of Surgery 244-250 (2003).

G. G. Porto, "Safety by Design: Ten Lessons From Human Factors Research," Journal of Healthcare Risk Management 43-50 (Fall 2011).

Russell, Scott M., Design Considerations for Nitinol Bone Staples, Journals of Materials Engineering and Performance, vol. 18(5-6), Aug. 2009, USA.

International Search Report for PCT/IB2021/050724, Apr. 22, 2021, PCT Application Counterpart to U.S. Appl. No. 16/775,577.

\* cited by examiner

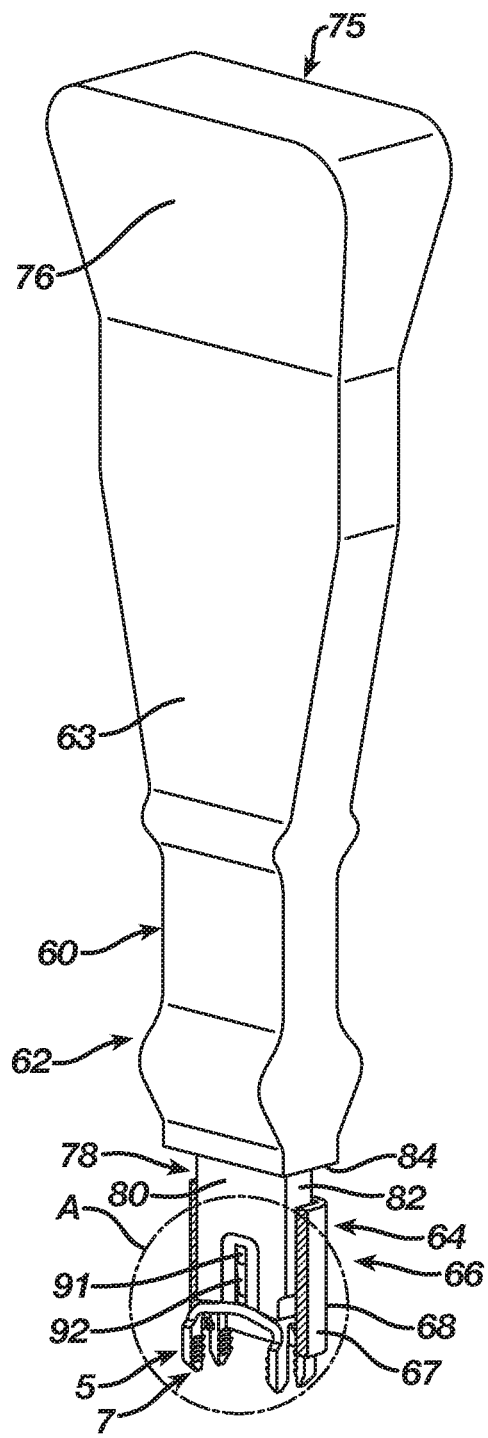
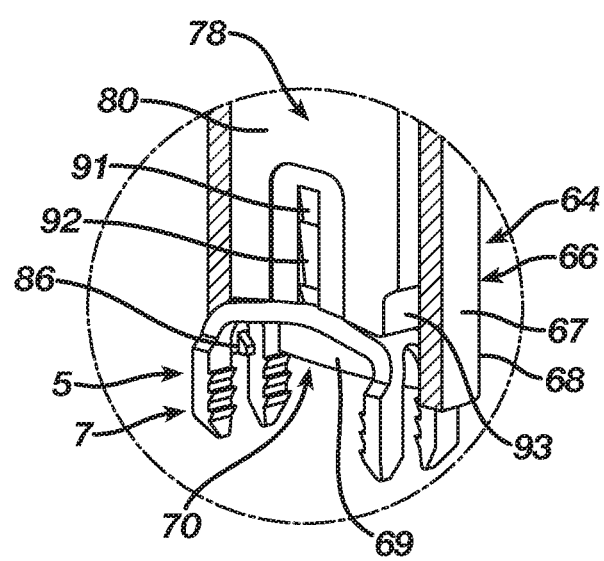
FIG. 5C
FIG. 5D

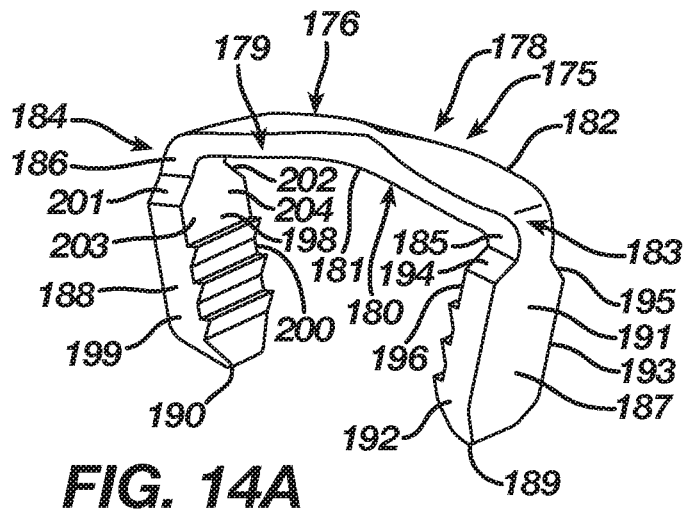
FIG. 14A
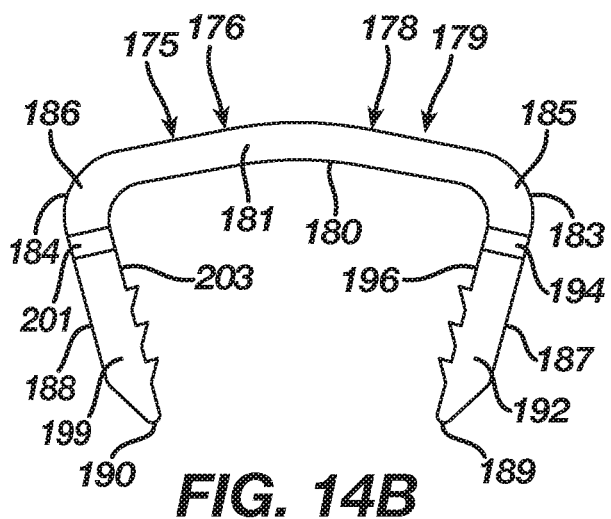
FIG. 14B
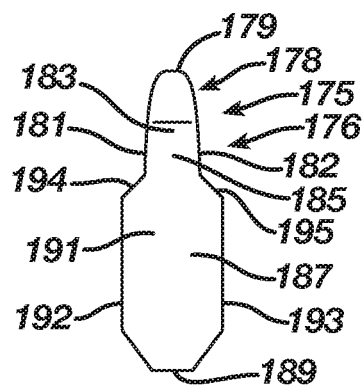
FIG. 14C
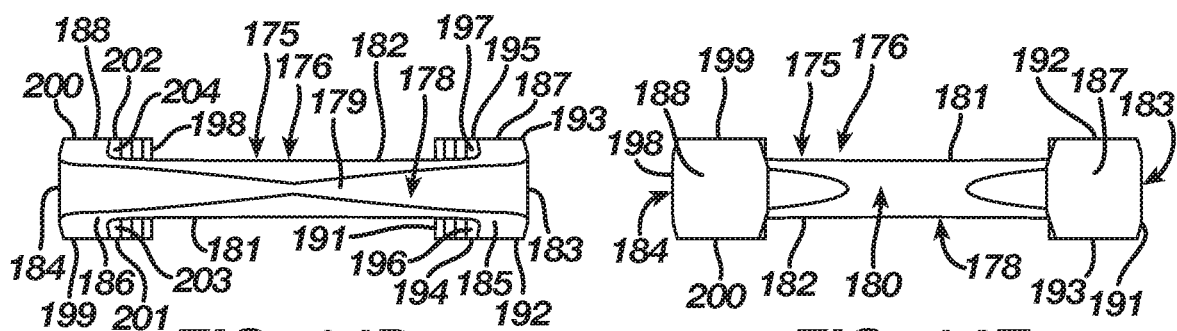
FIG. 14D
FIG. 14E

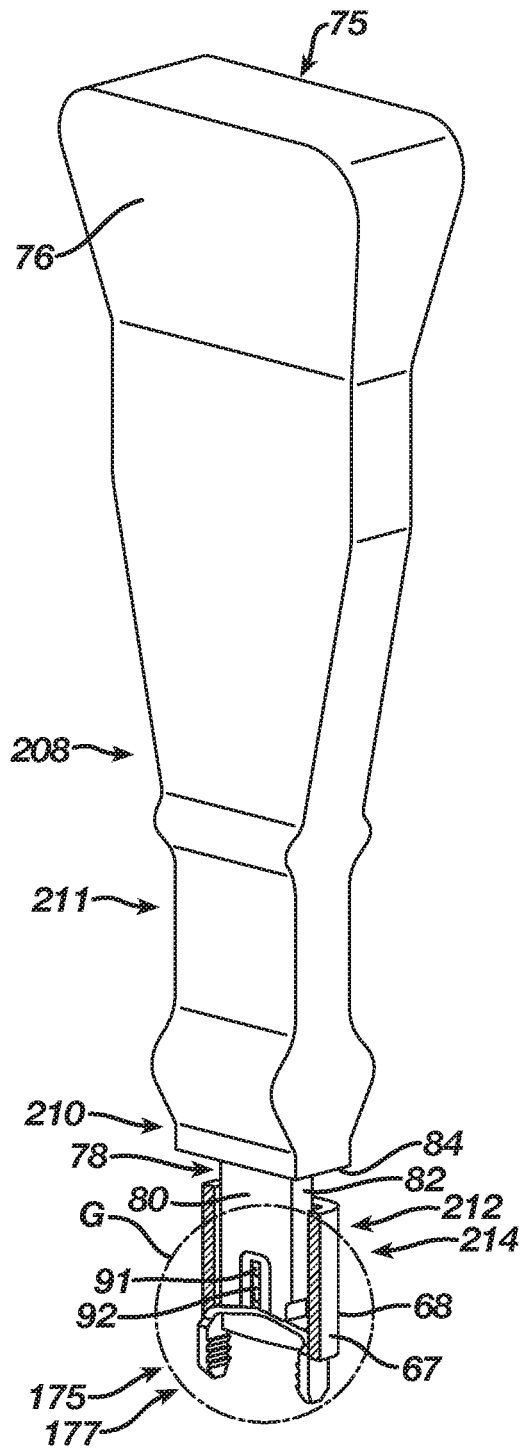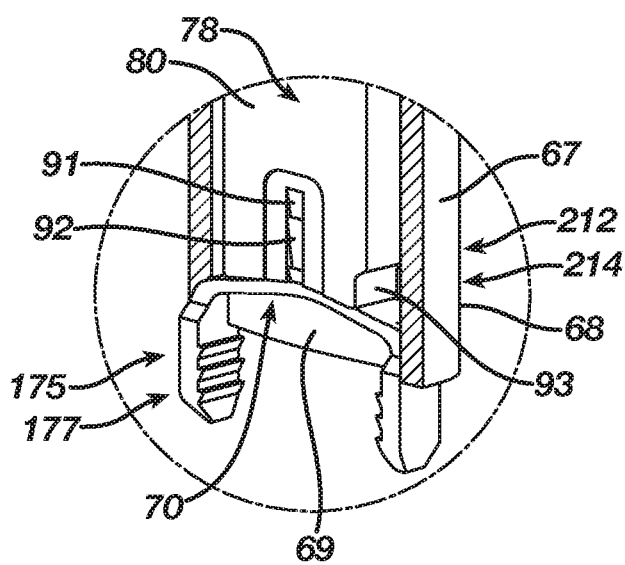
FIG. 18C
FIG. 18D

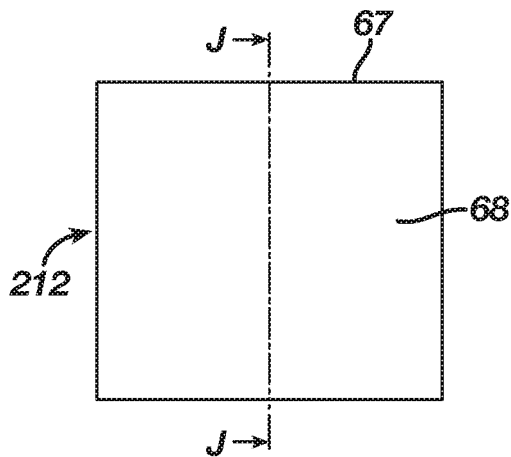
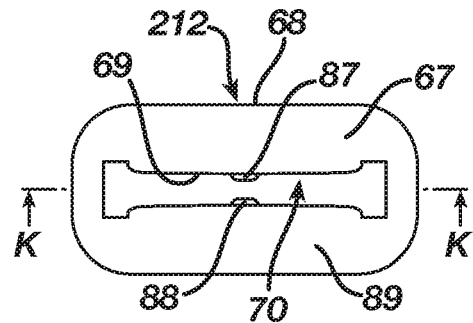
FIG. 20E    FIG. 20F
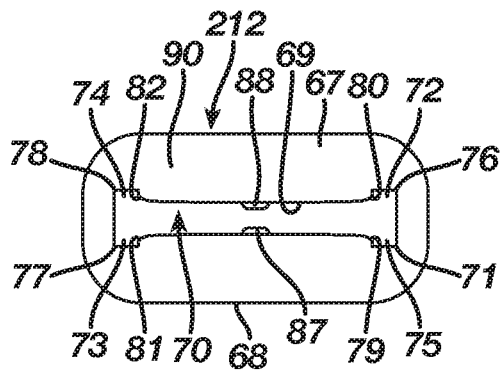
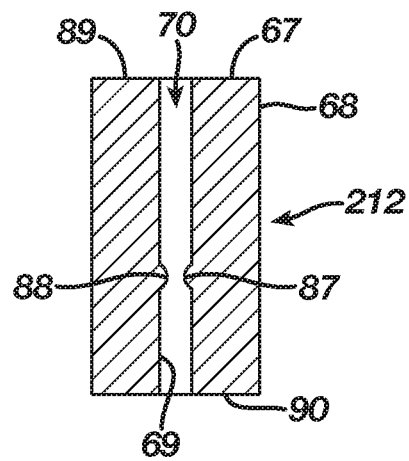
FIG. 20G    FIG. 20H
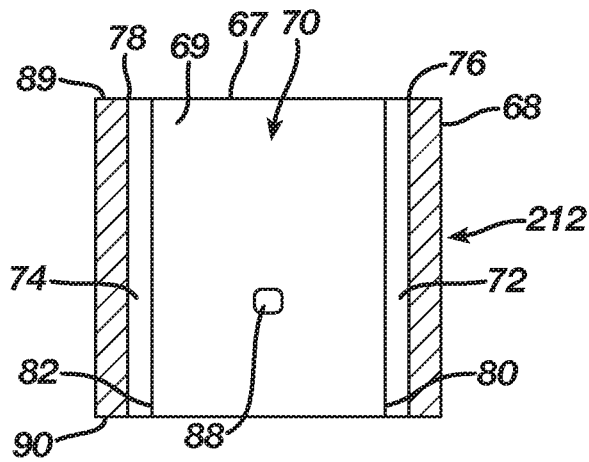
FIG. 20I

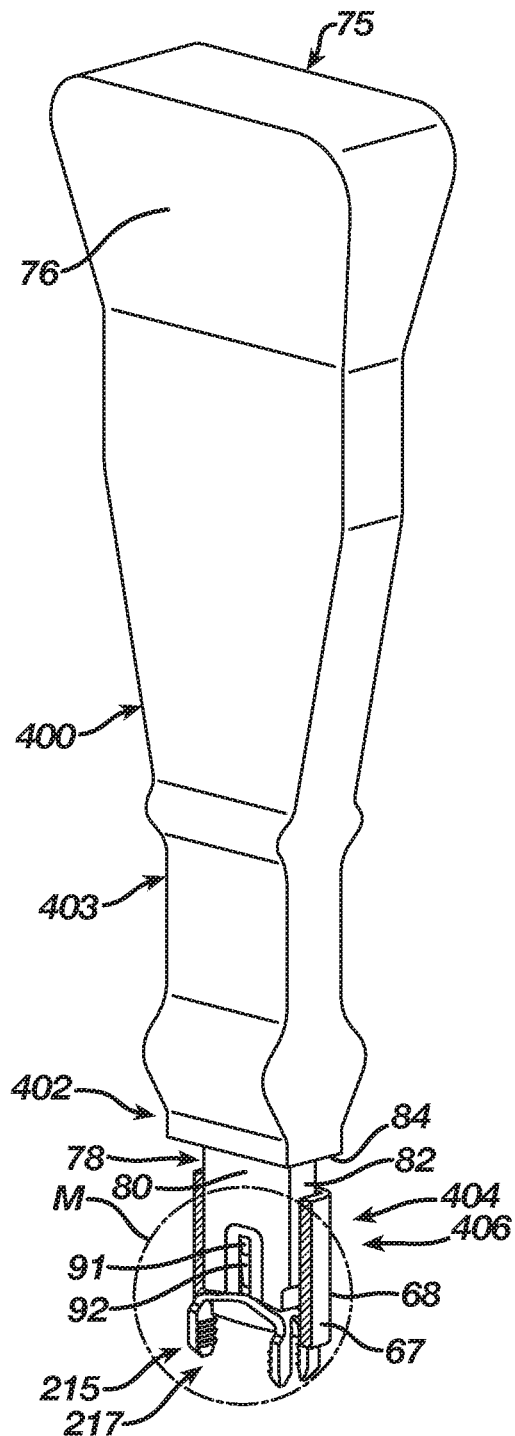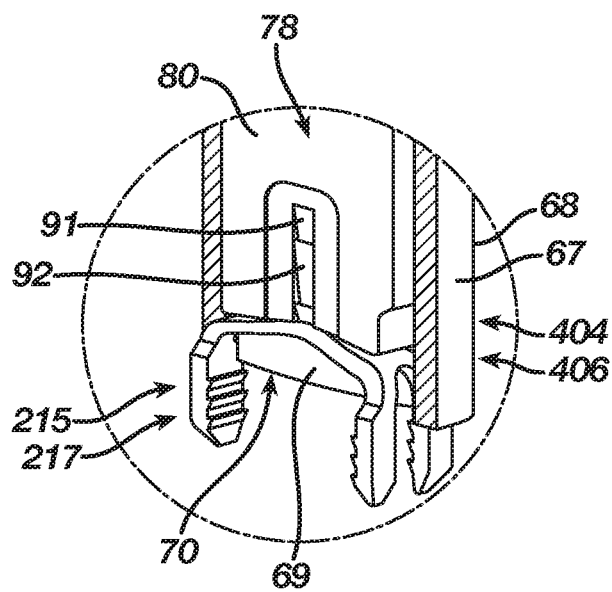
FIG. 31C
FIG. 31D

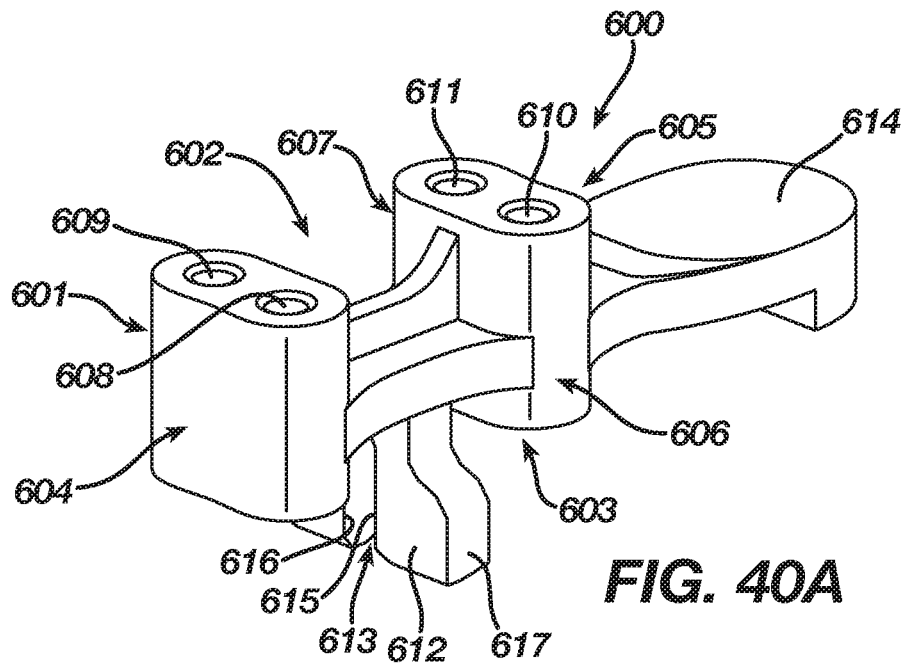
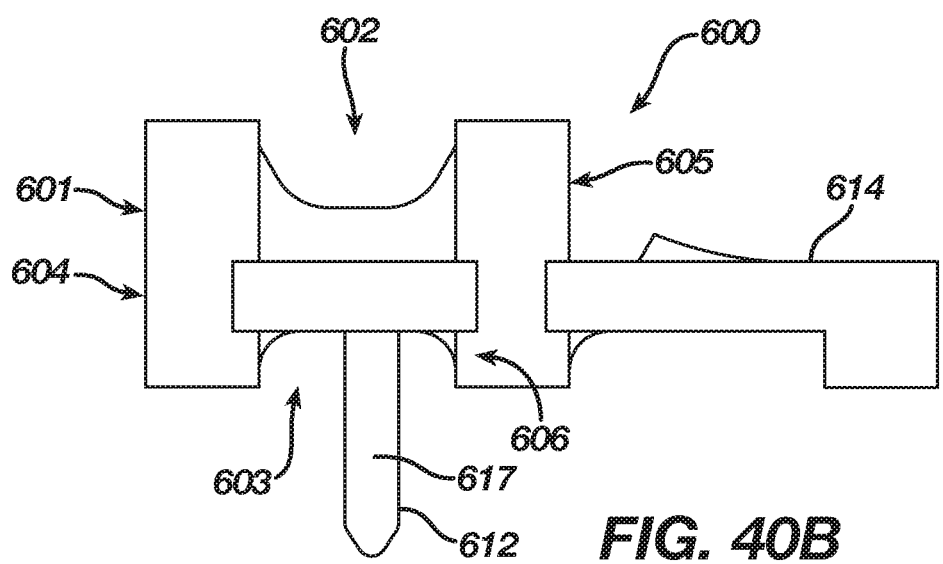

SHAPE MEMORY IMPLANTS AND METHODS AND APPARATUS FOR THE LOADING AND IMPLANTING THEREOF

BACKGROUND OF THE INVENTION

1. Field of the Invention

The present invention relates generally to shape memory implants and the implantation thereof using an implantation device and, more particularly, but not way of limitation, to an orthopedic fixation system including a shape memory implant and an implantation device designed for loading with the shape memory implant and for subsequent delivery of the shape memory implant utilizing the implantation device.

2. Description of the Related Art

Shape memory implants are commonly used in surgical procedures that require the reattachment or fusing of tissue or bone. Shape memory implants can be composed of a shape memory material such as Nitinol that allows the shape memory implants to have a first final shape and the ability to transform into a second shape. A shape memory implant can be either thermally activated, in which an external heating source or body temperature would be required to activate the implant, or mechanically activated, in which a constraining instrument would be required. A shape memory implant that requires mechanical constraint stores mechanical energy due to elastic recovery, and then releases the stored mechanical energy when the constraining instrument is removed. In these types of implants, the implants are mechanically moved into their second shape and maintained in their second shape by instrumentation such that, upon release from the instrumentation, the implants elastically return from their second shape into their first final shape.

In surgical procedures, the elastic property of constrained shape memory implants is used as follows. Bones that require fixating are aligned, and the shape memory implant, which has been mechanically deformed to its second shape, is maintained in instrumentation and inserted across the bones. After insertion, the shape memory implant is released from the instrumentation, whereupon the shape memory implant elastically tries to return to its first final shape such that the shape memory implant maintains the bones fixated together. The shape memory implant because it stores mechanical energy continuously applies force to the fixated bones as the shape memory implant tries to transition from the second shape to the first final shape, which aids in the healing process.

Various types of instrumentation can be used for either maintaining the shape memory implants in their second shape or moving an implant from its first final shape to a temporary second shape. Some companies used metal forceps to open and insert the shape memory implant. These forceps have to be sterilized by a hospital, and then a shape memory implant can be placed on the forceps, opened to a desired position, and used for inserting the implant. Although potentially effective, forceps require the implant to be loaded into the forceps during surgery, which might be cumbersome and time consuming. In addition, forceps might be large which could hinder implantation of the shape memory implant into a patient during surgery. It is also possible that a physician using the forceps might damage the shape memory implant in various ways, such as stretching the implant beyond the second shape, fatiguing the implant, or causing metal-on-metal scraping of the implant with the instrument. Furthermore, forceps can be expensive instruments that require cleaning and sterilization after each surgery.

Other instrumentation includes plastic and disposable tools to maintain a shape memory implant in the second shape. This type of instrumentation can be preloaded and sterilized with the implant already in the second shape, and the implant can be pre-activated so that it does not require heating with an external heater or body temperature after use. One type of plastic and disposable instrument operates by having the implant fit inside a passage that is substantially the same diameter as the shape memory implant. By using this method, the instrumentation allows the shape memory implant to be preloaded prior to surgery. However, using instrumentation that substantially conforms to the profile of the shape memory implant can create several problems for a surgeon. First, this type of instrumentation often makes disengagement of the shape memory staple after implantation problematic. In particular, the shape memory implant sticks to the instrumentation due to the frictional engagement between the shape memory implant, which is trying to compress, and the passage of the instrumentation, resulting in a more difficult surgical procedure and the potential for a less than satisfactory fixation of tissue or bone. Second, this type of instrumentation results in an abrupt and sudden release of stored mechanical energy as the implant is removed from the device. This type of instrumentation accordingly provides no method of slowly transitioning the stored energy in the implant from the instrumentation to the bones being fixated. Finally, this type of instrumentation can result in entanglement during release, in which the implant begins to compress upon release thereby making extraction of this type of instrumentation more difficult.

Another type of plastic and disposable instrument includes arms movable between a disengaged position and an engaged position. The arms terminate in jaws such that, when the arms reside in their engaged position, the jaws contact the shape memory implant to maintain the shape memory implant open for insertion. While the movable arms and jaws release the implant without entanglement and further allow the slow transitioning of the implant, the jaws, due to their location when contacting the shape memory implant as well as their path of travel during removal from the shape memory implant, leave the implant situated above the bone surface such that tamping of the implant to a position flush with the bone surface is required. As a result, the instrument can be impractical for certain surgeries because it is not always possible to tamp and thus seat the implant flush with a bone surface after its release from the instrument, particularly when the implant includes anchoring members of limited length.

Accordingly, an instrument that constrains a shape memory implant in its second shape, allows the shape memory implant to be preloaded and sterilized prior to surgery, controls the rate of tension release, simplifies removal of the shape memory implant after implantation, and releases the shape memory implant at a bone surface thereby eliminating tamping would be beneficial.

SUMMARY OF THE INVENTION

In accordance with the present invention, an orthopedic fixation system includes an implant and an implant insertion device. The implant transitions between a natural shape and an insertion shape. The implant insertion device moves between a loaded position that constrains the implant in its insertion shape and an unloaded position that releases the implant for attempted transition from its insertion shape to its natural shape. More particularly, the implant insertion device, when loading with the implant, by-passes a bridge of the implant and engages a segment of a first anchoring member for the implant at an engagement point and a segment of a second anchoring member for the implant at an engagement point such that the implant insertion device constrains the implant in its insertion shape.

The implant insertion device includes a body with a first end and a second end and an implant grip coupled with the body. The implant grip moves relative to the body between an engaged position and a disengaged position. The implant grip in its engaged position by-passes the bridge and engages the segment of the first anchoring member at its engagement point and the segment of the second anchoring member at its engagement point such that the implant grip constrains the implant in its insertion shape. The implant grip in its disengaged position releases the implant.

The implant in the present invention includes a bridge with first and second sides and first and second ends and anchoring members extending from the bridge in accordance with the following configurations. The implant in a first configuration includes a first anchoring member extending from the bridge at the first end thereof and a second anchoring member extending from the bridge at the second end thereof. The first anchoring member includes a width between sides thereof whereby a first segment extends exterior to the bridge at its first side to provide a first engagement point and a second segment extends exterior to the bridge at its second side to provide a second engagement point. The second anchoring member includes a width between sides thereof whereby a first segment extends exterior to the bridge at its first side to provide a first engagement point and a second segment extends exterior to the bridge at its second side to provide a second engagement point.

The implant in a second configuration includes a first anchoring member extending from the bridge at the first end of the bridge adjacent the first side of the bridge, a second anchoring member extending from the bridge at the second end thereof, and a third anchoring member extending from the bridge at the first end of the bridge adjacent the second side of the bridge. The first anchoring member includes a width between sides thereof whereby a segment of the first anchoring member extends exterior to the bridge at its first side to provide and engagement point. The second anchoring member includes a width between sides thereof whereby a first segment extends exterior to the bridge at its first side to provide a first engagement point and a second segment extends exterior to the bridge at its second side to provide a second engagement point. The third anchoring member includes a width between sides thereof whereby a segment of the third anchoring member extends exterior to the bridge at its second side to provide an engagement point.

The implant in a third configuration includes a first anchoring member extending from the bridge at the first end of the bridge adjacent the first side of the bridge, a second anchoring member extending from the bridge at the second end of the bridge adjacent the first side of the bridge, a third anchoring member extending from the bridge at the first end of the bridge adjacent the second side of the bridge, and a fourth anchoring member extending from the bridge at the second end of the bridge adjacent the second side of the bridge. The first anchoring member includes a width between sides thereof whereby a segment of the first anchoring member extends exterior to the bridge at its first side to provide an engagement point. The second anchoring member includes a width between sides thereof whereby a segment of the second anchoring member extends exterior to the bridge at its first side to provide an engagement point. The third anchoring member includes a width between sides thereof whereby a segment of the third anchoring member extends exterior to the bridge at its second side to provide an engagement point. The fourth anchoring member includes a width between sides thereof whereby a segment of the fourth anchoring member extends exterior to the bridge at its second side to provide an engagement point.

The implant insertion device for use with an implant having first and second anchoring members includes a body with a first end and a second end and an implant grip coupled with the body at its second end. The implant grip moves relative to the body between an engaged position and a disengaged position. The implant grip in its engaged position by-passes the bridge and engages the first and second segments of the first anchoring member at their first and second engagement points and the first and second segments of the second anchoring member at their first and second engagement points such that the implant grip constrains the implant in its insertion shape. The implant grip in its disengaged position releases the implant.

The implant grip includes a shell coupled with the body. The shell includes an exterior surface having an upper surface and a lower surface. The shell further includes an interior surface complimentary in shape with the implant such that the interior surface defines a passage through the shell complimentary in shape with the implant. The shell at its upper surface receives into the passage the body at its second end thereby coupling the shell with the body. The shell at its lower surface receives into the passage the implant. When receiving the implant, the shell at its interior surface by-passes the bridge and engages the first and second segments of the first anchoring member at their first and second engagement points and the first and second segments of the second anchoring member at their first and second engagement points thereby holding the implant in the shell and constraining the implant in its insertion shape.

The interior surface of the shell defines first, second, third, and fourth grooves. When the shell at its interior surface by-passes the bridge, each of the first, second, third, and fourth grooves receives therein one of the first and second segments of the first and second anchoring members. Moreover, the interior surface at the first, second, third, and fourth grooves engages the first and second anchoring members, thereby retaining the implant within the shell in its insertion shape. The interior surface in each of the first, second, third, and fourth grooves further defines a retention surface. When the first, second, third, and fourth grooves receive therein one of the first and second segments of the first and second anchoring members, each of the retention surfaces abuts one of the first and second engagement points of the first and second segments for the first and second anchoring members. The retention surfaces accordingly grip and constrain the first and second anchoring members such that the shell retains therein the implant in its insertion shape.

The body of the implant insertion device includes an implant grip receiver at the second end thereof that terminates in a tamp. The implant grip receiver is complimentary in shape with the interior surface of the shell such that the implant grip receiver inserts into the passage of the shell at its upper surface thereby coupling the implant grip receiver with the shell. When the implant grip resides in its engaged position, the tamp sits atop the bridge of the implant. Moreover, the tamp remains atop the bridge of the implant to prevent movement of the implant relative to the implant grip during progression of the implant grip from its engaged position to its disengaged position.

The implant grip receiver includes a first notch and a second notch, while the interior surface of the shell includes a detent engageable with the first and second notches. When the implant grip moves to its engaged position, the detent engages the first notch thereby locking the implant grip in its engaged position. Alternatively, when the implant grip moves to its disengaged position, the detent engages the second notch thereby locking the implant grip in its disengaged position.

The implant grip in an alternative embodiment of the implant insertion device includes an actuator coupled with the body and movable relative thereto whereby movement of the actuator progresses the implant grip between its engaged and disengaged positions. The implant grip further includes first and second blades securable with the actuator in an opposed relationship that defines a passage therebetween. The passage receives therein the bridge of the implant such that the first and second blades extend beyond the bridge and engage the first and second segments of the first and second anchoring members at their first and second engagement points thereby holding the implant and constraining the implant in its insertion shape. The actuator includes a first slider, a second slider, and a spacer. The first slider secures with the first blade, whereas the second slider secures with the second blade. The spacer secures between the first and second sliders such that the first and second blades are spaced apart to form the passage therebetween.

The body in an alternative embodiment of the implant insertion device defines a tamp at its second end. The body further defines a slot therethrough communicating exterior to the body that receives the spacer therein. The first slider secures with the spacer adjacent a first surface of the body, while the second slider secures with the spacer adjacent a second surface of the body. The first and second blades extend beyond the tamp such that the passage between the first and second blades is located adjacent the tamp. When the implant grip resides in its engaged position, the tamp sits atop the bridge of the implant. Moreover, the tamp remains atop the bridge of the implant to prevent movement of the implant relative to the implant grip during progression of the implant grip from its engaged position to its disengaged position.

The implant insertion device for use with an implant having first, second, and third anchoring members includes a body with a first end and a second end and an implant grip coupled with the body at its second end. The implant grip moves relative to the body between an engaged position and a disengaged position. The implant grip in its engaged position by-passes the bridge and engages the segments of the first and third anchoring members at their engagement points and the first and second segments of the second anchoring member at their first and second engagement points such that the implant grip constrains the implant in its insertion shape. The implant grip in its disengaged position releases the implant.

The implant grip includes a shell coupled with the body. The shell includes an exterior surface having an upper surface and a lower surface. The shell further includes an interior surface complimentary in shape with the implant such that the interior surface defines a passage through the shell complimentary in shape with the implant. The shell at its upper surface receives into the passage the body at its second end thereby coupling the shell with the body. The shell at its lower surface receives into the passage the implant. When receiving the implant, the shell at its interior surface by-passes the bridge and engages the segments of the first and third anchoring members at their engagement points and the first and second segments of the second anchoring member at their first and second engagement points thereby holding the implant in the shell and constraining the implant in its insertion shape.

The interior surface of the shell defines first, second, third, and fourth grooves. When the shell at its interior surface by-passes the bridge, each of the first, second, third, and fourth grooves receives therein one of the segments of the first and third anchoring members and the first and second segments of the second anchoring member. Moreover, the interior surface at the first, second, third, and fourth grooves engages the first, second, and third anchoring members, thereby retaining the implant within the shell in its insertion shape. The interior surface in each of the first, second, third, and fourth grooves further defines a retention surface. When the first, second, third, and fourth grooves receive therein one of the segments of the first and third anchoring members and the first and second segments of the second anchoring member, each of the retention surfaces abuts one of the engagement points of the segments for the first and third anchoring members and the first and second engagement points of the first and second segments for the second anchoring member. The retention surfaces accordingly grip and constrain the first, second, and third anchoring members such that the shell retains therein the implant in its insertion shape.

The interior surface of the shell includes projections that may be resilient. When the shell at its interior surface by-passes the bridge, the projections also by-pass the bridge and engage one of the first and third anchoring members such that the shell retains therein the implant in its insertion shape. The projections when they are resilient by-pass the bridge by moving relative thereto and engage one of the first and third anchoring members such that the shell retains therein the implant in its insertion shape.

The body of the implant insertion device includes an implant grip receiver at the second end thereof that terminates in a tamp. The implant grip receiver is complimentary in shape with the interior surface of the shell such that the implant grip receiver inserts into the passage of the shell at its upper surface thereby coupling the implant grip receiver with the shell. When the implant grip resides in its engaged position, the tamp sits atop the bridge of the implant. Moreover, the tamp remains atop the bridge of the implant to prevent movement of the implant relative to the implant grip during progression of the implant grip from its engaged position to its disengaged position.

The implant grip receiver includes a first notch and a second notch, while the interior surface of the shell includes a detent engageable with the first and second notches. When the implant grip moves to its engaged position, the detent engages the first notch thereby locking the implant grip in its engaged position. Alternatively, when the implant grip moves to its disengaged position, the detent engages the second notch thereby locking the implant grip in its disengaged position.

The implant grip in an alternative embodiment of the implant insertion device includes an actuator coupled with the body and movable relative thereto whereby movement of the actuator progresses the implant grip between its engaged and disengaged positions. The implant grip further includes first and second blades securable with the actuator in an opposed relationship that defines a passage therebetween. The passage receives therein the bridge of the implant such that the first and second blades extend beyond the bridge and engage the segments of the first and third anchoring members at their engagement points and the first and second segments of the second anchoring member at their first and second engagement points thereby holding the implant and constraining the implant in its insertion shape. The actuator includes a first slider, a second slider, and a spacer. The first slider secures with the first blade, whereas the second slider secures with the second blade. The spacer secures between the first and second sliders such that the first and second blades are spaced apart to form the passage therebetween.

The body in an alternative embodiment of the implant insertion device defines a tamp at its second end. The body further defines a slot therethrough communicating exterior to the body that receives the spacer therein. The first slider secures with the spacer adjacent a first surface of the body, while the second slider secures with the spacer adjacent a second surface of the body. The first and second blades extend beyond the tamp such that the passage between the first and second blades is located adjacent the tamp. When the implant grip resides in its engaged position, the tamp sits atop the bridge of the implant. Moreover, the tamp remains atop the bridge of the implant to prevent movement of the implant relative to the implant grip during progression of the implant grip from its engaged position to its disengaged position.

The implant insertion device for use with an implant having first, second, third, and fourth anchoring members includes a body with a first end and a second end and an implant grip coupled with the body at its second end. The implant grip moves relative to the body between an engaged position and a disengaged position. The implant grip in its engaged position by-passes the bridge and engages the segments of the first, second, third, and fourth anchoring members at their engagement points such that the implant grip constrains the implant in its insertion shape. The implant grip in its disengaged position releases the implant.

The implant grip includes a shell coupled with the body. The shell includes an exterior surface having an upper surface and a lower surface. The shell further includes an interior surface complimentary in shape with the implant such that the interior surface defines a passage through the shell complimentary in shape with the implant. The shell at its upper surface receives into the passage the body at its second end thereby coupling the shell with the body. The shell at its lower surface receives into the passage the implant. When receiving the implant, the shell at its interior surface by-passes the bridge and engages the segments of the first, second, third, and fourth anchoring members at their engagement points thereby holding the implant in the shell and constraining the implant in its insertion shape.

The interior surface of the shell defines first, second, third, and fourth grooves. When the shell at its interior surface by-passes the bridge, each of the first, second, third, and fourth grooves receives therein one of the segments of the first, second, third, and fourth anchoring members. Moreover, the interior surface at the first, second, third, and fourth grooves engages the first, second, third, and fourth anchoring members, thereby retaining the implant within the shell in its insertion shape. The interior surface in each of the first, second, third, and fourth grooves further defines a retention surface. When the first, second, third, and fourth grooves receive therein one of the segments of the first, second, third, and fourth anchoring members, each of the retention surfaces abuts one of the engagement points of the segments for the first, second, third, and fourth anchoring members. The retention surfaces accordingly grip and constrain the first, second, third, and fourth anchoring members such that the shell retains therein the implant in its insertion shape.

The interior surface of the shell includes projections that may be resilient. When the shell at its interior surface by-passes the bridge, the projections also by-pass the bridge and engage one of the first, second, third, and fourth anchoring members such that the shell retains therein the implant in its insertion shape. The projections when they are resilient by-pass the bridge by moving relative thereto and engage one of the first, second, third, and fourth anchoring members such that the shell retains therein the implant in its insertion shape.

The body of the implant insertion device includes an implant grip receiver at the second end thereof that terminates in a tamp. The implant grip receiver is complimentary in shape with the interior surface of the shell such that the implant grip receiver inserts into the passage of the shell at its upper surface thereby coupling the implant grip receiver with the shell. When the implant grip resides in its engaged position, the tamp sits atop the bridge of the implant. Moreover, the tamp remains atop the bridge of the implant to prevent movement of the implant relative to the implant grip during progression of the implant grip from its engaged position to its disengaged position.

The implant grip receiver includes a first notch and a second notch, while the interior surface of the shell includes a detent engageable with the first and second notches. When the implant grip moves to its engaged position, the detent engages the first notch thereby locking the implant grip in its engaged position. Alternatively, when the implant grip moves to its disengaged position, the detent engages the second notch thereby locking the implant grip in its disengaged position.

The implant grip in an alternative embodiment of the implant insertion device includes an actuator coupled with the body and movable relative thereto whereby movement of the actuator progresses the implant grip between its engaged and disengaged positions. The implant grip further includes first and second blades securable with the actuator in an opposed relationship that defines a passage therebetween. The passage receives therein the bridge of the implant such that the first and second blades extend beyond the bridge and engage the segments of the first, second, third, and fourth anchoring members at their engagement points thereby holding the implant and constraining the implant in its insertion shape. The actuator includes a first slider, a second slider, and a spacer. The first slider secures with the first blade, whereas the second slider secures with the second blade. The spacer secures between the first and second sliders such that the first and second blades are spaced apart to form the passage therebetween.

The body in an alternative embodiment of the implant insertion device defines a tamp at its second end. The body further defines a slot therethrough communicating exterior to the body that receives the spacer therein. The first slider secures with the spacer adjacent a first surface of the body, while the second slider secures with the spacer adjacent a second surface of the body. The first and second blades extend beyond the tamp such that the passage between the first and second blades is located adjacent the tamp. When the implant grip resides in its engaged position, the tamp sits atop the bridge of the implant. Moreover, the tamp remains atop the bridge of the implant to prevent movement of the implant relative to the implant grip during progression of the implant grip from its engaged position to its disengaged position.

The implant of the present invention with anchoring members extending from a bridge may be implanted through the use of drill holes created in bone, bones, or bone pieces. Moreover, it is often preferable to introduce the implant into the bone, bones, or bone pieces proximate to a fixation device holding the bone, bones, or bone pieces in a desired alignment. In order to permit such an implantation, a drill guide in various embodiments is configured for the drilling of drill holes into bone, bones, or bone pieces proximate to a fixation device.

The drill guide in one embodiment includes a body with first and second passages therethrough and a third passage and a fourth passage therethrough in alternative embodiments thereof. The drill guide includes a grip extending from the body and a template depending from the body between the first and second passages. The template includes a slot whereby the first passage resides exterior to the slot adjacent a first side thereof and the second passage resides exterior to the slot adjacent a second side thereof. In addition, a distance between the first and second passages substantially equals a distance between a first anchoring member of an implant and a second anchoring member of the implant when the implant resides in an insertion shape plus a distance equal to a thickness of the template.

A placement of the body on bone, bones, or bone pieces using the grip introduces the template at a fusion zone of the bone, bones, or bone pieces such that the slot receives therein a fixation device inserted into the bone, bones, or bone pieces. With the template at the fusion zone and the fixation device in the slot, the first passage resides on the bone, bones, or bone pieces adjacent a first side of the fusion zone proximate a first side of the fixation device and the second passage resides on the bone, bones, or bone pieces adjacent a second side of the fusion zone proximate a second side of the fixation device. Upon a drilling of drill holes in the bone, bones, or bone pieces using the first and second passages, the drill holes due to the positioning of the first and second passages on the bone, bones, or bone pieces are located proximate to the fixation device.

When the drill guide incorporates a third passage, the body includes the first passage therethrough located at a first end of the body adjacent a first side of the body, the second passage therethrough located at the first end of the body adjacent a second side of the body, and the third passage therethrough located at a second end of the body adjacent one of the first side of the body and the second side of the body. The drill guide includes the grip extending from the body and the template depending from the body between the first and second passages and the third passage. The template includes the slot whereby the first passage resides exterior to the slot adjacent the first side thereof, the second passage resides exterior to the slot adjacent the second side thereof, and the third passage resides exterior to the slot adjacent one of the first side thereof and the second side thereof. In addition, a distance between the first and second passages and the third passage substantially equals a distance between first and second anchoring members at a first end of an implant and a third anchoring member at a second end of the implant when the implant resides in an insertion shape plus a distance equal to a thickness of the template.

A placement of the body on bone, bones, or bone pieces using the grip introduces the template at a fusion zone of the bone, bones, or bone pieces such that the slot receives therein a fixation device inserted into the bone, bones, or bone pieces. With the template at the fusion zone and the fixation device in the slot, the first passage resides on the bone, bones, or bone piece adjacent a first side of the fusion zone proximate a first side of the fixation device, the second passage resides on the bone, bones, or bone piece adjacent the first side of the fusion zone proximate a second side of the fixation device, and the third passage resides on the bone, bones, or bone piece adjacent a second side of the fusion zone proximate one of the first side of the fixation device and the second side of the fixation device. Upon a drilling of drill holes in the bone, bones, or bone pieces using the first, second, and third passages, the drill holes due to the positioning of the first, second, and third passages on the bone, bones, or bone pieces are located proximate to the fixation device.

When the drill guide incorporates third and fourth passages, the body includes the first passage therethrough located at a first end of the body adjacent a first side of the body, the second passage therethrough located at the first end of the body adjacent a second side of the body, the third passage therethrough located at a second end of the body adjacent the first side of the body, and the fourth passage therethrough located at the second end of the body adjacent the second side of the body. The body includes the grip extending from the body the template depending from the body between the first and second passages and the third and fourth passages. The template includes the slot whereby the first and third passages reside exterior to the slot adjacent the first side thereof and the second and fourth passages reside exterior to the slot adjacent the second side thereof. In addition, a distance between the first and third passages and the second and fourth passages substantially equals a distance between first and second anchoring members at a first end of an implant and third and fourth anchoring members at a second end of the implant when the implant resides in an insertion shape plus a distance equal to a thickness of the template.

A placement of the body on bone, bones, or bone pieces using the grip introduces the template at a fusion zone of the bone, bones, or bone pieces such that the slot receives therein a fixation device inserted into the bone, bones, or bone pieces. With the template at the fusion zone and the fixation device in the slot, the first passage resides on the bone adjacent a first side of the fusion zone proximate a first side of the fixation device, the second passage resides on the bone adjacent the first side of the fusion zone proximate a second side of the fixation device, the third passage resides on the bone adjacent a second side of the fusion zone proximate the first side of the fixation device, and the fourth passage resides on the bone adjacent the second side of the fusion zone proximate the second side of the fixation device. Upon a drilling of drill holes in the bone, bones, or bone pieces using the first, second, third, and fourth passages, the drill holes due to the positioning of the first, second, third, and fourth passages on the bone, bones, or bone pieces are located proximate to the fixation device.

The drill guide in another embodiment includes a body with first and second passages therethrough and a third passage and a fourth passage therethrough in alternative embodiments thereof. The drill guide includes a first grip extending from the body adjacent the first passage and a first template depending from the first grip. The drill guide includes a second grip extending from the body adjacent the second passage and a second template depending from the second grip. The first and second templates each include a slot with first and second sides whereby the first passage resides exterior to the slots of the first and second templates at their first sides and the second passage resides exterior to the slots of the first and second templates at their second sides. In addition, a distance between the first and second passages substantially equals a distance between a first anchoring member of an implant and a second anchoring member of the implant when the implant resides in an insertion shape.

A placement of the body on bone, bones, or bone pieces across a fusion zone thereof using at least one of the first and second grips introduces the first template adjacent a first portion of the bone, bones, or bone pieces and the second template adjacent a second portion of the bone, bones, or bone pieces such that the slots of the first and second templates receive therein a fixation device inserted through the bone, bones, or bone pieces. With the first and second templates adjacent the bone, bones, or bone pieces and the fixation device in their respective slots, the first passage resides on the bone, bones, or bone pieces adjacent a first side of the fusion zone proximate a first side of the fixation device and the second passage resides on the bone, bones, or bone pieces adjacent a second side of the fusion zone proximate a second side of the fixation device. Upon a drilling of drill holes in the bone, bones, or bone pieces using the first and second passages, the drill holes due to the positioning of the first and second passages on the bone, bones, or bone pieces are located proximate to the fixation device.

When the drill guide incorporates a third passage, the body includes the first passage therethrough located at a first end of the body adjacent a first side of the body, the second passage therethrough located at the first end of the body adjacent a second side of the body, and the third passage therethrough located at a second end of the body adjacent one of the first side of the body and the second side of the body. The drill guide includes the first grip extending from the body adjacent the first and second passages and the first template depending from the first grip. The drill guide includes the second grip extending from the body adjacent the third passage and the second template depending from the second grip. The first and second templates each include the slot with first and second sides whereby the first passage resides exterior to the slots of the first and second templates at their first sides, the second passage resides exterior to the slots of the first and second templates at their second sides, and the third passage resides exterior to the slots of the first and second templates at one of their first sides and their second sides. In addition, a distance between the first and second passages and the third passage substantially equals a distance between first and second anchoring members at a first end of an implant and a third anchoring member at a second end of the implant when the implant resides in an insertion shape.

A placement of the body on bone, bones, or bone pieces across a fusion zone thereof using at least one of the first and second grips introduces the first template adjacent a first portion of the on bone, bones, or bone pieces and the second template adjacent a second portion of the on bone, bones, or bone pieces such that the slots of the first and second templates receive therein a fixation device inserted through the bone. With the first and second templates adjacent the bone, bones, or bone pieces and the fixation device in their respective slots, the first passage resides on the bone, bones, or bone pieces adjacent a first side of the fusion zone proximate a first side of the fixation device, the second passage resides on the bone, bones, or bone pieces adjacent the first side of the fusion zone proximate a second side of the fixation device, and the third passage resides on the bone, bones, or bone pieces adjacent a second side of the fusion zone proximate one of the first side of the fixation device and the second side of the fixation device. Upon a drilling of drill holes in the bone, bones, or bone pieces using the first, second, and third passages, the drill holes due to the positioning of the first, second, and third passages on the bone, bones, or bone pieces are located proximate to the fixation device.

When the drill guide incorporates third and fourth passages, the body includes the first passage therethrough located at a first end of the body adjacent a first side of the body, the second passage therethrough located at the first end of the body adjacent a second side of the body, the third passage therethrough located at a second end of the body adjacent the first side of the body, and the fourth passage therethrough the body located at the second end of the body adjacent the second side of the body. The drill guide includes the first grip extending from the body adjacent the first and second passages and the first template depending from the first grip. The drill guide includes the second grip extending from the body adjacent the third and fourth passages. The first and second templates each include the slot with first and second sides whereby the first and third passages reside exterior to the slots of the first and second templates at their first sides and the second and fourth passages reside exterior to the slots of the first and second templates at their second sides. In addition, a distance between the first and third passages and the second and fourth passages substantially equals a distance between first and second anchoring members at a first end of an implant and third and fourth anchoring members at a second end of the implant when the implant resides in an insertion shape.

A placement of the body on bone, bones, or bone pieces across a fusion zone thereof using at least one of the first and second grips introduces the first template adjacent a first portion of the bone, bones, or bone pieces and the second template adjacent a second portion of the bone, bones, or bone pieces such that the slots of the first and second templates receive therein a fixation device inserted through the bone, bones, or bone pieces. With the first and second templates adjacent the bone, bones, or bone pieces and the fixation device in their respective slots, the first passage resides on the bone, bones, or bone pieces adjacent a first side of the fusion zone proximate a first side of the fixation device, the second passage resides on the bone, bones, or bone pieces adjacent the first side of the fusion zone proximate a second side of the fixation device, the third passage resides on the bone, bones, or bone pieces adjacent a second side of the fusion zone proximate the first side of the fixation device, and the fourth passage resides on the bone, bones, or bone pieces adjacent the second side of the fusion zone proximate the second side of the fixation device. Upon a drilling of drill holes in the bone, bones, or bone pieces using the first, second, third, and fourth passages, the drill holes due to the positioning of the first, second, third, and fourth passages on the bone, bones, or bone pieces are located proximate to the fixation device.

In accordance with a method for an orthopedic fixation system including the implant with first and second anchoring members extending from the bridge, an implant insertion device loads with the implant. The implant insertion device by-passes the bridge and engages the segment of the first anchoring member at its engagement point and the segment of the second anchoring member at its engagement point such that the implant insertion device constrains the implant in its insertion shape. The implant utilizing the implant insertion device is positioned with its first anchoring member at a first bone, its second anchoring member at a second bone, and its bridge spanning a fusion zone of the first and second bones. The implant insertion device retracts from the segments of the first and second anchoring members while the implant insertion device is used to insert the first anchoring member into the first bone and the second anchoring member into the second bone until the bridge resides adjacent the first and second bones across the fusion zone thereof. Engagement of the implant insertion device with the segments of the first and second anchoring members is removed whereby the implant insertion device by-passes the bridge and releases the implant such that the implant attempts to transition from its insertion shape to its natural shape.

Loading the implant insertion device with the implant includes moving the implant grip relative to the body whereby the implant grip by-passes the bridge and engages the segment of the first anchoring member at its engagement point and the segment of the second anchoring member at its engagement point such that the implant grip constrains the implant in its insertion shape. Positioning and implanting the implant includes utilizing the body of the implant insertion device to place the implant with its first anchoring member at a first bone, its second anchoring member at a second bone, and its bridge spanning a fusion zone of the first and second bones. The implant grip moves relative to the body whereby the implant grip retracts from the segments of the first and second anchoring members. The first anchoring member inserts into the first bone and the second anchoring member inserts into the second bone utilizing the body until the bridge resides adjacent the first and second bones across the fusion zone thereof. The implant grip moves relative to the body until the implant grip releases the segments of the first and second anchoring members whereby the implant grip by-passes the bridge and releases the implant such that the implant attempts to transition from its insertion shape to its natural shape.

Positioning and implanting the implant includes utilizing the body of the implant insertion device to place the implant with its first anchoring member at a first bone, its second anchoring member at a second bone, and its bridge spanning a fusion zone of the first and second bones. The first anchoring member inserts into the first bone and the second anchoring member inserts into the second bone utilizing the body until the implant grip contacts the first and second bones. More particularly, pushing on the body results in the second end thereof via the bridge inserting the first anchoring member into the first bone and the second anchoring member into the second bone until the bridge resides adjacent the first and second bones across the fusion zone thereof. Moreover, the implant grip via its contact with the first and second bones moves relative to the body until the implant grip releases the segments of the first and second anchoring members whereby the implant grip by-passes the bridge and releases the implant such that the implant attempts to transition from its insertion shape to its natural shape.

Loading an implant insertion device according to an alternative embodiment includes positioning the body relative to the implant whereby the second end of the body abuts the bridge of the implant. The actuator and then moves relative to the body whereby the first and second blades extend beyond the bridge and respectively engage the segments of the first and second anchoring members at their engagement points such that the implant grip constrains the implant in its insertion shape.

Positioning and implanting the implant includes utilizing the body of the implant insertion device to place the implant with its first anchoring member at a first bone, its second anchoring member at a second bone, and its bridge spanning a fusion zone of the first and second bones. The actuator moves relative to the body whereby the first and second blades retract respectively from the segments of the first and second anchoring members The first anchoring member inserts into the first bone and the second anchoring member inserts into the second bone utilizing the body until the bridge resides adjacent the first and second bones across the fusion zone thereof. The actuator moves relative to the body until the first and second blades release respectively the segments of the first and second anchoring members whereby the first and second blades by-pass the bridge and release the implant such that the implant attempts to transition from its insertion shape to its natural shape.

When using a drill guide during implantation of the implant, a fixation device inserts into a first bone and a second bone across a fusion zone thereof. The template introduces into the fusion zone of the first and second bone utilizing the grip until the slot receives therein the fixation device, the first passage resides on the first bone adjacent a first side of the fusion zone proximate a first side of the fixation device, the second passage resides on the second bone adjacent a second side of the fusion zone proximate a second side of the fixation device, and the body spans the fusion zone. A first drill hole is formed in the first bone utilizing the first passage and a second drill hole is formed in the second bone using the second passage followed by a removal of the drill guide from the first and second bones. The first and second bones are compressed at their fusion zone thereby reducing a separation distance thereof. The implant insertion device positions the implant with its first anchoring member at the first drill hole of the first bone, its second anchoring member at the second drill hole of the second bone, and its bridge spanning the fusion zone of the first and second bones. The implant insertion device retracts from the segments of the first and second anchoring members while the implant insertion device inserts the first anchoring member into the first drill hole of the first bone and the second anchoring member into the second drill hole of the second bone until the bridge resides adjacent the first and second bones across the fusion zone thereof. Engagement of the implant insertion device with the segments of the first and second anchoring members is removed whereby the implant insertion device by-passes the bridge and releases the implant such that the implant attempts to transition from its insertion shape to its natural shape. If desired, the fixation device then is removed from the first and second bones. A distance between the first and second passages substantially equals a distance between the first anchoring member of the implant and the second anchoring member of the implant when the implant resides in its insertion shape plus a distance equal to a thickness of the template such that removing the template from the fusion zone and compressing the first and second bones at their fusion zone reduces a separation distance of the first drill hole from the second drill hole to a separation distance between the first anchoring member of the implant and the second anchoring member of the implant when the implant resides in its insertion shape.

When using an alternative drill guide during implantation of the implant, a fixation device inserts through a first bone and a second bone across a fusion zone thereof. The body of the drill guide is positioned on the first and second bones across the fusion zone thereof using at least one of the first and second grips whereby the first template resides adjacent the first bone and the second template resides adjacent the second bone such that the slots of the first and second templates receive therein the fixation device. With the body of the drill guide situated on the first and second bones, the first passage resides on the first bone adjacent a first side of the fusion zone proximate a first side of the fixation device, whereas the second passage resides on the second bone adjacent a second side of the fusion zone proximate a second side of the fixation device. A first drill hole is formed in the first bone utilizing the first passage and a second drill hole is formed in the second bone using the second passage followed by a removal of the drill guide from the first and second bones. The implant insertion device positions the implant with its first anchoring member at the first drill hole of the first bone, its second anchoring member at the second drill hole of the second bone, and its bridge spanning the fusion zone of the first and second bones. The implant insertion device retracts from the segments of the first and second anchoring members while the implant insertion device inserts the first anchoring member into the first drill hole of the first bone and the second anchoring member into the second drill hole of the second bone until the bridge resides adjacent the first and second bones across the fusion zone thereof. Engagement of the implant insertion device with the segments of the first and second anchoring members is removed whereby the implant insertion device by-passes the bridge and releases the implant such that the implant attempts to transition from its insertion shape to its natural shape. If desired, the fixation device then is removed from the first and second bones.

In accordance with a method for an orthopedic fixation system including the implant with first, second, and third anchoring members extending from the bridge, an implant insertion device loads with the implant. The implant insertion device by-passes the bridge and engages the segments of the first and third anchoring members at their engagement points and the first and second segments of the second anchoring member at its first and second engagement points such that the implant insertion device constrains the implant in its insertion shape. The implant utilizing the implant insertion device is positioned with its first and third anchoring members at a first bone, its second anchoring members at a second bone, and its bridge spanning a fusion zone of the first and second bones. The implant insertion device retracts from the segments of the first and third anchoring members and the first and second segments of the second anchoring member while the implant insertion device is used to insert the first and third anchoring members into the first bone and the second anchoring member into the second bone until the bridge resides adjacent the first and second bones across the fusion zone thereof. Engagement of the implant insertion device with the segments of the first and third anchoring members and the first and second segments of the second anchoring member is removed whereby the implant insertion device by-passes the bridge and releases the implant such that the implant attempts to transition from its insertion shape to its natural shape.

Loading the implant insertion device with the implant includes moving the implant grip relative to the body whereby the implant grip by-passes the bridge and engages the segments of the first and third anchoring members at their engagement points and the first and second segments of the second anchoring member at its first and second engagement points such that the implant grip constrains the implant in its insertion shape. Positioning and implanting the implant includes utilizing the body of the implant insertion device to place the implant with its first and third anchoring members at a first bone, its second anchoring member at a second bone, and its bridge spanning a fusion zone of the first and second bones. The implant grip moves relative to the body whereby the implant grip retracts from the segments of the first and third anchoring members and the first and second segments of the second anchoring member. The first and third anchoring members insert into the first bone and the second anchoring member inserts into the second bone utilizing the body until the bridge resides adjacent the first and second bones across the fusion zone thereof. The implant grip moves relative to the body until the implant grip releases the segments of the first and third anchoring members and the first and second segments of the second anchoring member whereby the implant grip by-passes the bridge and releases the implant such that the implant attempts to transition from its insertion shape to its natural shape.

Positioning and implanting the implant includes utilizing the body of the implant insertion device to place the implant with its first and third anchoring members at a first bone, its second anchoring member at a second bone, and its bridge spanning a fusion zone of the first and second bones. The first and third anchoring members insert into the first bone and the second anchoring member into the second bone utilizing the body until the implant grip contacts the first and second bones. More particularly, pushing on the body results in the second end of the body via the bridge inserting the first and third anchoring members into the first bone and the second anchoring member into the second bone until the bridge resides adjacent the first and second bones across the fusion zone thereof. The implant grip via its contact with the first and second bones moves relative to the body until the implant grip releases the segments of the first and third anchoring members and the first and second segments of the second anchoring member whereby the implant grip by-passes the bridge and releases the implant such that the implant attempts to transition from its insertion shape to its natural shape.

Loading an implant insertion device according to an alternative embodiment includes positioning the body relative to the implant whereby the second end of the body abuts the bridge of the implant. The actuator moves actuator relative to the body whereby the first and second blades extend beyond the bridge and respectively engage the segments of the first and third anchoring members at their engagement points and the first and second segments of the second anchoring member at its first and second engagement points such that the implant grip constrains the implant in its insertion shape.

Positioning and implanting the implant includes utilizing the body of the implant insertion device to place the implant with its first and third anchoring members at a first bone, its second anchoring member at a second bone, and its bridge spanning a fusion zone of the first and second bones. The actuator moves relative to the body whereby the first and second blades retract respectively from the segments of the first and third anchoring members and the first and second segments of the second anchoring member. The first and third anchoring members insert into the first bone and the second anchoring member inserts into the second bone utilizing the body until the bridge resides adjacent the first and second bones across the fusion zone thereof. The actuator moves relative to the body until the first and second blades release respectively the segments of the first and third anchoring members and the first and second segments of the second anchoring member whereby the first and second blades by-pass the bridge and release the implant such that the implant attempts to transition from its insertion shape to its natural shape.

When using a drill guide during implantation of the implant, a fixation device inserts into a first bone and a second bone across a fusion zone thereof. The template introduces into the fusion zone of the first and second bone utilizing the grip until the slot receives therein the fixation device, the first passage resides on the first bone adjacent a first side of the fusion zone proximate a first side of the fixation device, the second passage resides on the first bone adjacent the first side of the fusion zone proximate a second side of the fixation device, the third passage resides on the second bone adjacent a second side of the fusion zone proximate one of the first side of the fixation device and the second side of the fixation device, and the body spans the fusion zone. A first drill hole is formed in the first bone utilizing the first passage, a second drill hole is formed in the first bone using the second passage, and a drill hole is formed in the second bone utilizing the third passage followed by a removal of the drill guide from the first and second bones. The first and second bones are compressed at their fusion zone thereby reducing a separation distance thereof. The implant insertion device positions the implant with its first anchoring member at the first drill hole of the first bone, its second anchoring member at the second drill hole of the first bone, and its third anchoring member at the drill hole of the second bone, and its bridge spanning the fusion zone of the first and second bones. The implant insertion device retracts from the segments of the first, second, and third anchoring members while the implant insertion device inserts the first anchoring member into the first drill hole of the first bone, the second anchoring member into the second drill hole of the first bone, and the third anchoring member into the drill hole of the second bone until the bridge resides adjacent the first and second bones across the fusion zone thereof. Engagement of the implant insertion device with the segments of the first, second, and third anchoring members is removed whereby the implant insertion device by-passes the bridge and releases the implant such that the implant attempts to transition from its insertion shape to its natural shape. If desired, the fixation device then is removed from the first and second bones. A distance between the first and second passages and the third passage substantially equals a distance between the first and second anchoring members of the implant and the third anchoring member of the implant when the implant resides in its insertion shape plus a distance equal to a thickness of the template such that removing the template from the fusion zone and compressing the first and second bones at their fusion zone reduces a separation distance of the first and second drill holes of the first bone from the drill hole in the second bone to a separation distance between the first and second anchoring members of the implant and the third anchoring members of the implant when the implant resides in its insertion shape.

When using an alternative drill guide during implantation of the implant, a fixation device inserts through a first bone and a second bone across a fusion zone thereof. The body of the drill guide on the first and second bones is positioned across the fusion zone thereof using at least one of the first and second grips whereby the first template resides adjacent the first bone and the second template resides adjacent the second bone such that the slots of the first and second templates receive therein the fixation device. With the body of the drill guide situated on the first and second bones, the first passage resides on the first bone adjacent a first side of the fusion zone proximate a first side of the fixation device, the second passage resides on the first bone adjacent the first side of the fusion zone proximate a second side of the fixation device, and the third passage resides on the second bone adjacent a second side of the fusion zone proximate one of the first side of the fixation device and the second side of the fixation device. A first drill hole is formed in the first bone utilizing the first passage, a second drill hole is formed in the first bone using the second passage, and a drill hole is formed in the second bone utilizing the third passage followed by a removal of the drill guide from the first and second bones. The implant insertion device positions the implant with its first anchoring member at the first drill hole of the first bone, its second anchoring member at the second drill hole of the first bone, its third anchoring member at the drill hole of the second bone, and its bridge spanning the fusion zone of the first and second bones. The implant insertion device retracts from the segments of the first, second, and third anchoring members while the implant insertion device inserts the first anchoring member into the first drill hole of the first bone, the second anchoring member into the second drill hole of the first bone, the third anchoring member into the drill hole of the second until the bridge resides adjacent the first and second bones across the fusion zone thereof. Engagement of the implant insertion device with the segments of the first, second, and third anchoring members is removed whereby the implant insertion device by-passes the bridge and releases the implant such that the implant attempts to transition from its insertion shape to its natural shape. If desired, the fixation device then is removed the from the first and second bones.

In accordance with a method for an orthopedic fixation system including the implant with first, second, third, and fourth anchoring members extending from the bridge, an implant insertion device loads with the implant. The implant insertion device by-passes the bridge and engages the segments of the first, second, third, and fourth anchoring member at their engagement points such that the implant insertion device constrains the implant in its insertion shape. The implant utilizing the implant insertion device is positioned with its first and second anchoring members at a first bone, its third and fourth anchoring members at a second bone, and its bridge spanning a fusion zone of the first and second bones. The implant insertion device retracts from the segments of the first, second, third, and fourth anchoring members while the implant insertion device is used to insert the first and second anchoring members into the first bone and the third and fourth anchoring members into the second bone until the bridge resides adjacent the first and second bones across the fusion zone thereof. Engagement of the implant insertion device with the segments of the first, second, third, and fourth anchoring members is removed whereby the implant insertion device by-passes the bridge and releases the implant such that the implant attempts to transition from its insertion shape to its natural shape.

Loading the implant insertion device with the implant includes moving the implant grip relative to the body whereby the implant grip by-passes the bridge and engages the segments of the first, second, third, and fourth anchoring members at their engagement points such that the implant grip constrains the implant in its insertion shape. Positioning and implanting the implant includes utilizing the body of the implant insertion device to place the implant with its first and second anchoring members at a first bone, its third and fourth anchoring members at a second bone, and its bridge spanning a fusion zone of the first and second bones. The implant grip moves relative to the body whereby the implant grip retracts from the segments of the first, second, third, and fourth anchoring members. The first and second anchoring members insert into the first bone and the third and fourth anchoring members insert into the second bone utilizing the body until the bridge resides adjacent the first and second bones across the fusion zone thereof. The implant grip moves relative to the body until the implant grip releases the segments of the first, second, third, and fourth anchoring members whereby the implant grip by-passes the bridge and releases the implant such that the implant attempts to transition from its insertion shape to its natural shape.

Positioning and implanting the implant includes utilizing the body of the implant insertion device to place the implant with its first and second anchoring members at a first bone, its third and fourth anchoring members at a second bone, and its bridge spanning a fusion zone of the first and second bones. The first and second anchoring members insert into the first bone and the third and fourth anchoring members insert into the second bone utilizing the body until the implant grip contacts the first and second bones. More particularly, pushing on the body results in the second end of the body via the bridge inserting the first and second anchoring members into the first bone and the third and fourth anchoring members into the second bone until the bridge resides adjacent the first and second bones across the fusion zone thereof. The implant grip via its contact with the first and second bones moves relative to the body until the implant grip releases the segments of the first, second, third, and fourth anchoring members whereby the implant grip by-passes the bridge and releases the implant such that the implant attempts to transition from its insertion shape to its natural shape.

Loading an implant insertion device according to an alternative embodiment includes positioning the body relative to the implant whereby the second end of the body abuts the bridge of the implant. The actuator moves relative to the body whereby the first and second blades extend beyond the bridge and respectively engage the segments of the first, second, third, and fourth anchoring members at their engagement points such that the implant grip constrains the implant in its insertion shape.

Positioning and implanting the implant includes utilizing the body of the implant insertion device to place the implant with its first and second anchoring members at a first bone, its third and fourth anchoring members at a second bone, and its bridge spanning a fusion zone of the first and second bones. The actuator moves relative to the body whereby the first and second blades retract respectively from the segments of the first, second, third, and fourth anchoring members. The first and second anchoring members insert into the first bone and the third and fourth anchoring members insert into the second bone utilizing the body until the bridge resides adjacent the first and second bones across the fusion zone thereof. The actuator moves relative to the body until the first and second blades release respectively the segments of the first, second, third, and fourth anchoring members whereby the first and second blades by-pass the bridge and release the implant such that the implant attempts to transition from its insertion shape to its natural shape.

When using a drill guide during implantation of the implant, a fixation device inserts into a first bone and a second bone across a fusion zone thereof. The template introduces into the fusion zone of the first and second bone utilizing the grip until the slot receives therein the fixation device, the first passage resides on the first bone adjacent a first side of the fusion zone proximate a first side of the fixation device, the second passage resides on the first bone adjacent the first side of the fusion zone proximate a second side of the fixation device, the third passage resides on the second bone adjacent a second side of the fusion zone proximate the first side of the fixation device, the fourth passage resides on the second bone adjacent the second side of the fusion zone proximate the second side of the fixation device, and the body spans the fusion zone. A first drill hole is formed in the first bone utilizing the first passage, a second drill hole is formed in the first bone using the second passage, a first drill hole is formed in the second bone utilizing the third passage, and a second drill hole is formed in the second bone utilizing the fourth passage followed by a removal of the drill guide from the first and second bones. The first and second bones are compressed at their fusion zone thereby reducing a separation distance thereof. The implant insertion device positions the implant with its first anchoring member at the first drill hole of the first bone, its second anchoring member at the second drill hole of the first bone, its third anchoring member at the first drill hole of the second bone, its fourth anchoring member at the second drill hole of the second bone, and its bridge spanning the fusion zone of the first and second bones. The implant insertion device retracts from the segments of the first, second, third, and fourth anchoring members while the implant insertion device inserts the first anchoring member into the first drill hole of the first bone, the second anchoring member into the second drill hole of the first bone, the third anchoring member into the first drill hole of the second bone, and the fourth anchoring member into the second drill hole of the second bone until the bridge resides adjacent the first and second bones across the fusion zone thereof. Engagement of the implant insertion device with the segments of the first, second, third, and fourth anchoring members is removed whereby the implant insertion device by-passes the bridge and releases the implant such that the implant attempts to transition from its insertion shape to its natural shape. If desired, the fixation device then is removed from the first and second bones. A distance between the first and third passages and the second and fourth passages substantially equals a distance between the first and third anchoring members of the implant and the second and fourth anchoring members of the implant when the implant resides in its insertion shape plus a distance equal to a thickness of the template such that removing the template from the fusion zone and compressing the first and second bones at their fusion zone reduces a separation distance of the first drill hole of the first bone from the first drill hole in the second bone and the second drill hole of the first bone from the second drill hole of the second bone to a separation distance between the first and third anchoring members of the implant and the second and fourth anchoring members of the implant when the implant resides in its insertion shape.

When using an alternative drill guide during implantation of the implant, a fixation device inserts through a first bone and a second bone across a fusion zone thereof. The body of the drill guide is positioned on the first and second bones across the fusion zone thereof using at least one of the first and second grips whereby the first template resides adjacent the first bone and the second template resides adjacent the second bone such that the slots of the first and second templates receive therein the fixation device. With the body of the drill guide situated on the first and second bones, the first passage resides on the first bone adjacent a first side of the fusion zone proximate a first side of the fixation device, the second passage resides on the first bone adjacent the first side of the fusion zone proximate a second side of the fixation device, the third passage resides on the second bone adjacent a second side of the fusion zone proximate the first side of the fixation device, and the fourth passage resides on the second bone adjacent the second side of the fusion zone proximate the second side of the fixation device. A first drill hole is formed in the first bone utilizing the first passage, a second drill hole is formed in the first bone using the second passage, a first drill hole is formed in the second bone utilizing the third passage, and a second drill hole is formed in the second bone utilizing the fourth passage followed by a removal of the drill guide from the first and second bones. The implant insertion device positions the implant with its first anchoring member at the first drill hole of the first bone, its second anchoring member at the second drill hole of the first bone, its third anchoring member at the first drill hole of the second bone, its fourth anchoring member at the second drill hole of the second bone, and its bridge spanning the fusion zone of the first and second bones. The implant insertion device retracts from the segments of the first, second, third, and fourth anchoring members while the implant insertion device inserts the first anchoring member into the first drill hole of the first bone, the second anchoring member into the second drill hole of the first bone, the third anchoring member into the first drill hole of the second bone, and the fourth anchoring member into the second drill hole of the second bone until the bridge resides adjacent the first and second bones across the fusion zone thereof. Engagement of the implant insertion device with the segments of the first, second, third, and fourth anchoring members is removed whereby the implant insertion device by-passes the bridge and releases the implant such that the implant attempts to transition from its insertion shape to its natural shape. If desired, the fixation device then is removed from the first and second bones.

In accordance with an implantation method including a drill guide with first and second passages, a fixation device inserts into a first bone and a second bone across a fusion zone thereof. The template introduces into the fusion zone of the first and second bone utilizing the grip until the slot receives therein the fixation device. As a result, the first passage resides on the first bone adjacent a first side of the fusion zone proximate a first side of the fixation device, the second passage resides on the second bone adjacent a second side of the fusion zone proximate a second side of the fixation device, and the body spans the fusion zone. A drill hole is formed in the first bone utilizing the first passage, while a drill hole is formed in the second bone using the second passage. The drill guide removes from the first and second bones followed by a compressing of the first and second bones at their fusion zone thereby reducing a separation distance thereof. A first anchoring member of an implant inserts into the drill hole of the first bone and a second anchoring member of the implant inserts into the drill hole of the second bone until a bridge of the implant resides adjacent the first and second bones across the fusion zone thereof, whereby the implant attempts to transition from an insertion shape to a natural shape. If desired, the fixation device then is removed from the first and second bones. A distance between the first and second passages substantially equals a distance between the first anchoring member of the implant and the second anchoring member of the implant when the implant resides in its insertion shape plus a distance equal to a thickness of the template such that removing the template from the fusion zone and compressing the first and second bones at their fusion zone reduces a separation distance of the drill hole of the first bone from the drill hole of the second bone to a separation distance between the first anchoring member of the implant and the second anchoring member of the implant when the implant resides in its insertion shape.

In accordance with an implantation method including an alternative drill guide with first and second passages, a fixation device inserts through a first bone and a second bone across a fusion zone thereof. The body of the drill guide is positioned on the first and second bones across the fusion zone thereof using at least one of the first and second grips whereby the first template resides adjacent the first bone and the second template resides adjacent the second bone such that the slots of the first and second templates receive therein the fixation device. With the body of the drill guide situated on the first and second bones, the first passage resides on the first bone adjacent a first side of the fusion zone proximate a first side of the fixation device, whereas and the second passage resides on the second bone adjacent a second side of the fusion zone proximate a second side of the fixation device. A drill hole is formed in the first bone utilizing the first passage while a drill hole is formed in the second bone using the second passage followed by a removal of the drill guide from the first and second bones. A first anchoring member of an implant inserts into the drill hole of the first bone and a second anchoring member of the implant inserts into the drill hole of the second bone until a bridge of the implant resides adjacent the first and second bones across the fusion zone thereof, whereby the implant attempts to transition from an insertion shape to a natural shape. If desired, the fixation device then is removed from the first and second bones.

In accordance with an implantation method including a drill guide with first, second, and third passages, a fixation device inserts into a first bone and a second bone across a fusion zone thereof. The template introduces into the fusion zone of the first and second bone utilizing the grip until the slot receives therein the fixation device. As a result, the first passage resides on the first bone adjacent a first side of the fusion zone proximate a first side of the fixation device, the second passage resides on the first bone adjacent the first side of the fusion zone proximate a second side of the fixation device, the third passage resides on the second bone adjacent a second side of the fusion zone proximate one of the first side of the fixation device and the second side of the fixation device, and the body spans the fusion zone. A first drill hole is formed in the first bone utilizing the first passage, a second drill hole is formed in the first bone using the second passage, and a drill hole is formed in the second bone utilizing the third passage. The drill guide is removed from the first and second bones followed by a compressing of the first and second bones at their fusion zone thereby reducing a separation distance thereof. A first anchoring member of an implant inserts into the first drill hole of the first bone, a second anchoring member of the implant inserts into the second drill hole of the first bone, and a third anchoring member of the implant inserts into the drill hole of the second bone until a bridge of the implant resides adjacent the first and second bones across the fusion zone thereof, whereby the implant attempts to transition from an insertion shape to a natural shape. If desired, the fixation device is then removed from the first and second bones. A distance between the first and second passages and the third passage substantially equals a distance between the first and second anchoring members of the implant and the third anchoring member of the implant when the implant resides in its insertion shape plus a distance equal to a thickness of the template such that removing of the template from the fusion zone and compressing the first and second bones at their fusion zone reduces a separation distance of the first and second drill holes of the first bone from the drill hole in the second bone to a separation distance between the first and second anchoring members of the implant and the third anchoring members of the implant when the implant resides in its insertion shape.

In accordance with an implantation method including an alternative drill guide with first, second, and third passages, a fixation device inserts through a first bone and a second bone across a fusion zone thereof. The body of the drill guide is positioned on the first and second bones across the fusion zone thereof using at least one of the first and second grips whereby the first template resides adjacent the first bone and the second template resides adjacent the second bone such that the slots of the first and second templates receive therein the fixation device. With the body of the drill guide situated on the first and second bones, the first passage resides on the first bone adjacent a first side of the fusion zone proximate a first side of the fixation device, the second passage resides on the first bone adjacent the first side of the fusion zone proximate a second side of the fixation device, and the third passage resides on the second bone adjacent a second side of the fusion zone proximate one of the first side of the fixation device and the second side of the fixation device. A first drill hole is formed in the first bone utilizing the first passage, a second drill hole is formed in the first bone using the second passage, and a drill hole is formed in the second bone utilizing the third passage followed by a removal of the drill guide from the first and second bones. A first anchoring member of an implant inserts into the first drill hole of the first bone, a second anchoring member of the implant inserts into the second drill hole of the first bone, and a third anchoring member of the implant inserts into the drill hole of the second bone until a bridge of the implant resides adjacent the first and second bones across the fusion zone thereof, whereby the implant attempts to transition from an insertion shape to a natural shape. If desired, the fixation device then is removed from the first and second bones.

In accordance with an implantation method including a drill guide with first, second, third, and fourth passages, a fixation device inserts into a first bone and a second bone across a fusion zone thereof. The template introduces into the fusion zone of the first and second bone utilizing the grip until the slot receives therein the fixation device. As a result, the first passage resides on the first bone adjacent a first side of the fusion zone proximate a first side of the fixation device, the second passage resides on the first bone adjacent the first side of the fusion zone proximate a second side of the fixation device, the third passage resides on the second bone adjacent a second side of the fusion zone proximate a first side of the fixation device, the fourth passage resides on the second bone adjacent the second side of the fusion zone proximate a second side of the fixation device, and the body spans the fusion zone. A first drill hole is formed in the first bone utilizing the first passage, a second drill hole is formed in the first bone using the second passage, a first drill hole is formed in the second bone utilizing the third passage, and a second drill hole is formed in the second bone utilizing the fourth passage. The drill guide is removed from the first and second bones followed by a compressing of the first and second bones at their fusion zone thereby reducing a separation distance thereof. A first anchoring member of an implant inserts into the first drill hole of the first bone, a second anchoring member of the implant inserts into the second drill hole of the first bone, a third anchoring member of the implant inserts into the first drill hole of the second bone, and a fourth anchoring member of the implant inserts into the second drill hole of the second bone until a bridge of the implant resides adjacent the first and second bones across the fusion zone thereof, whereby the implant attempts to transition from an insertion shape to a natural shape. If desired, the fixation device is then removed from the first and second bones. A distance between the first and third passages and the second and fourth passages substantially equals a distance between the first and third anchoring members of the implant and the second and fourth anchoring members of the implant when the implant resides in its insertion shape plus a distance equal to a thickness of the template such that removing the template from the fusion zone and compressing the first and second bones at their fusion zone reduces a separation distance of the first drill hole of the first bone from the first drill hole in the second bone and the second drill hole of the first bone from the second drill hole of the second bone to a separation distance between the first and third anchoring members of the implant and the second and fourth anchoring members of the implant when the implant resides in its insertion shape.

In accordance with an implantation method including an alternative drill guide with first, second, third, and fourth passages, a fixation device inserts through a first bone and a second bone across a fusion zone thereof. The body of the drill guide on the first and second bones is positioned across the fusion zone thereof using at least one of the first and second grips whereby the first template resides adjacent the first bone and the second template resides adjacent the second bone such that the slots of the first and second templates receive therein the fixation device. With the body of the drill guide situated on the first and second bones, the first passage resides on the first bone adjacent a first side of the fusion zone proximate a first side of the fixation device, the second passage resides on the first bone adjacent the first side of the fusion zone proximate a second side of the fixation device, the third passage resides on the second bone adjacent a second side of the fusion zone proximate the first side of the fixation device, and the fourth passage resides on the second bone adjacent the second side of the fusion zone proximate the second side of the fixation device. A first drill hole is formed in the first bone utilizing the first passage, a second drill hole is formed in the first bone using the second passage, a first drill hole is formed in the second bone utilizing the third passage, and a second drill hole is formed in the second bone utilizing the fourth passage followed by a removal of the drill guide from the first and second bones. A first anchoring member of an implant inserts into the first drill hole of the first bone, a second anchoring member of the implant inserts into the second drill hole of the first bone, a third anchoring member of the implant inserts into the first drill hole of the second bone, and a fourth anchoring member of the implant inserts into the second drill hole of the second bone until a bridge of the implant resides adjacent the first and second bones across the fusion zone thereof, whereby the implant attempts to transition from an insertion shape to a natural shape. If desired, the fixation device then is removed from the first and second bones.

It is therefore an object of the present invention to provide an implant with a bridge and anchoring members including a segment exterior of the bridge whereby the implant transitions between a natural shape and an insertion shape.

It is another object of the present invention to provide an implant insertion device that engages the implant at the segments of its anchoring members in order to constrain the implant in its insertion shape.

It is a further object of the present invention to provide the implant insertion device whereby the implant insertion device delivers the implant at a surface of bone, bones, or bone pieces such that tamping of the implant is eliminated.

It is still a further object of the present invention to provide a drill guide that facilitates introduction of an implant into bone, bones, or bone pieces proximate to a fixation device holding the bone, bones, or bone pieces in a desired alignment.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTION OF DRAWINGS

FIG. 5C is an isometric view in partial cross-section illustrating the implant insertion device in its loaded position that constrains the shape memory implant in its insertion shape.

FIG. 5D is an isometric view in cross-section taken along line A of FIG. 5C illustrating the implant insertion device in its loaded position that constrains the shape memory implant in its insertion shape.

FIG. 14A is an isometric view illustrating a shape memory implant according to a second embodiment in a natural shape.

FIG. 14B is a side view thereof.

FIG. 14C is an end view thereof.

FIG. 14D is a top view thereof.

FIG. 14E is a bottom view thereof.

FIG. 18C is an isometric view in partial cross-section illustrating the implant insertion device in its loaded position that constrains the shape memory implant in its insertion shape.

FIG. 18D is an isometric view in cross-section taken along line G of FIG. 18C illustrating the implant insertion device in its loaded position that constrains the shape memory implant in its insertion shape.

FIG. 20E is a front view illustrating the implant grip of the implant insertion device.

FIG. 20F is a top view illustrating the implant grip of the implant insertion device.

FIG. 20G is a bottom view illustrating the implant grip of the implant insertion device.

FIG. 20H is an end view in cross-section taken along lines J-J of FIG. 20E illustrating the implant grip of the implant insertion device.

FIG. 20I is a front view in cross-section taken along lines K-K of FIG. 20F illustrating the implant grip of the implant insertion device.

FIG. 31C is an isometric view in partial cross-section illustrating the implant insertion device in its loaded position that constrains the shape memory implant in its insertion shape.

FIG. 31D is an isometric view in cross-section taken along line M of FIG. 31C illustrating the implant insertion device in its loaded position that constrains the shape memory implant in its insertion shape.

FIG. 33F is a top view illustrating the implant grip of the implant insertion device.

FIG. 33G is a bottom view illustrating the implant grip of the implant insertion device.

FIG. 33H is an end view in cross-section taken along lines P-P of FIG. 33E illustrating the implant grip of the implant insertion device.

FIG. 33I is an end view in cross-section taken along lines Q-Q of FIG. 33E illustrating the implant grip of the implant insertion device.

FIG. 33J is a front view in cross-section taken along lines R-R of FIG. 33F illustrating the implant grip of the implant insertion device.

FIG. 34A is front view illustrating the implant grip of the implant insertion device according to the fifth embodiment constraining the shape memory implant in its insertion shape.

FIG. 34B is a bottom view in cross-section taken along lines S-S of FIG. 33A illustrating the implant grip of the implant insertion device constraining the shape memory implant in its insertion shape.

FIGS. 35A-35B are isometric views in cross-section illustrating the implant grip of the implant insertion device constraining the shape memory implant in its insertion shape.

FIG. 36A is an isometric view illustrating an implant insertion device according to a sixth embodiment in an unloaded position and a shape memory implant according to the third embodiment in its natural shape.

FIG. 36B is a front view illustrating the implant insertion device in its unloaded position and the shape memory implant.

FIG. 36C is an end view illustrating the implant insertion device in its unloaded position and the shape memory implant.

FIG. 36D is a bottom view illustrating the implant insertion device in its unloaded position.

Figure 37A:
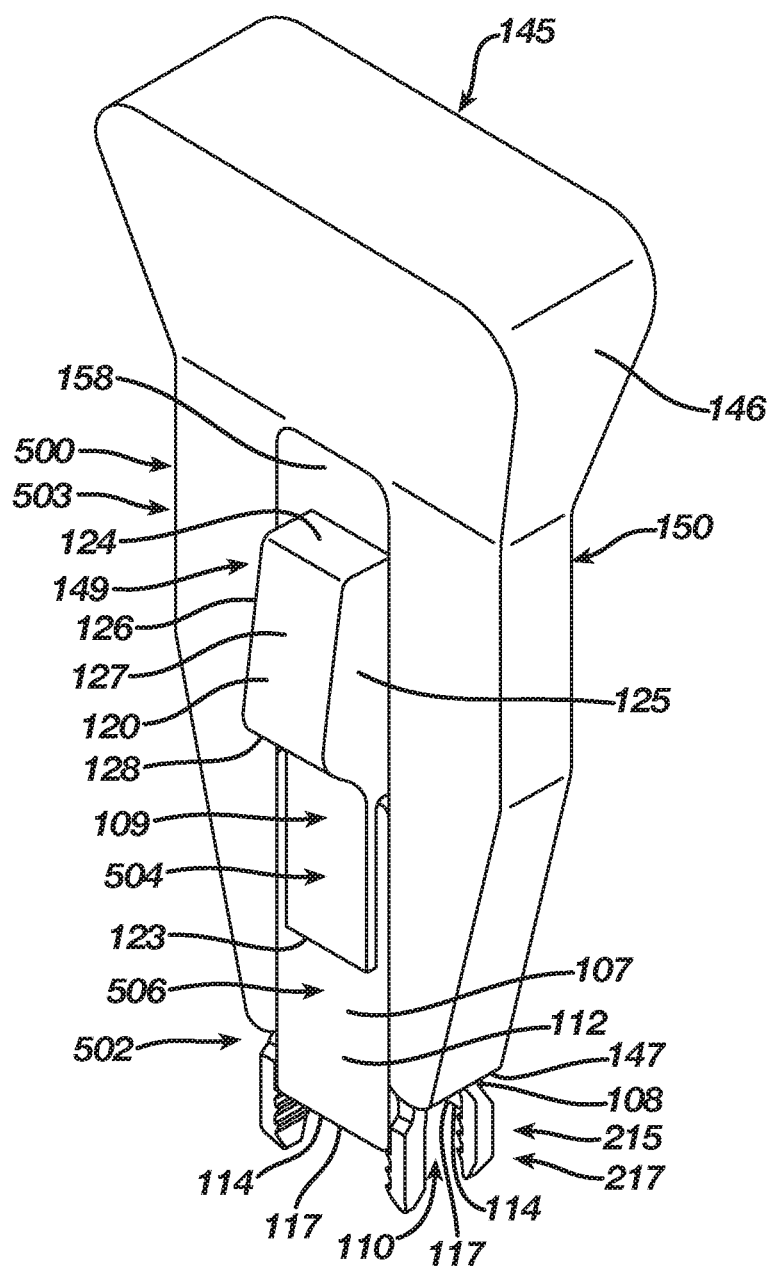

FIG. 37A is an isometric view illustrating the implant insertion device according to the sixth embodiment in a loaded position that constrains the shape memory implant according to the third embodiment in its insertion shape.

Figure 37B:
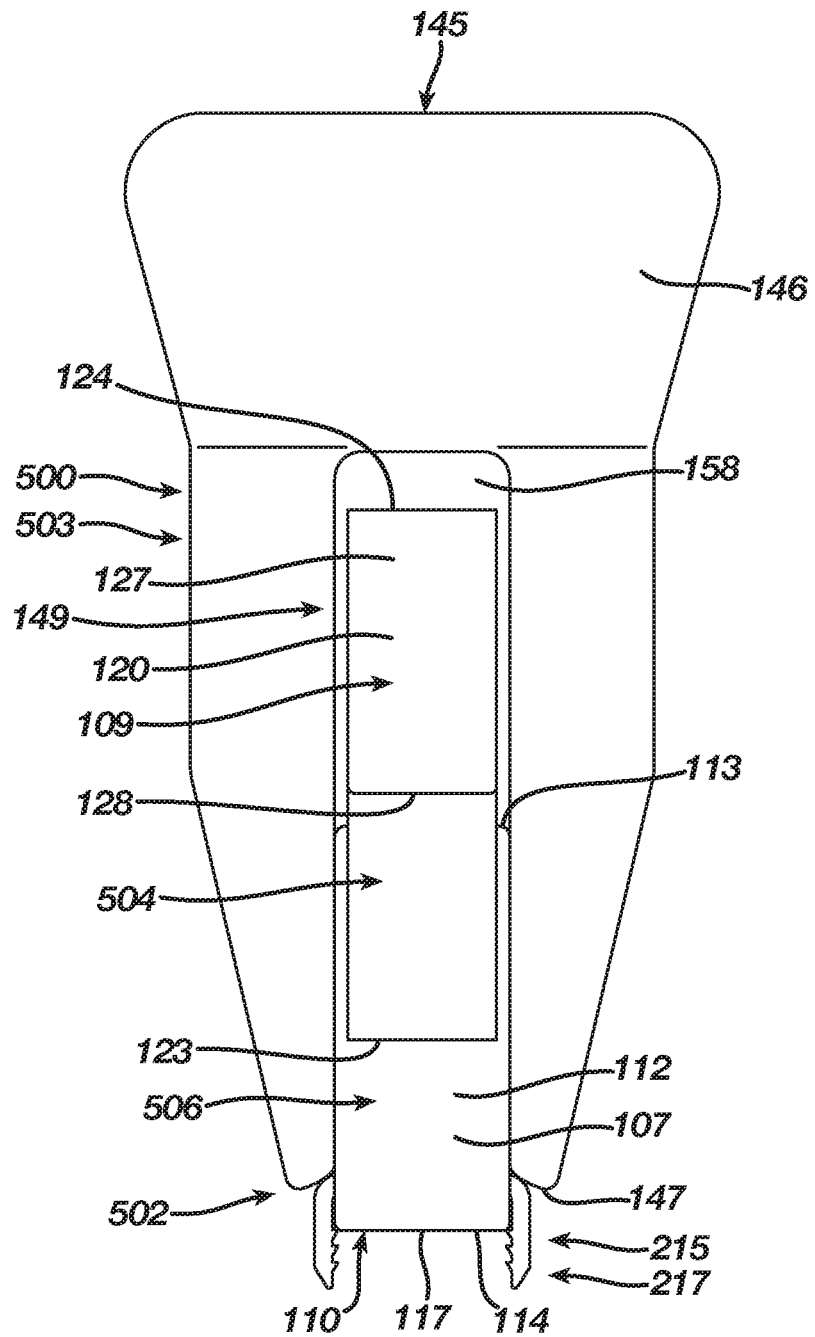

FIG. 37B is a front view illustrating the implant insertion device in its loaded position that constrains the shape memory implant in its insertion shape.

Figure 37C:
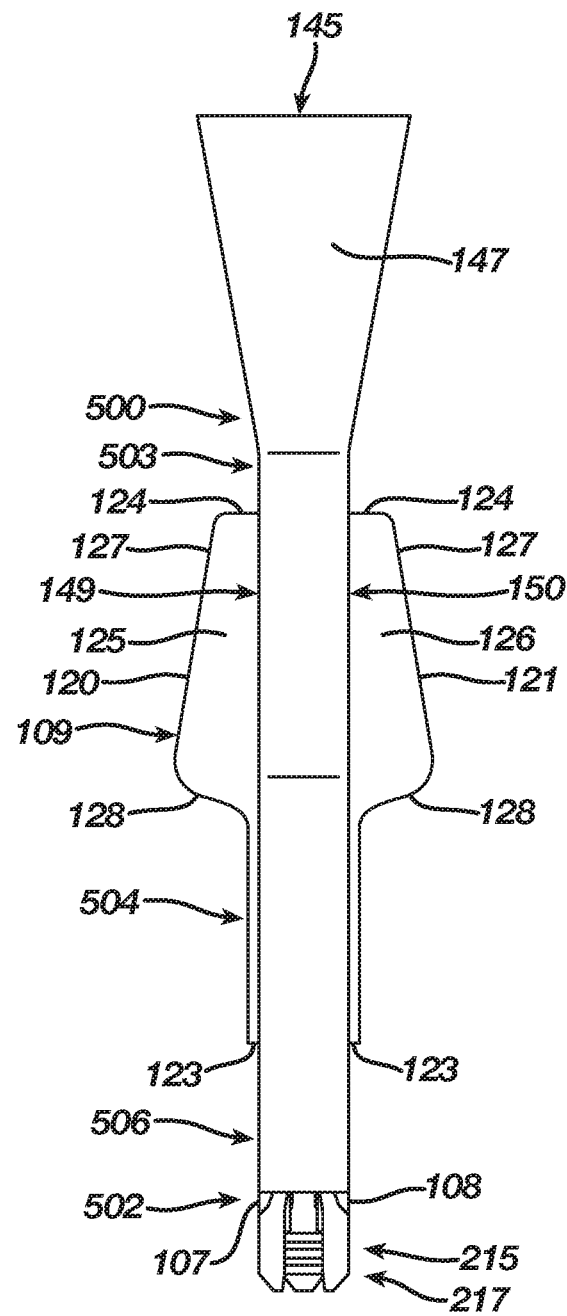

FIG. 37C is an end view illustrating the implant insertion device in its loaded position that constrains the shape memory implant in its insertion shape.

Figure 37D:
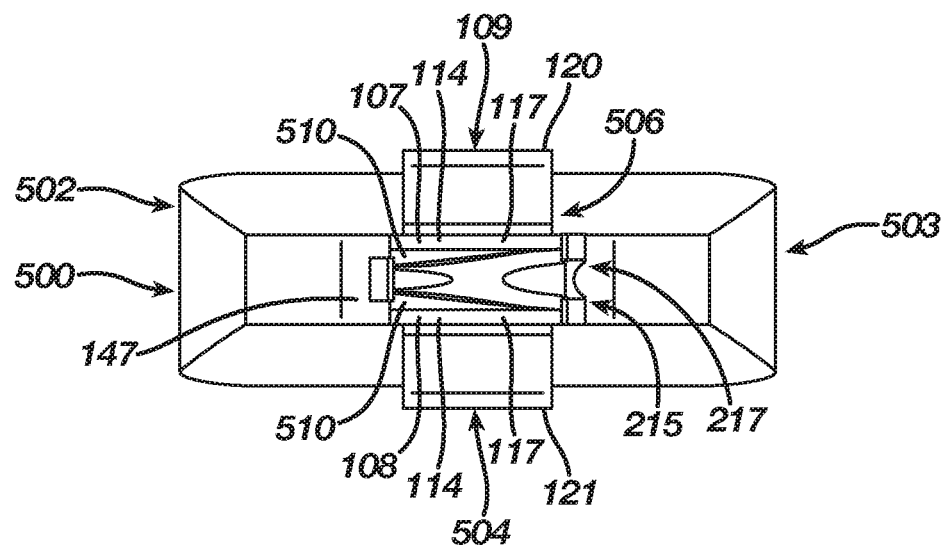

FIG. 37D is a bottom view illustrating the implant insertion device in its loaded position that constrains the shape memory implant in its insertion shape.

Figure 38A:
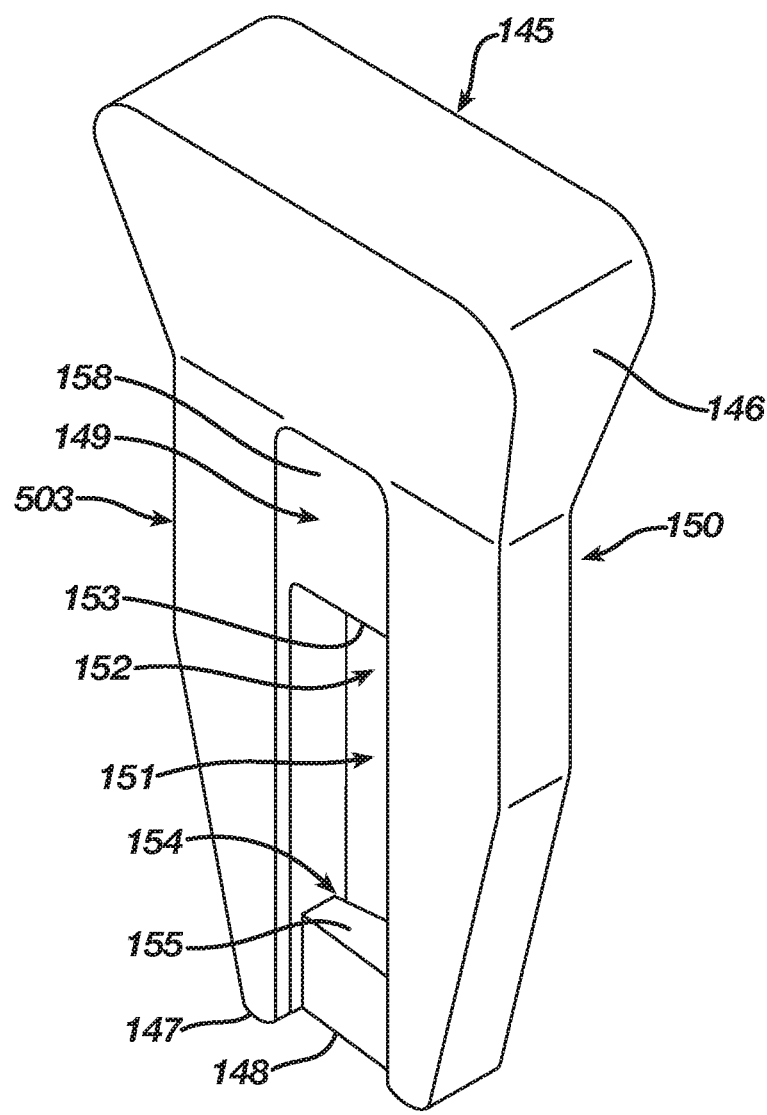

FIG. 38A is an isometric view illustrating a body of the implant insertion device according to the sixth embodiment.

Figure 38B:
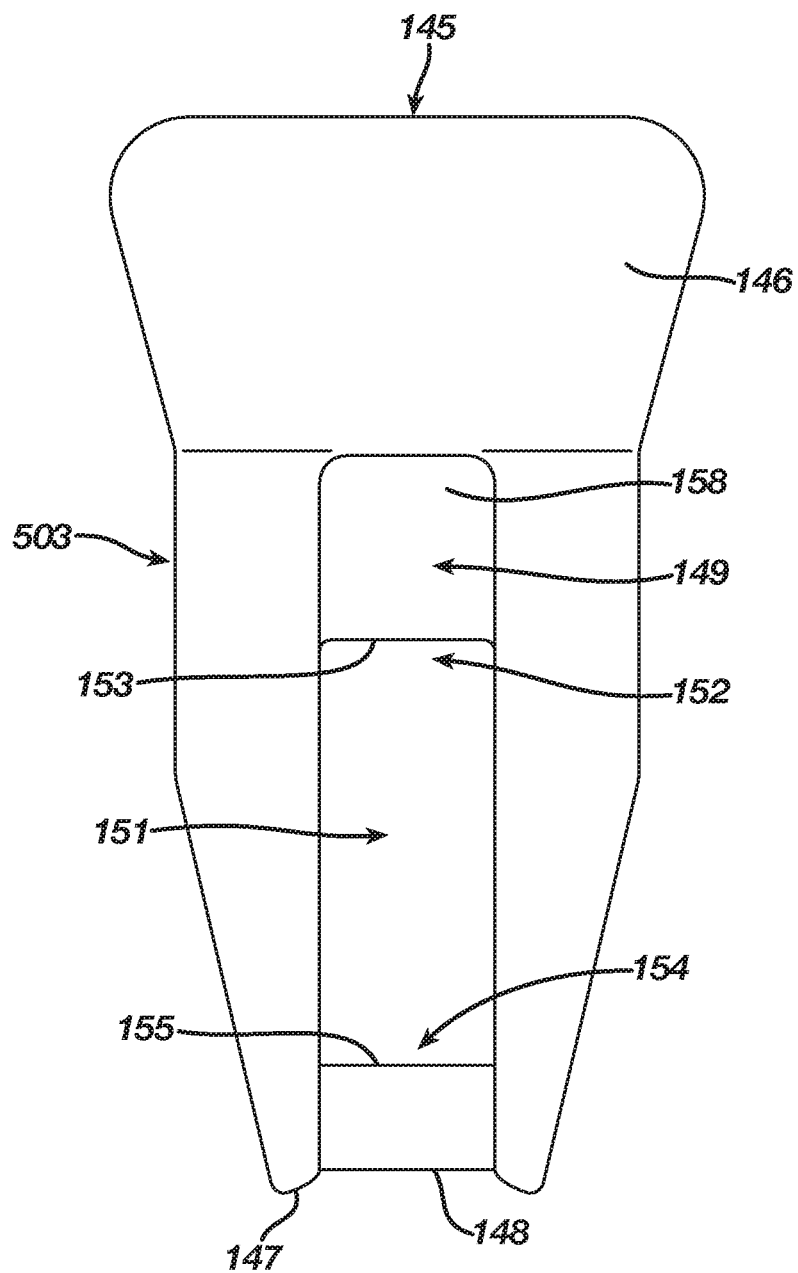

FIG. 38B is a front view illustrating the body of the implant insertion device.

Figure 39A:
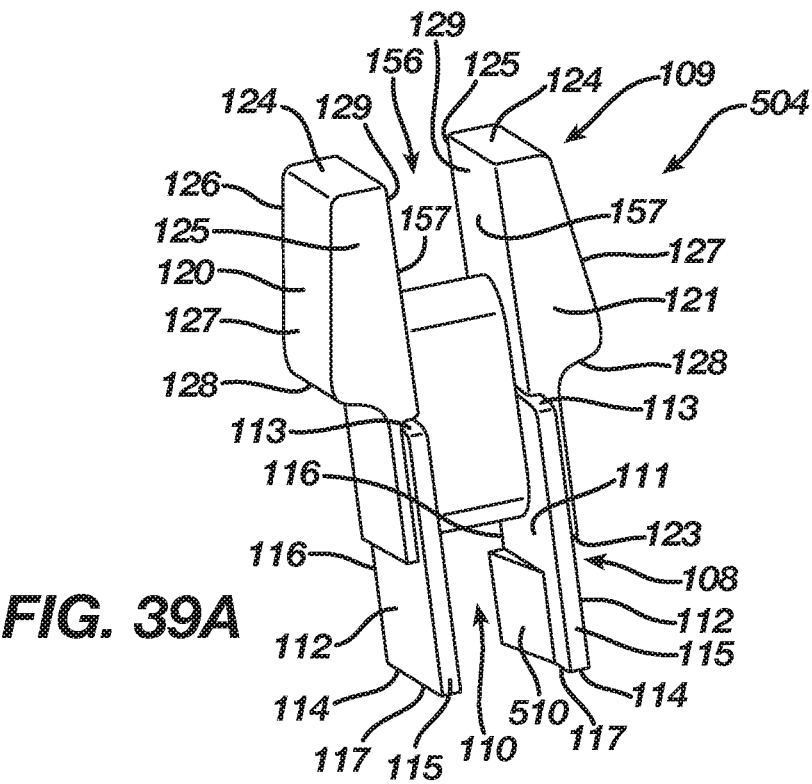

FIG. 39A is an isometric view illustrating an implant grip of the implant insertion device according to the sixth embodiment.

Figure 39B:
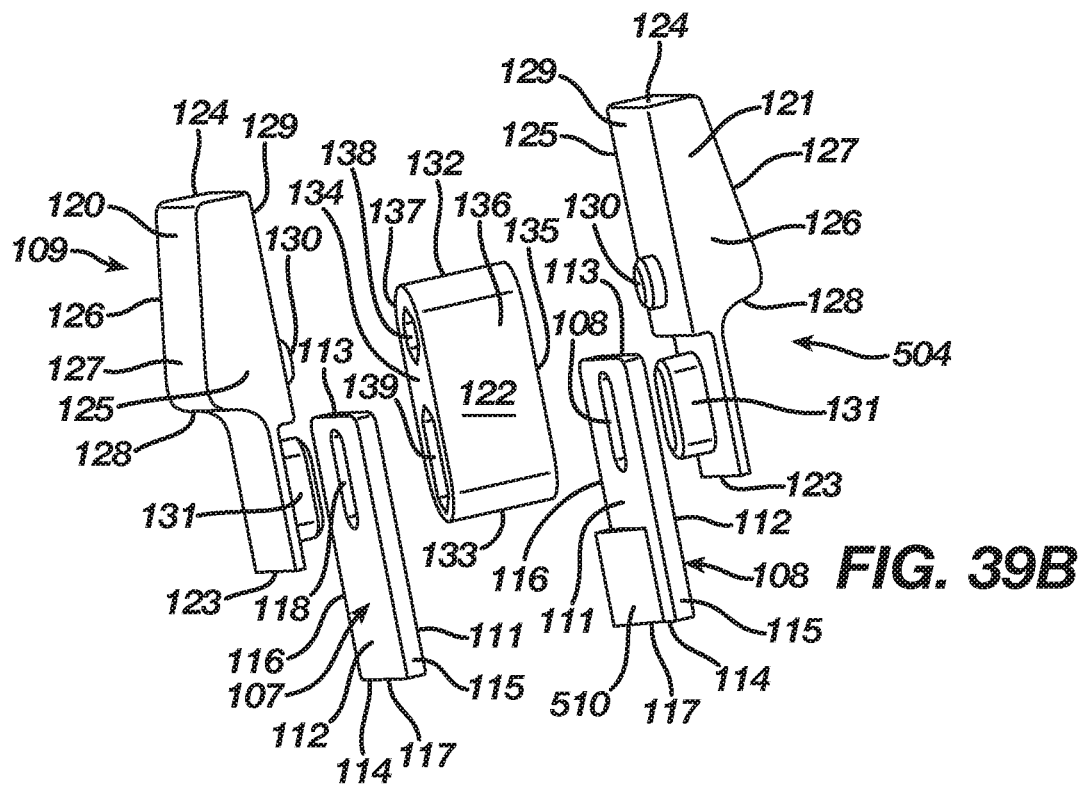

FIG. 39B is an exploded isometric view illustrating the implant grip of the implant insertion device according to the sixth embodiment.

FIG. 40A is an isometric view illustrating a drill guide according to a first embodiment used during implantation of a shape memory implant according to the first embodiment.

FIG. 40B is a side view thereof.

Figure 40C:
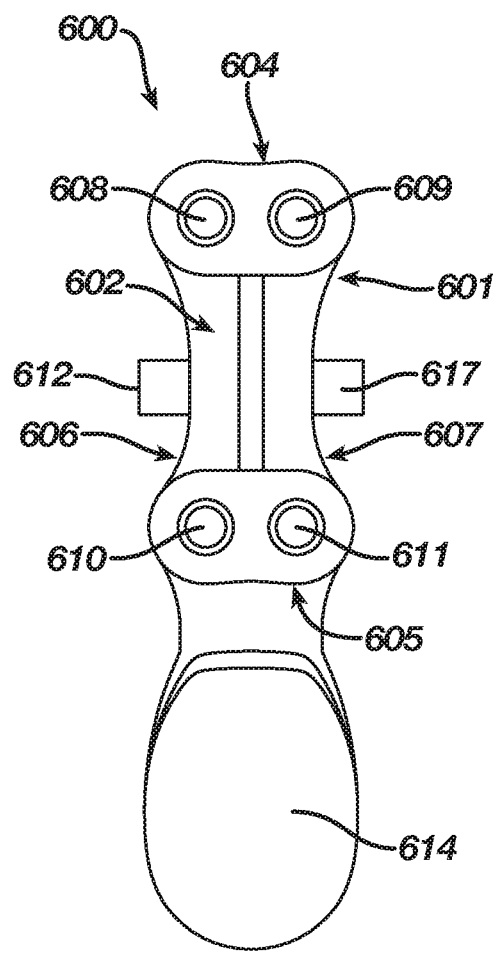

FIG. 40C is a top view thereof.

Figure 40D:
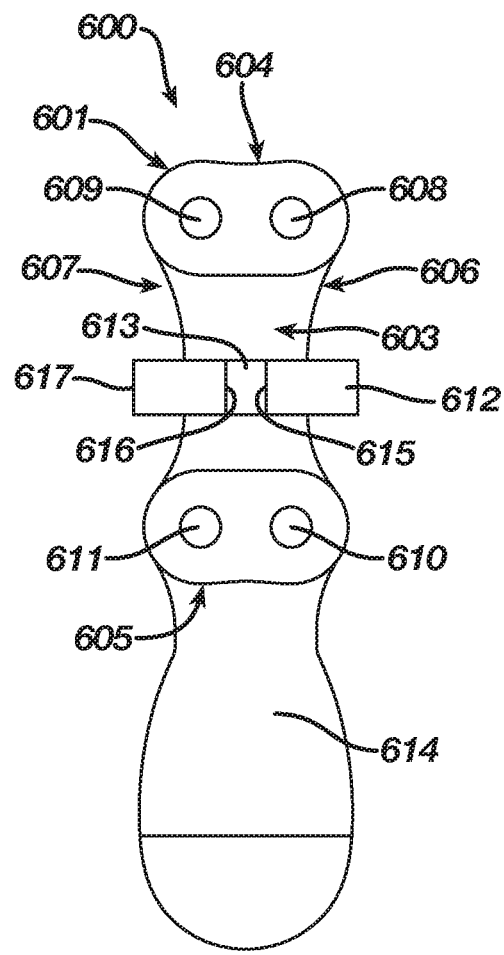

FIG. 40D is a bottom view thereof.

Figure 40E:
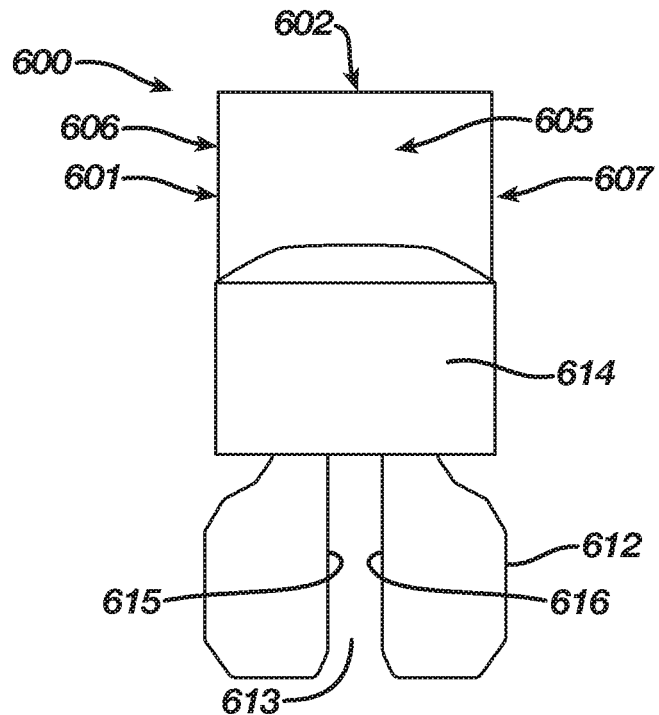

FIG. 40E is a rear view thereof.

Figure 40F:
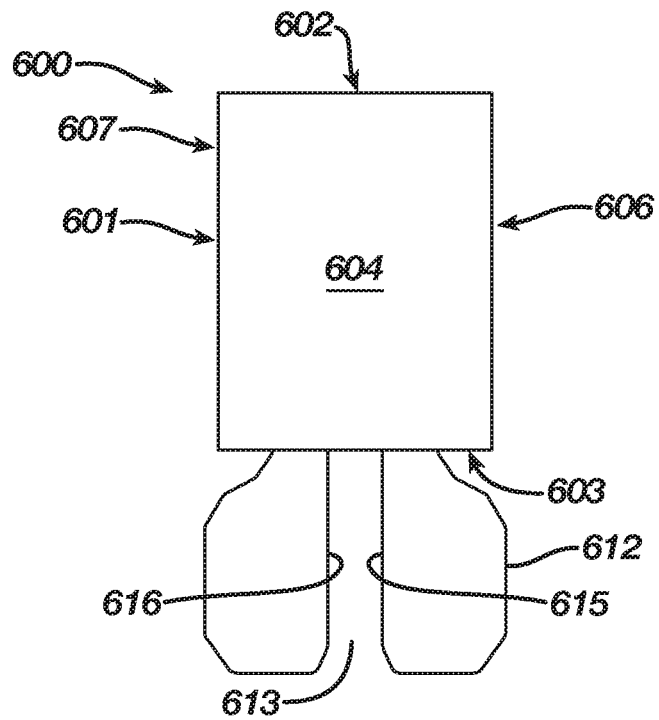

FIG. 40F is a front view thereof.

Figure 41:
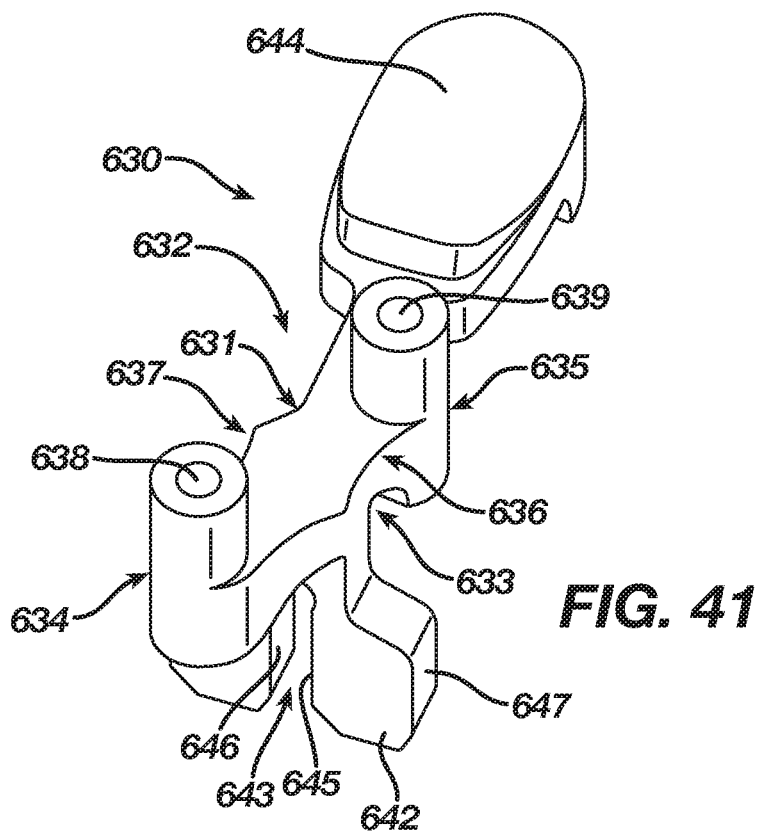

FIG. 41 is an isometric view illustrating a drill guide according to a second embodiment used during implantation of a shape memory implant according to the second embodiment.

Figure 42:
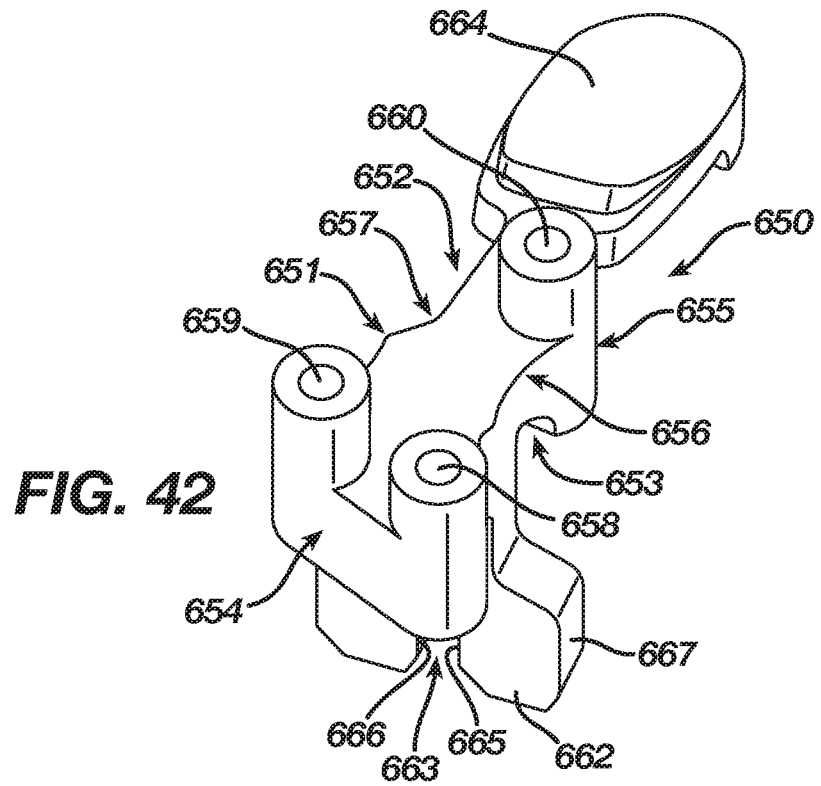

FIG. 42 is an isometric view illustrating a drill guide according to a third embodiment used during implantation of a shape memory implant according to the third embodiment.

Figure 43A:
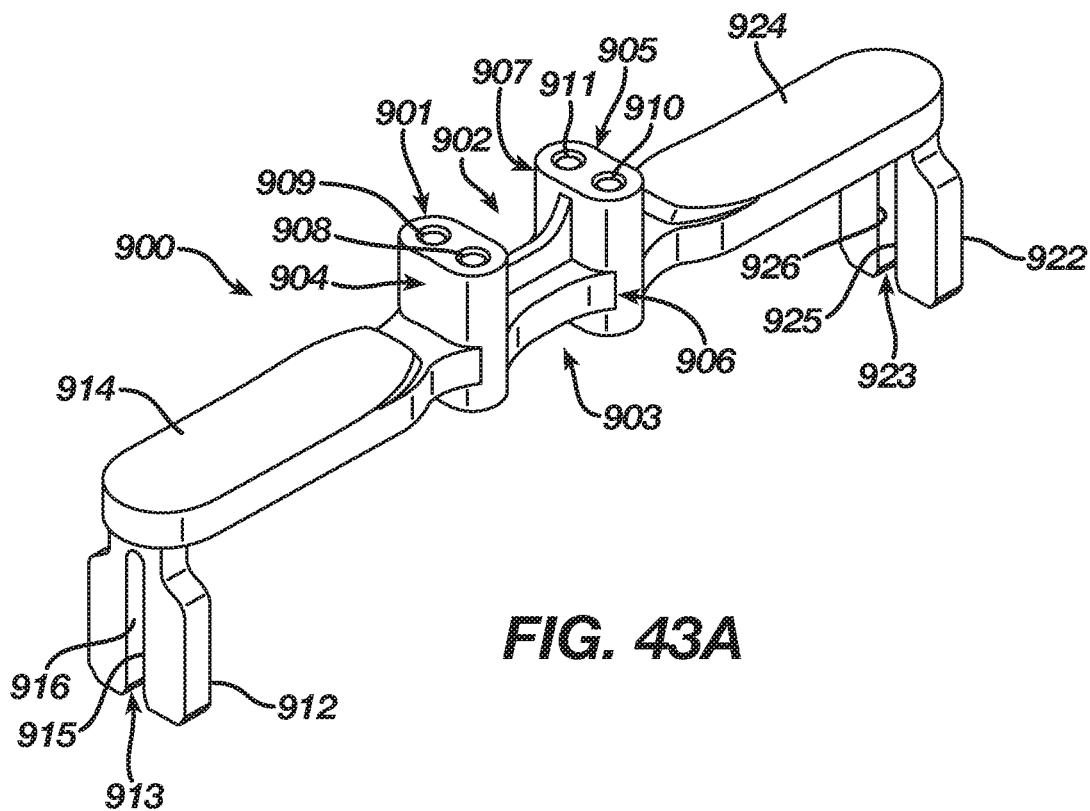

FIG. 43A is an isometric view illustrating a drill guide according to a fourth embodiment used during implantation of a shape memory implant according to the first embodiment.

Figure 43B:
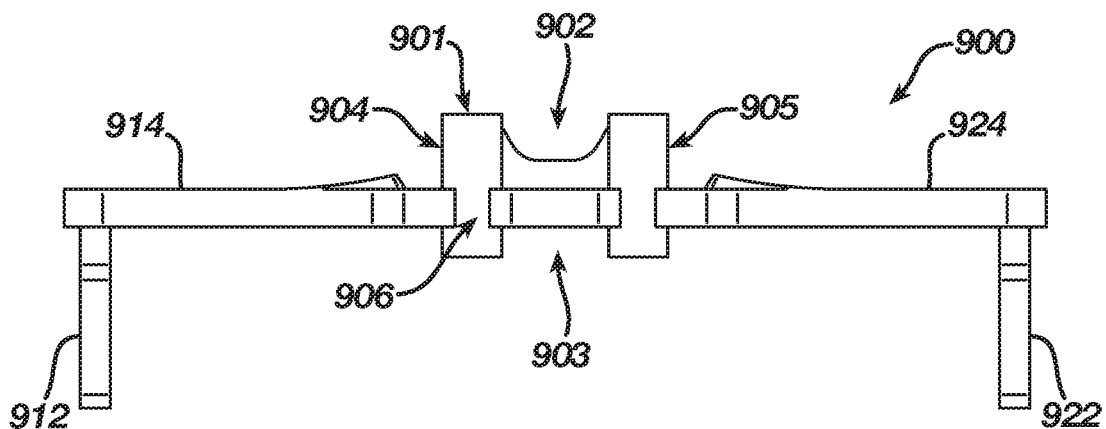

FIG. 43B is a side view thereof.

Figure 43C:
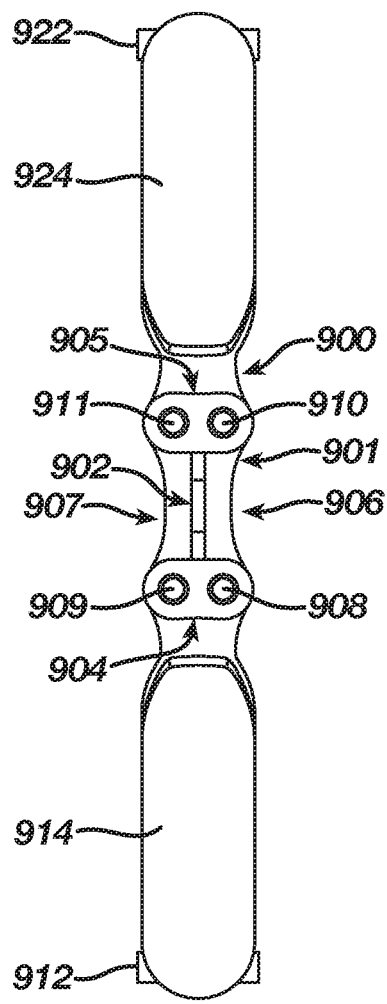

FIG. 43C is a top view thereof.

Figure 43D:
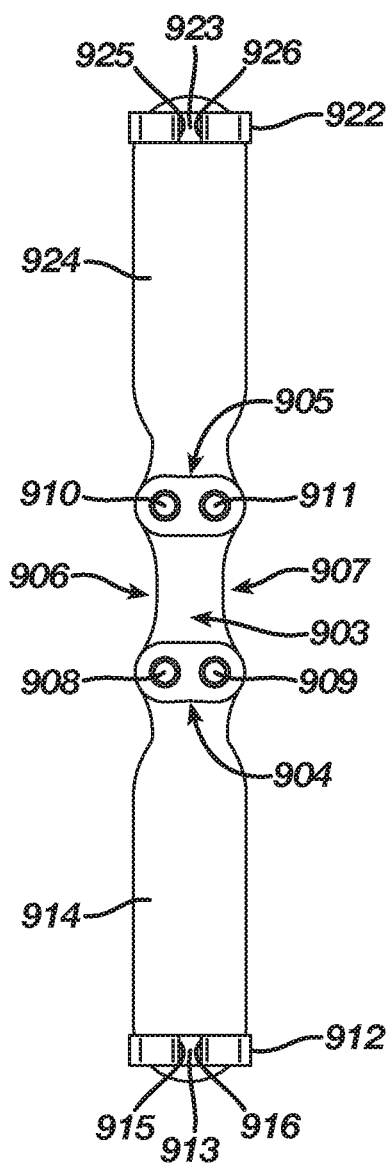

FIG. 43D is a bottom view thereof.

Figure 43E:
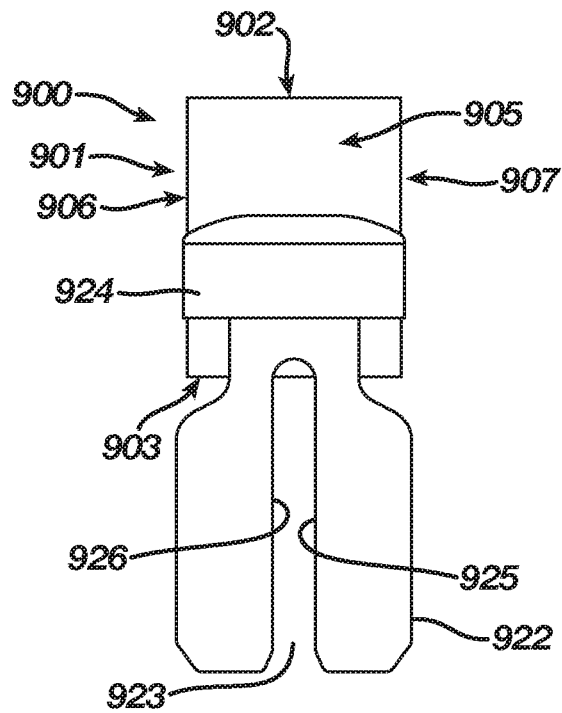

FIG. 43E is a rear view thereof.

Figure 43F:
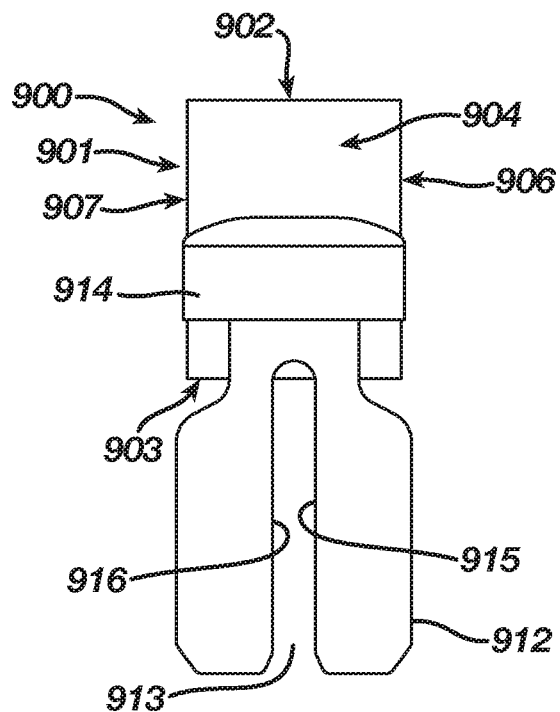

FIG. 43F is a front view thereof.

Figure 44:
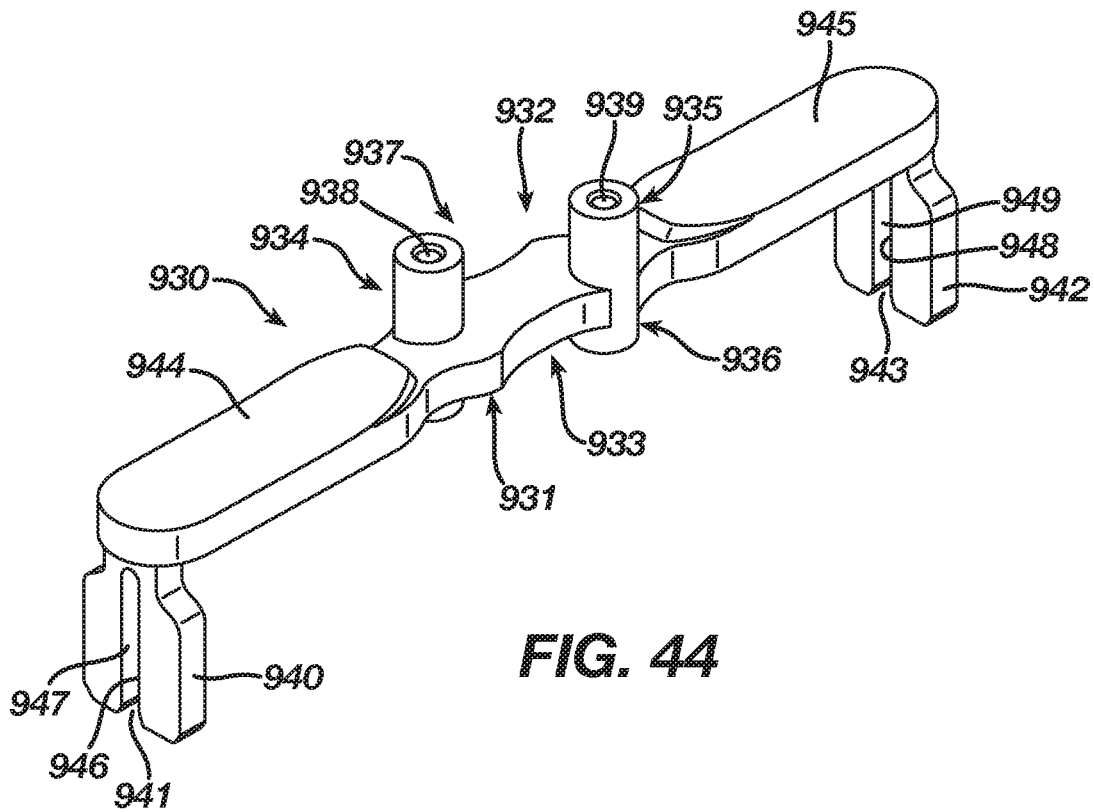

FIG. 44 is an isometric view illustrating a drill guide according to a fifth embodiment used during implantation of a shape memory implant according to the second embodiment.

Figure 45:
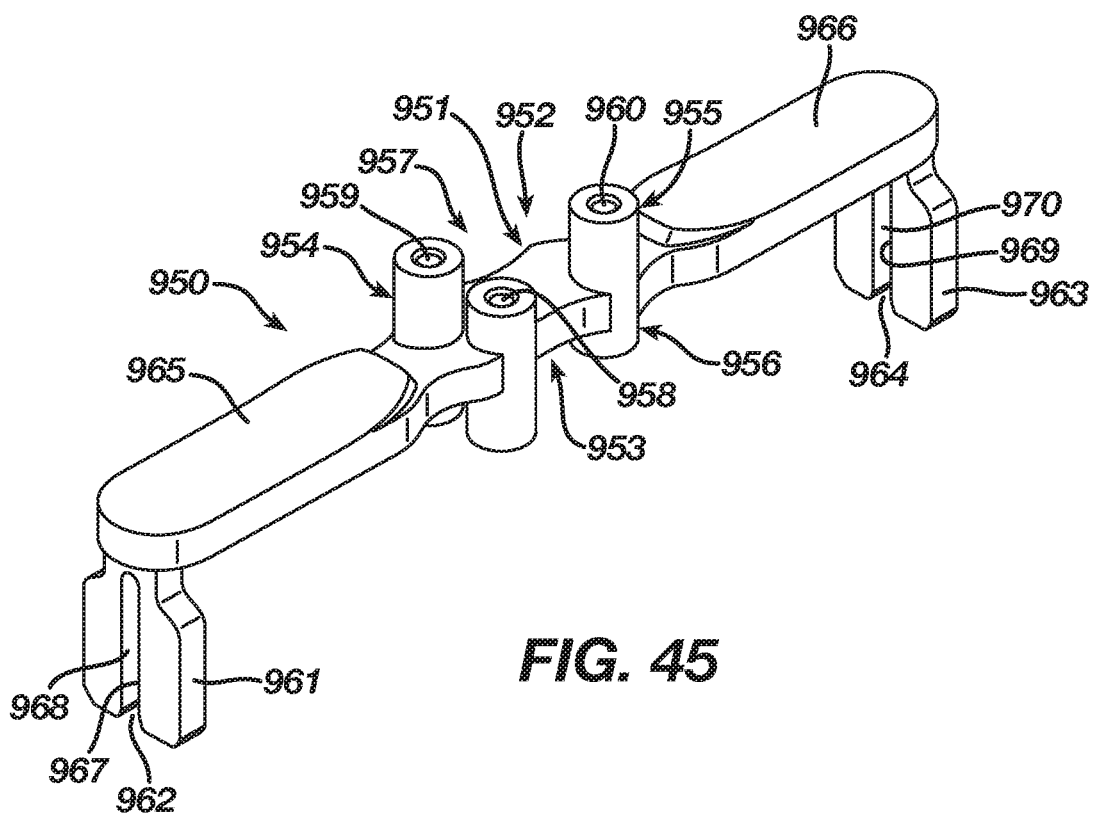

FIG. 45 is an isometric view illustrating a drill guide according to a sixth embodiment used during implantation of a shape memory implant according to the third embodiment.

FIGS. 46-49 are isometric views illustrating insertion of a shape memory implant according to the first embodiment into bone, bones, or bone pieces using an implant insertion device according to the first embodiment.

FIGS. 50A-54 are isometric views illustrating insertion of a shape memory implant according to the first embodiment into bone, bones, or bone pieces using a drill guide according to the first embodiment and an implant insertion device according to the first embodiment.

FIGS. 55A-59 are isometric views illustrating insertion of a shape memory implant according to the first embodiment into bone, bones, or bone pieces using a drill guide according to the fourth embodiment and an implant insertion device according to the first embodiment.

DETAILED DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

FIGS. 1A-1E illustrate an orthopedic implant 5 according to a first embodiment in a natural shape 6, whereas FIGS. 2A-2E illustrate the orthopedic implant 5 in an insertion shape 7. The implant 5 in the first embodiment may be manufactured from a shape memory material with superelastic or temperature dependent properties (e.g., Nitinol) such that the implant 5 transitions between its natural shape 6 and its insertion shape 7. The implant 5 when deformed from its natural shape 6 to its insertion shape 7 stores energy deliverable to bone, bones, or bone pieces. In accordance with its manufacture from shape memory material, the implant 5 begins in its natural shape 6, is transitionable to its insertion shape 7, and, once implanted in bone, bones, or bone pieces, attempts to transition from its insertion shape 7 to its natural shape 6 whereby the implant 5 delivers the energy stored therein to the bone, bones, or bone pieces in order to affix the bone, bones, or bone pieces and promote a healing thereof. In the first embodiment, attempted transition of the implant 5 from its insertion shape 7 to its natural shape 6 continuously compresses the bone, bones, or bone pieces to promote fusion thereof.

The implant 5 includes a bridge 8 with upper and lower surfaces 9 and 10, first and second sides 11 and 12, and first and second ends 13 and 14 defining a perimeter in alignment with a longitudinal axis of the bridge. The first and second sides 11 and 12 and the first and second ends 13 and 14 in the first embodiment of the implant 5 include a respective concave section 11a, 12a, 13a, and 14a along at least a portion thereof. The implant 5 further includes transition sections 15 and 16 at the first end 13 of the bridge 8 and transition sections 17 and 18 at the second end 14 of the bridge 8. More particularly, in the first embodiment, the transition section 15 resides at a corner 19 of the bridge 8 at its first end 13, whereas the transition section 16 resides at a corner 20 of the bridge 8 at its first end 13. Similarly, the transition section 17 resides at a corner 21 of the bridge 8 at its first end 14, whereas the transition section 18 resides at a corner 22 of the bridge 8 at its first end 14.

The implant 5 in the first embodiment includes an anchoring member in the form of a leg 23 extending from the lower surface 10 of the bridge 8 at the corner 19 interior to the first end 13 of the bridge 8 and, in particular, the transition section 15 at the corner 19; an anchoring member in the form of a leg 24 extending from the lower surface 10 of the bridge 8 at the corner 20 interior to the first end 13 of the bridge 8 and, in particular, the transition section 16 at the corner 20; an anchoring member in the form of a leg 25 extending from the lower surface 10 of the bridge 8 at the corner 21 interior to the second end 14 of the bridge 8 and, in particular, the transition section 17 at the corner 21; and an anchoring member in the form of a leg 26 extending from the lower surface 10 of the bridge 8 at the corner 22 interior to the second end 14 of the bridge 8 and, in particular, the transition section 18 at the corner 22. In the first embodiment, the legs 23-26 are formed integrally with the bridge 8 at a respective corner 19-22 and, in particular, at a respective transition section 15-18. Each leg 23-26, which has a respective tip 27-30, may include barbs thereon that improve the pull-out resistance of the implant 5. The implant 5 includes anchoring members in the form of the legs 23-26 in order to facilitate a securing of the implant 5 with bone, bones, or bone pieces whereby the bridge 8 between the legs 23-26 traverses a fixation zone of the bone, bones, or bone pieces such that the implant 5, after its insertion and attempted transition from the insertion shape 7 to the natural shape 6, delivers energy to the bone, bones, or bone pieces at the fixation zone.

The leg 23 in the first embodiment includes a width 31 between sides 32 and 33 such that a segment 34 of the leg 23 extends interior to the perimeter of the bridge 8 at the first end 13 and exterior to the perimeter of the bridge 8 at its first side 11 in order to provide an engagement point 35 whereby an implant engagement device by-passes the bridge 8 at its first side 11 and abuts the engagement point 35. The leg 24 in the first embodiment includes a width 36 between sides 37 and 38 such that a segment 39 of the leg 24 extends interior to the perimeter of the bridge 8 at the first end 13 and exterior to the perimeter of the bridge 8 at its second side 12 in order to provide an engagement point 40 whereby an implant engagement device by-passes the bridge 8 at its second side 12 and abuts the engagement point 40. The leg 25 in the first embodiment includes a width 41 between sides 42 and 43 such that a segment 44 of the leg 25 extends interior to the perimeter of the bridge 8 at the second end 14 and exterior to the perimeter of the bridge 8 at its first side 11 in order to provide an engagement point 45 whereby an implant engagement device by-passes the bridge 8 at its first side 11 and abuts the engagement point 45. The leg 26 in the first embodiment includes a width 46 between sides 47 and 48 such that a segment 49 of the leg 26 extends interior to the perimeter of the bridge 8 at the second end 14 and exterior to the perimeter of the bridge 8 at its second side 12 in order to provide an engagement point 50 whereby an implant engagement device by-passes the bridge 8 at its second side 12 and abuts the engagement point 50.

The regular inherent shape of the implant 5, as illustrated in FIGS. 1A-1E, is its natural shape 6 where the transition sections 15-18 locate the bridge 8 in a natural form that places the legs 23-26 in a natural position whereby the legs 23-26 are convergent and spaced apart at a first distance. Nevertheless, as illustrated in FIGS. 2A-2E, the implant 5 is deformable under the action of superelasticity or temperature dependent shape memory to an insertion shape 7 where the transition sections 15-18 deform to store energy while also moving the bridge 8 from its natural form to an insertion form that places the legs 23-26 in an insertion position whereby the legs 23-26 are substantially parallel and spaced apart at a second distance that is greater than the first distance. Since the insertion shape 7 is not the regular inherent shape of the implant 5, the bridge 8 typically is mechanically constrained using an implant insertion device whereby the implant insertion device maintains the bridge 8 in its insertion form. In order to facilitate engagement of an implant insertion device with the implant 5, the legs 23-26, respectively, include the engagement points 35, 40, 45, and 50 that receive the implant insertion device. The implant insertion device by-passes the bridge 8 at its first and second sides 11 and 12 and abuts the engagement points 35, 40, 45, and 50. In particular, the implant insertion device extends beyond the bridge 8 at its first and second sides 11 and 12 and abuts the engagement points 35, 40, 45, and 50 such that the implant insertion device engages and then holds the legs 23-26, resulting in the implant insertion device constraining the deformed transition sections 15-18 in order to maintain the implant 5 in its insertion shape 7. After implantation into bone, bones, or bone pieces and a release of the implant insertion device, including if necessary a heating of the implant 5, the implant 5 delivers the energy stored in the transition sections 15-18 whereby the bridge 8 attempts to transition from its insertion form to its natural form, which causes an attempt of the legs 23-26 to move from their insertion position to their natural position such that the implant 5 affixes the bone, bones, or bone pieces through an application of a compressive force thereto.

Figure 1A:
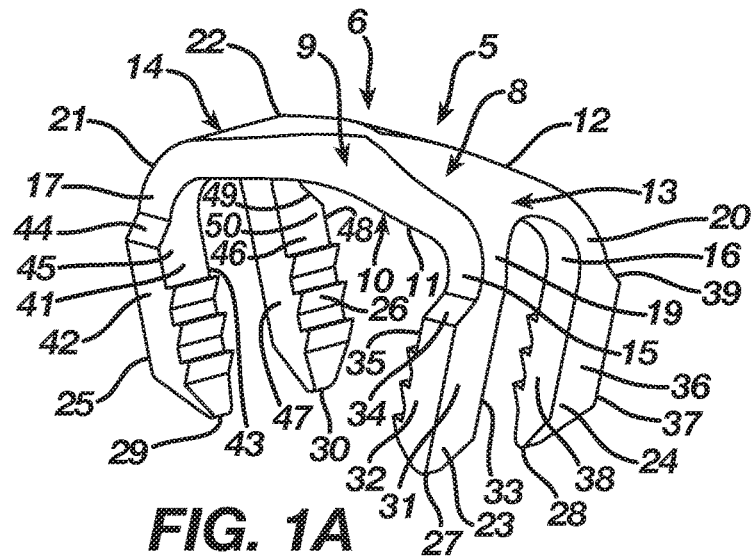
FIG. 1A is an isometric view illustrating a shape memory implant according to a first embodiment in a natural shape.
Figure 1B:
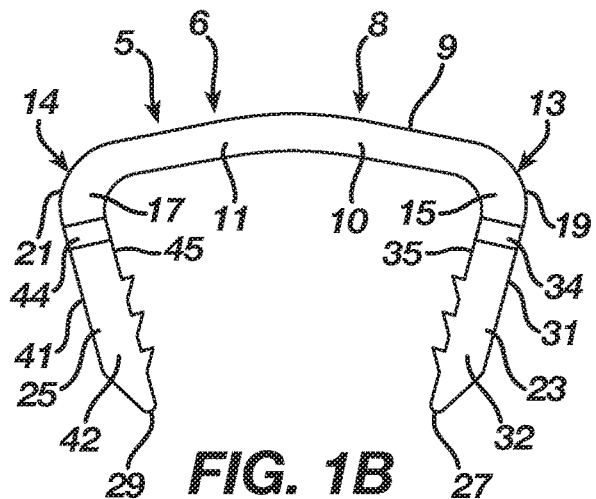
FIG. 1B is a side view thereof.
Figure 1C:
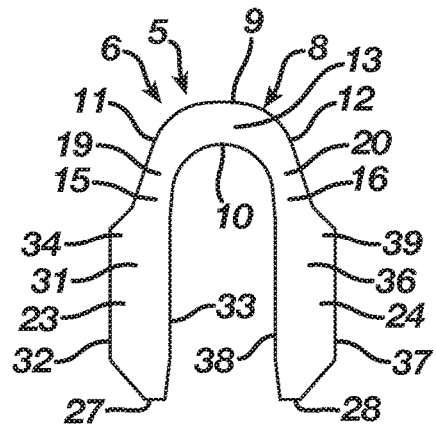
FIG. 1C is an end view thereof.
Figure 1D:
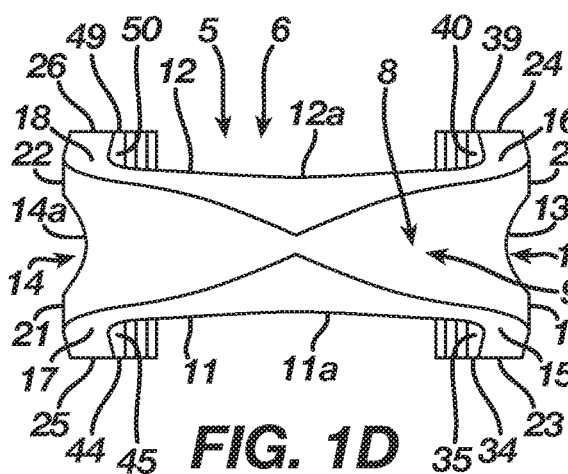
FIG. 1D is a top view thereof.
Figure 1E:
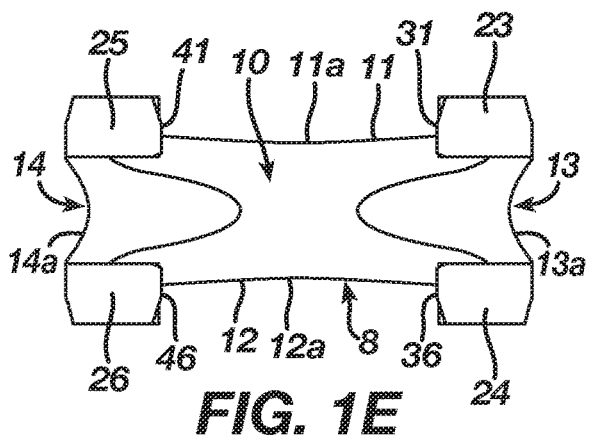
FIG. 1E is a bottom view thereof.
Figure 2A:
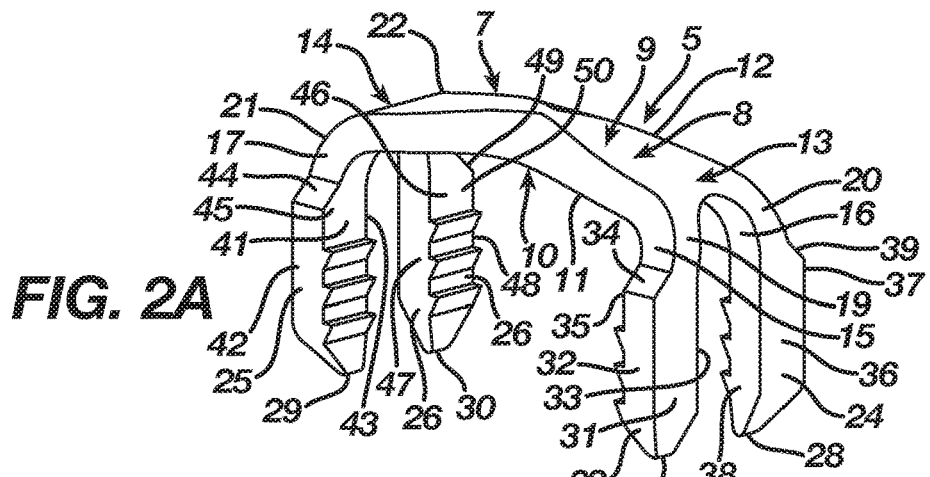
FIG. 2A is an isometric view illustrating the shape memory implant according to the first embodiment in an insertion shape.
Figure 2B:
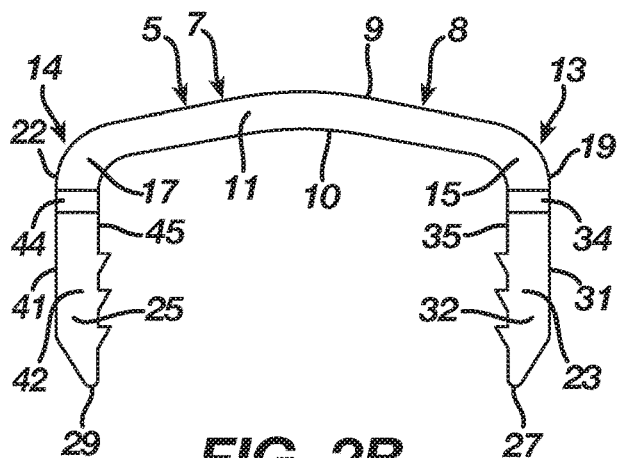
FIG. 2B is a side view thereof.
Figure 2C:
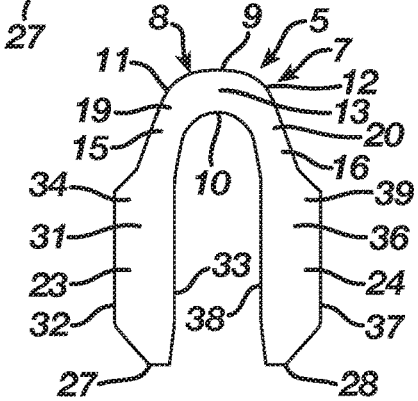
FIG. 2C is an end view thereof.
Figure 2D:
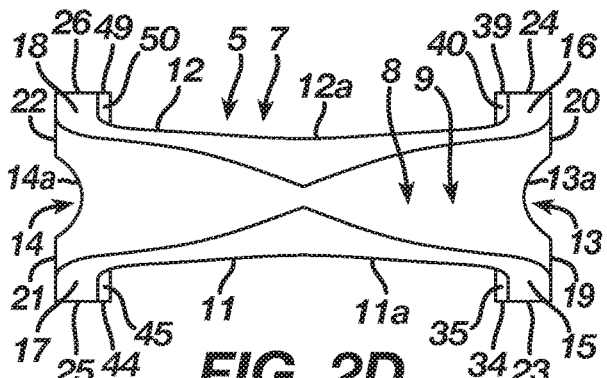
FIG. 2D is a top view thereof.
Figure 2E:
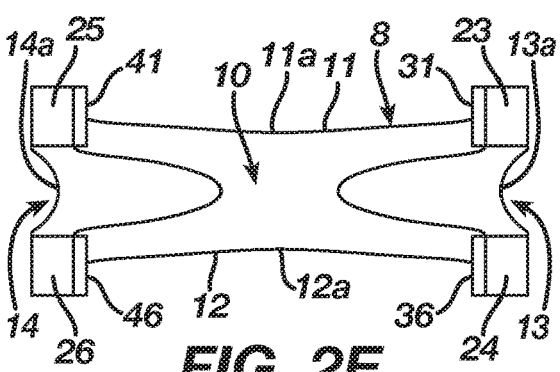
FIG. 2E is a bottom view thereof.
Figure 2F:
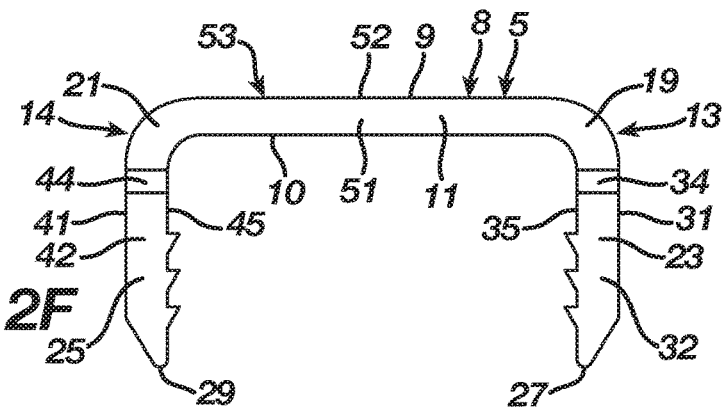
FIG. 2F is a side view illustrating an alternative insertion shape for the shape memory implant according to the first embodiment.

Although the bridge 8 of the implant 5 according to the first embodiment includes the transition sections 15-18, the bridge 8, alternatively, may include a transition section 51 located at a center section 52 of the implant 5 and thus the bridge 8. The regular inherent shape of the implant 5, as illustrated in FIGS. 1A-1E, is its natural shape 6 where the transition section 51 locates the bridge 8 in a natural form consisting of a closed or angular profile whereby the first and second ends 13 and 14 reside at a first distance and the legs 23-26 reside in a natural position whereby the legs 23-26 are convergent and spaced apart at a first distance. Nevertheless, as illustrated in FIG. 2F, the implant 5 is deformable under the action of superelasticity or temperature dependent shape memory to an insertion shape 53 where the transition section 51 deforms to store energy while also moving the bridge 8 from its natural form to an insertion form which is an open or substantially linear profile whereby the first and second ends 13 and 14 reside at a second distance that is greater than the first distance and the legs 23-26 reside in an insertion position whereby the legs 23-26 are substantially parallel and spaced apart at a second distance that is greater than the first distance. Since the insertion shape 53 is not the regular inherent shape of the implant 5, the bridge 8 typically is mechanically constrained using an implant insertion device whereby the implant insertion device maintains the bridge 8 in its insertion form. In order to facilitate engagement of an implant insertion device with the implant 5, the legs 23-26, respectively, include the engagement points 35, 40, 45, and 50 that receive the implant insertion device. The implant insertion device by-passes the bridge 8 at its first and second sides 11 and 12 and abuts the engagement points 35, 40, 45, and 50. In particular, the implant insertion device extends beyond the bridge 8 at its first and second sides 11 and 12 and abuts the engagement points 35, 40, 45, and 50 such that the implant insertion device engages and then holds the legs 23-26, resulting in the implant insertion device constraining the deformed transition section 51 in order to maintain the implant 5 in its insertion shape 7. After implantation into bone, bones, or bone pieces and a release of the implant insertion device, including if necessary a heating of the implant 5, the implant 5 delivers the energy stored in the transition section 51 whereby the bridge 8 attempts to transition from its insertion form to its natural form, which causes an attempt of the legs 23-26 to move from their insertion position to their natural position such that the implant 5 affixes the bone, bones, or bone pieces through an application of a compressive force thereto.

While the first embodiment of the implant 5 includes either the transition sections 15-18 or the transition section 51 to produce deformation thereof, one of ordinary skill in the art will recognize that the bridge 8 of the implant 5 may include both the transition sections 15-18 and the transition section 51 to produce deformation thereof. Moreover, while the bridge 8 in the first embodiment includes an angular profile in the natural shape of the implant 5, it should be understood by one of ordinary skill in the art that a bridge 8 incorporating the transition sections 15-18 may include a substantially linear profile for the natural shape of the implant 5.

FIGS. 3A-5D illustrate an implant insertion device 60 that engages an implant 5 and retains the implant 5 in its insertion shape 7 or 53. FIGS. 4A-4B illustrate the implant insertion device 60 in an unloaded position 61 prior to its loading with the implant 5 or after its delivery of the implant 5 whereby the implant 5 releases from the implant insertion device 60 without obstruction. FIGS. 5A-5D illustrate the implant insertion device 60 in a loaded position 62 whereby the implant insertion device 60 may be loaded with the implant 5 such that the implant insertion device 60 constrains the implant 5 in its insertion shape 7 or 53. The implant insertion device 60 allows a surgeon to manipulate the implant 5 and insert the implant 5 into bone, bones, or bone pieces requiring fixation. FIGS. 6A-6D illustrate a body 63 of the implant insertion device 60, whereas FIGS. 7A-9B illustrate an implant grip 64 of the implant insertion device 60 that is coupled with the body 63 and is movable relative to the body 63 between a disengaged position 65 shown in FIGS. 4A-4B and an engaged position 66 shown in FIGS. 5A-5D.

The implant grip 64 as illustrated in FIGS. 7A-9B includes a shell 67 with a passage 70 therethrough that permits the implant grip 64 to interface with the implant 5 and the body 63. The shell 67 includes an exterior surface 68 with an upper surface 89 and a lower surface 90 and an interior surface 69 that defines the passage 70 therethrough whereby the passage 70 at the lower surface 90 receives therein the implant 5 and the passage 70 at the upper surface 89 receives therein the body 63. The interior surface 69 of the shell 67 and thus the passage 70 include a shape complimentary with the implant 5 and, in particular, with the first and second sides 11 and 12 and the first and second ends 13 and 14 of the implant 5 whereby the shell 67 grips the implant 5 and retains the implant 5 therein. More particularly, the implant 5 inserts into the shell 67 via the passage 70 beginning at the lower surface 90 and is held therein due to a frictional engagement of the interior surface 69 with the implant 5 such that the shell 67 encloses the implant 5 and constrains the implant 5 in its insertion shape 7 or 53. The interior surface 69 of the shell 67 and thus the passage 70 due to their shape complimentary with the implant 5 define a groove 71-74 located at a respective corner 75-78 of the interior surface 69 that respectively receives therein a segment 34, 39, 44, and 49 of the legs 23-26 whereby the interior surface 69 at the grooves 71-74 respectively frictionally engages the legs 23-26 of the implant 5 thereby retaining the implant 5 within the shell 67. The interior surface 69 in each groove 71-74 further defines a retention surface 79-82 that respectively abuts an engagement point 35, 40, 44, and 50 of the legs 23-26 in order to grip and then constrain the legs 23-26 such that the shell 67 retains the implant 5 in its insertion shape 7 or 53. While the frictional engagement between the interior surface 69 and the implant 5 and, in particular, between the interior surface 69 at its grooves 71-74 and retention surfaces 79-82 with the legs 23-26 and their segments 34, 39, 44, and 49 retains the implant 5 within the shell 67, the shell 67 at its interior surface 69, in order to provide additional retention of the implant 5 within the shell 67, includes projections 83-86 that grip a respective leg 23-26 opposite to the segments 34, 39, 44, and 49. Upon the insertion of the implant 5 into the passage 70, the projections 83-86 by-pass respectively the bridge 8 at its first and second ends 13 and 14 via the concave sections 13a and 14a thereof and then frictionally engage a respective leg 23-26 opposite to the segments 34, 39, 44, and 49, thereby assisting in retaining the implant 5 within the shell 67. Alternatively, the projections 83-86 may be resilient whereby, during the insertion of the implant 5 into the passage 70, the projections 83-86 move relative to bridge 8 at its first and second ends 13 and 14 and then return to frictionally engage a respective leg 23-26 opposite to the segments 34, 39, 44, and 49, thereby assisting in retaining the implant 5 within the shell 67 including operating as a stop relative to the bridge 8 that prevents accidental release of the implant 5 from the implant grip 64. The shell 67 at its interior surface 69 includes detents 87 and 88 that engage the body 63 to assist in coupling the shell 67 with the body 63 and further to limit the motion of the shell 67 relative to the body 63 as the implant grip 64 moves between its disengaged position 65 and its engaged position 66.

The body 63 as illustrated in FIGS. 6A-6D includes a first end 75 defining a handle 76 and a second end 77 defining an implant grip receiver 78 and a stop 84 adjacent the implant grip receiver 78 that limits the movement of the implant grip 64 relative to the implant grip receiver 78. The handle 76 facilitates grasping of the implant insertion device 60 during its use in implanting the implant 5 into bone, bones, or bone pieces requiring fixation. The implant grip receiver 78 includes first and second sides 80 and 81, first and second ends 82 and 83, and a tamp 79 configured to engage the bridge 8 when the implant 5 resides in its insertion shape 7 or its insertion shape 53. The implant grip receiver 78 and thus the first and second sides 80 and 81 and the first and second ends 82 and 83 thereof include a shape complimentary with the implant grip 64 and, in particular, with the interior surface 69 of the shell 67 whereby the implant grip receiver 78 retains the implant grip 64 thereon. More particularly, the implant grip receiver 78 inserts into the shell 67 via the passage 70 beginning at the upper surface 89 such that the implant grip receiver 78 holds the shell 67 thereon due to a frictional engagement between the first and second sides 80 and 81 and the first and second ends 82 and 83 of the implant grip receiver 78 with the interior surface 69 of the shell 67. While the frictional engagement between the first and second sides 80 and 81 and the first and second ends 82 and 83 of the implant grip receiver 78 and the interior surface 69 of the implant grip 64 retains the shell 67 on the implant grip receiver 78, the implant grip receiver 78 defines on both its first and second sides 80 and 81 notches 91 and 92 that aid in retaining the shell 67 on the implant grip receiver 78 and further locate the implant grip 64 in either its disengaged position 65 or its engaged position 66. In particular, the detents 87 and 88 on the interior surface 69 of the shell 67, during insertion of the implant grip receiver 78 into the shell 67, move respectively into the notches 92 thereby locking the implant grip 64 in its engaged position 66 relative to the implant grip receiver 78 or into the notches 91 thereby locking the implant grip 64 in its disengaged position 65 relative to the implant grip receiver 78. The first and second ends 82 and 83 define respectively indentations 93 and 94 that prevent the implant grip receiver 78 from contacting the projections 83-86 when the implant grip 64 resides in its disengaged position 65. In the first embodiment of the implant insertion device 60, the length of the implant grip receiver 78 for the body 63 substantially equals the length of the implant grip 64. With the implant insertion device 60 in its unloaded position 61, the implant grip receiver 78 inserts substantially, completely within the implant grip 64 until the implant grip 64 reaches its disengaged position 65 whereby the tamp 79 of the implant grip receiver 78 resides at the lower surface 90 of the implant grip 64 such that the tamp 79 facilitates delivery of the implant 5 from the implant grip 64 into bone, bones, or bone pieces. With the implant insertion device 60 in its loaded position 62, the implant grip receiver 78 moves within the implant grip 64 relative thereto until the implant grip 64 reaches its engaged position 66 whereby the implant 5 inserts into the implant grip 64 such that the tamp 79 of the implant grip receiver 78 resides adjacent the bridge 8 of the implant 5.

Figure 3A:
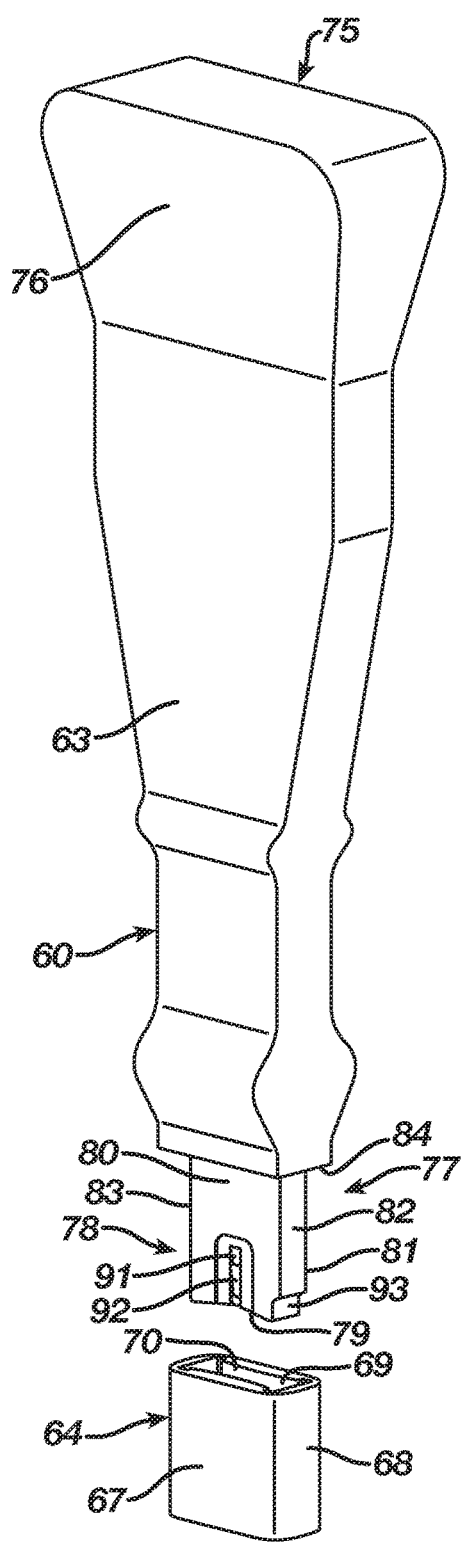
FIG. 3A is an exploded isometric view illustrating an implant insertion device according to a first embodiment and a shape memory implant according to the first embodiment in its natural shape.
Figure 3B:
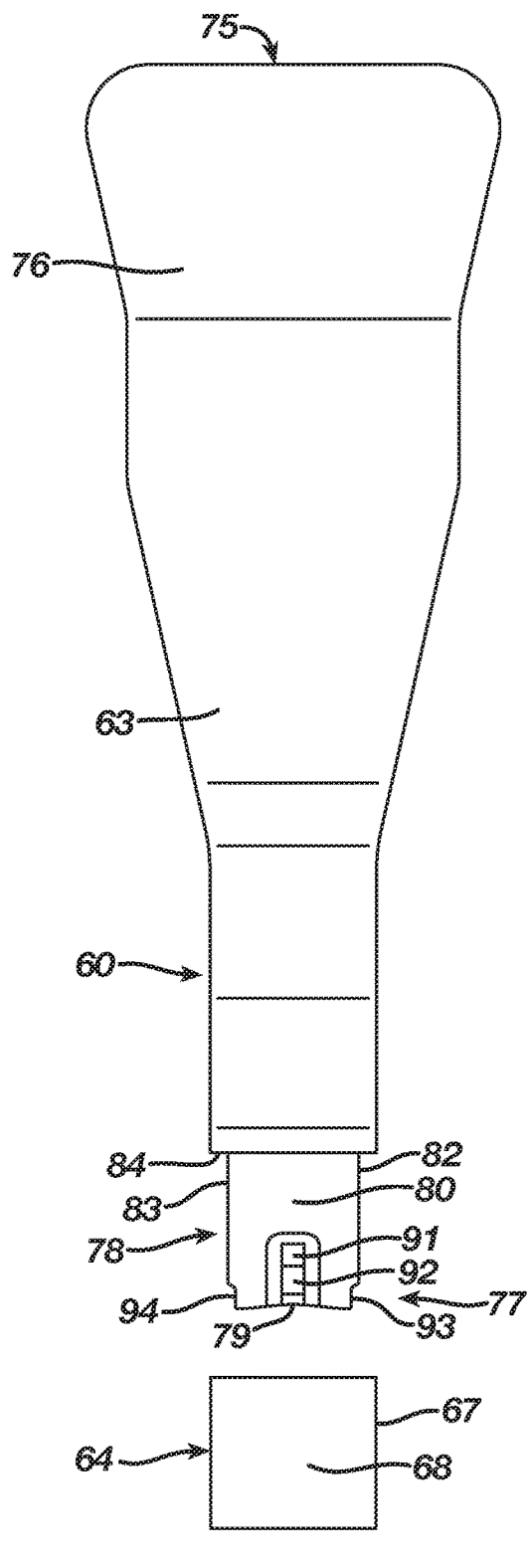
FIG. 3B is an exploded front view illustrating the implant insertion device and the shape memory implant.

Loading the implant insertion device 60 with the implant 5 includes the implant grip receiver 78 receiving thereon the implant grip 64. As illustrated in FIGS. 3A and 3B, the implant grip receiver 78 inserts into the implant grip 64 beginning with its tamp 79 being located at the upper surface 89 of the shell 67. After insertion into the implant grip 64, the implant grip receiver 78 moves within the shell 67 via the passage 70 whereby a frictional engagement of the first and second sides 80 and 81 and the first and second ends 82 and 83 for the implant grip receiver 78 retains the implant grip 64 on the implant grip receiver 78. The implant grip receiver 78 moves within the shell 67 via the passage 70 until the detents 88 and 89 respectively slide into the notches 92 thereby locking the implant grip 64 in its engaged position 66 relative to the implant grip receiver 78. The detents 88 and 89 and the notches 92 cooperate to prevent removal of the implant grip 64 from the implant grip receiver 78 without application of a removal force imparted to the implant grip 64 and the implant grip receiver 78. After insertion of the implant grip receiver 78 into the implant grip 64, the implant grip receiver 78 further inserts into the implant grip 64 via the passage 70 of the shell 67 until the upper surface 89 of the shell 67 abuts the stop 84 of the body 63 whereby the detents 88 and 89 disengage from the notches 92 and respectively slide into the notches 91 thereby locking the implant grip 64 in its disengaged position 65 relative to the implant grip receiver 78.

Figure 4A:
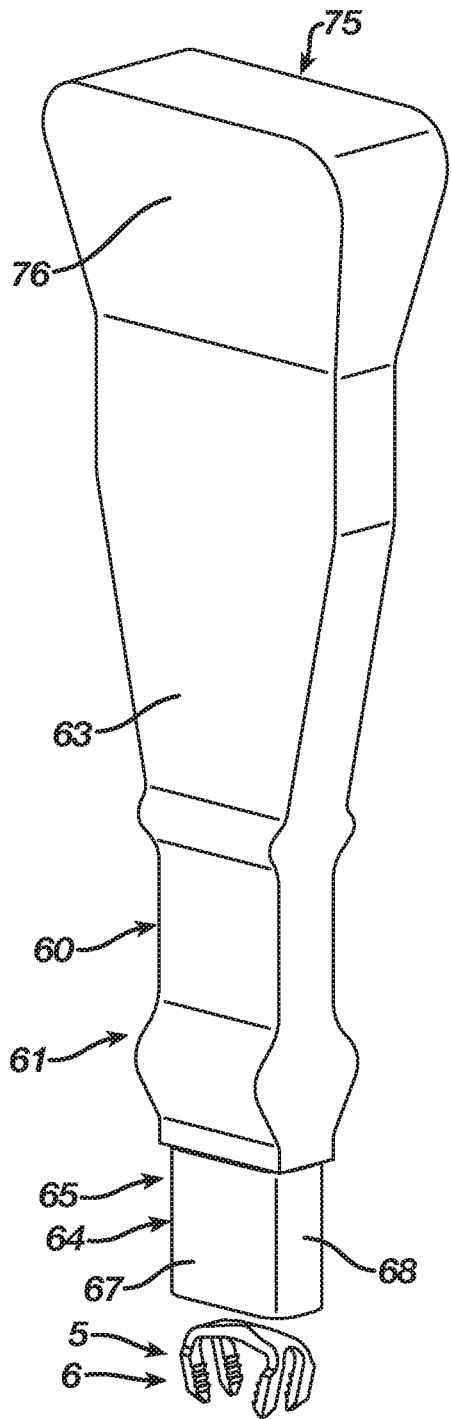
FIG. 4A is an isometric view illustrating the implant insertion device according to the first embodiment in an unloaded position and the shape memory implant according to the first embodiment in its natural shape.
Figure 4B:
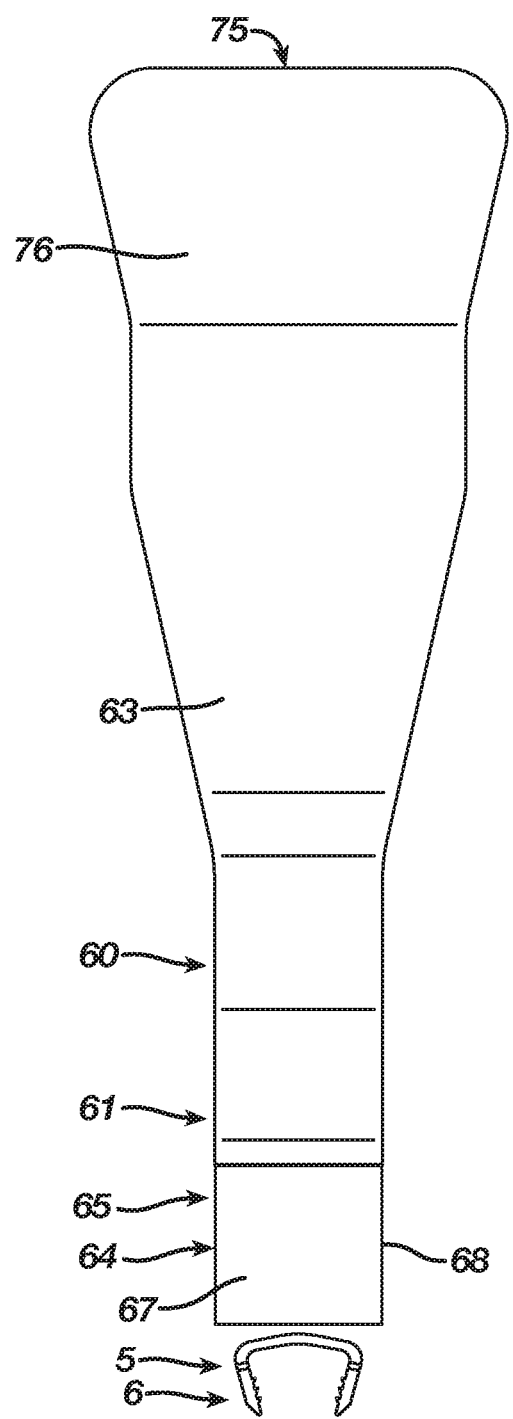
FIG. 4B is a front view illustrating the implant insertion device in its unloaded position and the shape memory implant.
Figure 5A:
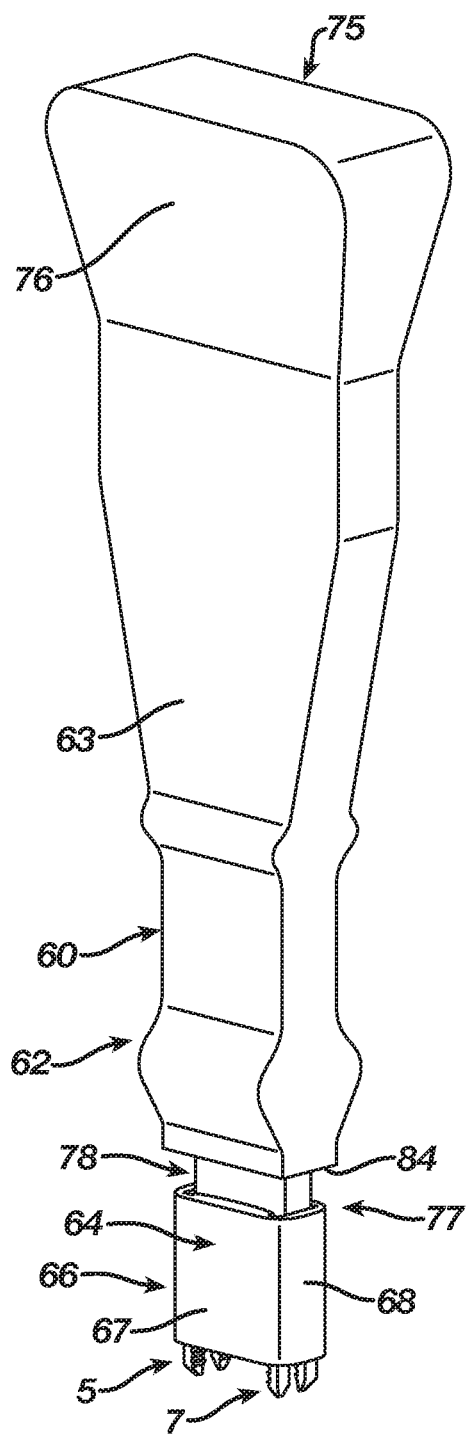
FIG. 5A is an isometric view illustrating the implant insertion device according to the first embodiment in a loaded position that constrains the shape memory implant according to the first embodiment in its insertion shape.
Figure 5B:
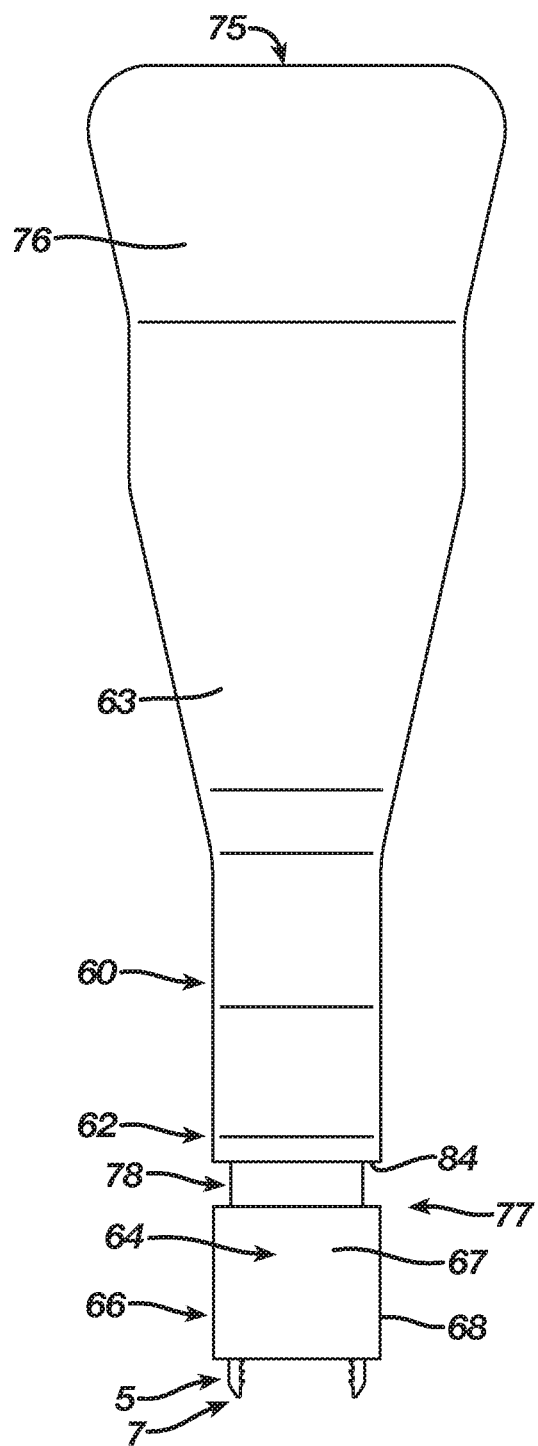
FIG. 5B is a front view illustrating the implant insertion device in its loaded position that constrains the shape memory implant in its insertion shape.
Figure 6A:
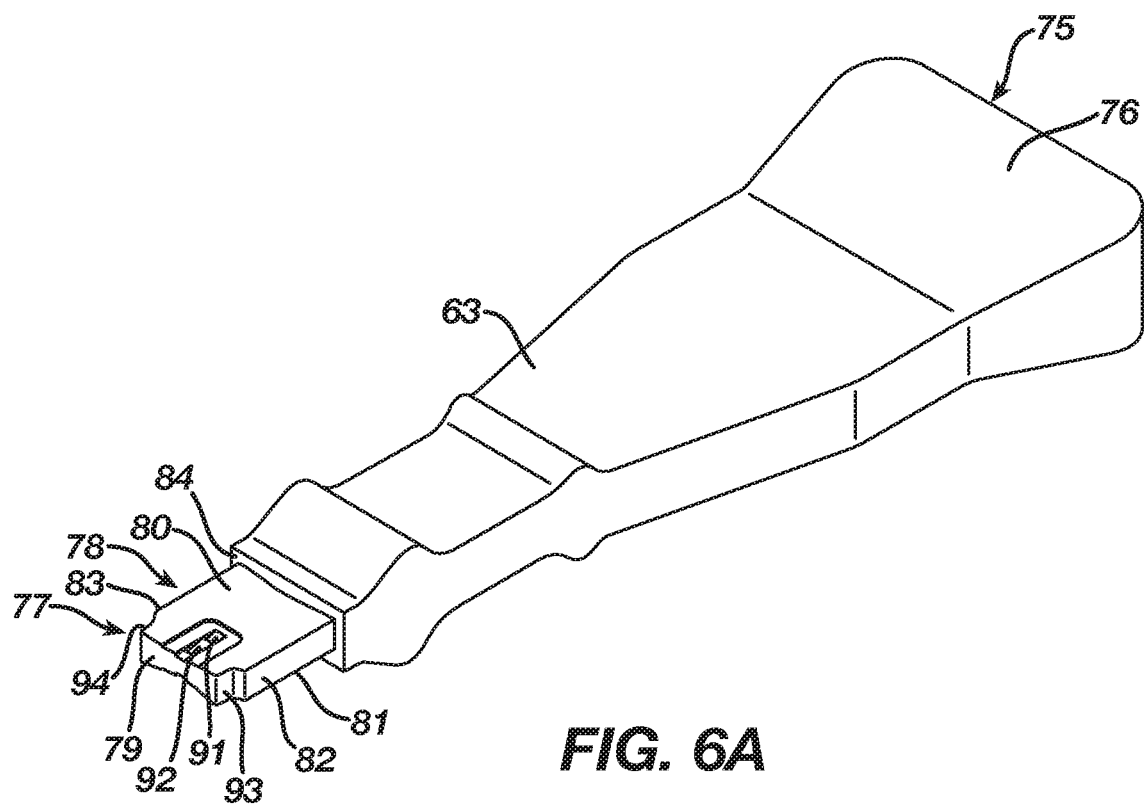
FIGS. 6A-6B are isometric views illustrating a body of the implant insertion device according to the first embodiment.
Figure 6B:
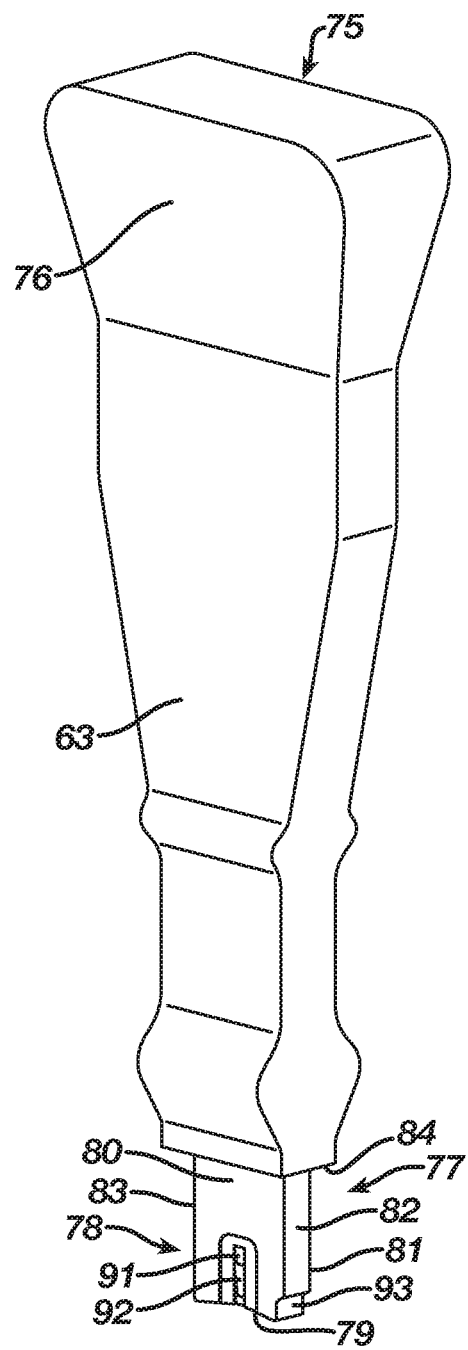
Figure 6C:
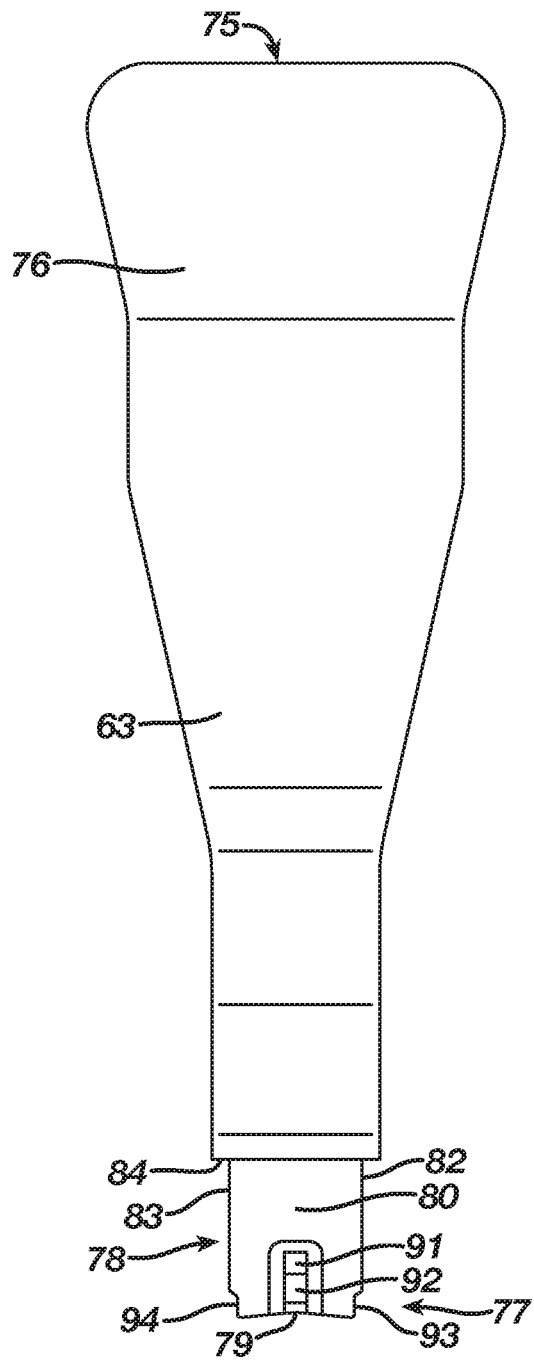
FIG. 6C is a front view illustrating the body of the implant insertion device.
Figure 6D:
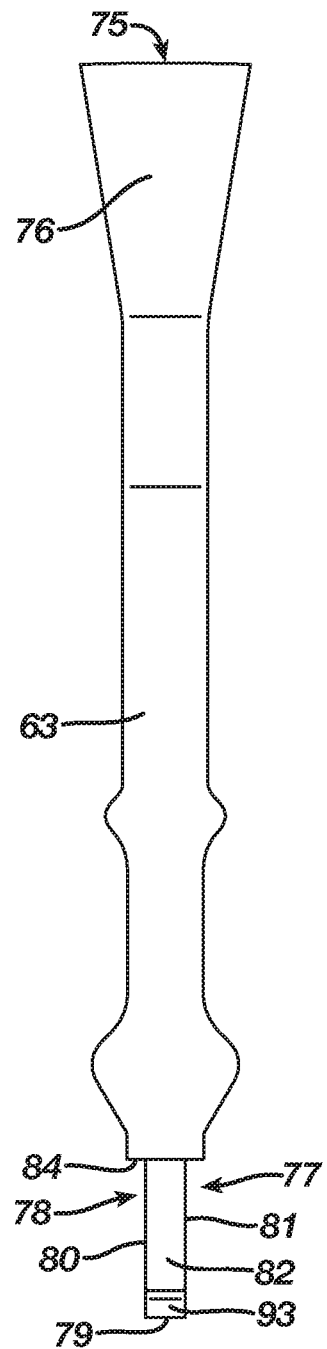
FIG. 6D is an end view illustrating the body of the implant insertion device.
Figure 7A:
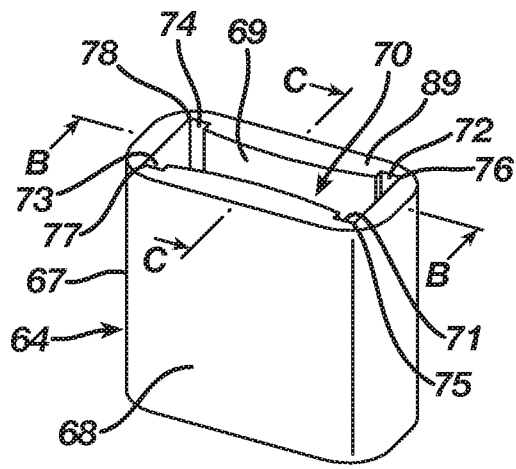
FIG. 7A is an isometric view illustrating an implant grip of the implant insertion device according to the first embodiment.
Figure 7B:
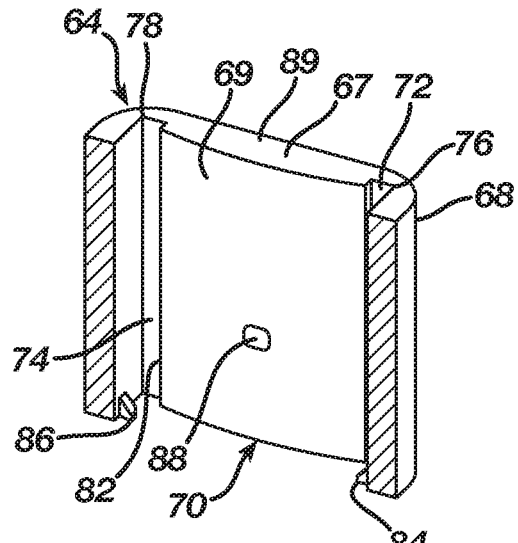
FIG. 7B is an isometric view in cross-section taken along lines B-B of FIG. 7A illustrating the implant grip of the implant insertion device.
Figure 7C:
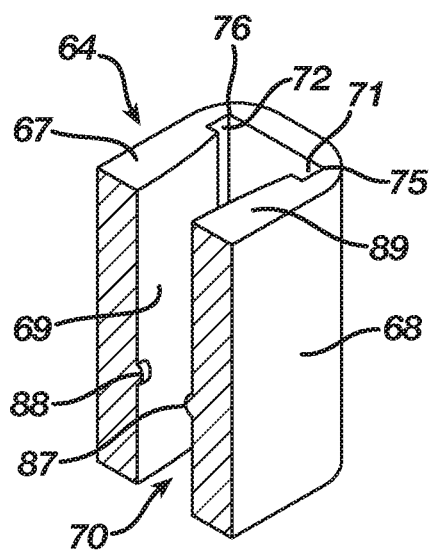
FIG. 7C is a top isometric view in cross-section taken along lines C-C of FIG. 7A illustrating the implant grip of the implant insertion device.
Figure 7D:
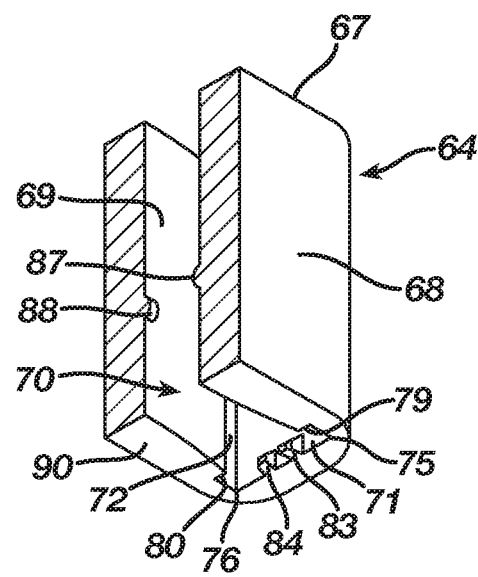
FIG. 7D is a bottom isometric view in cross-section taken along lines C-C of FIG. 7A illustrating the implant grip of the implant insertion device.
Figure 7E:
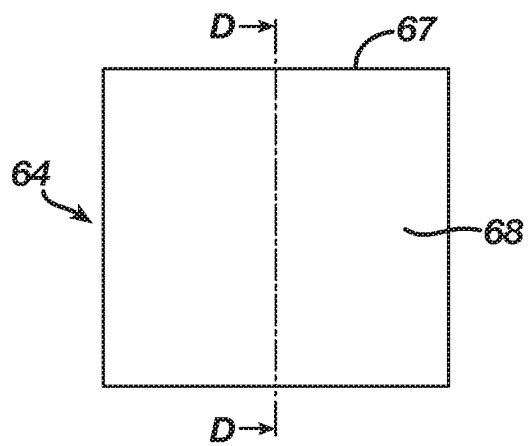
FIG. 7E is a front view illustrating the implant grip of the implant insertion device.
Figure 7F:
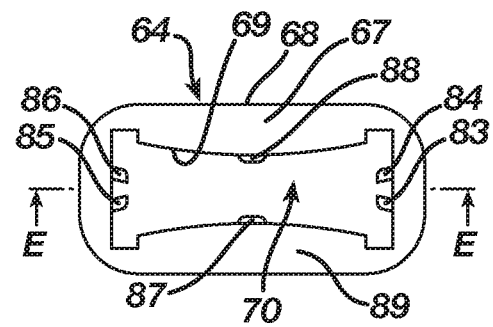
FIG. 7F is a top view illustrating the implant grip of the implant insertion device.
Figure 7G:
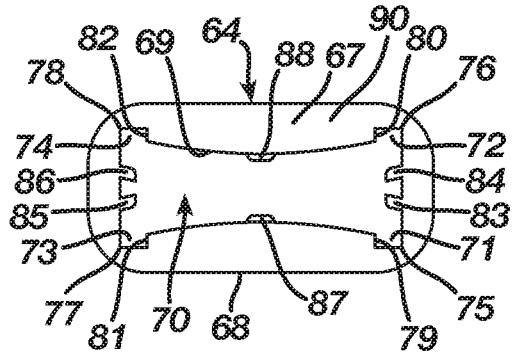
FIG. 7G is a bottom view illustrating the implant grip of the implant insertion device.
Figure 7H:
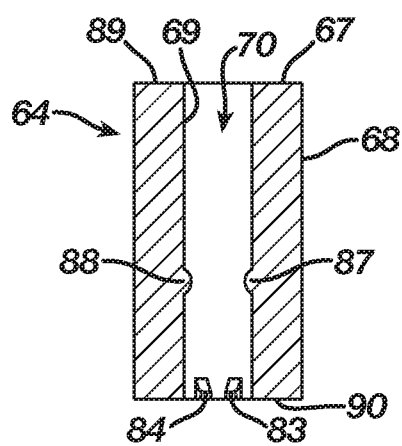
FIG. 7H is an end view in cross-section taken along lines D-D of FIG. 7E illustrating the implant grip of the implant insertion device.
Figure 7I:
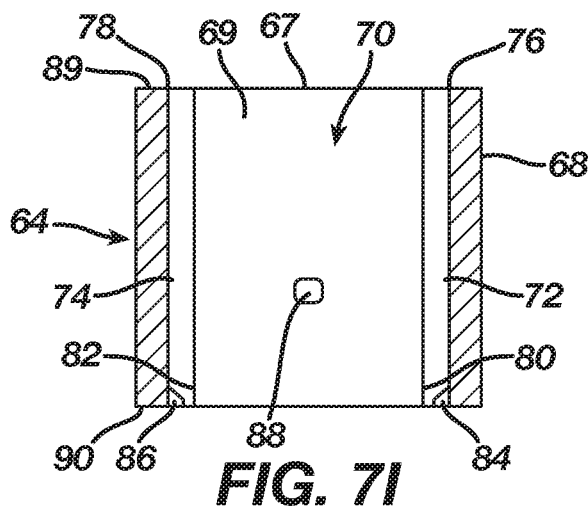
FIG. 7I is a front view in cross-section taken along lines E-E of FIG. 7F illustrating the implant grip of the implant insertion device.

When receiving the implant 5 in an orthopedic fixation system, the implant insertion device 60 as illustrated in FIGS. 4A and 4B begins in its unloaded position 61 wherein the implant grip 64 resides in its disengaged position 65. The implant 5 is mechanically deformed from its natural shape 6 to its insertion shape 7 as illustrated in FIGS. 2A-2E or its insertion shape 53 as illustrated in FIG. 2F such that the implant 5 stores mechanical energy. Mechanical deformation of the implant 5 may include cooling of the implant 5 such that the implant 5 transitions from its austenite phase to its martensite phase prior to loading of the implant 5 on the implant insertion device 60. After deformation of the implant 5, the deformed implant 5 is positioned adjacent the implant insertion device 60 whereby the implant 5 resides at the passage 70 of the shell 67 interior of the lower surface 90 for the implant grip 64 such that the tamp 79 of the implant grip receiver 78 for the body 63 resides atop the bridge 8 of the implant 5.

Figure 8A:
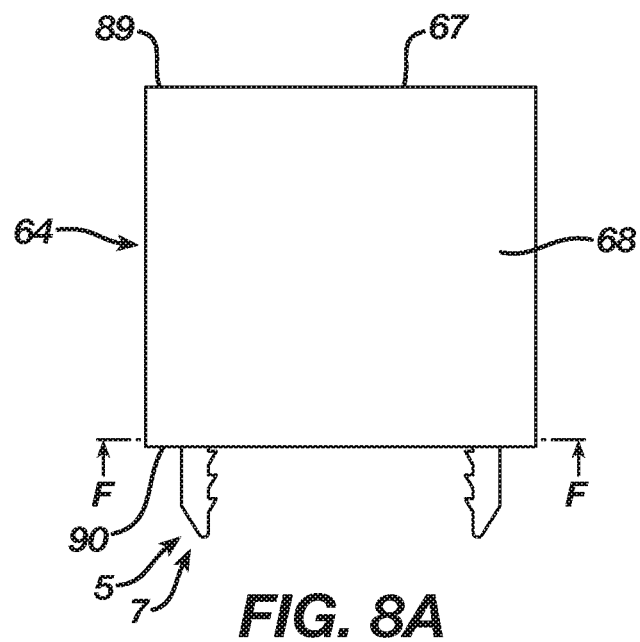
FIG. 8A is front view illustrating the implant grip of the implant insertion device according to the first embodiment constraining the shape memory implant in its insertion shape.
Figure 8B:
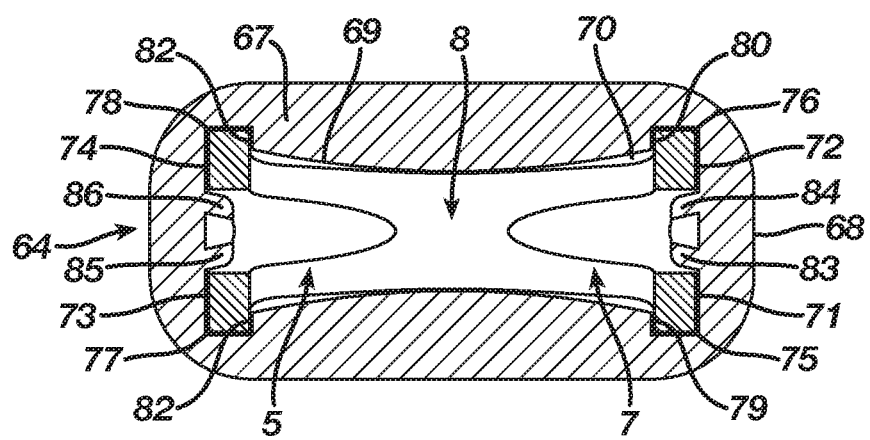
FIG. 8B is a bottom view in cross-section taken along lines F-F of FIG. 8A illustrating the implant grip of the implant insertion device constraining the shape memory implant in its insertion shape.
Figure 9A:
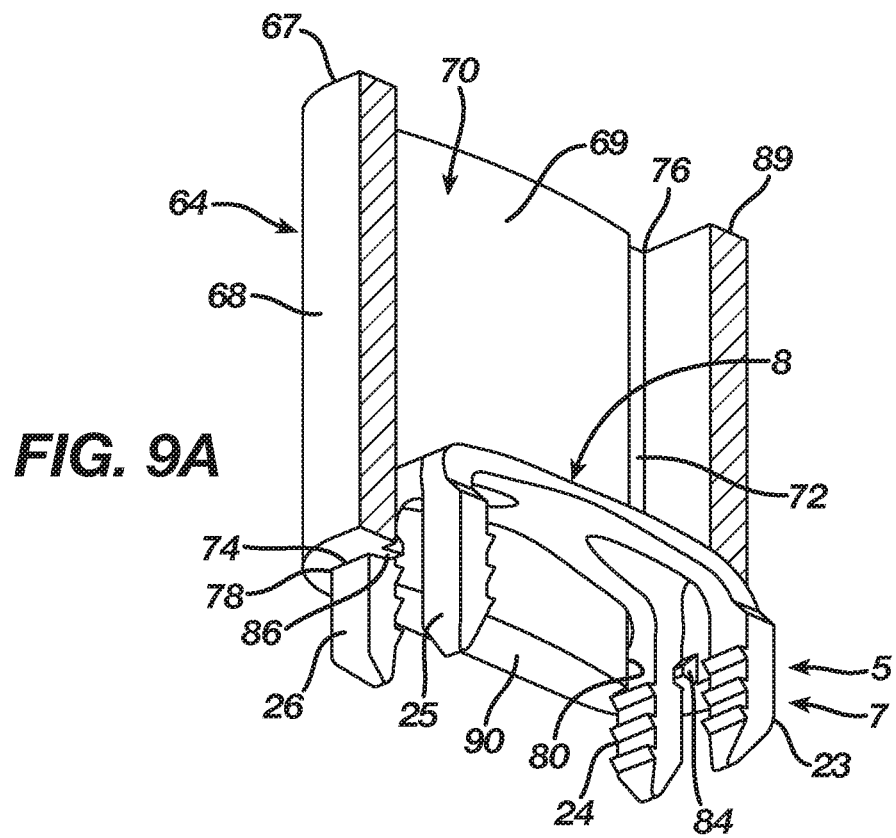
FIGS. 9A-9B are isometric views in cross-section illustrating the implant grip of the implant insertion device constraining the shape memory implant in its insertion shape.
Figure 9B:
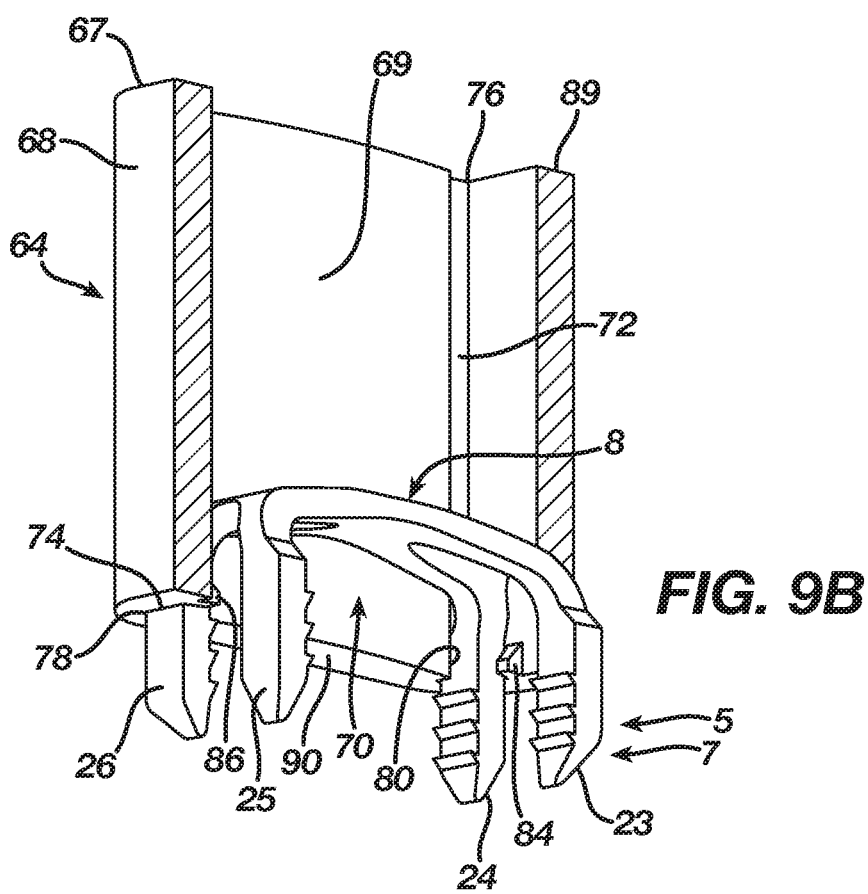
Figure 10A:
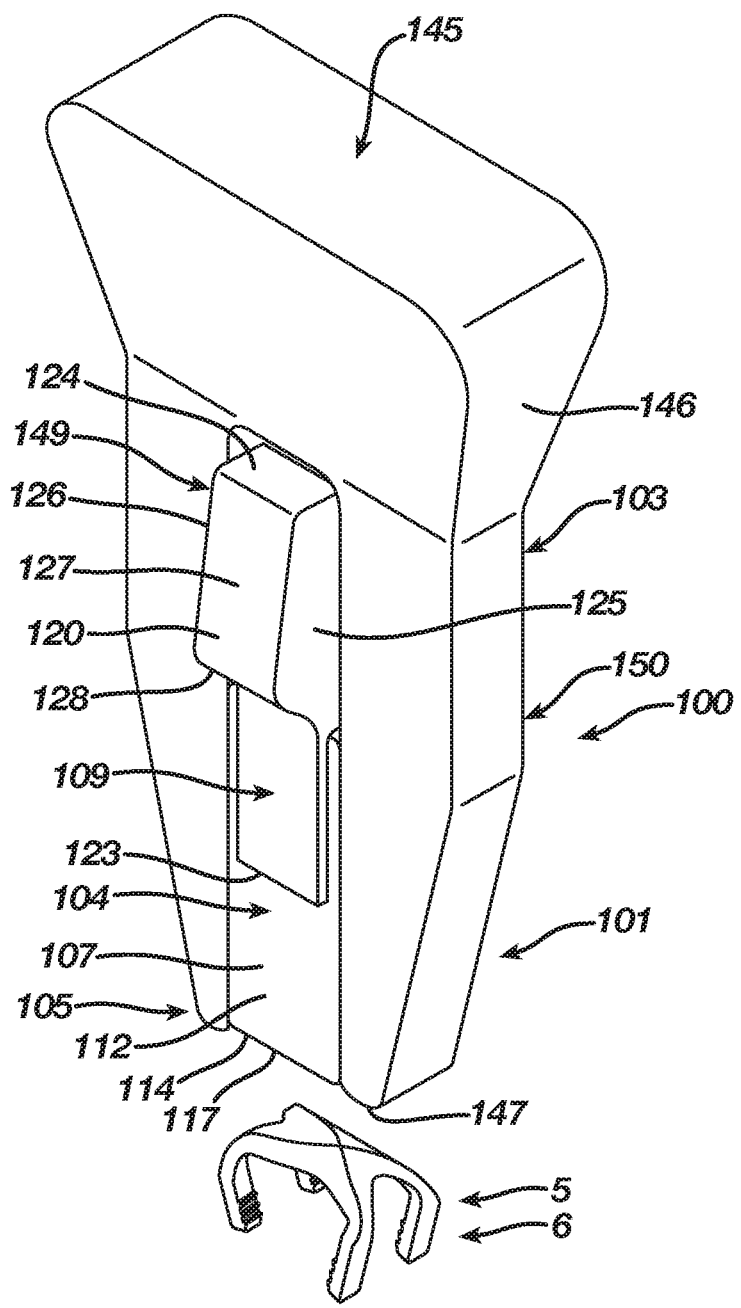
FIG. 10A is an isometric view illustrating an implant insertion device according to a second embodiment in an unloaded position and a shape memory implant according to the first embodiment in its natural shape.
Figure 10B:
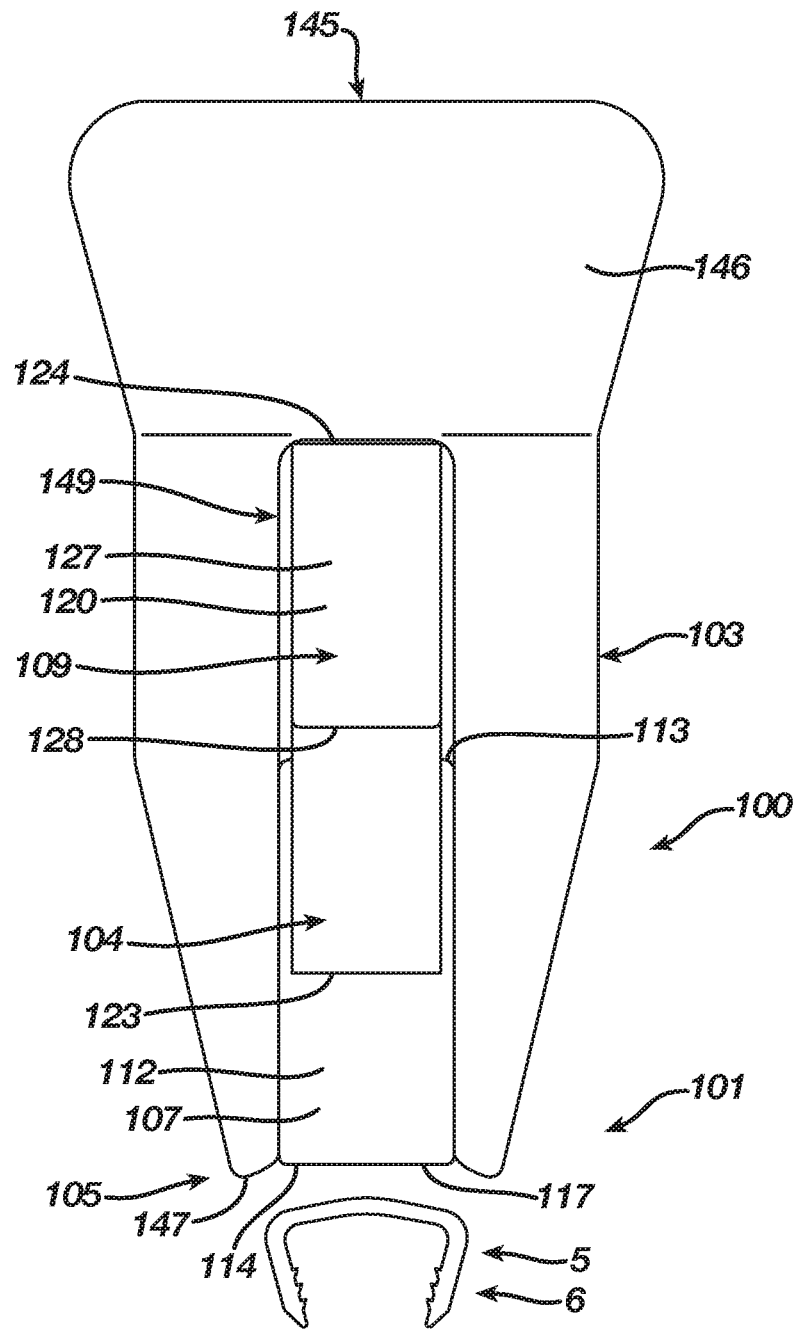
FIG. 10B is a front view illustrating the implant insertion device in its unloaded position and the shape memory implant.
Figure 10C:
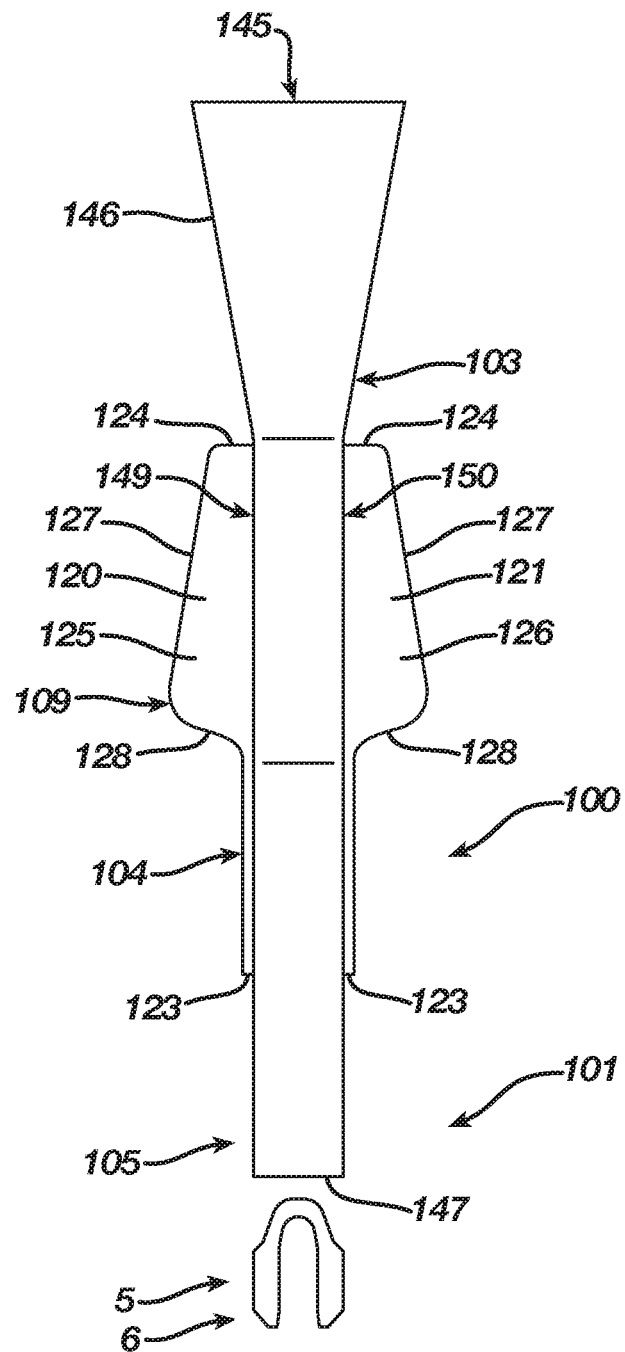
FIG. 10C is an end view illustrating the implant insertion device in its unloaded position and the shape memory implant.
Figure 10D:
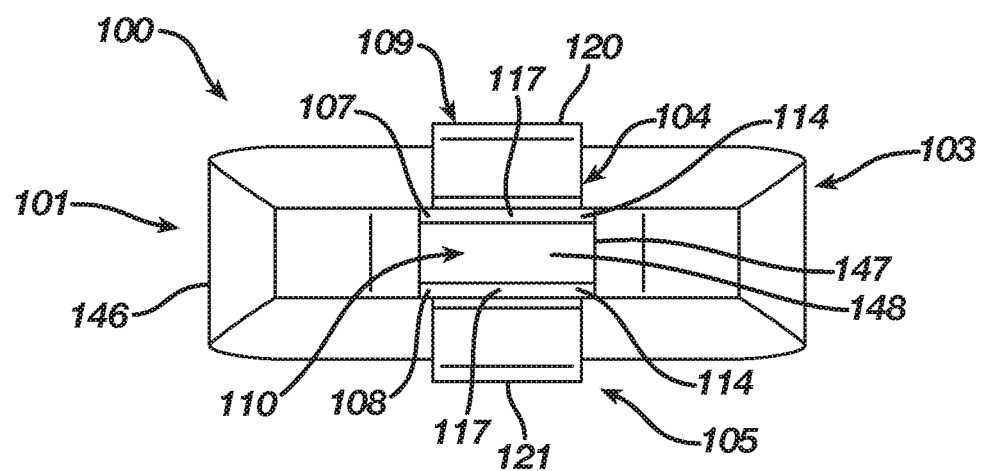
FIG. 10D is a bottom view illustrating the implant insertion device in its unloaded position.
Figure 11A:
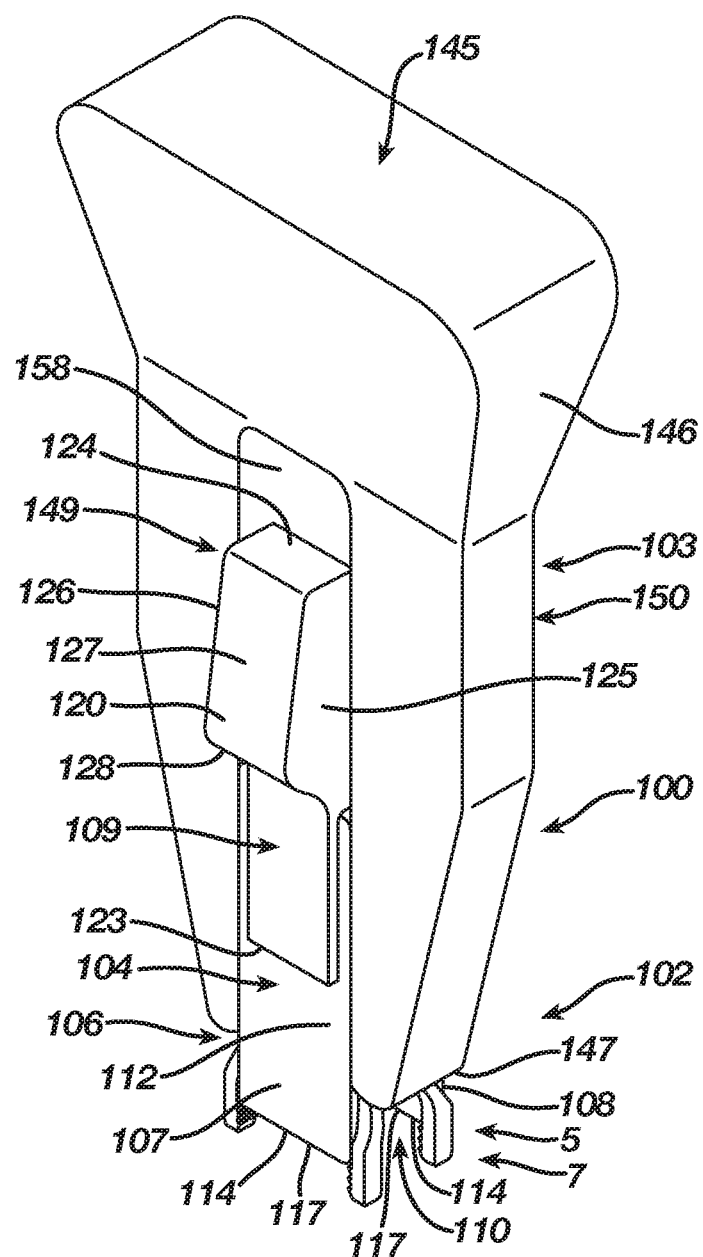
FIG. 11A is an isometric view illustrating the implant insertion device according to the second embodiment in a loaded position that constrains the shape memory implant according to the first embodiment in its insertion shape.
Figure 11B:
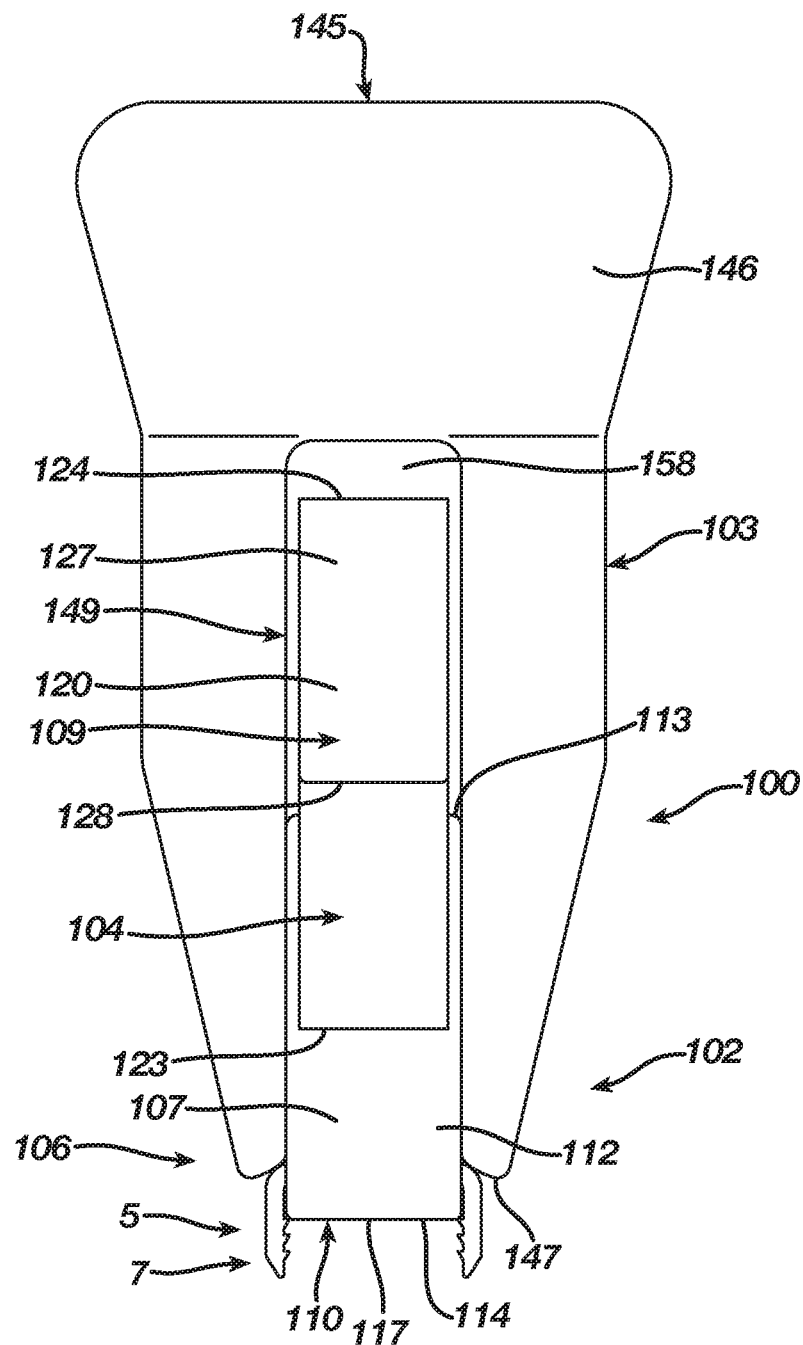
FIG. 11B is a front view illustrating the implant insertion device in its loaded position that constrains the shape memory implant in its insertion shape.
Figure 11C:
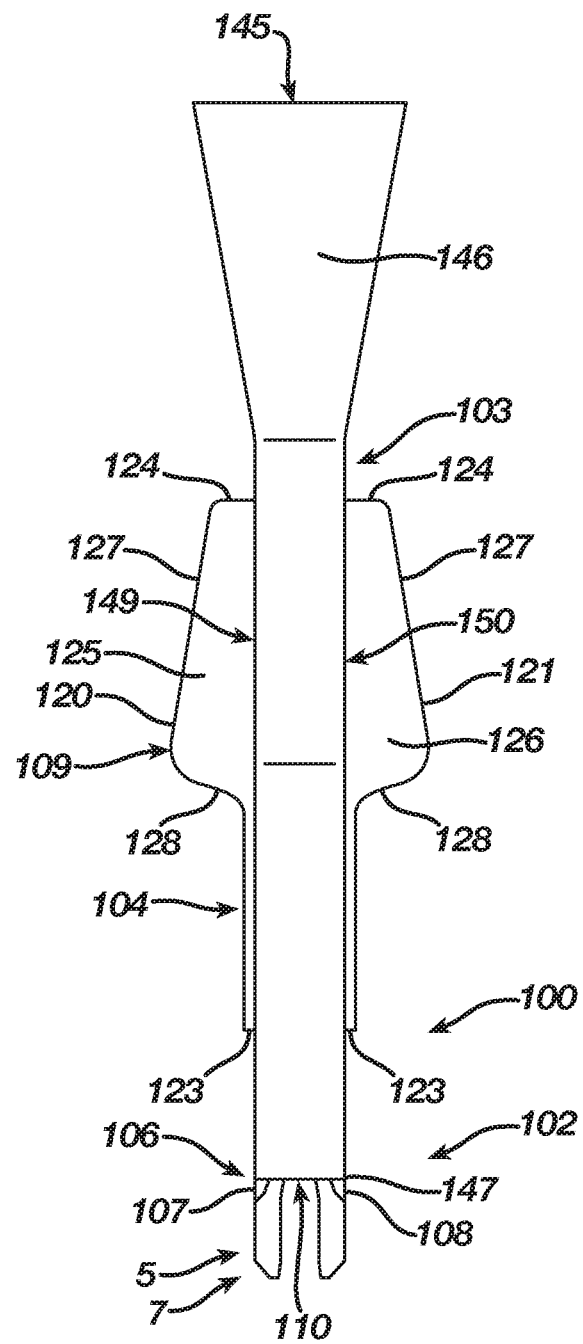
FIG. 11C is an end view illustrating the implant insertion device in its loaded position that constrains the shape memory implant in its insertion shape.
Figure 11D:
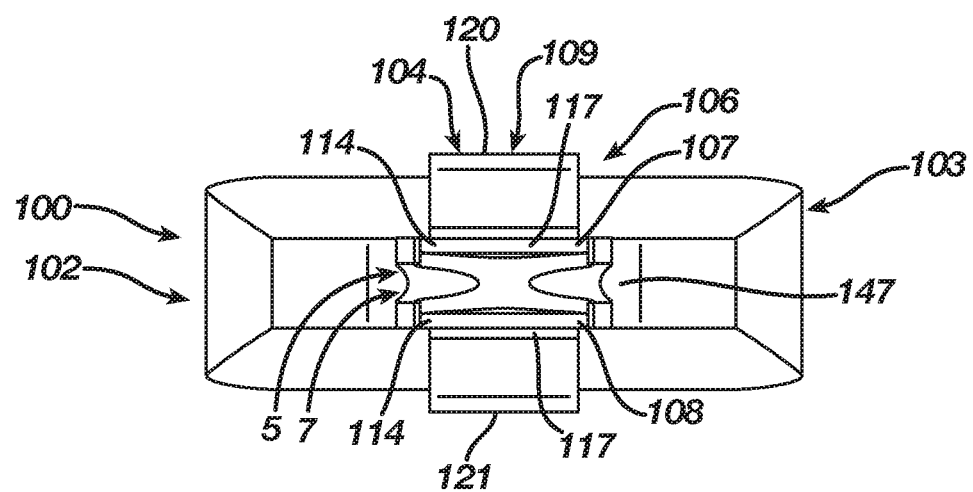
FIG. 11D is a bottom view illustrating the implant insertion device in its loaded position that constrains the shape memory implant in its insertion shape.

Once the shell 67 of the implant grip 64 aligns with the bridge 8 such that the implant 5 resides at the passage 70 of the implant grip 64, a force applied to the implant grip 64 transitions the implant insertion device 60 from its unloaded position 61 to its loaded position 62 as illustrated in FIGS. 5A-5D, 8A-8B, and 9A-9B whereby the implant insertion device 60 retains the implant 5 in its insertion shape 7 or 53. In particular, the force applied to the implant grip 64 moves the implant grip 64 relative to the implant grip receiver 78 of the body 63 from its disengaged position 65 to its engaged position 66, resulting in the detents 88 and 89 disengaging from the notches 91 and respectively sliding into the notches 92 thereby locking the implant grip 64 in its engaged position 66 relative to the implant grip receiver 78. The movement of the implant grip 64 relative to the body 63 from its disengaged position 65 to its engaged position 66 inserts the implant 5 into the passage 70 of the shell 67 thereby seating the implant 5 within the implant grip 64 with the shell 67 disposed thereabout. The passage 70 receives the implant 5 such that the shell 67 retains the implant 5 therein due to the interior surface 69 of the shell 67 and thus the passage 70 including a shape complimentary with the implant 5 whereby the interior surface 69 is sized to permit introduction of the implant 5 while also frictionally engaging the implant 5 as illustrated in FIG. 8B. The bridge 8 of the implant 5 at its first and second sides 11 and 12 and its first and second ends 13 and 14 inserts into the passage 70 of the shell 67 whereas the interior surface 69 of the shell 67 frictionally engages the first and second sides 11 and 12 of the bridge 8 at their concave sections 11a and 12a in order to retain the bridge 8 in the implant grip 64. When the implant 5 inserts into the implant grip 64 during transition of the implant grip 64 from its disengaged position 65 to its engaged position 66, the shell 67 at its interior surface 69 receives the bridge 8 therein and progresses beyond the bridge 8 such that a groove 71-74 of the interior surface 69 for the shell 67 respectively receives therein a segment 34, 39, 44, and 49 of the legs 23-26 whereby the interior surface 69 at the grooves 71-74 respectively frictionally engages the legs 23-26 of the implant 5 thereby retaining the implant 5 within the shell 67 in its insertion shape 7 or 53. Moreover, a retention surface 79-82 disposed in each of the grooves 71-74 respectively abuts an engagement point 35, 40, 44, and 50 of the legs 23-26 in order to grip and then constrain the legs 23-26 wherein the shell 67 retains the implant 5 in its insertion shape 7 or 53. In addition, during the insertion of the implant 5 into the passage 70 of the shell 67, the projections 83-86 of the interior surface 69 by-pass respectively the bridge 8 at its first and second ends 13 and 14 via the concave sections 13a and 14a thereof and then frictionally engage a respective leg 23-26 opposite from the segments 34, 39, 44, and 49, thereby assisting in retaining the implant 5 within the shell 67 in its insertion shape 7 or 53. The projections 83-86, when they resiliently by-pass the bridge 8, further prevent release of the implant 5 from the implant grip 64 without application of an extrusion force exerted against the implant 5 using the tamp 79 of the implant grip receiver 78 and the body 63. After the implant grip 64 reaches its engaged position 66 with the detents 88 and 89 retained in the notches 92, the tamp 79 of the implant grip receiver 78 for the body 63 remains atop the bridge 8 of the implant 5 while concurrently the grooves 71-74 and the projections 83-86 maintain the implant 5 within the implant grip 64 and the retention surfaces 79-82 in each of the grooves 71-74 defined by the shell 67 constrain the legs 23-26 such that the shell 67 holds the implant 5 in its insertion shape 7 or 53.

When receiving the implant 5 in an orthopedic fixation system, the implant insertion device 60 alternatively may begin in its loaded position 62 wherein the implant grip 64 resides in its engaged position 66 with the detents 88 and 89 retained in the notches 92. Upon mechanical deformation of the implant 5 from its natural shape 6 to its insertion shape 7 or 53, the deformed implant 5 is positioned adjacent the implant insertion device 60 whereby the implant 5 resides at the passage 70 of the shell 67 interior of the lower surface 90 for the implant grip 64. After the shell 67 of the implant grip 64 aligns with the bridge 8 such that the implant 5 resides at the passage 70 of the implant grip 64, the implant grip 64 is held while a force applied to the body 63 fits the shell 67 over the implant 5 until the tamp 79 of the implant grip receiver 78 for the body 63 abuts the bridge 8 of the implant 5 and the implant insertion device 60 retains the implant 5 in its insertion shape 7 or 53. In particular, the force applied to the body 63 with the implant grip 64 held in place inserts the implant 5 into the passage 70 of the shell 67 thereby seating the implant 5 within the implant grip 64 with the shell 67 disposed thereabout. The passage 70 receives the implant 5 such that the shell 67 retains the implant 5 therein due to the interior surface 69 of the shell 67 and thus the passage 70 including a shape complimentary with the implant 5 whereby the interior surface 69 is sized to permit introduction of the implant 5 while also frictionally engaging the implant 5 as illustrated in FIG. 8B. The bridge 8 of the implant 5 at its first and second sides 11 and 12 and its first and second ends 13 and 14 inserts into the passage 70 of the shell 67 whereas the interior surface 69 of the shell 67 frictionally engages the first and second sides 11 and 12 of the bridge 8 at their concave sections 11a and 12a in order to retain the bridge 8 in the implant grip 64. During insertion of the implant 5 into the implant grip 64, the shell 67 at its interior surface 69 receives the bridge 8 therein and progresses beyond the bridge 8 such that a groove 71-74 of the interior surface 69 for the shell 67 respectively receives therein a segment 34, 39, 44, and 49 of the legs 23-26 whereby the interior surface 69 at the grooves 71-74 respectively frictionally engages the legs 23-26 of the implant 5 thereby retaining the implant 5 within the shell 67 in its insertion shape 7 or 53. Moreover, a retention surface 79-82 disposed in each of the grooves 71-74 respectively abuts an engagement point 35, 40, 44, and 50 of the legs 23-26 in order to grip and then constrain the legs 23-26 wherein the shell 67 retains the implant 5 in its insertion shape 7 or 53. In addition, during the insertion of the implant 5 into the passage 70 of the shell 67, the projections 83-86 of the interior surface 69 by-pass respectively the bridge 8 at its first and second ends 13 and 14 via the concave sections 13*a* and 14*a* thereof and then frictionally engage a respective leg 23-26 opposite from the segments 34, 39, 44, and 49, thereby assisting in retaining the implant 5 within the shell 67 in its insertion shape 7 or 53. The projections 83-86, when they resiliently by-pass the bridge 8, further prevent release of the implant 5 from the implant grip 64 without application of an extrusion force exerted against the implant 5 using the tamp 79 of the implant grip receiver 78 and the body 63. After the tamp 79 of the implant grip receiver 78 for the body 63 reaches and sits atop the bridge 8 of the implant 5, the grooves 71-74 and the projections 83-86 maintain the implant 5 within the implant grip 64 and the retention surfaces 79-82 in each of the grooves 71-74 defined by the shell 67 constrain the legs 23-26 such that the shell 67 holds the implant 5 in its insertion shape 7 or 53.

While the implant 5 may be mechanically deformed from its natural shape 6 to its insertion shape 7 or 53 prior to its loading on the implant insertion device 60 in an orthopedic fixation system, the implant insertion device 60 may be employed during its loading with the implant 5 to mechanically deform the implant 5 from its natural shape 6 to its insertion shape 7 or 53. The implant 5 in its natural shape 6 is positioned adjacent the implant insertion device 60 whereby the implant 5 resides at the passage 70 of the shell 67 interior of the lower surface 90 for the implant grip 64 such that the tamp 79 of the implant grip receiver 78 for the body 63 resides atop the bridge 8 of the implant 5. Once the shell 67 of the implant grip 64 aligns with the bridge 8 such that the implant 5 resides at the passage 70 of the implant grip 64, a force applied to the implant grip 64 transitions the implant insertion device 60 from its unloaded position 61 to its loaded position 62 as illustrated in FIGS. 5A-5D, 8A-8B, and 9A-9B whereby the implant insertion device 60 moves the implant 5 from its natural shape 6 to its insertion shape 7 or 53 and then retains the implant 5 in its insertion shape 7 or 53. In particular, the force applied to the implant grip 64 moves the implant grip 64 relative to the body 63 from its disengaged position 65 to its engaged position 66, resulting in the detents 88 and 89 disengaging from the notches 91 and respectively sliding into the notches 92 thereby locking the implant grip 64 in its engaged position 66 relative to the implant grip receiver 78. The movement of the implant grip 64 relative to the body 63 from its disengaged position 65 to its engaged position 66 inserts the implant 5 into the passage 70 of the shell 67 thereby seating the implant 5 within the implant grip 64 with the shell 67 disposed thereabout. The passage 70 receives the implant 5 such that the shell 67 retains the implant 5 therein due to the interior surface 69 of the shell 67 and thus the passage 70 including a shape complimentary with the implant 5 whereby the interior surface 69 is sized to permit introduction of the implant 5 while also frictionally engaging the implant 5 as illustrated in FIG. 8B. The bridge 8 of the implant 5 at its first and second sides 11 and 12 and its first and second ends 13 and 14 inserts into the passage 70 of the shell 67 whereas the interior surface 69 of the shell 67 frictionally engages the first and second sides 11 and 12 of the bridge 8 at their concave sections 11*a* and 12*a* in order to retain the bridge 8 in the implant grip 64. When the implant 5 inserts into the implant grip 64 during transition of the implant grip 64 from its disengaged position 65 to its engaged position 66, the shell 67 at its interior surface 69 receives the bridge 8 therein and progresses beyond the bridge 8 such that a groove 71-74 of the interior surface 69 for the shell 67 respectively receives therein a segment 34, 39, 44, and 49 of the legs 23-26 whereby the interior surface 69 at the grooves 71-74 respectively frictionally engages the legs 23-26 of the implant 5. Moreover, a retention surface 79-82 disposed in each of the grooves 71-74 respectively abuts an engagement point 35, 40, 44, and 50 of the legs 23-26 in order to grip the legs 23-26 at the engagement points 35, 40, 44, and 50 and further to impart a force into the implant 5 that facilitates transition of the implant 5 from its natural shape 6 to its insertions shape 7 or 53 as the implant grip 64 travels to its engaged position 66. The abutment of the retention surfaces 79-82 of the grooves 71-74 respectively with the engagement points 35, 40, 44, and 50 of the legs 23-26 additionally constrains the legs 23-26 wherein the shell 67 retains the implant 5 in its insertion shape 7 or 53. Furthermore, during the insertion of the implant 5 into the passage 70 of the shell 67, the projections 83-86 of the interior surface 69 by-pass respectively the bridge 8 at its first and second ends 13 and 14 via the concave sections 13*a* and 14*a* thereof and then frictionally engage a respective leg 23-26 opposite from the segments 34, 39, 44, and 49, thereby assisting in retaining the implant 5 within the shell 67 in its insertion shape 7 or 53. The projections 83-86, when they resiliently by-pass the bridge 8, further prevent release of the implant 5 from the implant grip 64 without application of an extrusion force exerted against the implant 5 using the tamp 79 of the implant grip receiver 78 and the body 63. After the implant grip 64 reaches its engaged position 66 with the detents 88 and 89 retained in the notches 92, the tamp 79 of the implant grip receiver 78 for the body 63 remains atop the bridge 8 of the implant 5 while concurrently the grooves 71-74 and the projections 83-86 maintain the implant 5 within the implant grip 64 and the retention surfaces 79-82 in each of the grooves 71-74 defined by the shell 67 constrain the legs 23-26 such that the shell 67 holds the implant 5 in its insertion shape 7 or 53.

When receiving the implant 5 in an orthopedic fixation system, the implant insertion device 60 alternatively may begin in its loaded position 62 wherein the implant grip 64 resides in its engaged position 66 with the detents 88 and 89 retained in the notches 92. The implant 5 in its natural shape 6 is positioned adjacent the implant insertion device 60 whereby the implant 5 resides at the passage 70 of the shell 67 interior of the lower surface 90 for the implant grip 64. After the shell 67 of the implant grip 64 aligns with the bridge 8 such that the implant 5 resides at the passage 70 of the implant grip 64, the implant grip 64 is held while a force applied to the body 63 fits the shell 67 over the implant 5 until the tamp 79 of the implant grip receiver 78 for the body 63 abuts the bridge 8 of the implant 5 and the implant insertion device 60 moves the implant 5 from its natural shape 6 to its insertion shape 7 or 53 and then retains the implant 5 in its insertion shape 7 or 53. In particular, the force applied to the body 63 with the implant grip 64 held in place inserts the implant 5 into the passage 70 of the shell 67 thereby seating the implant 5 within the implant grip 64 with the shell 67 disposed thereabout. The passage 70 receives the implant 5 such that the shell 67 retains the implant 5 therein due to the interior surface 69 of the shell 67 and thus the passage 70 including a shape complimentary with the implant 5 whereby the interior surface 69 is sized to permit introduction of the implant 5 while also frictionally engaging the implant 5 as illustrated in FIG. 8B. The bridge 8 of the implant 5 at its first and second sides 11 and 12 and its first and second ends 13 and 14 inserts into the passage 70 of the shell 67 whereas the interior surface 69 of the shell 67 frictionally engages the first and second sides 11 and 12 of the bridge 8 at their concave sections 11a and 12a in order to retain the bridge 8 in the implant grip 64. During insertion of the implant 5 into the implant grip 64, the shell 67 at its interior surface 69 receives the bridge 8 therein and progresses beyond the bridge 8 such that a groove 71-74 of the interior surface 69 for the shell 67 respectively receives therein a segment 34, 39, 44, and 49 of the legs 23-26 whereby the interior surface 69 at the grooves 71-74 respectively frictionally engages the legs 23-26 of the implant 5. Moreover, a retention surface 79-82 disposed in each of the grooves 71-74 respectively abuts an engagement point 35, 40, 44, and 50 of the legs 23-26 in order to grip the legs 23-26 at the engagement points 35, 40, 44, and 50 and further to impart a force into the implant 5 that facilitates transition of the implant 5 from its natural shape 6 to its insertions shape 7 or 53 as the implant grip 64 receives the implant 5 therein until the tamp 79 of the implant grip receiver 78 for the body 63 abuts the bridge 8 of the implant 5. The abutment of the retention surfaces 79-82 of the grooves 71-74 respectively with the engagement points 35, 40, 44, and 50 of the legs 23-26 additionally constrains the legs 23-26 wherein the shell 67 retains the implant 5 in its insertion shape 7 or 53. Furthermore, during the insertion of the implant 5 into the passage 70 of the shell 67, the projections 83-86 of the interior surface 69 by-pass respectively the bridge 8 at its first and second ends 13 and 14 via the concave sections 13a and 14a thereof and then frictionally engage a respective leg 23-26 opposite from the segments 34, 39, 44, and 49, thereby assisting in retaining the implant 5 within the shell 67 in its insertion shape 7 or 53. The projections 83-86, when they resiliently by-pass the bridge 8, further prevent release of the implant 5 from the implant grip 64 without application of an extrusion force exerted against the implant 5 using the tamp 79 of the implant grip receiver 78 and the body 63. After the tamp 79 of the implant grip receiver 78 for the body 63 reaches and sits atop the bridge 8 of the implant 5, the grooves 71-74 and the projections 83-86 maintain the implant 5 within the implant grip 64 and the retention surfaces 79-82 in each of the grooves 71-74 defined by the shell 67 constrain the legs 23-26 such that the shell 67 holds the implant 5 in its insertion shape 7 or 53.

When delivering the implant 5 to bone, bones, or bone pieces, the implant insertion device 60 as illustrated in FIGS. 5A-5D begins in its loaded position 62 wherein the implant grip 64 in its engaged position 66 constrains the implant 5 in its insertion shape 7 or 53. In order to release the implant 5 from the implant insertion device 60, a force applied to the implant grip 64, either at the lower surface 90 of the shell 67 as described herein or directly to the implant grip 64, progresses the implant grip 64 from its engaged position 66 to its disengaged position 65 abutting the stop 84 adjacent the implant grip receiver 78, resulting in the detents 88 and 89 disengaging from the notches 92 and respectively sliding into the notches 91 thereby locking the implant grip 64 in its disengaged position 65. The tamp 79 of the implant grip receiver 78 for the body 63 remains atop the bridge 8 of the implant 5 to prevent movement of the implant 5 relative to the implant grip 64 during progression of the implant grip 64 from its engaged position 66 to its disengaged position 65. As a consequence, the projections 83-86 of the interior surface 69, when the implant grip 64 moves from its engaged position 66 to its disengaged position 65, by-pass respectively the bridge 8 at its first and second ends 13 and 14 via the concave sections 13a and 14a thereby releasing a respective leg 23-26 opposite from the segments 34, 39, 44, and 49. The projections 83-86 insert into the indentations 93 and 94 in the implant grip receiver 78 to prevent the projections 83-86 from impeding movement of the implant grip 64 relative to the implant grip receiver 78 such that the tamp 79 ultimately reaches a position adjacent the lower surface 90 of the shell 67. Similarly, the retention surfaces 79-82 disposed in each of the grooves 71-74 respectively release an engagement point 35, 40, 44, and 50 of the legs 23-26, while the grooves 71-74 of the interior surface 69 for the shell 67 respectively disengage from a segment 34, 39, 44, and 49 of the legs 23-26. Moreover, the interior surface 69 of the shell 67 disengages from the first and second sides 11 and 12 of the bridge 8 at their concave sections 11a and 12a, whereas the interior surface 69 of the shell 67 further by-passes the bridge 8 of the implant 5 at its first and second sides 11 and 12 and its first and second ends 13 and 14 such that the implant 5 exits the passage 70 of the shell 67, resulting in the discharge of the implant 5 from the implant grip 64 and a subsequent attempted transition of the implant 5 from its insertion shape 7 or 53 to its natural shape 6 whereby the implant 5 delivers the energy stored therein to the bone, bones, or bone pieces.

Figure 12A:
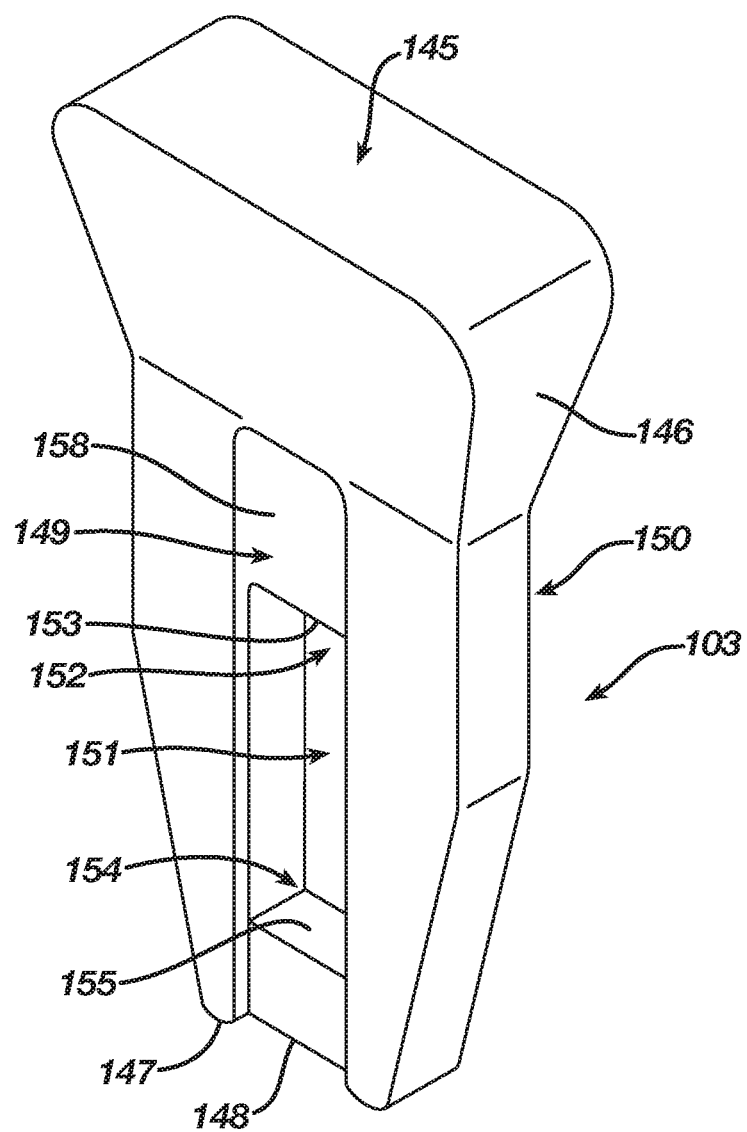
FIG. 12A is an isometric view illustrating a body of the implant insertion device according to the second embodiment.
Figure 12B:
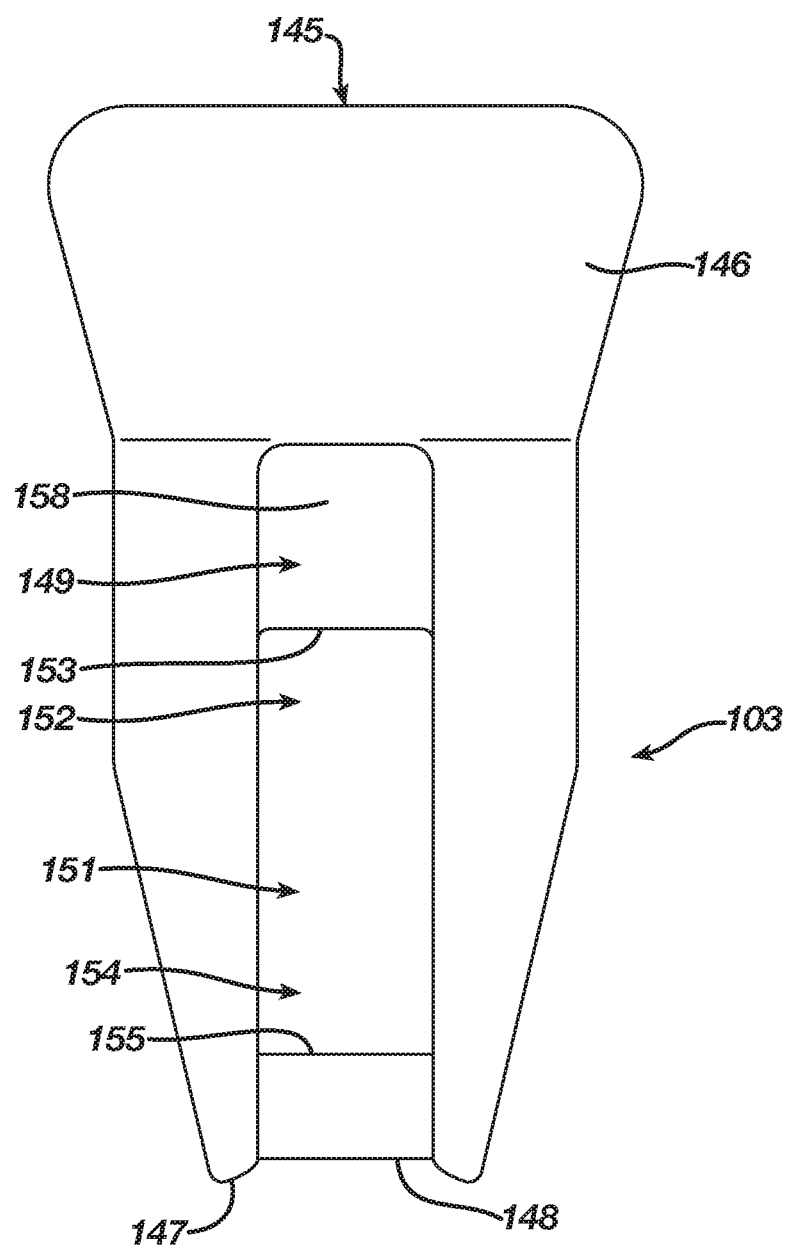
FIG. 12B is a front view illustrating the body of the implant insertion device.

FIGS. 10A-11D illustrate an implant insertion device 100 according to a second embodiment that engages the implant 5 and retains the implant 5 in its insertion shape 7 or 53. FIGS. 10A-10D illustrate the implant insertion device 100 in an unloaded position 101 prior to its loading with the implant 5 or after its delivery of the implant 5 whereby the implant 5 releases from the implant insertion device 100 without obstruction. FIGS. 11A-11D illustrate the implant insertion device 100 in a loaded position 102 whereby the implant insertion device 100 may be loaded with the implant 5 such that the implant insertion device 100 retains the implant 5 in its insertion shape 7 or 53. The implant insertion device 100 allows a surgeon to manipulate the implant 5 and insert the implant 5 into bone, bones, or bone pieces requiring fixation. FIGS. 12A-12B illustrate a body 103 of the implant insertion device 100, whereas FIGS. 13A-13B illustrate an implant grip 104 of the implant insertion device 100 that is coupled with the body 103 and is movable relative to the body 103 between a disengaged position 105 shown in FIGS. 10A-10D and an engaged position 106 shown in FIGS. 11A-11D.

Figure 13A:
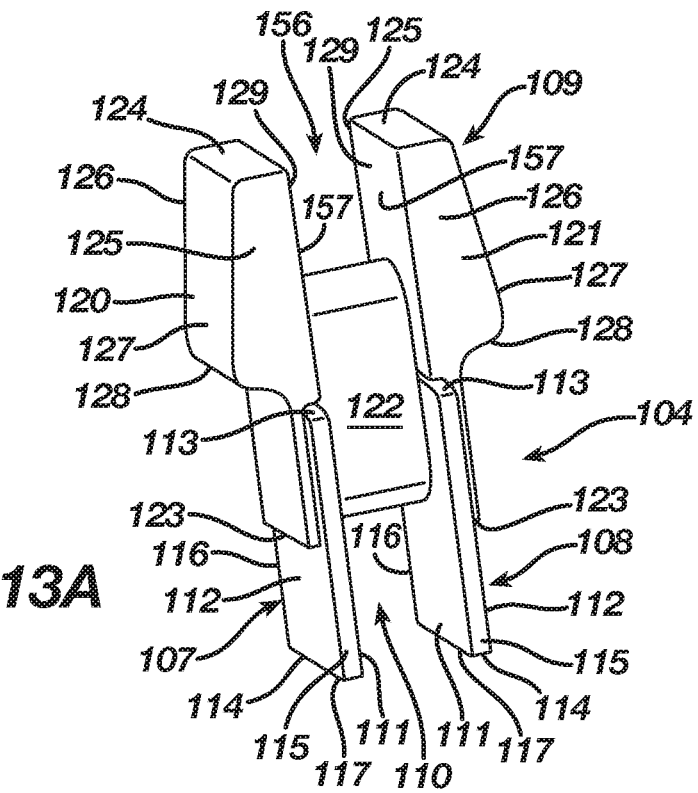
FIG. 13A is an isometric view illustrating an implant grip of the implant insertion device according to the second embodiment.
Figure 13B:
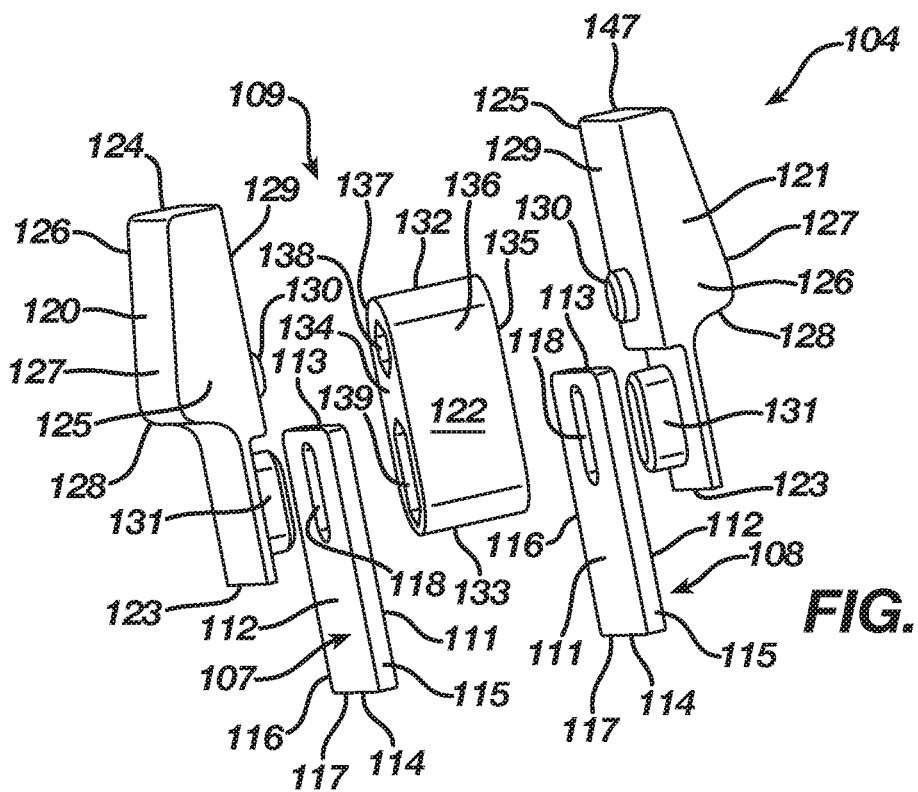
FIG. 13B is an exploded isometric view illustrating the implant grip of the implant insertion device according to the second embodiment.

The implant grip 104 as illustrated in FIGS. 13A-13B includes a first blade 107 and a second blade 108 whereby the first and second blades 107 and 108 are secured with an actuator 109 in an opposed relationship defining a passage 110 therebetween. The first blade 107 and the second blade 108 in the second embodiment each include a first face 111, a second face 112, a first side 115, a second side 116, a first end 113, and a second end 114 that defines a leading edge 117 between the first and second sides 115 and 116. The first end 113 of the first and second blades 107 and 108 includes an aperture 118 therethrough that facilitates securing of the first blade 107 and the second blade 108 with the actuator 109. The passage 110 between the first and second blades 107 and 108 in the second embodiment receives the bridge 8 of the implant 5 therein whereby the first and second blades 107 and 108 at their leading edges 117 extend beyond the bridge 8 such that the first and second blades 107 and 108 at their first and second sides 115 and 116 respectively abut the engagement points 35, 40, 44, and 50 of the legs 23-26, thereby constraining the implant 5 in its insertion shape 7 or 53.

The actuator 109 as illustrated in FIGS. 13A-13B includes a first slider 120, a second slider 121, and a spacer 122 whereby the first and second sliders 120 and 121 couple with the spacer 122 in opposed relationship to form the actuator 109 secured with the first and second blades 107 and 108. The first and second sliders 120 and 121 each include first and second ends 123 and 124, first and second sides 125 and 126, and a front surface 127 defining a protrusion 128 that allows manipulation of the first and second sliders 120 and 121, and a rear surface 129 defining a pin 130 and a peg 131. The spacer 122 includes first and second ends 132 and 133, first and second sides 134 and 135, a front surface 136, and a rear surface 137. The spacer 122 further includes an opening 138 therethrough extending from its first side 134 to its second side 135 and a channel 139 therethrough extending from its first side 134 to its second side 135. The pins 130 of the first and second sliders 120 and 121 are complementary in shape and produce a complementary fit with the opening 138, whereas the pegs 131 of the first and second sliders 120 and 121 are complementary in shape and produce a complementary fit with both the aperture 118 of the first and second blades 107 and 108 and the channel 139. The first slider 120 at its peg 131 receives thereon the first blade 107 via its aperture 118, while the first slider 120 aligns with the spacer 122 at its first side 134 such that its pin 130 inserts into the opening 138 at the first side 134 of the spacer 122 and the peg 131 with the first blade 107 thereon inserts into the channel 139 at the first side 134 of the spacer 122. Likewise, the second slider 121 at its peg 131 receives thereon the second blade 108 via its aperture 118, while the second slider 121 aligns with the spacer 122 at its second side 135 such that its pin 130 inserts into the opening 138 at the second side 135 of the spacer 122 and the peg 131 with the second blade 108 thereon inserts into the channel 139 at the second side 135 of the spacer 122. The securing of the first slider 120 at the first side 134 of the spacer 122 along with the first blade 107 in combination with the securing of the second slider 121 at the second side 135 of the spacer 122 along with the second blade 108 constructs the implant grip 104. The spacer 122 in the second embodiment is dimensioned whereby the spacer 122 locates the first and second blades 107 and 108 such that the passage 110 therebetween receives therein the bridge 8 of the implant 5.

The body 103 as illustrated in FIGS. 12A-12B includes a first end 145 defining a handle 146 that facilitates grasping of the implant insertion device 100 during its use in implanting the implant 5 into bone, bones, or bone pieces requiring fixation. The body 103 includes a second end 147 defining a tamp 148 configured to engage the bridge 8 when the implant 5 resides in its insertion shape 7 or 53. The body 103 includes a first surface 149 and a second surface 150, which, in the second embodiment, are symmetrical and identical in shape. The body 103 defines a slot 151 therethrough communicating exterior to the body 103 that receives the implant grip 104 such that the implant grip 104 secures with the body 103 and is movable between its disengaged position 105 and its engaged position 106. The slot 151 within the body 103 at an upper end 152 terminates in a first stop 153 and at a lower end 154 terminates in a second stop 155. The slot 151 in the second embodiment is sized and shaped to receive therein the spacer 122 of the actuator 109 whereby the spacer 122 in combination with the first and second sliders 120 and 121 of the actuator 109 and the first and second blades 107 and 108 couple with the body 103 to form the actuator 109 and the implant grip 104. The body 103 in the second embodiment may be a single piece or two symmetrical halves secured together using any suitable means such as an adhesive.

The slot 151 of the body 103 receives the implant grip 104 and secures the implant grip 104 with the body 103 as follows. The spacer 122 of the actuator 109 inserts into the slot 151 with the spacer 122 oriented whereby its first side 134 and the opening 138 and the channel 139 communicate exterior to the slot 151 at the first surface 149 of the body 103 and its second side 135 and the opening 138 and the channel 139 communicate exterior to the slot 151 at the second surface 150 of the body 103. The first slider 120 at its peg 131 receives thereon the first blade 107 via its aperture 118 followed by placement of the first slider 120 adjacent the first surface 149 of the body 103 over the slot 151 such that its pin 130 inserts into the opening 138 at the first side 134 of the spacer 122 and the peg 131 with the first blade 107 thereon inserts into the channel 139 at the first side 134 of the spacer 122. Likewise, the second slider 121 at its peg 131 receives thereon the second blade 108 via its aperture 118 followed by placement of the second slider 121 adjacent the second surface 150 of the body 103 over the slot 151 such that its pin 130 inserts into the opening 138 at the second side 135 of the spacer 122 and the peg 131 with the second blade 108 thereon inserts into the channel 139 at the second side 135 of the spacer 122. The first and second sliders 120 and 121 at their pins 130 and pegs 131 accordingly frictionally engage the spacer 122 thereby forming the actuator 109 and coupling the actuator with the body 103 while also locating the first blade 107 at the first surface 149 of the body 103 and the second blade 108 at the second surface 150 of the body 103 to form the implant grip 104; although an adhesive if desired may be introduced to aid in the securing of the first slider 120 with the second slider 121.

With the first and second sliders 120 and 121 coupled together over the spacer 122 to form the actuator 109, the actuator 109 frictionally engages the body 103 in order to introduce a resistance to the movement of the actuator 109 along the body 103 such that a force must be applied to the actuator 109 when moving the implant grip 104 between its disengaged position 105 and its engaged position 106. In particular, the rear surfaces 129 of the first and second sliders 120 and 121 adjacent the pins 130 form a clasp 156 including a clasp surface 157 whereby the clasp 156 frictionally engages the body 103 in that the clasp surface 157 of the first slider 120 contacts the first surface 149 of the body 103 located about the slot 151 and the clasp surface 157 of the second slider 121 contacts the second surface 150 of the body 103 located about the slot 151. The first and second surfaces 149 and 150 of the body 103 in the second embodiment may define a clasp receiver 158 configured specifically for frictional contact respectively with the clasp surface 157 of the clasp 156 defined by the first and second sliders 120 and 121.

The coupling of the implant grip 104 with the first end 132 of the spacer 122 for the actuator 109 located adjacent the first stop 153 of the slot 151 produces the implant grip 104 configured in its disengaged position 105 as illustrated in FIGS. 10A-10D. Furthermore, the frictional engagement of the clasp 156 for the actuator 109 with the body 103 prevents involuntary movement of the implant grip 104 from its disengaged position 105 such that the first and second blades 107 and 108 remain positioned at the second end 147 of the body 103 adjacent the tamp 148 and thus retracted relative to the body 103. An application of a force to the actuator 109 (e.g., pushing on the actuator 109) progresses the implant grip 104 from its disengaged position 105 to its engaged position 106 as illustrated in FIGS. 11A-11D. More particularly, the actuator 109 moves along the body 103 towards the second stop 155 of the body 103 until the spacer 122 of the actuator 109 at its second end 133 contacts the second stop 155 such that the actuator 109 via its connection with the first and second blades 107 and 108 advances the first and second blades 107 and 108 exterior to the body 103. In the second embodiment, the second stop 155 and the tamp 148 define a rectangular shape similar to the bridge 8 of the implant 5 but are dimensioned smaller than the passage 110 between the first and second blades 107 and 108 in order to allow the first and second blades 107 and 108 to by-pass the second stop 155 and the tamp 148 and extend exterior relative to the body 103. An application of a force to the actuator 109 (e.g., pulling on the actuator 109) or to first and second blades 107 and 108 at their leading edges 117 progresses the implant grip 104 from its engaged position 106 to its disengaged position 105. More particularly, the actuator 109 moves along the body 103 away from the second stop 155 and towards 103 the first stop 153 until the spacer 122 of the actuator 109 at its first end 132 contacts the first stop 153 such that the actuator 109 retracts the first and second blades 107 and 108 to a position at the second end 147 of the body 103 adjacent the tamp 148. When moving the implant grip 104 between its disengaged position 105 and its engaged position 106, one of ordinary skill in the art will recognize that the actuator 109 due to its frictional engagement with the body 103 may be released at any point between the first stop 153 and the second stop 155 such that the first and second blades 107 and 108 extend from the body 103 at any location between the disengaged position 105 and the engaged position 106.

When receiving the implant 5 in an orthopedic fixation system, the implant insertion device 100 as illustrated in FIGS. 10A-10D begins in its unloaded position 101 wherein the implant grip 104 resides in its disengaged position 105. The implant 5 is mechanically deformed from its natural shape 6 to its insertion shape 7 as illustrated in FIGS. 2A-2E or its insertion shape 53 as illustrated in FIG. 2F such that the implant 5 stores mechanical energy. Mechanical deformation of the implant 5 may include cooling of the implant 5 such that the implant 5 transitions from its austenite phase to its martensite phase prior to loading of the implant 5 on the implant insertion device 100. After deformation of the implant 5, the implant insertion device 100 is positioned adjacent the deformed implant 5 whereby the tamp 148 of the body 103 contacts the bridge 8.

Once the body 103 of the implant insertion device 100 aligns with the bridge 8 of the implant 5, a force applied to the implant grip 104 moves the implant grip 104 relative to the body 103 from its disengaged position 105 to its engaged position 106 resulting in the implant insertion device 100 as illustrated in FIGS. 11A-11D transitioning from its unloaded position 101 to its loaded position 102 whereby the implant insertion device 100 retains the implant 5 in its insertion shape 7 or 53. The implant grip 104 extends from the body 103 whereby the passage 110 between the first and second blades 107 and 108 permits the first and second blades 107 and 108 at their leading edges 117 to by-pass and then extend beyond the bridge 8 such that the first and second blades 107 and 108 respectively engage the legs 23-26 at their engagement points 35, 40, 44, and 50. More particularly, a force applied to the actuator 109 progresses the actuator 109 along the body 103 towards the second stop 155 of the body 103 until the spacer 122 of the actuator 109 at its second end 133 contacts the second stop 155 whereby the actuator 109 extends the first and second blades 107 and 108 exterior to the body 103 such that the first and second blades 107 and 108 at their first and second sides 115 and 116 respectively abut the engagement points 35, 40, 44, and 50 of the legs 23-26, thereby constraining the implant 5 in its insertion shape 7 or 53. In the second embodiment, the first and second blades 107 and 108 at their first faces 111 defining the passage 110 may be spaced apart a distance that allows the first and second blades 107 and 108 at their first faces 111 to frictionally engage the bridge 8 at its first and second sides 11 and 12.

While the implant 5 may be mechanically deformed from its natural shape 6 to its insertion shape 7 or 53 prior to its loading on the implant insertion device 100, the implant insertion device 100 may be employed during its loading with the implant 5 to mechanically deform the implant 5 from its natural shape 6 to its insertion shape 7 or 53. The implant insertion device 100 is positioned adjacent the implant 5 in its natural shape 6 whereby the tamp 148 of the body 103 contacts the bridge 8. Once the body 103 of the implant insertion device 100 aligns with the bridge 8 of the implant 5, a force applied to the implant grip 104 moves the implant grip 104 relative to the body 103. As a result, the implant grip 104 extends from the body 103 such that the passage 110 between the first and second blades 107 and 108 receives the bridge 8 therein while the first and second blades 107 and 108 at their leading edges 117 by-pass and then extend beyond the bridge 8 to respectively engage the legs 23-26 at their engagement points 35, 40, 44, and 50. More particularly, a force applied to the actuator 109 progresses the actuator 109 along the body 103 towards the second stop 155 of the body 103 until the spacer 122 of the actuator 109 at its second end 133 contacts the second stop 155 whereby the actuator 109 extends the first and second blades 107 and 108 exterior to the body 103 such that the first and second blades 107 and 108 at their first and second sides 115 and 116 respectively abut the engagement points 35, 40, 44, and 50 of the legs 23-26. Moreover, due to the force imparted to the first and second blades 107 and 108 via the actuator 109, the first and second blades 107 and 108 via their abutment with the engagement points 35, 40, 44, and 50 of the legs 23-26 deform the implant 5, thereby transitioning the implant 5 from its natural shape 6 to its insertion shape 7 or 53 and constraining the implant 5 as illustrated in FIGS. 11A-11D.

When delivering the implant 5 to bone, bones, or bone pieces, the implant insertion device 100 as illustrated in FIGS. 11A-11D begins in its loaded position 102 wherein the implant grip 104 in its engaged position 106 constrains the implant 5 in its insertion shape 7 or 53. In order to release the implant 5 from the implant insertion device 100, a force applied to the implant grip 104 either at the leading edges 117 of the first and second blades 107 and 108 or the actuator 109 progresses the implant grip 104 from its engaged position 106 to its disengaged position 105. The implant grip 104 disengages from the implant 5 and retracts relative to the body 103 such that the implant grip 104 releases the legs 23-26 at their engagement points 35, 40, 44, and 50 and also the bridge 8 if engaged therewith resulting in an attempted transition of the implant 5 from its insertion shape 7 or 53 to its natural shape 6 whereby the implant 5 delivers the energy stored therein to the bone, bones, or bone pieces. More particularly, progression of the actuator 109 along the body 103 to the first stop 154 thereof moves the first and second blades 107 and 108 such that the first and second blades 107 and 108 at their first and second sides 115 and 116 respectively release the engagement points 35, 40, 44, and 50 of the legs 23-26 while, if engaged, the first and second blades 107 and 108 at their first faces 111 also release the bridge 8. The first and second blades 107 and 108 retract to a position at the second end 147 of the body 103 adjacent the tamp 148 whereby the released implant 5 delivers the energy stored therein to the bone, bones, or bone pieces.

FIGS. 14A-14E illustrate an orthopedic implant 175 according to a second embodiment in a natural shape 176, whereas FIGS. 15A-15E illustrate the orthopedic implant 175 in an insertion shape 177. The implant 175 in the second embodiment may be manufactured from a shape memory material with superelastic or temperature dependent properties (e.g., Nitinol) such that the implant 175 transitions between its natural shape 176 and its insertion shape 177. The implant 175 when deformed from its natural shape 176 to its insertion shape 177 stores energy deliverable to bone, bones, or bone pieces. In accordance with its manufacture from shape memory material, the implant 175 begins in its natural shape 176, is transitionable to its insertion shape 177, and, once implanted in bone, bones, or bone pieces, attempts to transition from its insertion shape 177 to its natural shape 176 whereby the implant 175 delivers the energy stored therein to the bone, bones, or bone pieces in order to affix the bone, bones, or bone pieces and promote a healing thereof. In the first embodiment, attempted transition of the implant 175 from its insertion shape 177 to its natural shape 176 continuously compresses the bone, bones, or bone pieces to promote fusion thereof.

The implant 175 includes a bridge 178 with upper and lower surfaces 179 and 180, first and second sides 181 and 182, and first and second ends 183 and 184. The implant 175 further includes a transition section 185 at the first end 183 of the bridge 178 and a transition sections 186 at the second end 184 of the bridge 178. The implant 175 in the second embodiment includes an anchoring member in the form of a leg 187 extending from the first end 183 and, in particular, the transition section 185 and an anchoring member in the form of a leg 188 extending from the second end 184 and, in particular, the transition section 186. In the second embodiment, the legs 187-188 are formed integrally with the bridge 8 at a respective first and second end 183-184 and, in particular, at a respective transition section 185-186. Each leg 187-188, which has a respective tip 189-190, may include barbs thereon that improve the pull-out resistance of the implant 175. The implant 175 includes anchoring members in the form of the legs 187-188 in order to facilitate a securing of the implant 175 with bone, bones, or bone pieces whereby the bridge 178 between the legs 187-188 traverses a fixation zone of the bone, bones, or bone pieces such that the implant 175, after its insertion and attempted transition from the insertion shape 177 to the natural shape 176, delivers energy to the bone, bones, or bone pieces at the fixation zone.

The leg 187 in the second embodiment includes a width 191 between sides 192 and 193 such that a first segment 194 of the leg 187 extends exterior to the bridge 178 at its first side 181 and a second segment 195 of the leg 187 extends exterior to the bridge 178 at its second side 182. The first segment 194 provides an engagement point 196 whereby an implant engagement device by-passes the bridge 178 at its first side 181 and abuts the engagement point 196. Likewise, the second segment 195 provides an engagement point 197 whereby an implant engagement device by-passes the bridge 178 at its second side 182 and abuts the engagement point 197. The leg 188 in the second embodiment includes a width 198 between sides 199 and 200 such that a first segment 201 of the leg 188 extends exterior to the bridge 178 at its first side 181 and a second segment 202 of the leg 188 extends exterior to the bridge 178 at its second side 182. The first segment 201 provides an engagement point 203 whereby an implant engagement device by-passes the bridge 178 at its first side 181 and abuts the engagement point 203. Likewise, the second segment 202 provides an engagement point 204 whereby an implant engagement device by-passes the bridge 178 at its second side 182 and abuts the engagement point 204. While the legs 187-188 in the second embodiment respectively include engagement points 196-197 and 203-204, one of ordinary skill in the art will recognize that legs 187-188 respectively may include one engagement point 196 or 197 and 203 or 204 whereby an implant engagement device by-passes the bridge 178 and abuts respectively one the engagement points 196 or 197 and 203 or 204.

The regular inherent shape of the implant 175, as illustrated in FIGS. 14A-14E, is its natural shape 176 where the transition sections 185-186 locate the bridge 178 in a natural form that places the legs 187-188 in a natural position whereby the legs 187-188 are convergent and spaced apart at a first distance. Nevertheless, as illustrated in FIGS. 15A-15E, the implant 175 is deformable under the action of superelasticity or temperature dependent shape memory to an insertion shape 177 where the transition sections 185-186 deform to store energy while also moving the bridge 178 from its natural form to an insertion form that places the legs 187-188 in an insertion position whereby the legs 187-188 are substantially parallel and spaced apart at a second distance that is greater than the first distance. Since the insertion shape 177 is not the regular inherent shape of the implant 175, the bridge 178 typically is mechanically constrained using an implant insertion device whereby the implant insertion device maintains the bridge 178 in its insertion form. In order to facilitate engagement of an implant insertion device with the implant 175, the legs 187-188, respectively, include engagement points 196-197 and 203-204 that receive the implant insertion device. The implant insertion device by-passes the bridge 178 at its first and second sides 181 and 182 and abuts the engagement points 196-197 and 203-204. In particular, the implant insertion device extends beyond the bridge 178 at its first and second sides 181 and 182 and abuts the engagement points 196-197 and 203-204 such that the implant insertion device engages and then holds the legs 187-188, resulting in the implant insertion device constraining the deformed transition sections 185-186 in order to maintain the implant 175 in its insertion shape 177. After implantation into bone, bones, or bone pieces and a release of the implant insertion device, including if necessary a heating of the implant 175, the implant 175 delivers the energy stored in the transition sections 185-186 whereby the bridge 178 attempts to transition from its insertion form to its natural form, which causes an attempt of the legs 187-188 to move from their insertion position to their natural position such that the implant 175 affixes the bone, bones, or bone pieces through an application of a compressive force thereto.

Figure 15A:
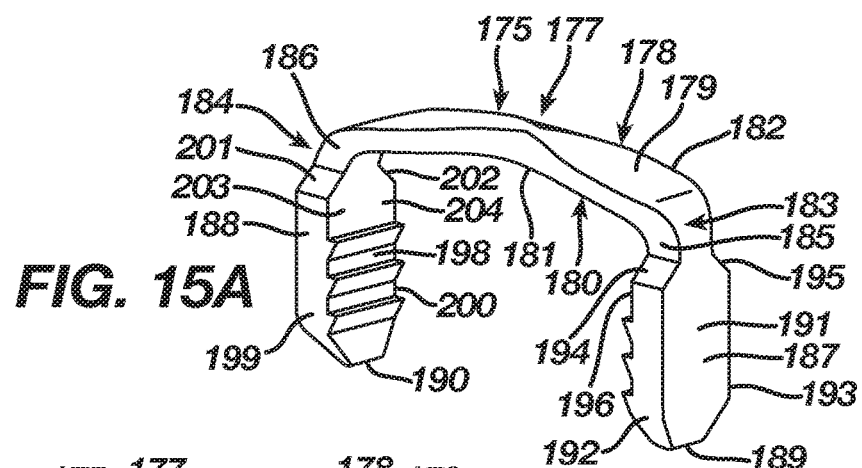
FIG. 15A is an isometric view illustrating the shape memory implant according to the second embodiment in an insertion shape.
Figure 15B:
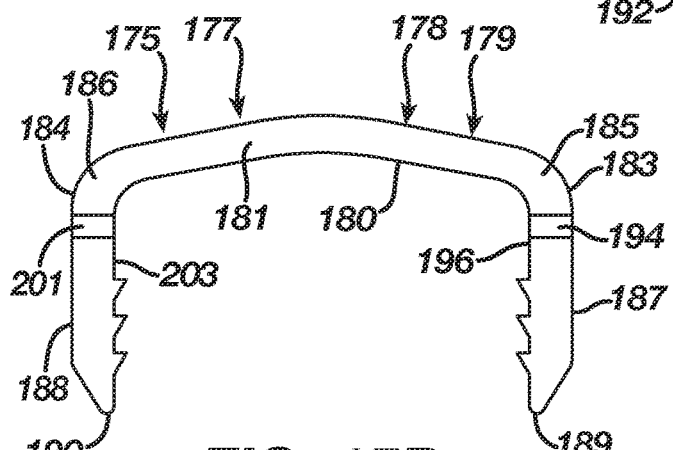
FIG. 15B is a side view thereof.
Figure 15C:
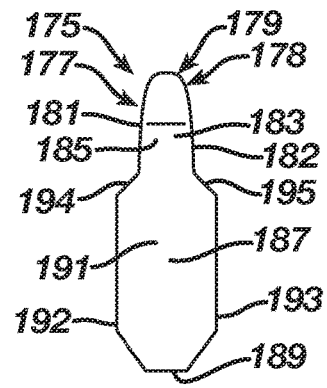
FIG. 15C is an end view thereof.
Figure 15D:
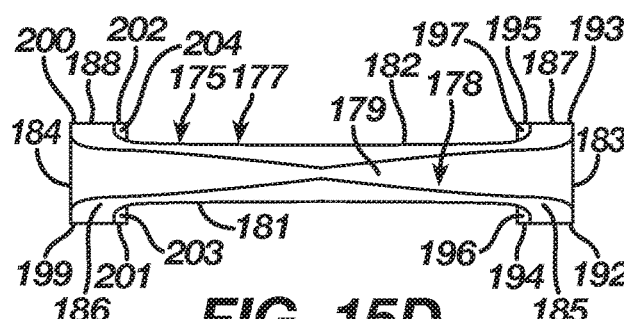
FIG. 15D is a top view thereof.
Figure 15E:
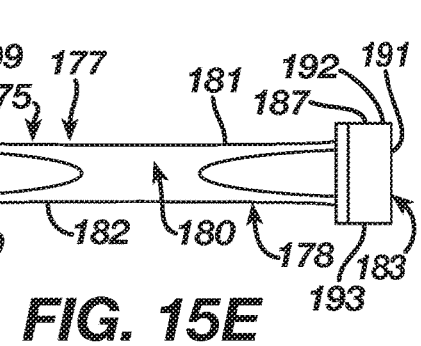
FIG. 15E is a bottom view thereof.
Figure 15F:
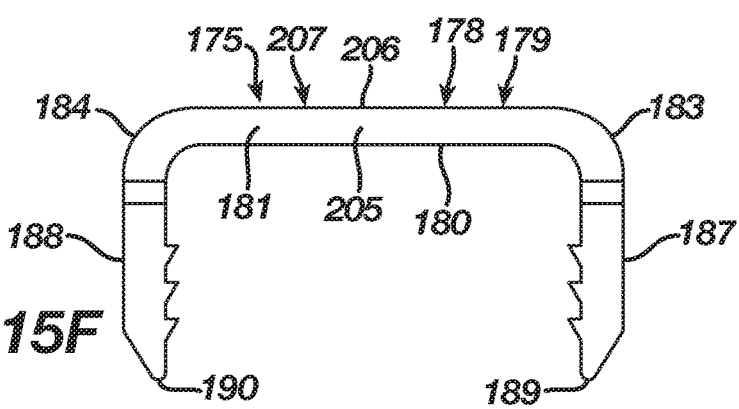
FIG. 15F is a side view illustrating an alternative insertion shape for the shape memory implant according to the second embodiment.
Figure 16A:
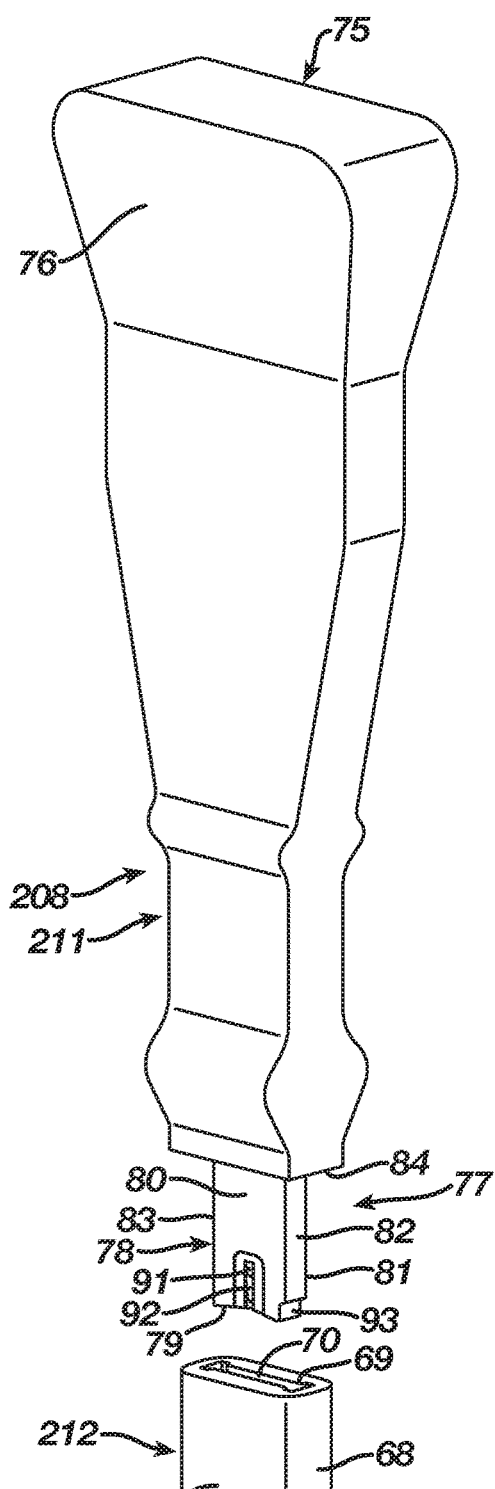
FIG. 16A is an exploded isometric view illustrating an implant insertion device according to a third embodiment and a shape memory implant according to the second embodiment in its natural shape.
Figure 16B:
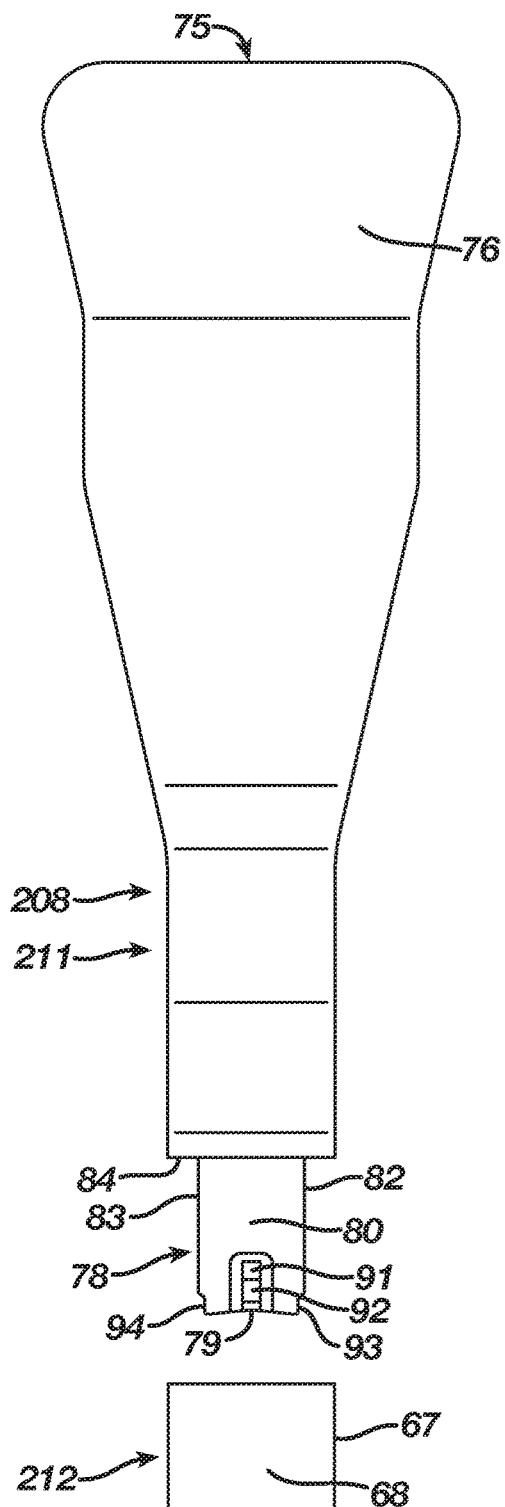
FIG. 16B is an exploded front view illustrating the implant insertion device and the shape memory implant.
Figure 17A:
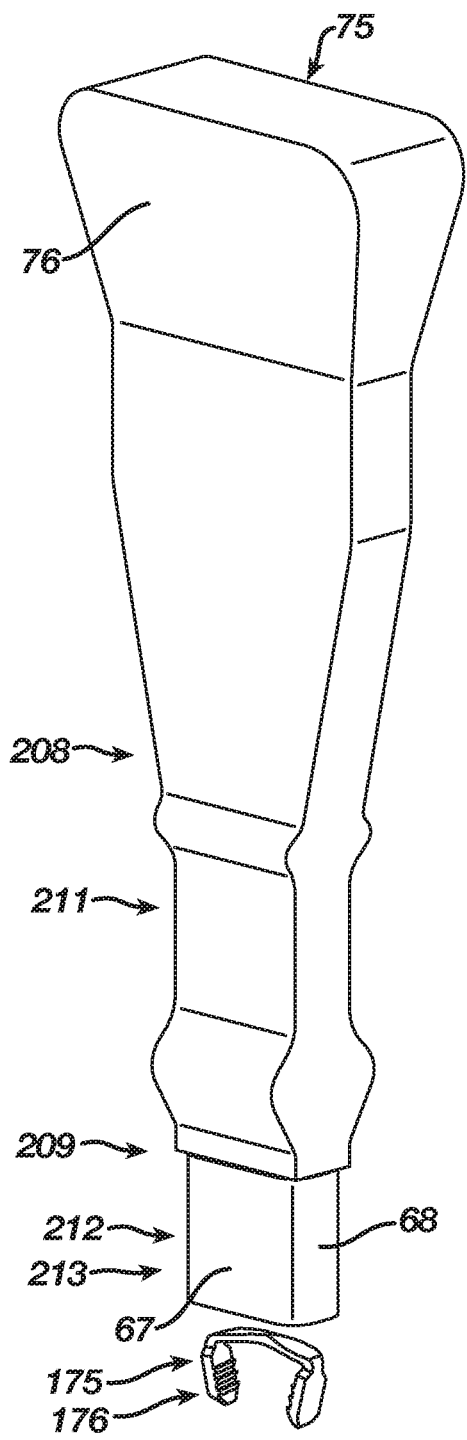
FIG. 17A is an isometric view illustrating the implant insertion device according to the third embodiment in an unloaded position and the shape memory implant according to the second embodiment in its natural shape.
Figure 17B:
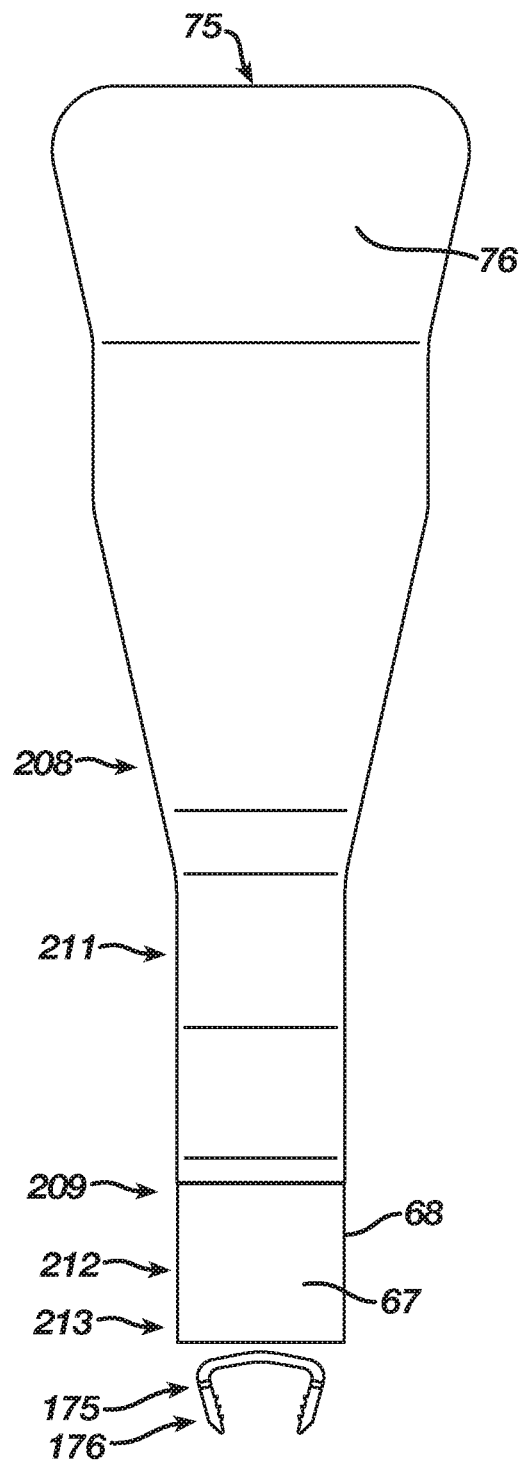
FIG. 17B is a front view illustrating the implant insertion device in its unloaded position and the shape memory implant.
Figure 18A:
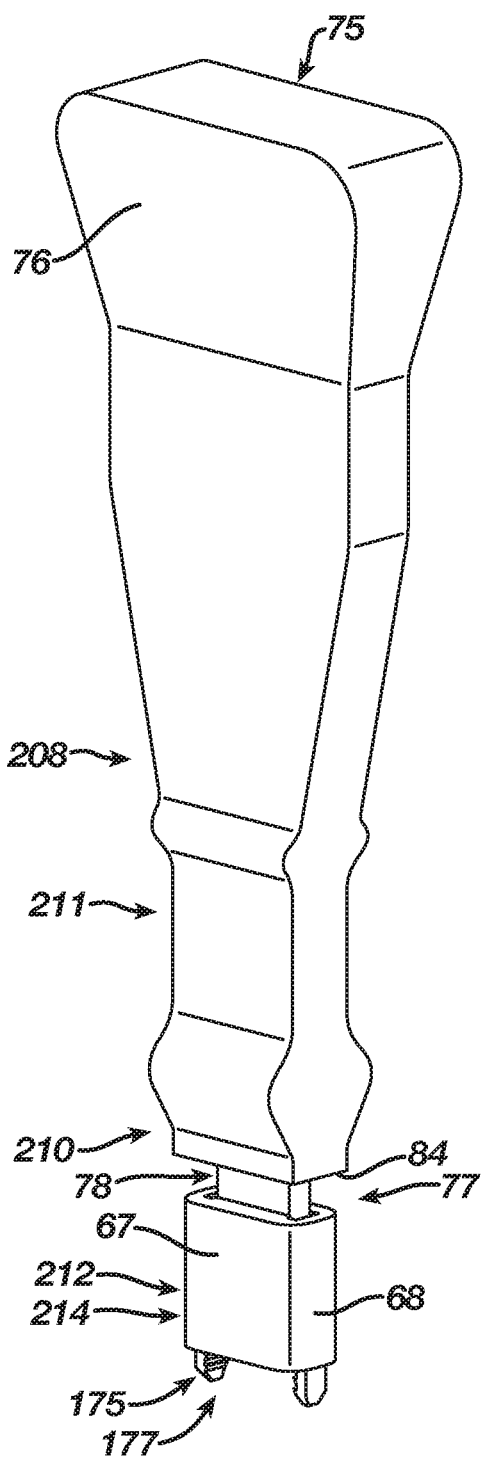
FIG. 18A is an isometric view illustrating the implant insertion device according to the third embodiment in a loaded position that constrains the shape memory implant according to the second embodiment in its insertion shape.
Figure 18B:
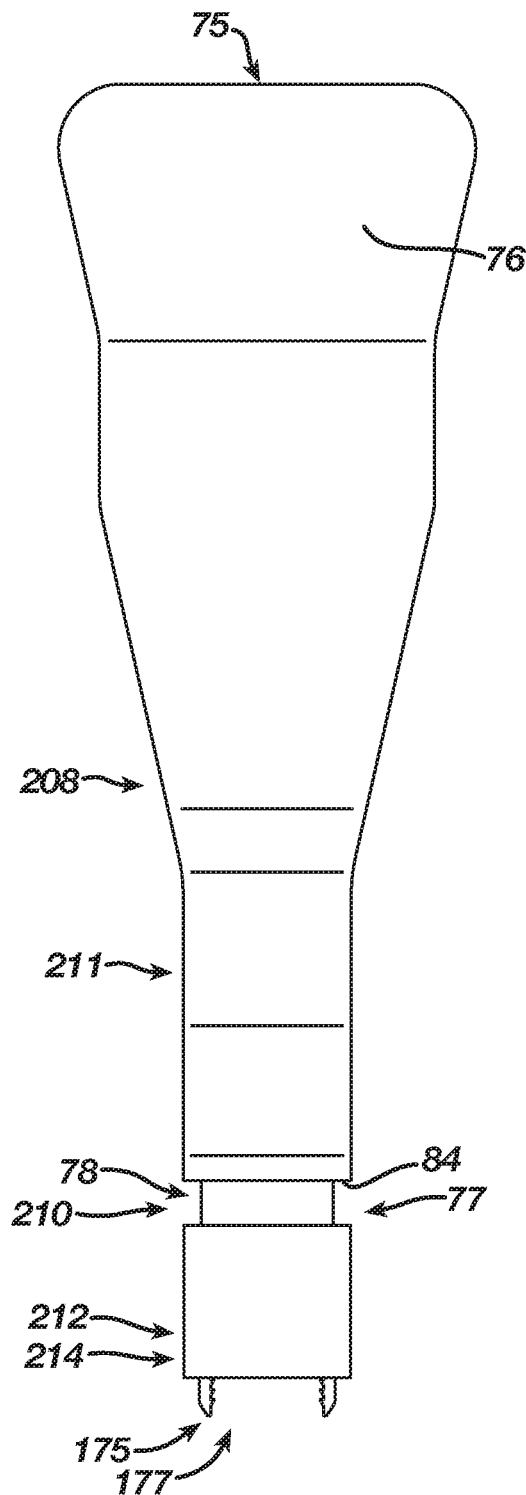
FIG. 18B is a front view illustrating the implant insertion device in its loaded position that constrains the shape memory implant in its insertion shape.
Figure 19A:
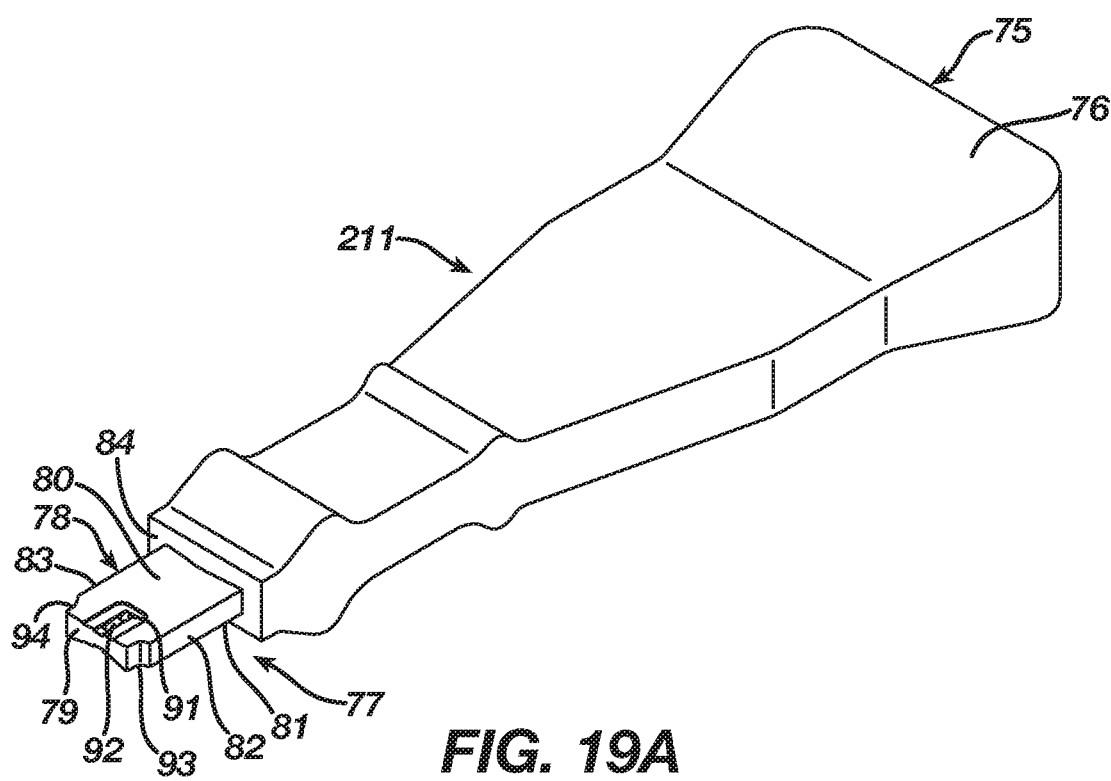
FIGS. 19A-19B are isometric views illustrating a body of the implant insertion device according to the third embodiment.
Figure 19B:
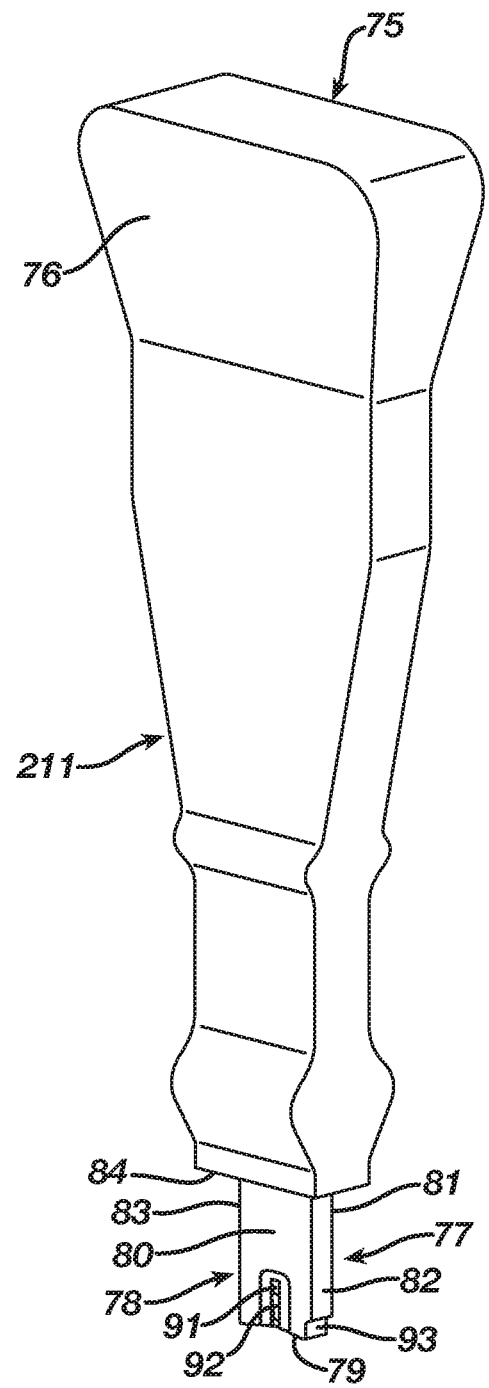
Figure 19C:
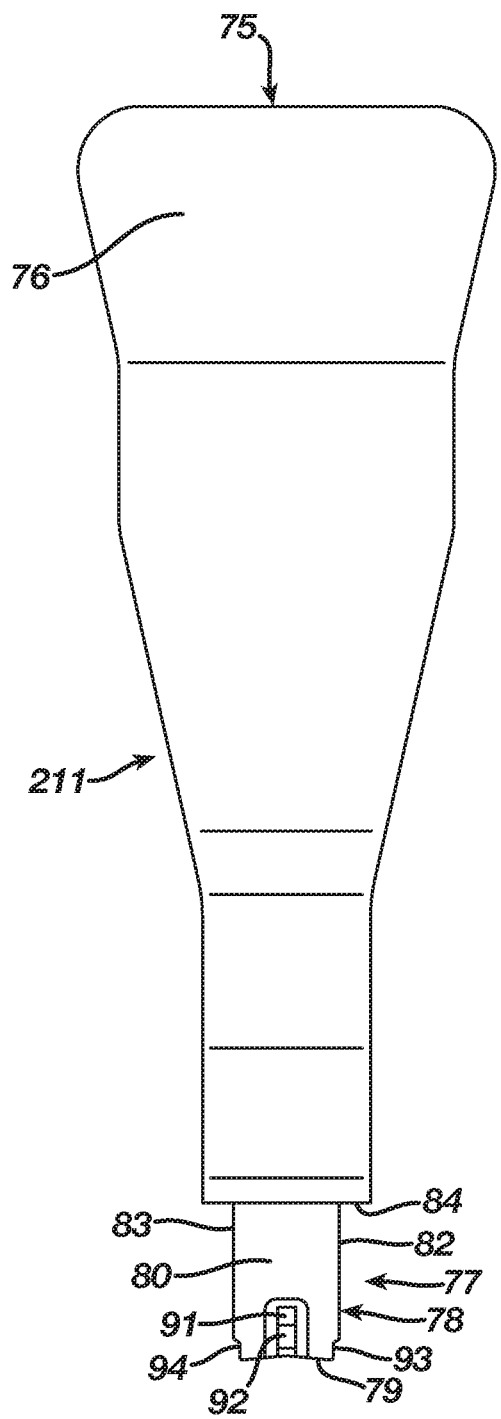
FIG. 19C is a front view illustrating the body of the implant insertion device.
Figure 19D:
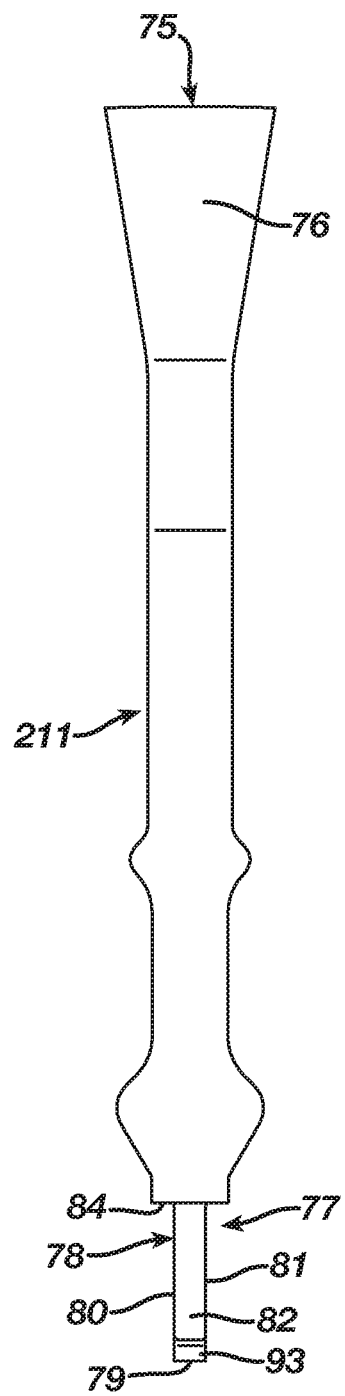
FIG. 19D is an end view illustrating the body of the implant insertion device.
Figure 20A:
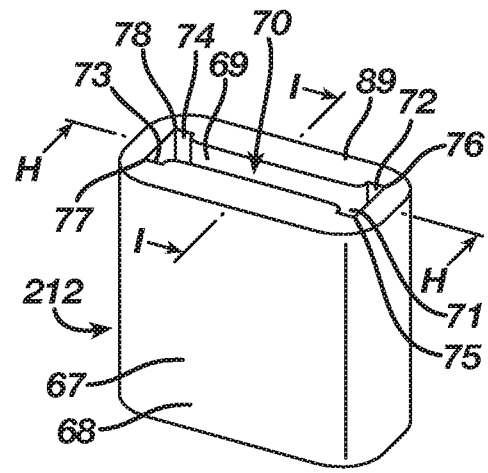
FIG. 20A is an isometric view illustrating an implant grip of the implant insertion device according to the third embodiment.
Figure 20B:
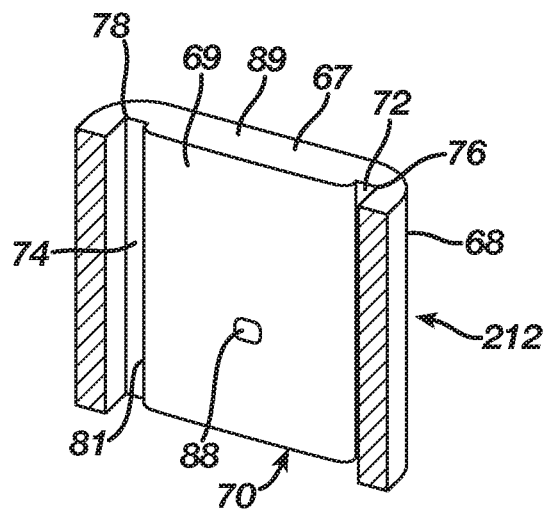
FIG. 20B is an isometric view in cross-section taken along lines H-H of FIG. 20A illustrating the implant grip of the implant insertion device.
Figure 20C:
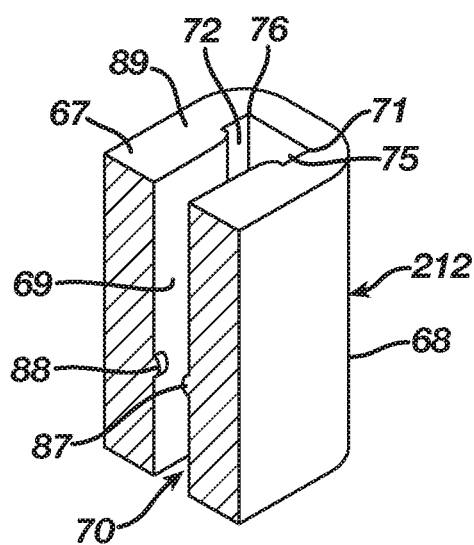
FIG. 20C is a top isometric view in cross-section taken along lines I-I of FIG. 20A illustrating the implant grip of the implant insertion device.
Figure 20D:
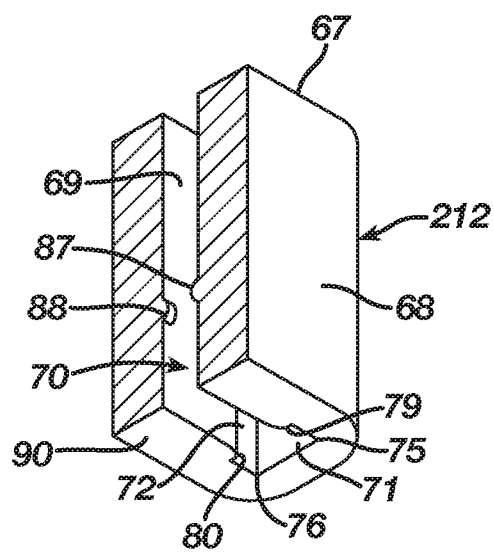
FIG. 20D is a bottom isometric view in cross-section taken along lines I-I of FIG. 20A illustrating the implant grip of the implant insertion device.
Figure 21A:
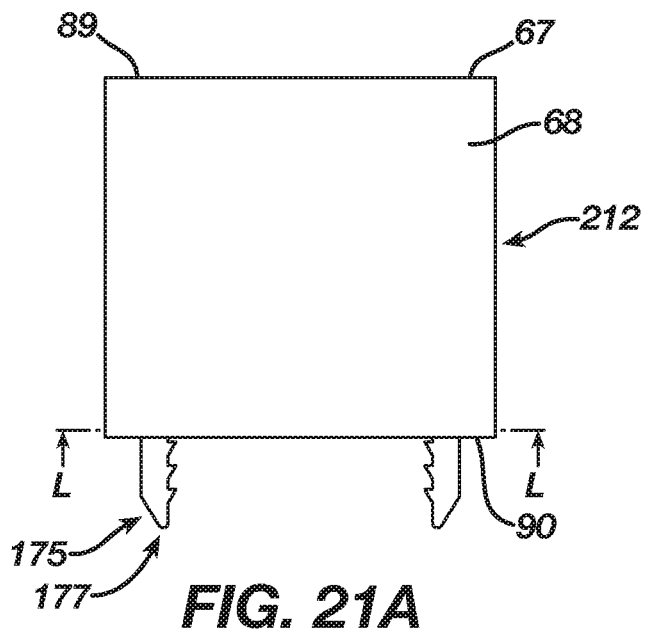
FIG. 21A is front view illustrating the implant grip of the implant insertion device according to the third embodiment constraining the shape memory implant in its insertion shape.
Figure 21B:
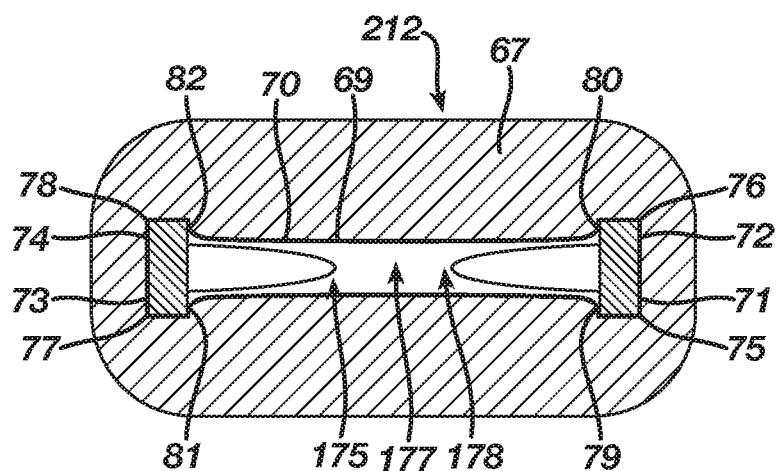
FIG. 21B is a bottom view in cross-section taken along lines L-L of FIG. 21A illustrating the implant grip of the implant insertion device constraining the shape memory implant in its insertion shape.
Figure 22A:
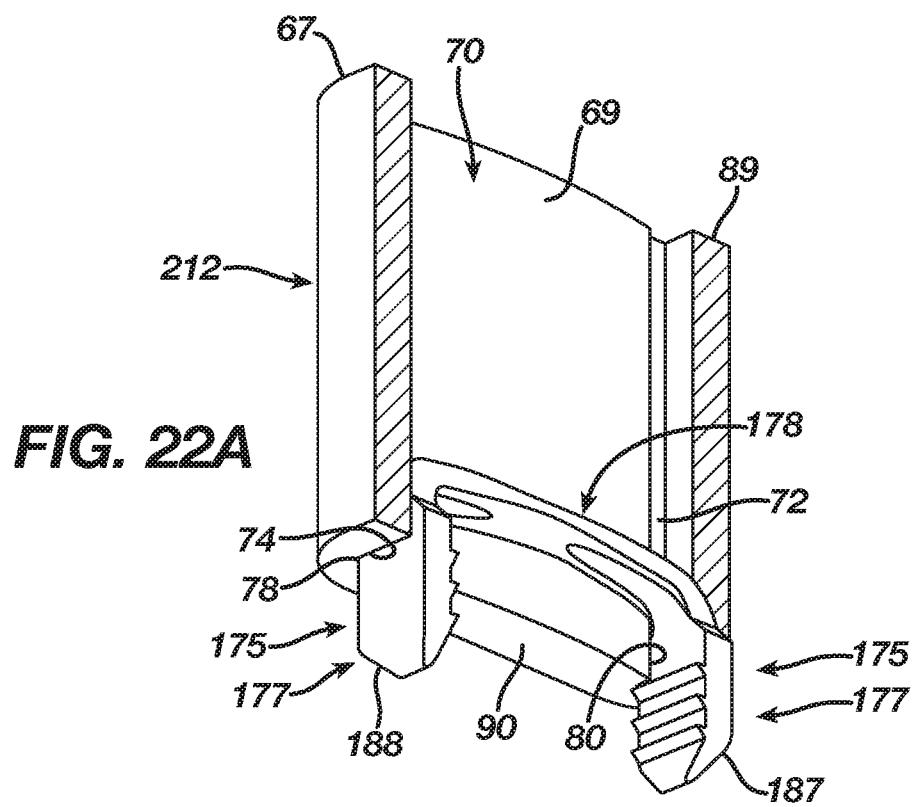
FIGS. 22A-22B are isometric views in cross-section illustrating the implant grip of the implant insertion device constraining the shape memory implant in its insertion shape.
Figure 22B:
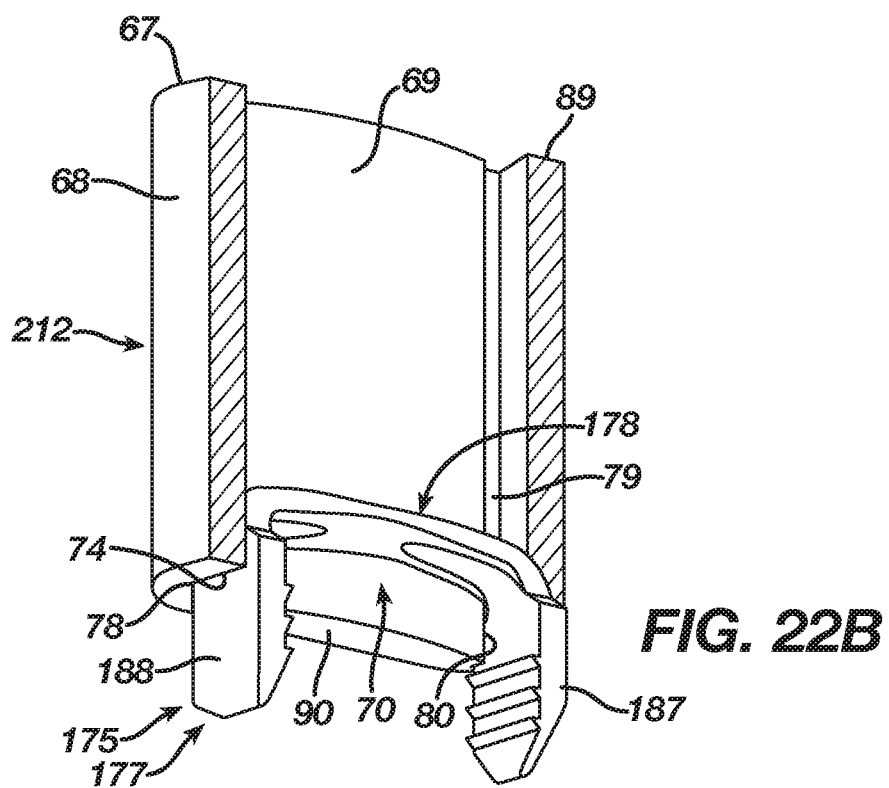
Figure 23A:
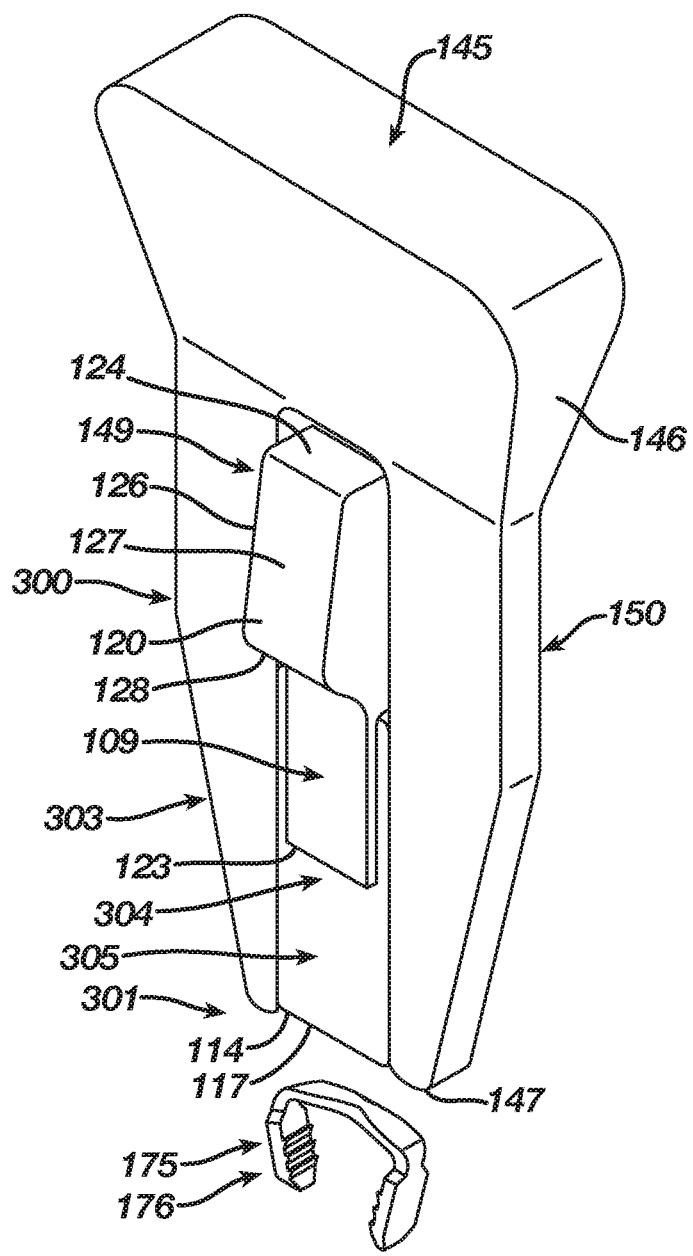
FIG. 23A is an isometric view illustrating an implant insertion device according to a fourth embodiment in an unloaded position and a shape memory implant according to the second embodiment in its natural shape.
Figure 23B:
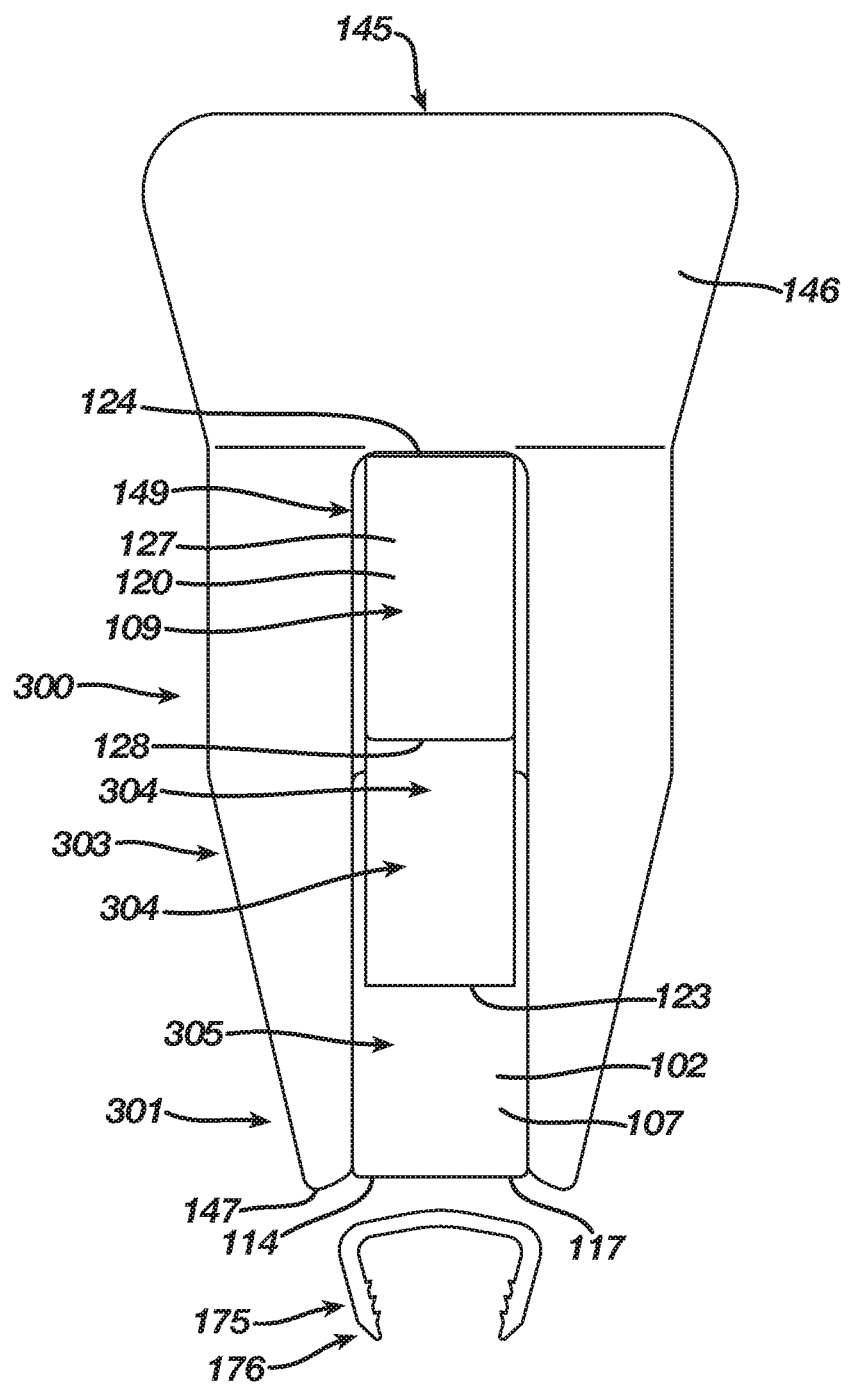
FIG. 23B is a front view illustrating the implant insertion device in its unloaded position and the shape memory implant.
Figure 23C:
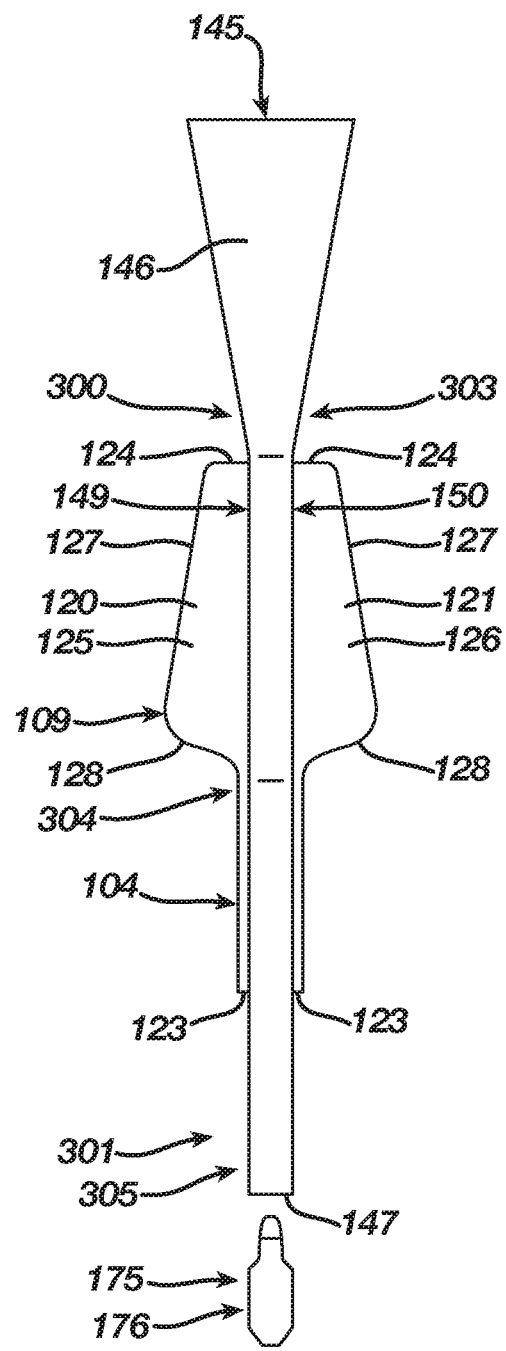
FIG. 23C is an end view illustrating the implant insertion device in its unloaded position and the shape memory implant.
Figure 23D:
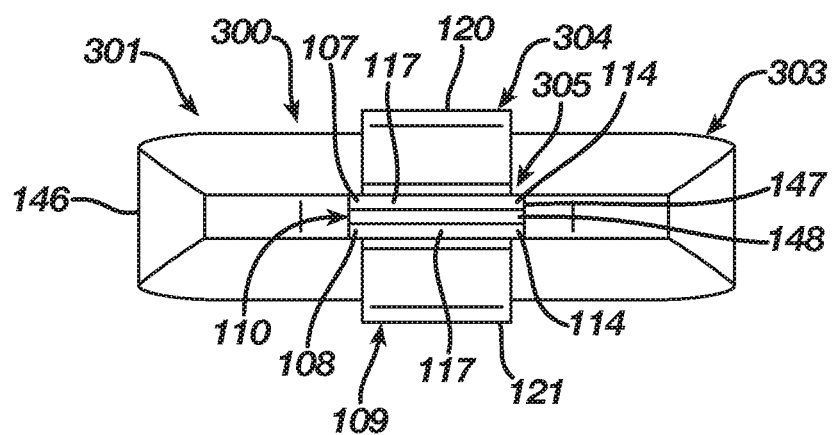
FIG. 23D is a bottom view illustrating the implant insertion device in its unloaded position.
Figure 24A:
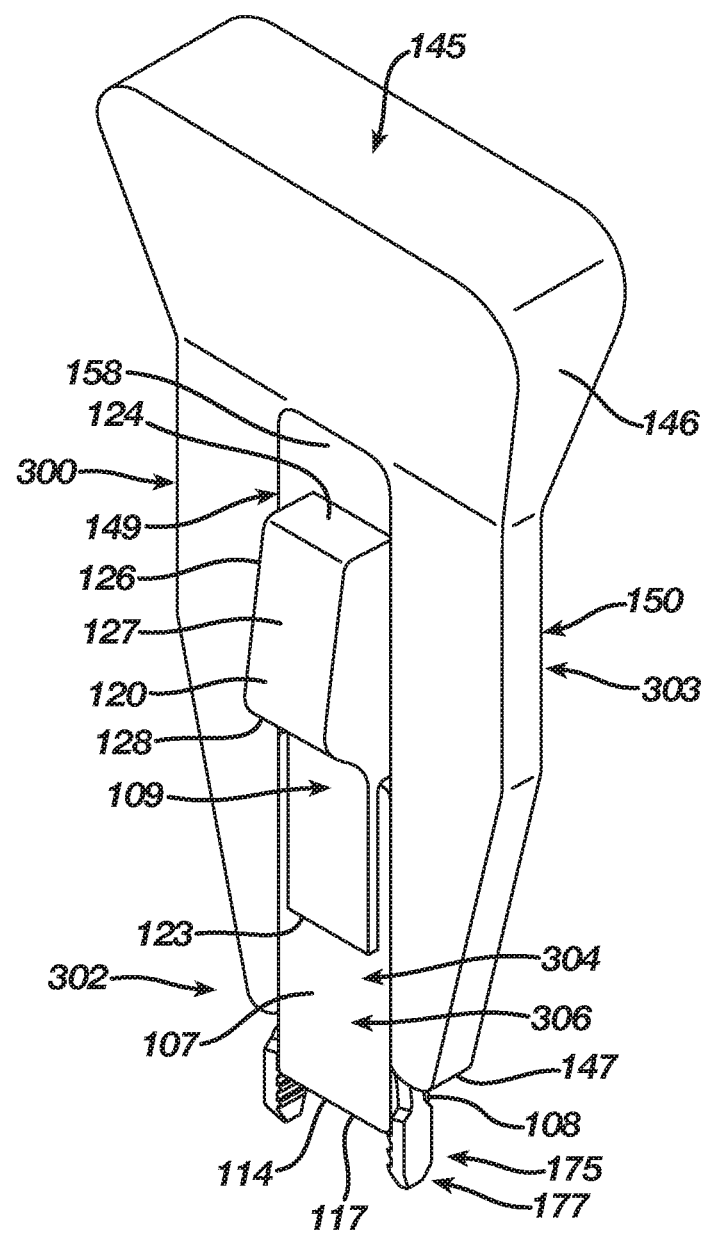
FIG. 24A is an isometric view illustrating the implant insertion device according to the fourth embodiment in a loaded position that constrains the shape memory implant according to the second embodiment in its insertion shape.
Figure 24B:
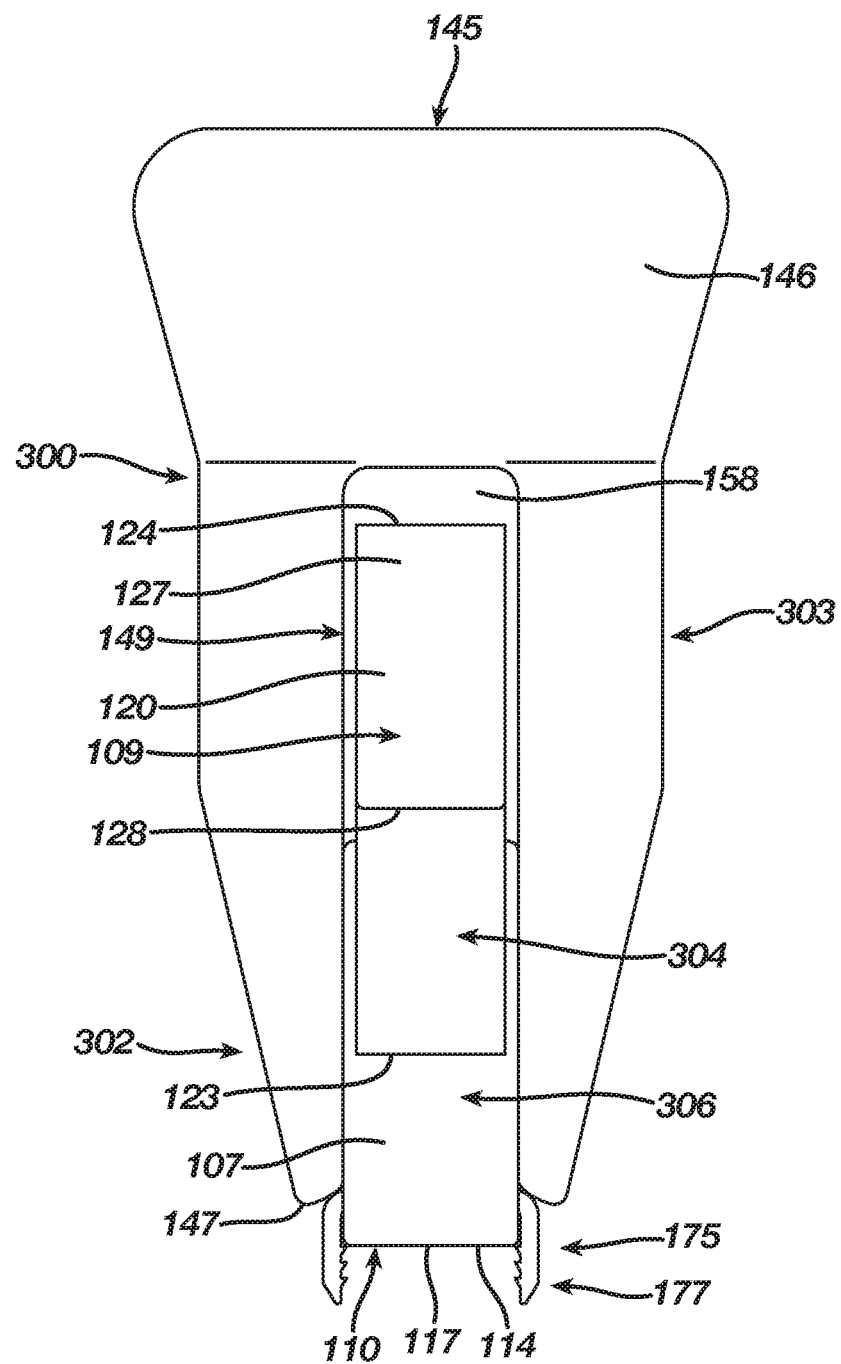
FIG. 24B is a front view illustrating the implant insertion device in its loaded position that constrains the shape memory implant in its insertion shape.
Figure 24C:
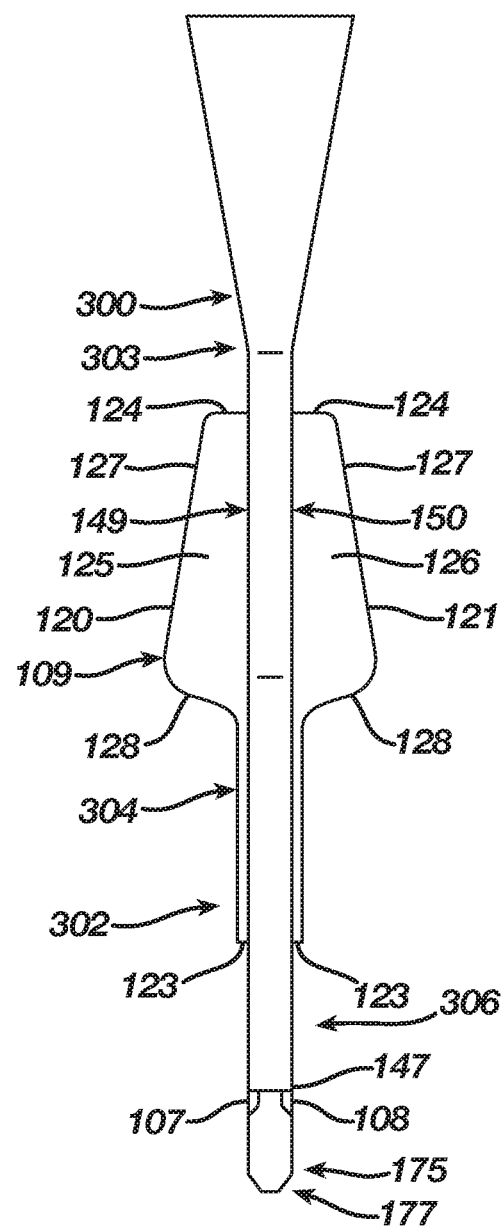
FIG. 24C is an end view illustrating the implant insertion device in its loaded position that constrains the shape memory implant in its insertion shape.
Figure 24D:
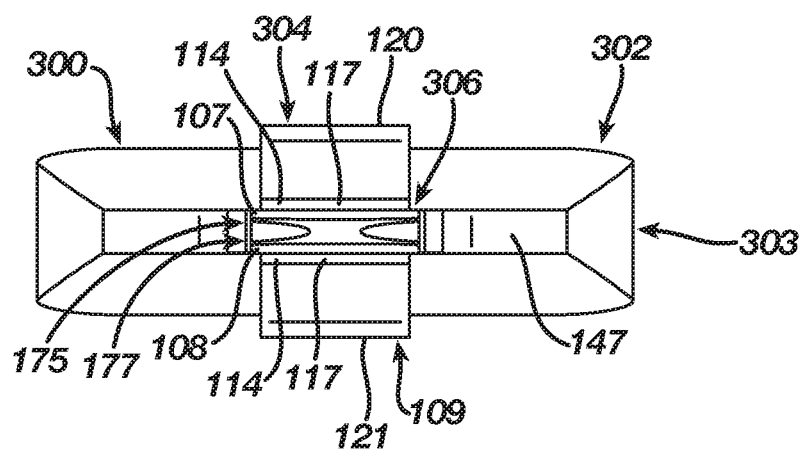
FIG. 24D is a bottom view illustrating the implant insertion device in its loaded position that constrains the shape memory implant in its insertion shape.

Although the bridge 178 of the implant 175 according to the second embodiment includes the transition sections 185-186, the bridge 178, alternatively, may include a transition section 205 located at a center section 206 of the implant 175 and thus the bridge 178. The regular inherent shape of the implant 175, as illustrated in FIGS. 14A-14E, is its natural shape 6 where the transition section 205 locates the bridge 178 in a natural form consisting of a closed or angular profile whereby the first and second ends 183 and 184 reside at a first distance and the legs 187-188 reside in a natural position whereby the legs 187-188 are convergent and spaced apart at a first distance. Nevertheless, as illustrated in FIG. 15F, the implant 175 is deformable under the action of superelasticity or temperature dependent shape memory to an insertion shape 207 where the transition section 205 deforms to store energy while also moving the bridge 178 from its natural form to an insertion form which is an open or substantially linear profile whereby the first and second ends 183 and 184 reside at a second distance that is greater than the first distance and the legs 187-188 reside in an insertion position whereby the legs 187-188 are substantially parallel and spaced apart at a second distance that is greater than the first distance. Since the insertion shape 207 is not the regular inherent shape of the implant 175, the bridge 178 typically is mechanically constrained using an implant insertion device whereby the implant insertion device maintains the bridge 178 in its insertion form. In order to facilitate engagement of an implant insertion device with the implant 175, the legs 187-188, respectively, include the engagement points 196-197 and 203-204 that receive the implant insertion device. The implant insertion device bypasses the bridge 178 at its first and second sides 181 and 182 and abuts the engagement points 196-197 and 203-204. In particular, the implant insertion device extends beyond the bridge 178 at its first and second sides 181 and 182 and abuts the engagement points 196-197 and 203-204 such that the implant insertion device engages and then holds the legs 187-188, resulting in the implant insertion device constraining the deformed transition section 205 in order to maintain the implant 175 in its insertion shape 177. After implantation into bone, bones, or bone pieces and a release of the implant insertion device, including if necessary a heating of the implant 175, the implant 175 delivers the energy stored in the transition section 205 whereby the bridge 178 attempts to transition from its insertion form to its natural form, which causes an attempt of the legs 187-188 to move from their insertion position to their natural position such that the implant 175 affixes the bone, bones, or bone pieces through an application of a compressive force thereto.

While the second embodiment of the implant 175 includes either the transition sections 185-186 or the transition section 205 to produce deformation thereof, one of ordinary skill in the art will recognize that the bridge 178 of the implant 175 may include both the transition sections 185-186 and the transition section 205 to produce deformation thereof. Moreover, while the bridge 178 in the second embodiment includes an angular profile in the natural shape of the implant 175, it should be understood by one of ordinary skill in the art that a bridge 178 incorporating the transition sections 185-186 may include a substantially linear profile for the natural shape of the implant 175.

FIGS. 16A-18D illustrate an implant insertion device 208 according to a third embodiment that engages an implant 175 and retains the implant 175 in its insertion shape 177 or 207. FIGS. 17A-17B illustrate the implant insertion device 208 in an unloaded position 209 prior to its loading with the implant 175 or after its delivery of the implant 175 whereby the implant 175 releases from the implant insertion device 208 without obstruction. FIGS. 18A-18D illustrate the implant insertion device 208 in a loaded position 210 whereby the implant insertion device 208 may be loaded with the implant 175 such that the implant insertion device 208 constrains the implant 175 in its insertion shape 177 or 207. The implant insertion device 208 allows a surgeon to manipulate the implant 175 and insert the implant 175 into bone, bones, or bone pieces requiring fixation. FIGS. 19A-19D illustrate a body 211 of the implant insertion device 208, whereas FIGS. 20A-22B illustrates an implant grip 212 of the implant insertion device 208 that is coupled with the body 211 and is movable relative to the body 211 between a disengaged position 213 shown in FIGS. 17A-17B and an engaged position 214 shown in FIGS. 18A-18D.

The implant insertion device 208 according to the third embodiment, including its body 211 and implant grip 212, is substantially similar in design and operation relative to the implant insertion device 60 according to the first embodiment, including its body 63 and implant grip 64, such that, for the sake of brevity, only differences therebetween will be described herein. Moreover, one of ordinary skill in the art will recognize that like parts of the body 211 and the implant grip 212 for the implant insertion device 208 labeled with like numerals of the body 63 and the implant grip 64 for the implant insertion device 60 incorporate a design and function as previously set forth in the detailed description of the implant insertion device 60 according to the first embodiment.

The implant grip 212 as illustrated in FIGS. 20A-22B is substantially similar to the implant grip 64 with the exception of the following. The implant grip 212, which includes the shell 67 with the interior surface 69 defining the passage 70 therethrough, the grooves 71-74, the retention surfaces 79-82, and the detents 87 and 88, interfaces with the implant 175 and the body 211, whereas the implant grip 64 interfaces with the implant 5 and the body 63. In accordance therewith, the interior surface 69 of the shell 67 and thus the passage 70 include a shape complimentary with the implant 175 and, in particular, with the first and second sides 181 and 182 and the first and second ends 183 and 184 of the bridge 178 whereby the shell 67 grips the implant 175 and retains therein the implant 175 in its insertion shape 177 or 207. The grooves 71-72 located respectively at the corners 75-76 of the interior surface 69 respectively receive therein the segments 194-195 of the leg 187 for the implant 175 and frictionally engage the segments 194-195 thereby retaining the implant 175 within the shell 67, while the grooves 73-74 located respectively at the corners 77-78 of the interior surface 69 respectively receive therein the segments 201-202 of the leg 188 for the implant 175 and frictionally engage the segments 201-202 thereby retaining the implant 175 within the shell 67. The retention surfaces 79-80 respectively abut an engagement point 196-197 of the leg 187 for the implant 175 in order to grip and then constrain the leg 187 such that the shell 67 retains the implant 175 in its insertion shape 177 or 207, while the retention surfaces 81-82 respectively abut an engagement point 203-204 of the leg 188 for the implant 175 in order to grip and then constrain the leg 188 such that the shell 67 retains the implant 175 in its insertion shape 177 or 207. The detents 87-88 engage the body 211 to assist in coupling the shell 67 with the body 211 and further to limit the motion of the shell 67 relative to the body 211 as the implant grip 212 moves between its disengaged position 213 and its engaged position 214. The shell 67 for the implant grip 212 at its interior surface 69 does not incorporate the projections 83-86 on the basis the implant 175 includes only two legs 187-188.

The body 211 as illustrated in FIGS. 19A-19D is substantially similar to the body 63 with the exception of the following. The body 211, which includes the first end 75 defining the handle 76 and the second end 77 defining the implant grip receiver 78 with the tamp 79 and a stop 84, interfaces with the implant grip 212 and the implant 175, whereas the body 63 interfaces with the implant grip 64 and the implant 5. In accordance therewith, the implant grip receiver 78 and thus the first and second sides 80 and 81 and the first and second ends 82 and 83 thereof include a shape complimentary with the implant grip 212 and, in particular, with the interior surface 69 of the shell 67 whereby the implant grip receiver 78 receives and then retains the implant grip 212 thereon. The tamp 79 includes a configuration for engagement with the bridge 178 when the implant 175 resides in its insertion shape 177 or its insertion shape 207. The notches 91 and 92 aid in retaining the shell 67 on the implant grip receiver 78 and further locate the implant grip 212 in either its disengaged position 213 or its engaged position 214. In the third embodiment of the implant insertion device 208, the length of the implant grip receiver 78 for the body 211 substantially equals the length of the implant grip 212.

The implant insertion device 208 according to the third embodiment loads with the implant 175, constrains the implant 175 in its insertion position 177 or 207, and transitions from its loaded position 210 to its unloaded position 209 thereby delivering the implant 175 to bone, bones, or bone pieces substantially identical to the implant insertion device 60 according to the first embodiment as previously set forth in the detailed description thereof. During loading of the implant insertion device 208 with the implant 175 and a subsequent retention thereof, the tamp 79 of the implant grip receiver 78 for the body 211 sits atop the bridge 178 of the implant 175, while the grooves 71-74 maintain the implant 175 within the implant grip 212 and the retention surfaces 79-82 in each of the grooves 71-74 defined by the shell 67 constrain the legs 187-188 such that the shell 67 holds the implant 175 in its insertion shape 177 or 207. When delivering the implant 175 to bone, bones, or bone pieces, the retention surfaces 79-82 disposed in each of the grooves 71-74 respectively release an engagement point 196-197 and 203-204 of the legs 187-188, while the grooves 71-74 of the interior surface 69 for the shell 67 respectively disengage from a segment 194-195 and 201-202 of the legs 187-188. Moreover, the interior surface 69 of the shell 67 disengages from the first and second sides 181 and 182 of the bridge 178, whereas the interior surface 69 of the shell 67 further by-passes the bridge 178 of the implant 175 at its first and second sides 181 and 182 and its first and second ends 183 and 184 such that the implant 175 exits the passage 70 of the shell 67, resulting in the discharge of the implant 175 from the implant grip 212 and a subsequent attempted transition of the implant 175 from its insertion shape 177 or 207 to its natural shape 176 whereby the implant 175 delivers the energy stored therein to the bone, bones, or bone pieces.

Figure 25A:
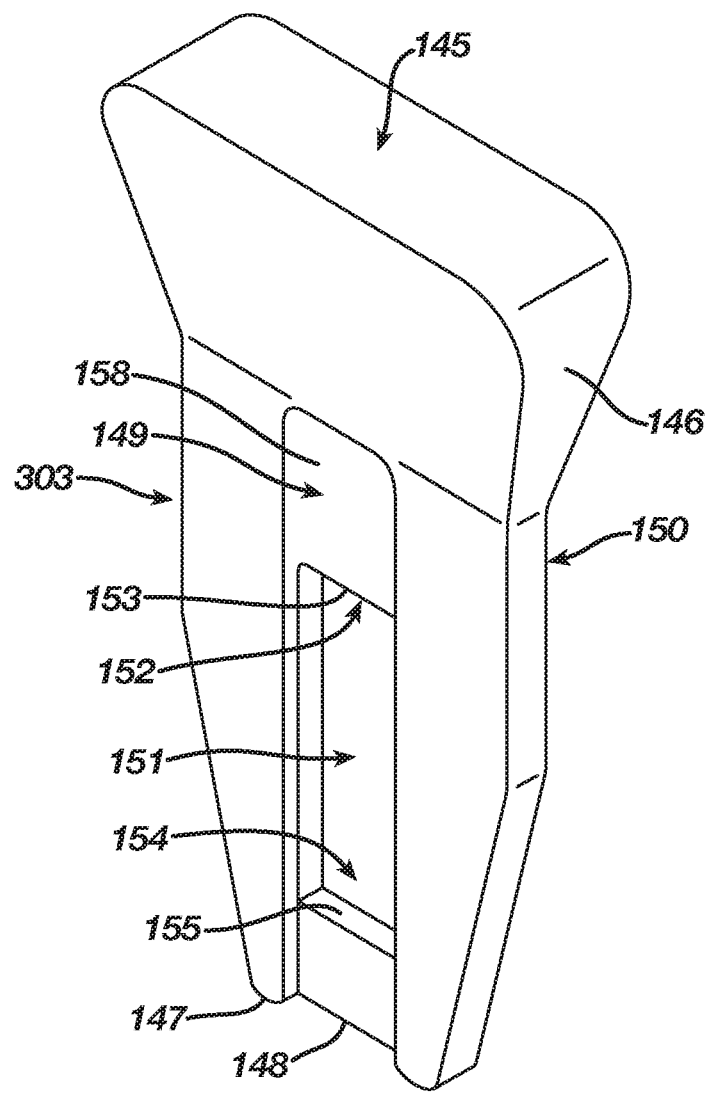
FIG. 25A is an isometric view illustrating a body of the implant insertion device according to the fourth embodiment.
Figure 25B:
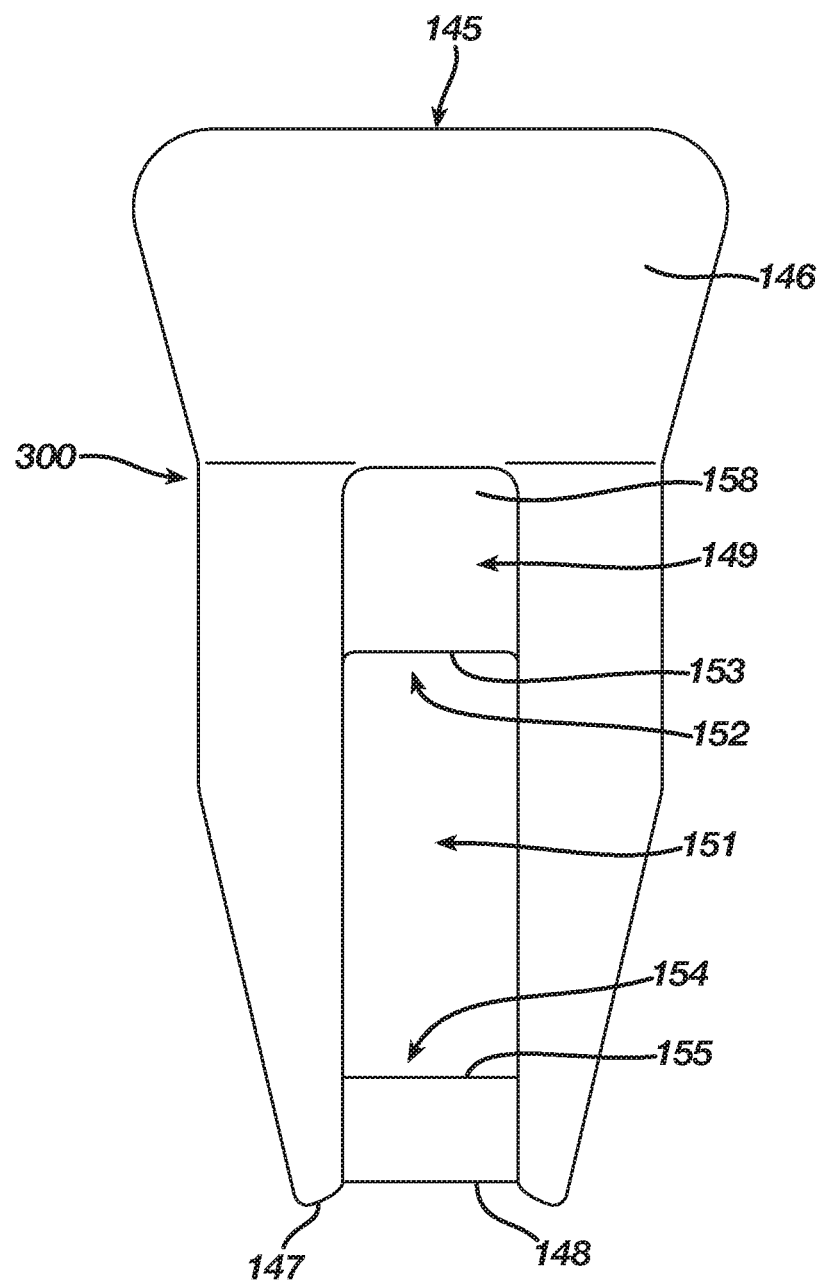
FIG. 25B is a front view illustrating the body of the implant insertion device.

FIGS. 23A-24D illustrate an implant insertion device 300 according to a fourth embodiment that engages the implant 175 and retains the implant 175 in its insertion shape 177 or 207. FIGS. 23A-23D illustrate the implant insertion device 300 in an unloaded position 301 prior to its loading with the implant 175 or after its delivery of the implant 175 whereby the implant 175 releases from the implant insertion device 300 without obstruction. FIGS. 24A-24D illustrate the implant insertion device 300 in a loaded position 302 whereby the implant insertion device 300 may be loaded with the implant 175 such that the implant insertion device 300 retains the implant 175 in its insertion shape 177 or 207. The implant insertion device 300 allows a surgeon to manipulate the implant 175 and insert the implant 175 into bone, bones, or bone pieces requiring fixation. FIGS. 25A-25B illustrate a body 303 of the implant insertion device 300, whereas FIGS. 26A-26B illustrate an implant grip 304 of the implant insertion device 300 that is coupled with the body 303 and is movable relative to the body 303 between a disengaged position 305 shown in FIGS. 23A-23D and an engaged position 306 shown in FIGS. 24A-24D.

The implant insertion device 300 according to the fourth embodiment, including its body 303 and implant grip 304, is substantially similar in design and operation relative to the implant insertion device 100 according to the second embodiment, including its body 103 and implant grip 104, such that, for the sake of brevity, only differences therebetween will be described herein. Moreover, one of ordinary skill in the art will recognize that like parts of the body 303 and the implant grip 304 for the implant insertion device 300 labeled with like numerals of the body 103 and the implant grip 104 for the implant insertion device 100 incorporate a design and function as previously set forth in the detailed description of the implant insertion device 100 according to the second embodiment.

Figure 26A:
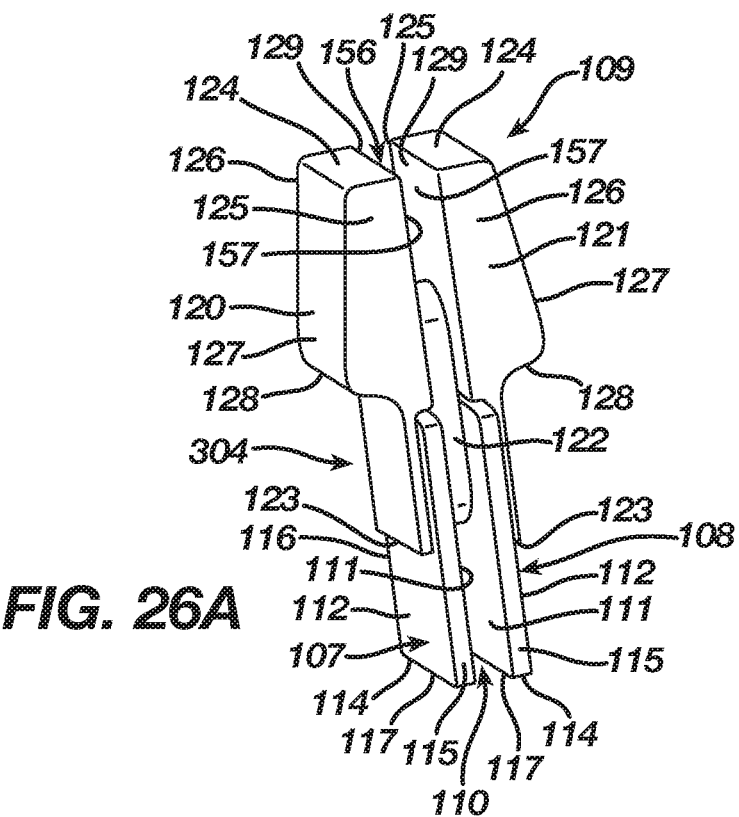
FIG. 26A is an isometric view illustrating an implant grip of the implant insertion device according to the fourth embodiment.
Figure 26B:
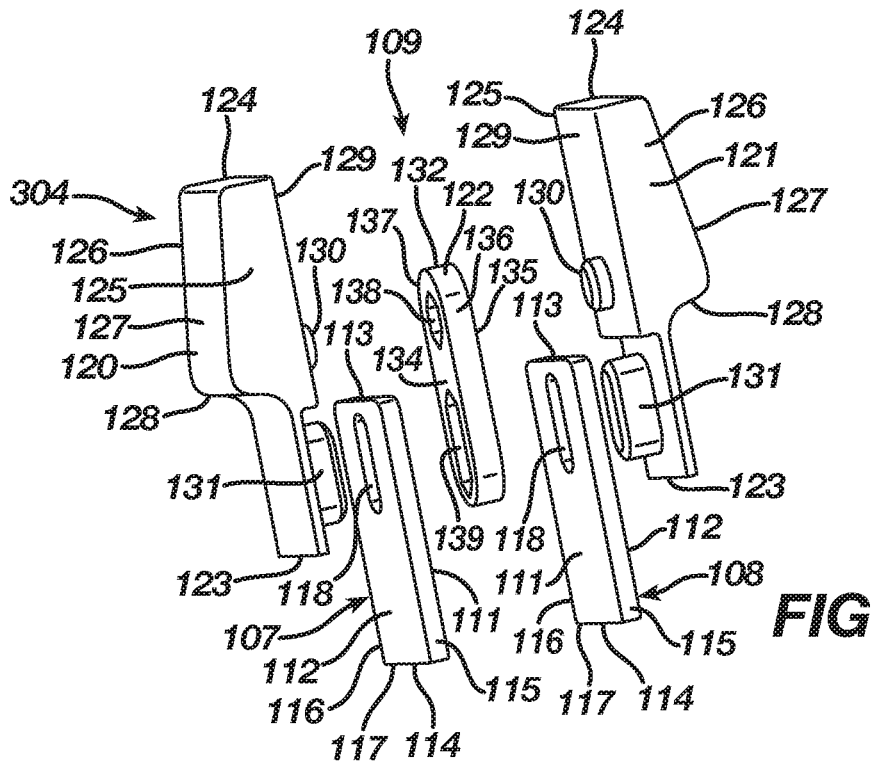
FIG. 26B is an exploded isometric view illustrating the implant grip of the implant insertion device according to the fourth embodiment.
Figure 27A:
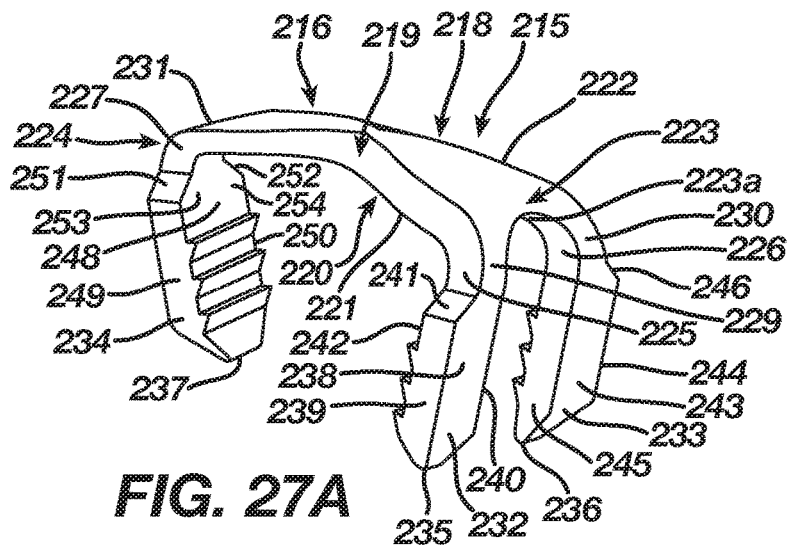
FIG. 27A is an isometric view illustrating a shape memory implant according to a third embodiment in a natural shape.
Figure 27B:
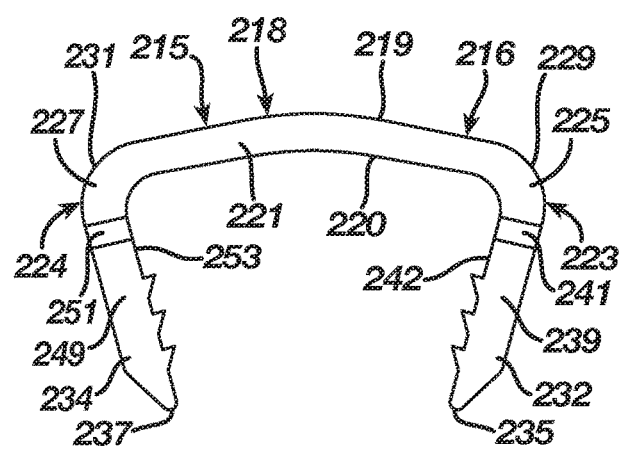
FIG. 27B is a side view thereof.
Figure 27C:
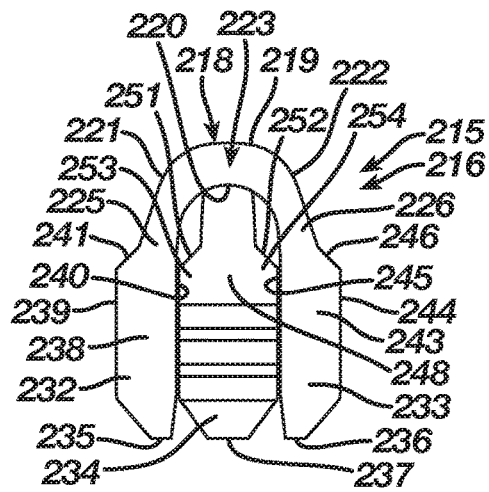
FIG. 27C is an end view thereof.
Figure 27D:
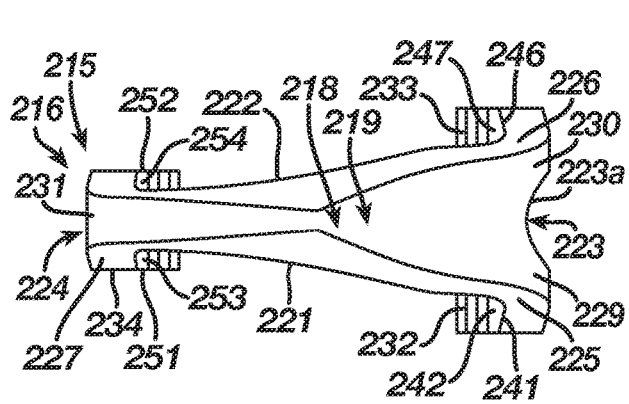
FIG. 27D is a top view thereof.
Figure 27E:
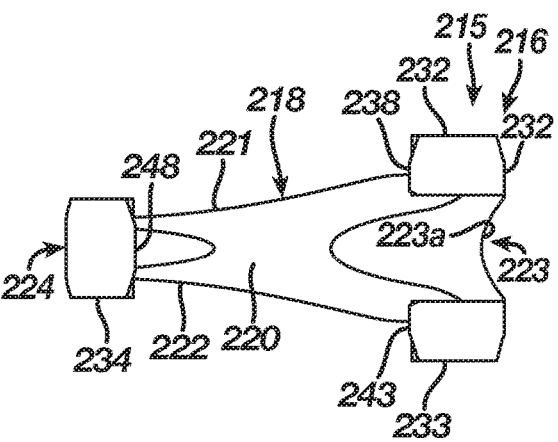
FIG. 27E is a bottom view thereof.

The implant grip 304 as illustrated in FIGS. 26A-26B is substantially similar to the implant grip 104 with the exception of the following. The implant grip 304, which includes the first and second blades 107 and 108 defining the passage 110 therebetween and the actuator 109, interfaces with the implant 175 and the body 303, whereas the implant grip 104 interfaces with the implant 175 and the body 103. In accordance therewith, the actuator 109 in the fourth embodiment and, more particularly, the spacer 122 thereof is dimensioned whereby the spacer 122 locates the first and second blades 107 and 108 such that the passage 110 therebetween receives therein the bridge 178 of the implant 175. The passage 110 in the fourth embodiment therefore is dimensioned to receive therein the bridge 178 of the implant 175 whereby the first and second blades 107 and 108 at their leading edges 117 extend beyond the bridge 178 such that the first blade 107 at its first and second sides 115 and 116 respectively abuts the engagement points 196 and 203 of the legs 187-188 for the implant 175 and the second blade 108 at its first and second sides 115 and 116 respectively abut the engagement points 197-204 of the legs 187-188 for the implant 175, thereby constraining the implant 175 in its insertion shape 177 or 207.

The body 303 as illustrated in FIGS. 25A-25B is substantially similar to the body 103 with the exception of the following. The body 303, which includes the first end 145 defining the handle 146 and the second end 147 defining the tamp 148, interfaces with the implant grip 304 and the implant 175, whereas the body 103 interfaces with the implant grip 104 and the implant 5. In accordance therewith, the body 303 is dimensioned relative to the implant 175 such that the tamp 79 is configured to engage the bridge 178 when the implant 175 resides in its insertion shape 177 or its insertion shape 207. Likewise, the body 303 and, more particularly, the slot 151 is dimensioned relative to the implant grip 304 such that the spacer 122 of the actuator 109 inserts into the slot 151 with the spacer 122 oriented whereby its first side 134 and the opening 138 and the channel 139 communicate exterior to the slot 151 at the first surface 149 of the body 303 and its second side 135 and the opening 138 and the channel 139 communicate exterior to the slot 151 at the second surface 150 of the body 303. Moreover, the second stop 155 and the tamp 148 of the body 303 in the fourth embodiment define a rectangular shape similar to the bridge 178 of the implant 175 but are dimensioned smaller than the passage 110 between the first and second blades 107 and 108 in order to allow the first and second blades 107 and 108 to by-pass the second stop 155 and the tamp 148 and extend exterior relative to the body 303.

The implant insertion device 300 according to the fourth embodiment loads with the implant 175, constrains the implant 175 in its insertion position 177 or 207, and transitions from its loaded position 302 to its unloaded position 301 thereby delivering the implant 175 to bone, bones, or bone pieces substantially identical to the implant insertion device 100 according to the second embodiment as previously set forth in the detailed description thereof. During loading of the implant insertion device 300 with the implant 175 and a subsequent retention thereof, the tamp 148 of the body 303 sits atop the bridge 178 of the implant 175, while the actuator 109 progresses along the body 303 towards the second stop 155 of the body 303 until the spacer 122 of the actuator 109 at its second end 133 contacts the second stop 155 whereby the actuator 109 extends the first and second blades 107 and 108 exterior to the body 303 such that the first and second blades 107 and 108 at their first and second sides 115 and 116 respectively abut the engagement points 196-197 and 203-204 of the legs 187-188 for the implant 175, thereby constraining the implant 175 in its insertion shape 177 or 207. When delivering the implant 175 to bone, bones, or bone pieces, the actuator 109 progresses along the body 303 to the first stop 154 thereof such that the first and second blades 107 and 108 at their first and second sides 115 and 116 respectively release the engagement points 196-197 and 203-204 of the legs 187-188 for the implant 175 while, if engaged, the first and second blades 107 and 108 at their first faces 111 also release the bridge 178, resulting in the discharge of the implant 175 from the implant grip 304 and a subsequent attempted transition of the implant 175 from its insertion shape 177 or 207 to its natural shape 176 whereby the implant 175 delivers the energy stored therein to the bone, bones, or bone pieces.

FIGS. 27A-27E illustrate an orthopedic implant 215 according to a third embodiment in a natural shape 216, whereas FIGS. 28A-28E illustrate the orthopedic implant 215 in an insertion shape 217. The implant 215 in the third embodiment may be manufactured from a shape memory material with superelastic or temperature dependent properties (e.g., Nitinol) such that the implant 215 transitions between its natural shape 216 and its insertion shape 217. The implant 215 when deformed from its natural shape 216 to its insertion shape 217 stores energy deliverable to bone, bones, or bone pieces. In accordance with its manufacture from shape memory material, the implant 215 begins in its natural shape 216, is transitionable to its insertion shape 217, and, once implanted in bone, bones, or bone pieces, attempts to transition from its insertion shape 217 to its natural shape 216 whereby the implant 215 delivers the energy stored therein to the bone, bones, or bone pieces in order to affix the bone, bones, or bone pieces and promote a healing thereof. In the first embodiment, attempted transition of the implant 215 from its insertion shape 217 to its natural shape 216 continuously compresses the bone, bones, or bone pieces to promote fusion thereof.

The implant 215 includes a bridge 218 with upper and lower surfaces 219 and 220, first and second sides 221 and 222, and first and second ends 223 and 224. The first and second sides 221 and 222 and the first and second ends 223 and 224 in the third embodiment of the implant 215 define a substantially triangular shape. The bridge 218 at its first end 223 includes a concave section 223a. The implant 215 further includes transition sections 225 and 226 at the first end 223 of the bridge 218 and a transition section 227 at the second end 224 of the bridge 218. More particularly, in the third embodiment, the transition section 225 resides at a corner 229 of the bridge 218 at its first end 223, whereas the transition section 226 resides at a corner 230 of the bridge 218 at its first end 223. Similarly, the transition section 227 resides at a corner 231 of the bridge 218 at its first end 224.

The implant 215 in the third embodiment includes an anchoring member in the form of a leg 232 extending from the corner 229 and, in particular, the transition section 225 at the corner 229; an anchoring member in the form of a leg 233 extending from the corner 230 and, in particular, the transition section 226 at the corner 230; and an anchoring member in the form of a leg 234 extending from the corner 231 and, in particular, the transition section 227 at the corner 231. In the third embodiment, the legs 232-234 are formed integrally with the bridge 218 at a respective corner 229-231 and, in particular, at a respective transition section 225-227. Each leg 232-234, which has a respective tip 235-237, may include barbs thereon that improve the pull-out resistance of the implant 215. The implant 215 includes anchoring members in the form of the legs 232-234 in order to facilitate a securing of the implant 215 with bone, bones, or bone pieces whereby the bridge 218 between the legs 232-234 traverses a fixation zone of the bone, bones, or bone pieces such that the implant 215, after its insertion and attempted transition from the insertion shape 217 to the natural shape 216, delivers energy to the bone, bones, or bone pieces at the fixation zone.

The leg 232 in the third embodiment includes a width 238 between sides 239 and 240 such that a segment 241 of the leg 232 extends exterior to the bridge 218 at its first side 221 in order to provide an engagement point 242 whereby an implant engagement device by-passes the bridge 218 at its first side 221 and abuts the engagement point 242. The leg 233 in the third embodiment includes a width 243 between sides 244 and 245 such that a segment 246 of the leg 233 extends exterior to the bridge 218 at its second side 222 in order to provide an engagement point 247 whereby an implant engagement device by-passes the bridge 218 at its second side 222 and abuts the engagement point 247. The leg 234 in the third embodiment includes a width 248 between sides 249 and 250 such that a first segment 251 of the leg 234 extends exterior to the bridge 218 at its first side 221 and a second segment 252 of the leg 234 extends exterior to the bridge 218 at its second side 222. The first segment 251 provides an engagement point 253 whereby an implant engagement device by-passes the bridge 218 at its first side 221 and abuts the engagement point 253. Likewise, the second segment 252 provides an engagement point 254 whereby an implant engagement device by-passes the bridge 218 at its second side 222 and abuts the engagement point 254. While the leg 234 in the third embodiment includes engagement points 253-254, one of ordinary skill in the art will recognize that leg may include one engagement point 253 or 254 whereby an implant engagement device by-passes the bridge 218 and abuts one of the engagement points 253 or 254.

The regular inherent shape of the implant 215, as illustrated in FIGS. 27A-27E, is its natural shape 216 where the transition sections 225-227 locate the bridge 218 in a natural form that places the legs 232-234 in a natural position whereby the legs 232-233 are convergent with the leg 234 and spaced apart from the leg 234 at a first distance. Nevertheless, as illustrated in FIGS. 28A-28E, the implant 215 is deformable under the action of superelasticity or temperature dependent shape memory to an insertion shape 217 where the transition sections 225-227 deform to store energy while also moving the bridge 218 from its natural form to an insertion form that places the legs 232-234 in an insertion position whereby the legs 232-233 are substantially parallel with the leg 234 and spaced apart from the leg 234 at a second distance that is greater than the first distance. Since the insertion shape 217 is not the regular inherent shape of the implant 215, the bridge 218 typically is mechanically constrained using an implant insertion device whereby the implant insertion device maintains the bridge 218 in its insertion form. In order to facilitate engagement of an implant insertion device with the implant 215, the legs 232-233, respectively, include the engagement points 242 and 247 and the leg 234 respectively includes the engagement points 253 and 254 that receive the implant insertion device. The implant insertion device by-passes the bridge 218 at its first and second sides 221 and 222 and abuts the engagement points 242, 247, 253, and 254. In particular, the implant insertion device extends beyond the bridge 218 at its first and second sides 221 and 222 and abuts the engagement points 242, 247, 253, and 254 such that the implant insertion device engages and then holds the legs 232-234, resulting in the implant insertion device constraining the deformed transition sections 225-227 in order to maintain the implant 215 in its insertion shape 217. After implantation into bone, bones, or bone pieces and a release of the implant insertion device, including if necessary a heating of the implant 215, the implant 215 delivers the energy stored in the transition sections 225-227 whereby the bridge 218 attempts to transition from its insertion form to its natural form, which causes an attempt of the legs 232-234 to move from their insertion position to their natural position such that the implant 215 affixes the bone, bones, or bone pieces through an application of a compressive force thereto.

Figure 28A:
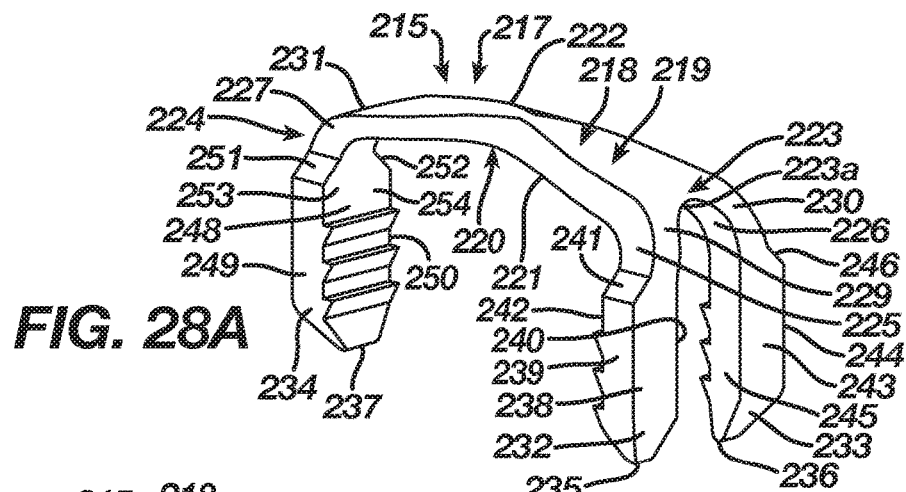
FIG. 28A is an isometric view illustrating the shape memory implant according to the third embodiment in an insertion shape.
Figure 28B:
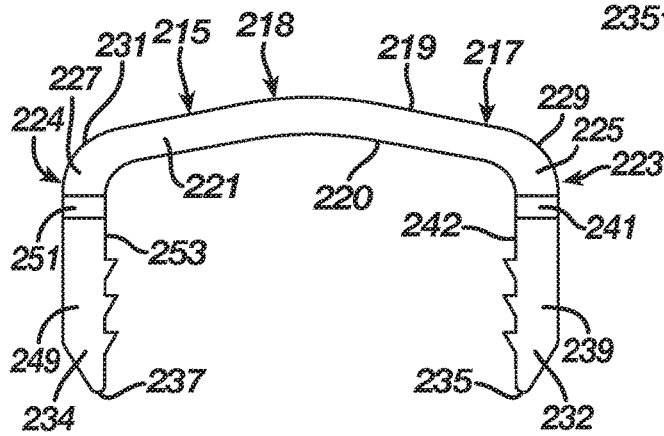
FIG. 28B is a side view thereof.
Figure 28C:
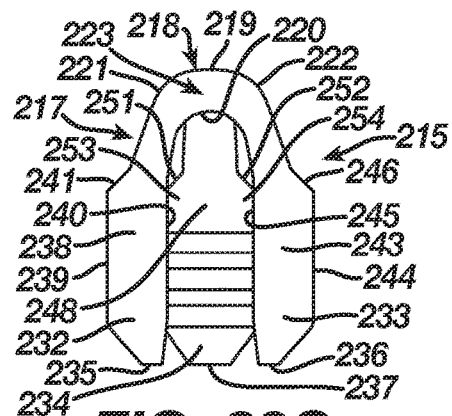
FIG. 28C is an end view thereof.
Figure 28D:
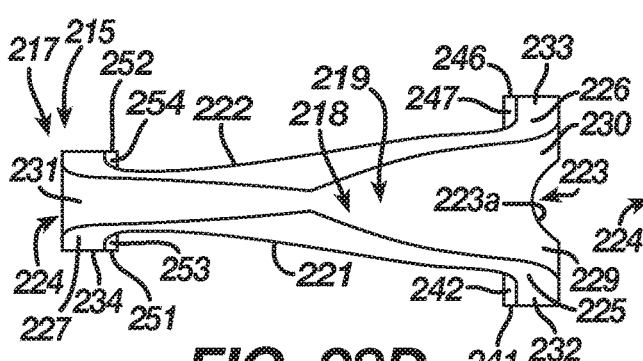
FIG. 28D is a top view thereof.
Figure 28E:
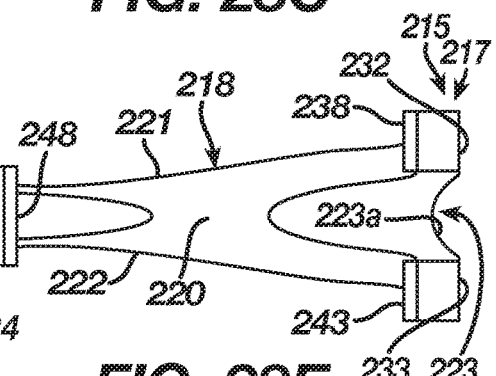
FIG. 28E is a bottom view thereof.
Figure 28F:
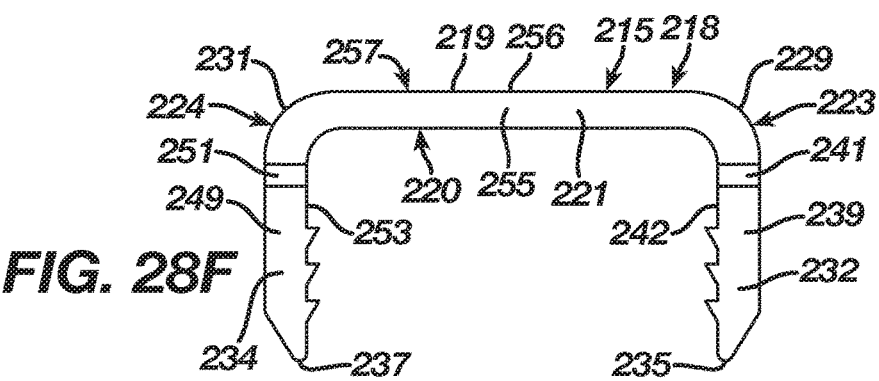
FIG. 28F is a side view illustrating an alternative insertion shape for the shape memory implant according to the third embodiment.
Figure 29A:
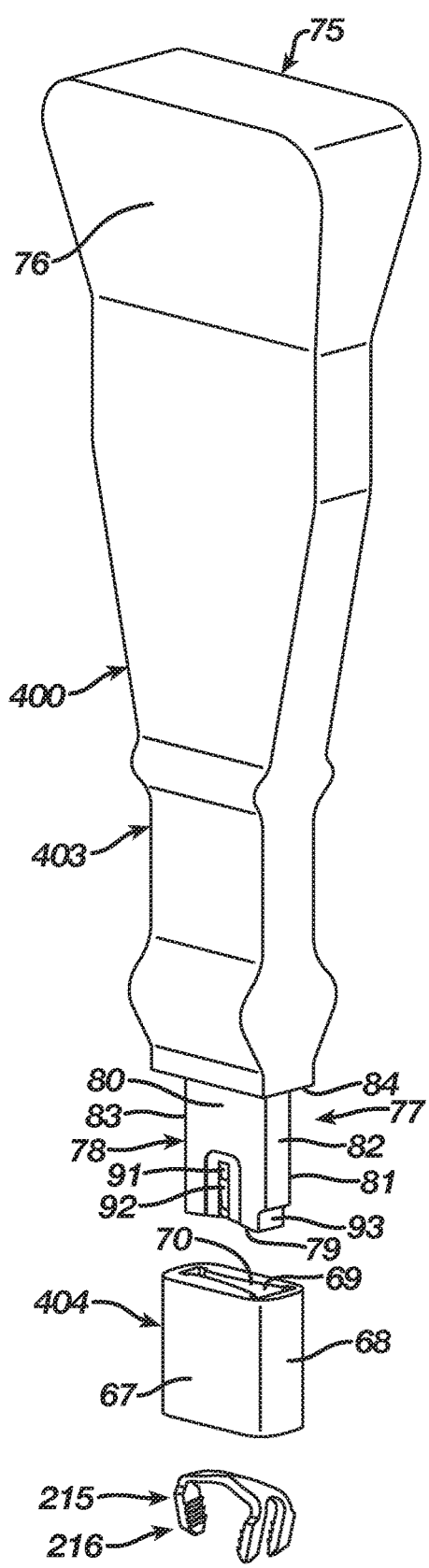
FIG. 29A is an exploded isometric view illustrating an implant insertion device according to a fifth embodiment and a shape memory implant according to the third embodiment in its natural shape.
Figure 29B:
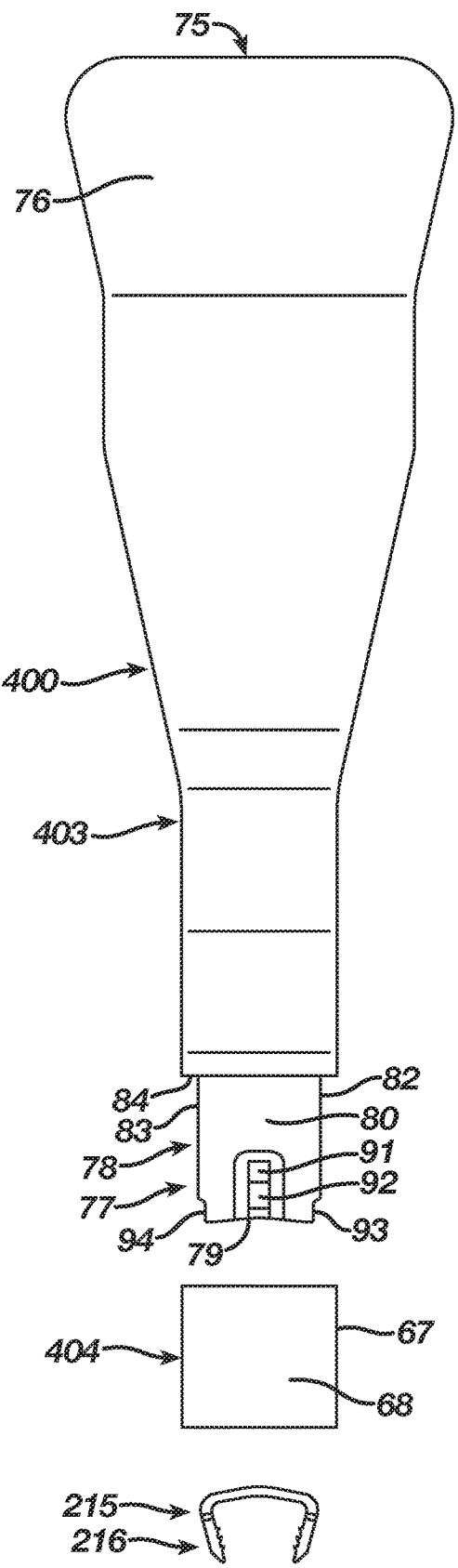
FIG. 29B is an exploded front view illustrating the implant insertion device and the shape memory implant.
Figure 30A:
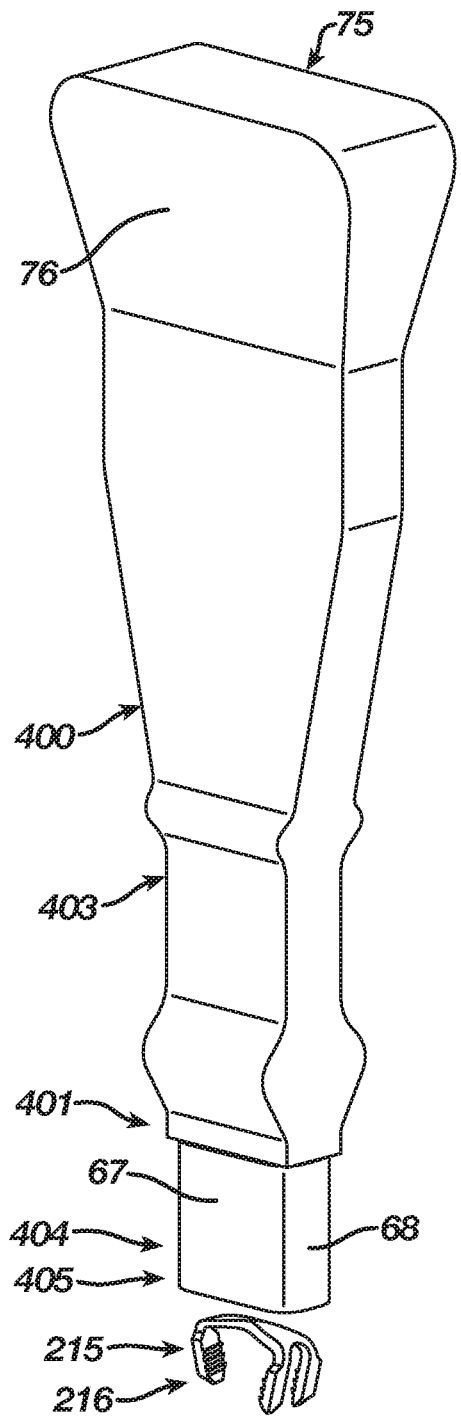
FIG. 30A is an isometric view illustrating the implant insertion device according to the fifth embodiment in an unloaded position and the shape memory implant according to the third embodiment in its natural shape.
Figure 30B:
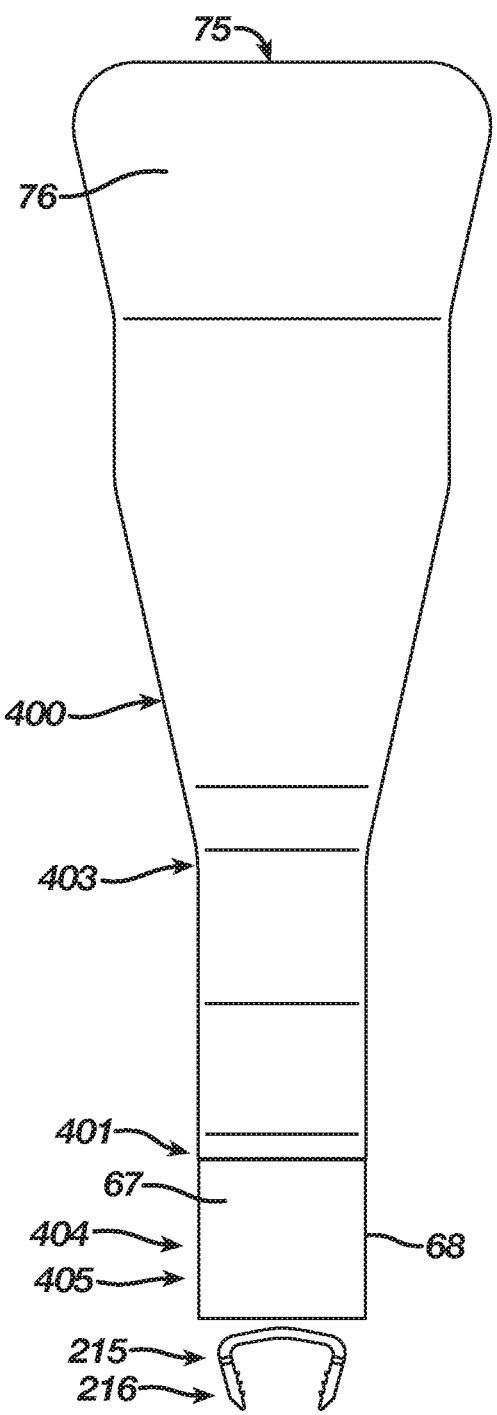
FIG. 30B is a front view illustrating the implant insertion device in its unloaded position and the shape memory implant.
Figure 31A:
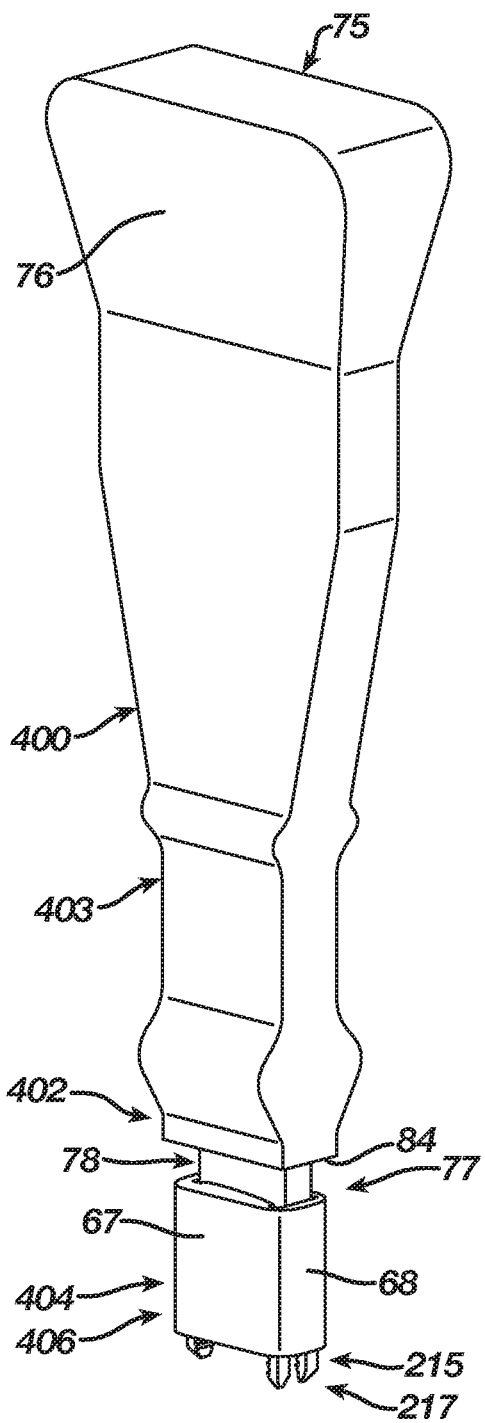
FIG. 31A is an isometric view illustrating the implant insertion device according to the fifth embodiment in a loaded position that constrains the shape memory implant according to the third embodiment in its insertion shape.
Figure 31B:
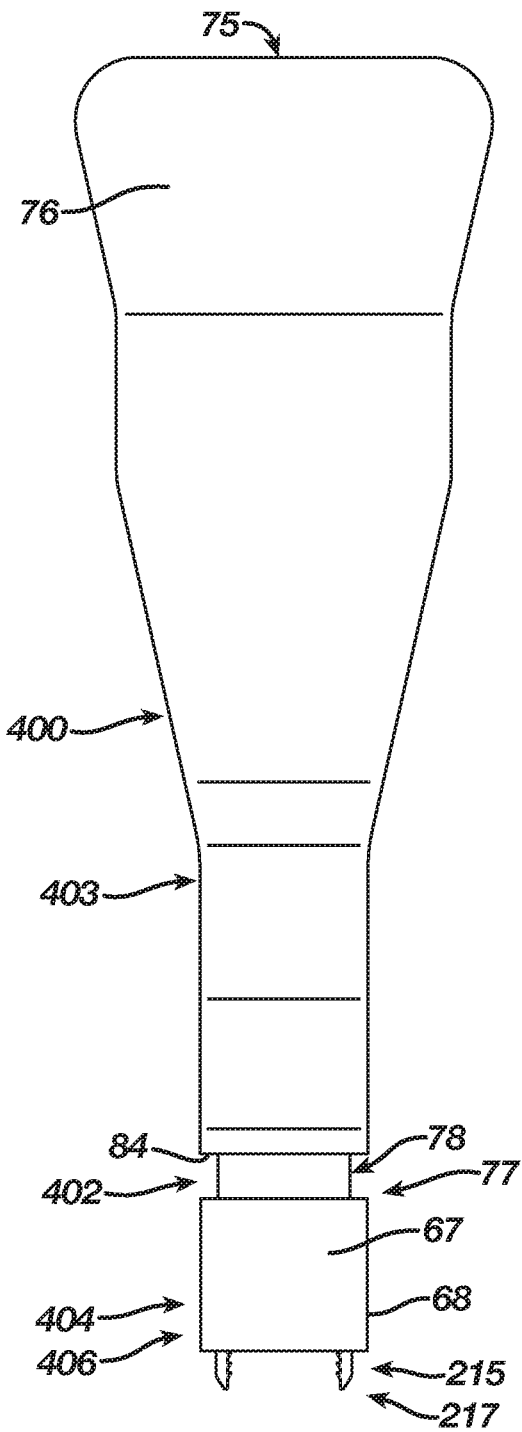
FIG. 31B is a front view illustrating the implant insertion device in its loaded position that constrains the shape memory implant in its insertion shape.
Figure 32A:
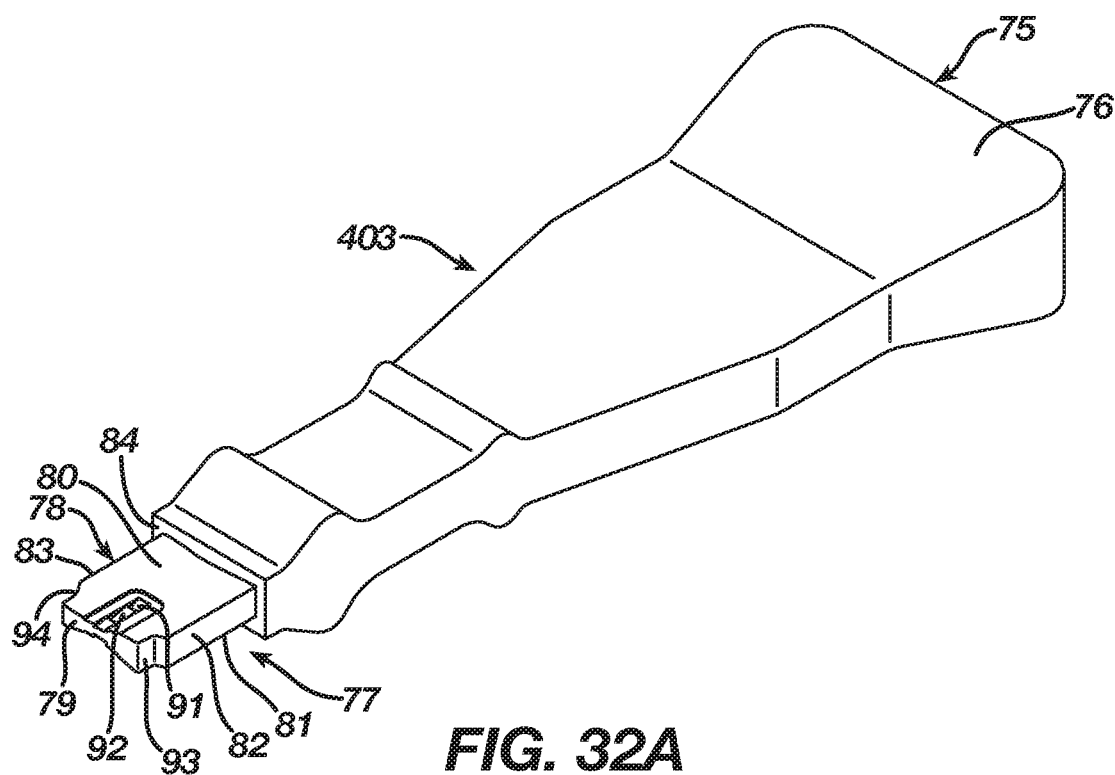
FIGS. 32A-32B are isometric views illustrating a body of the implant insertion device according to the fifth embodiment.
Figure 32B:
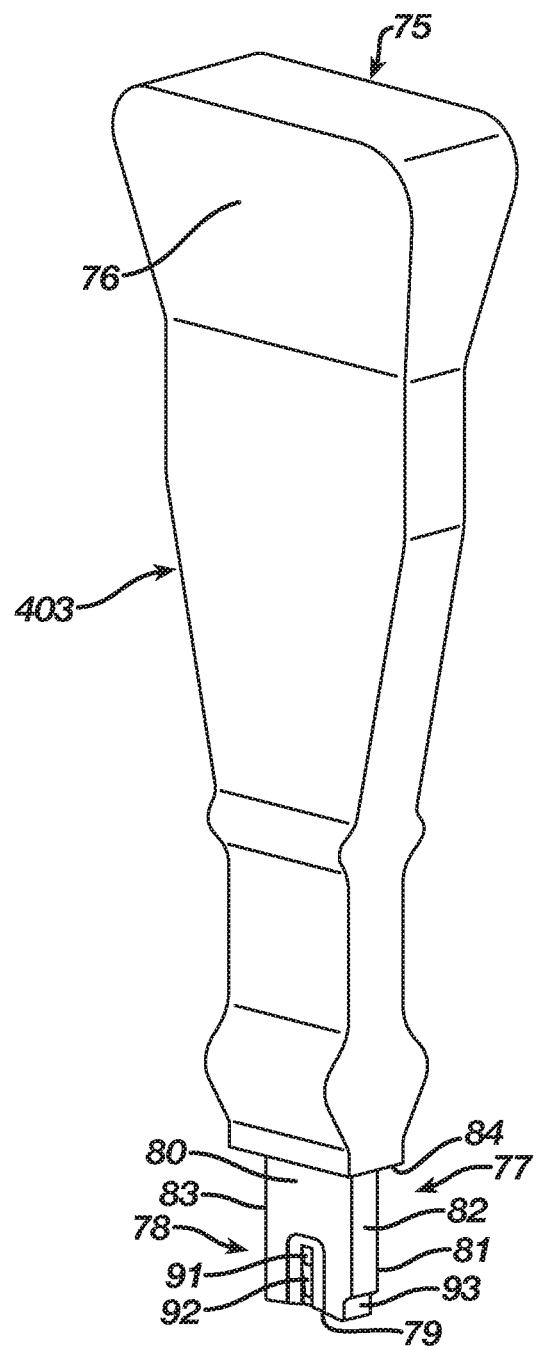
Figure 32C:
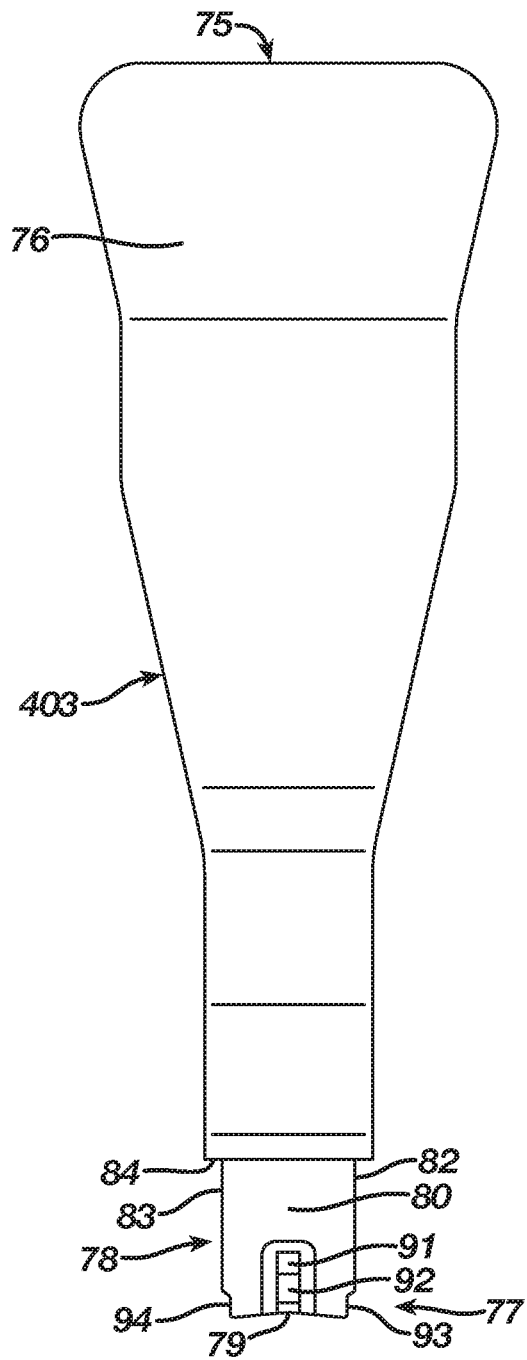
FIG. 32C is a front view illustrating the body of the implant insertion device.
Figure 32D:
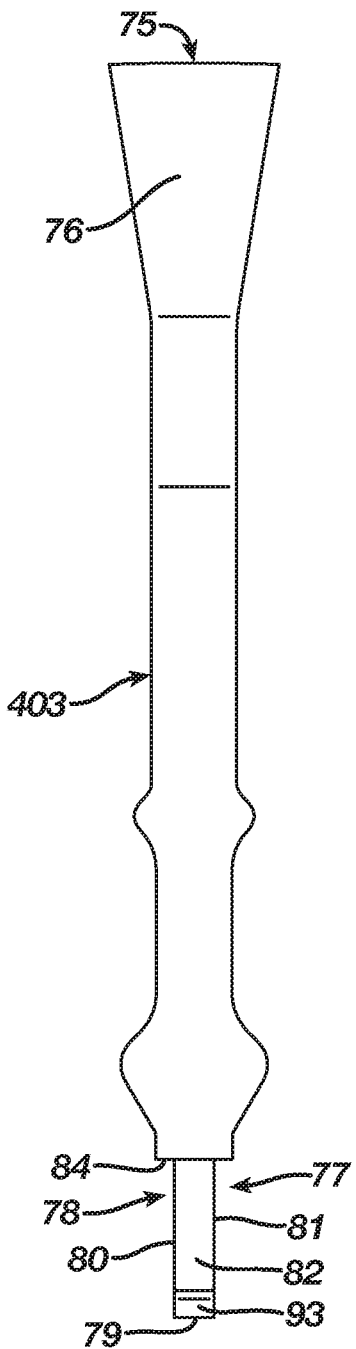
FIG. 32D is an end view illustrating the body of the implant insertion device.
Figure 33A:
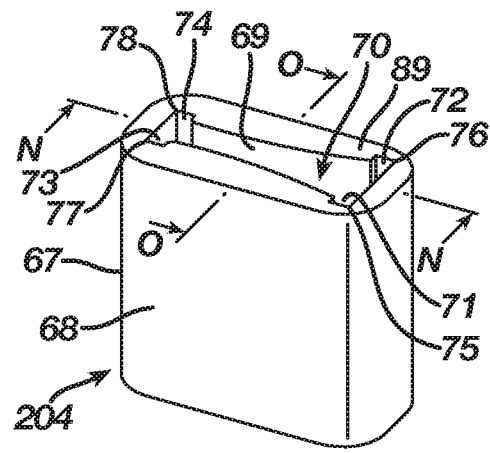
FIG. 33A is an isometric view illustrating an implant grip of the implant insertion device according to the fifth embodiment.
Figure 33B:
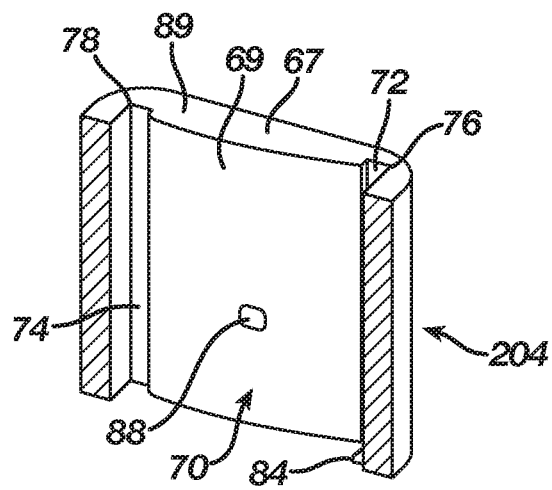
FIG. 33B is an isometric view in cross-section taken along lines N-N of FIG. 33A illustrating the implant grip of the implant insertion device.
Figure 33C:
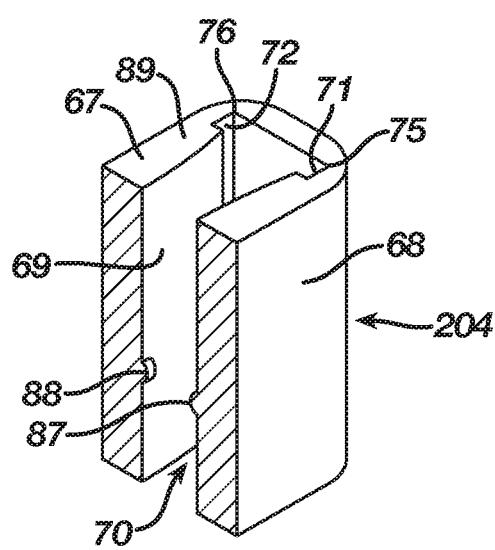
FIG. 33C is a top isometric view in cross-section taken along lines O-O of FIG. 33A illustrating the implant grip of the implant insertion device.
Figure 33D:
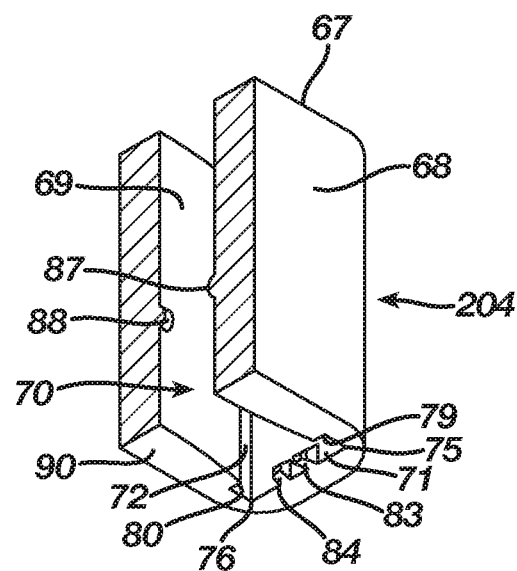
FIG. 33D is a bottom isometric view in cross-section taken along lines O-O of FIG. 33A illustrating the implant grip of the implant insertion device.
Figure 33E:
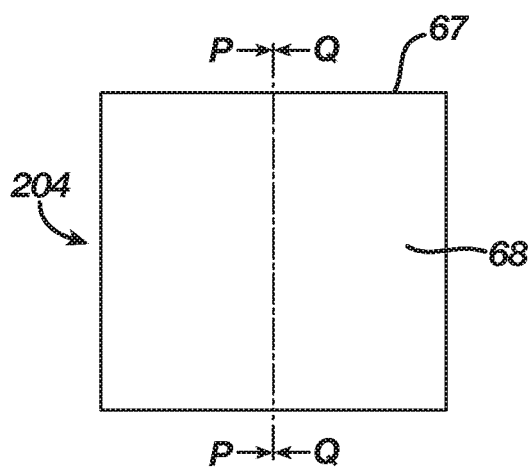
FIG. 33E is a front view illustrating the implant grip of the implant insertion device.
Figure 33F:
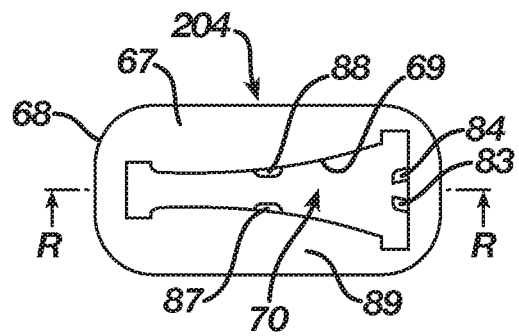
Figure 33G:
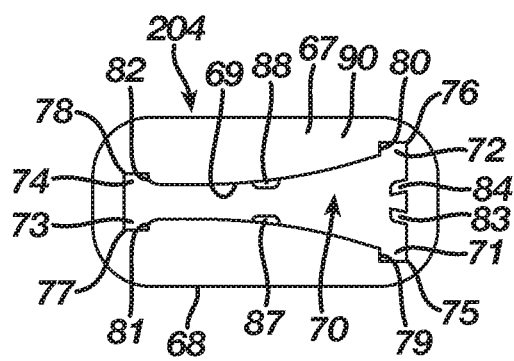
Figure 33H:
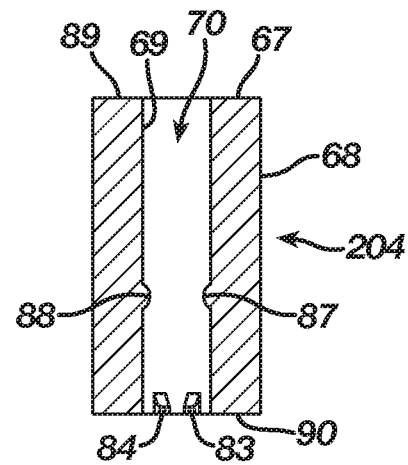
Figure 33I:
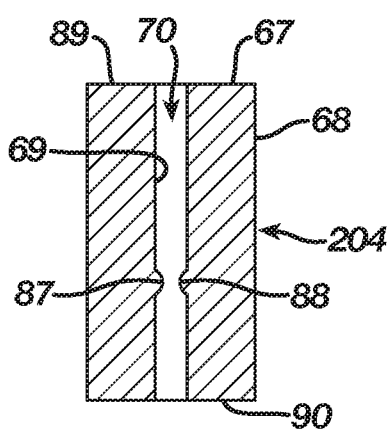
Figure 33J:
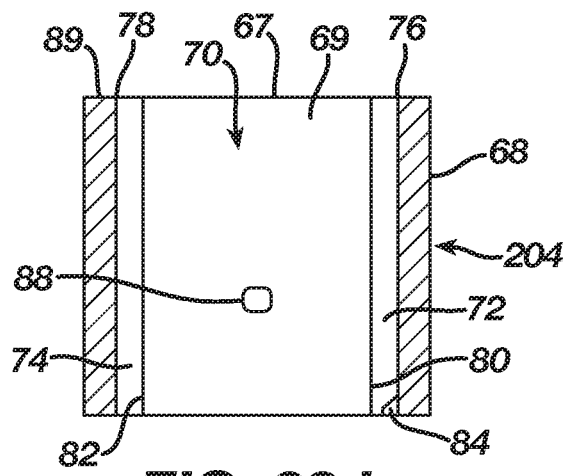
Figure 34A:
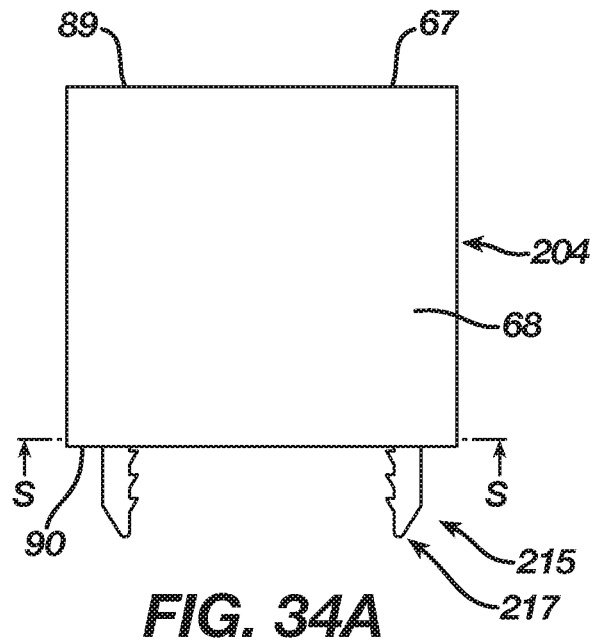
Figure 34B:
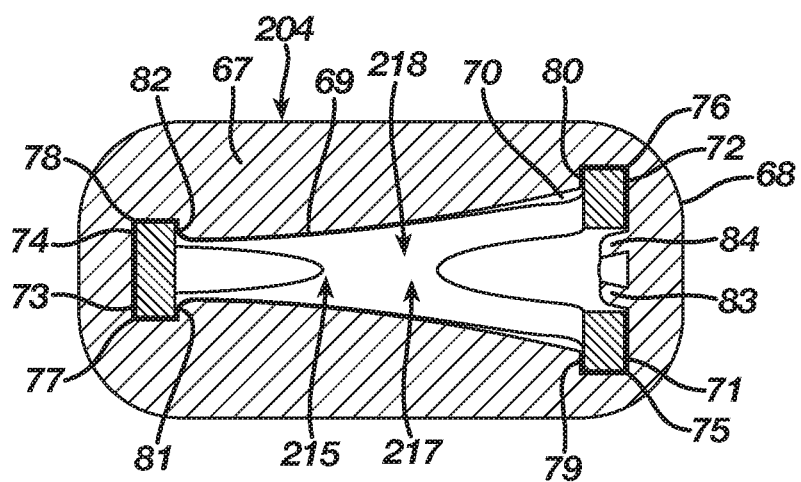
Figure 35A:
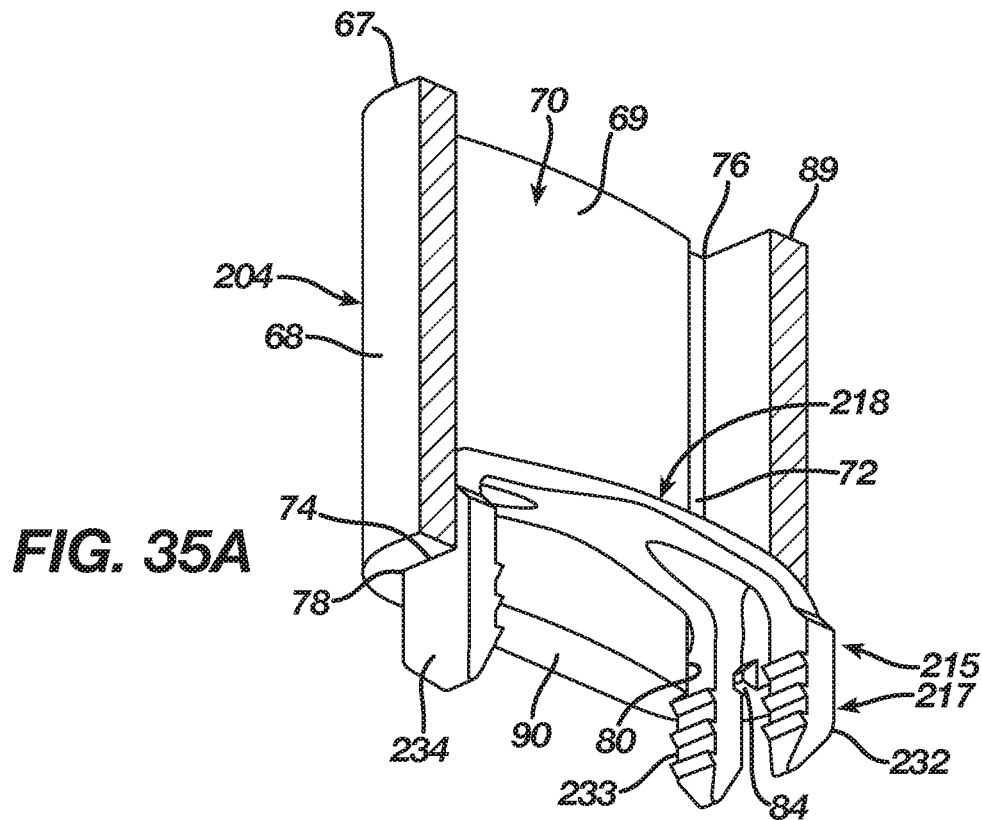
Figure 35B:
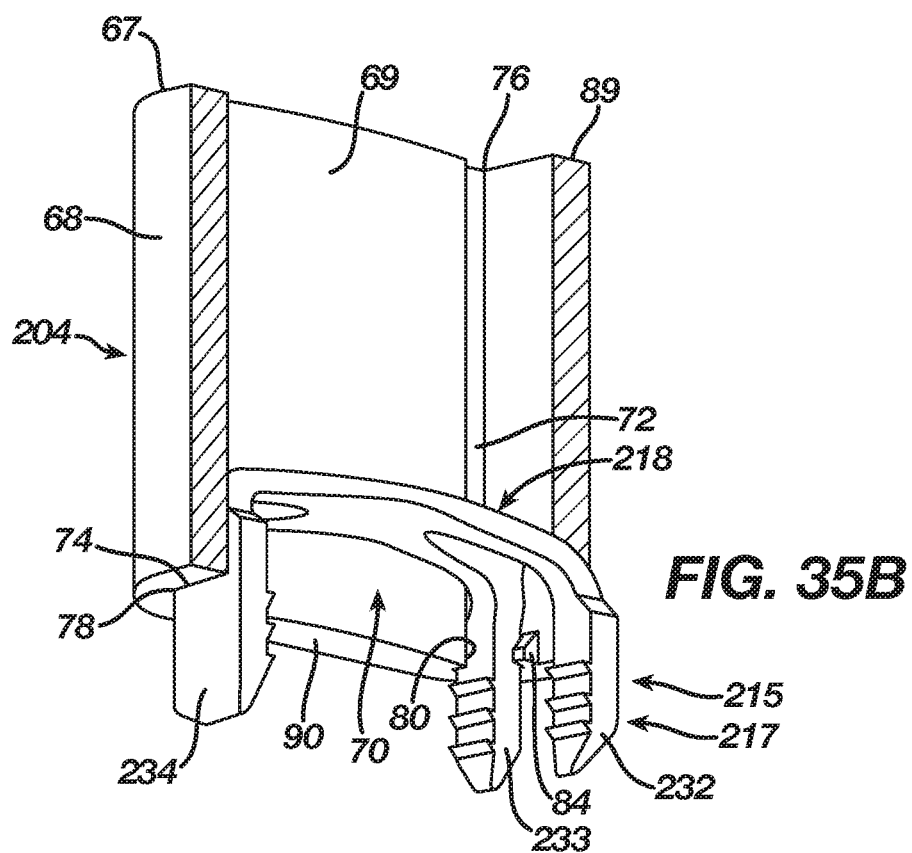
Figure 36A:
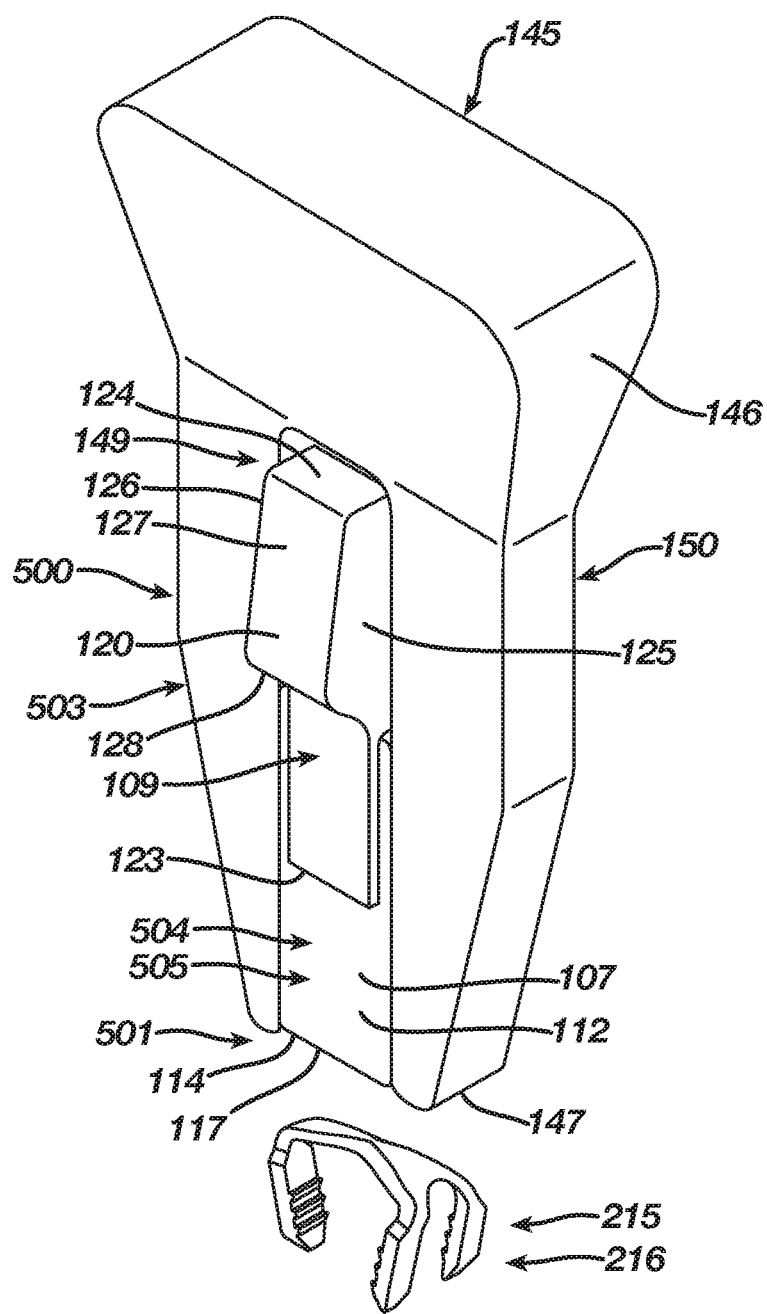
Figure 36B:
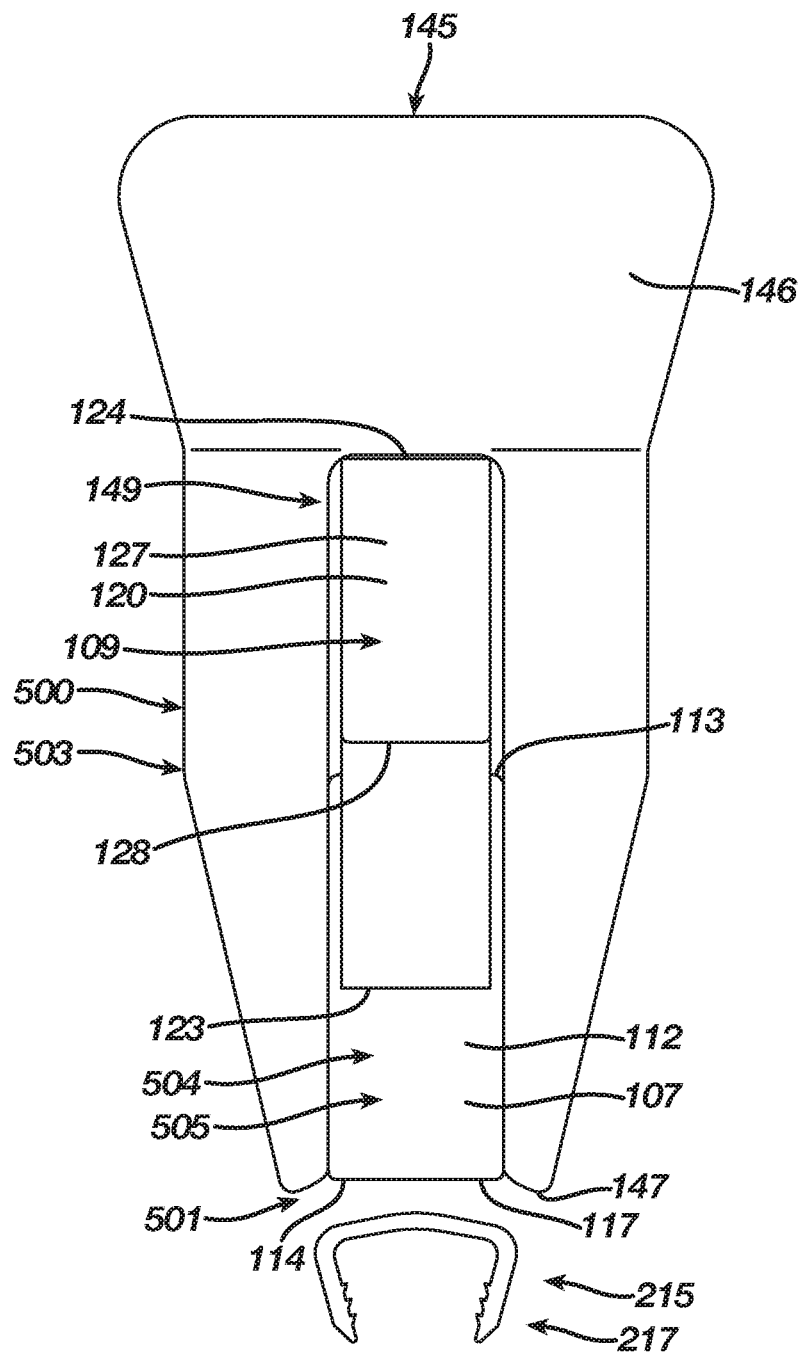
Figure 36C:
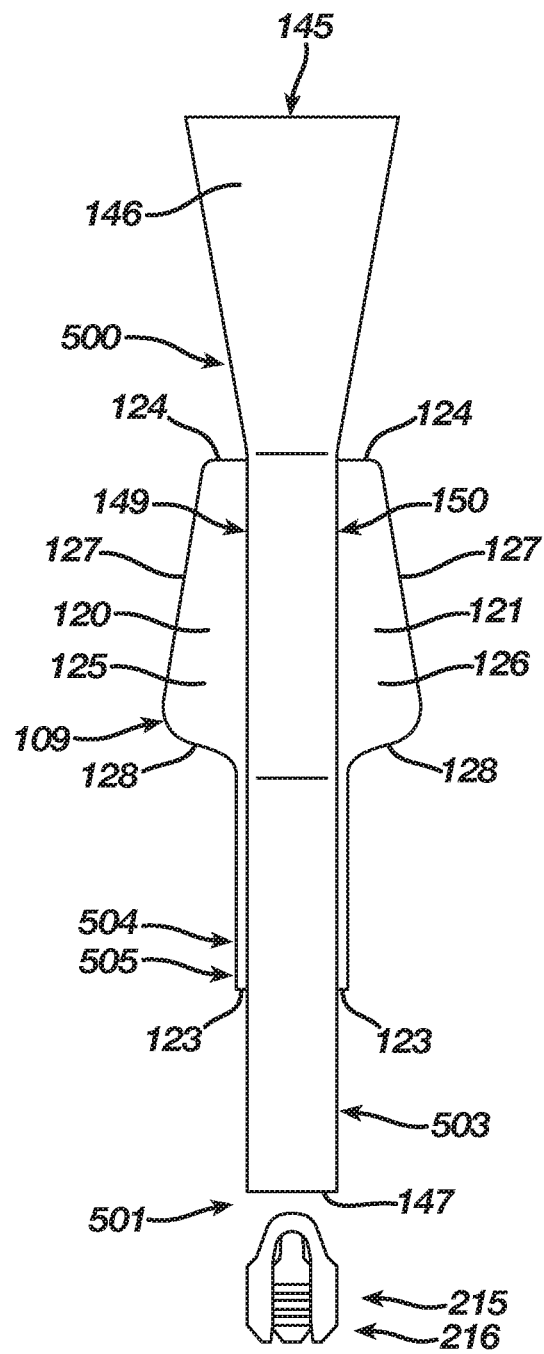
Figure 36D:
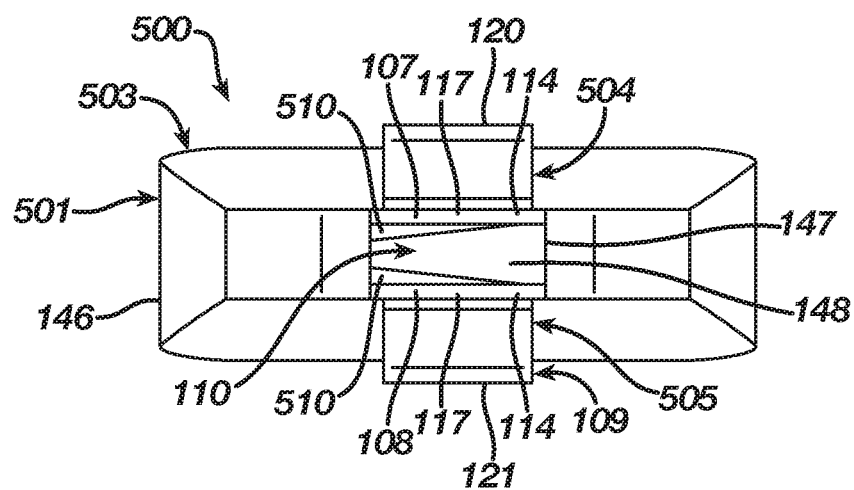

Although the bridge 218 of the implant 215 according to the third embodiment includes the transition sections 225-227, the bridge 218, alternatively, may include a transition section 255 located at a center section 256 of the implant 215 and thus the bridge 218. The regular inherent shape of the implant 215, as illustrated in FIGS. 27A-27E, is its natural shape 216 where the transition section 255 locates the bridge 218 in a natural form consisting of a closed or angular profile whereby the first and second ends 223 and 224 reside at a first distance and the legs 232-234 reside in a natural position whereby the legs 232-233 are convergent with the leg 234 and spaced apart from the leg 234 at a first distance. Nevertheless, as illustrated in FIG. 28F, the implant 215 is deformable under the action of superelasticity or temperature dependent shape memory to an insertion shape 257 where the transition section 255 deforms to store energy while also moving the bridge 218 from its natural form to an insertion form which is an open or substantially linear profile whereby the first and second ends 223 and 224 reside at a second distance that is greater than the first distance and the legs 232-234 reside in an insertion position whereby the legs 232-233 are substantially parallel with the leg 234 and spaced apart from the leg 234 at a second distance that is greater than the first distance. Since the insertion shape 257 is not the regular inherent shape of the implant 215, the bridge 218 typically is mechanically constrained using an implant insertion device whereby the implant insertion device maintains the bridge 218 in its insertion form. In order to facilitate engagement of an implant insertion device with the implant 215, the legs 232-233, respectively, include the engagement points 242 and 247 and the leg 234 respectively includes the engagement points 253 and 254 that receive the implant insertion device. The implant insertion device by-passes the bridge 218 at its first and second sides 221 and 222 and abuts the engagement points 242, 247, 253, and 254. In particular, the implant insertion device extends beyond the bridge 218 at its first and second sides 221 and 222 and abuts the engagement points 242, 247, 253, and 254 such that the implant insertion device engages and then holds the legs 232-234, resulting in the implant insertion device constraining the deformed transition section 255 in order to maintain the implant 215 in its insertion shape 257. After implantation into bone, bones, or bone pieces and a release of the implant insertion device, including if necessary a heating of the implant 215, the implant 215 delivers the energy stored in the transition section 255 whereby the bridge 218 attempts to transition from its insertion form to its natural form, which causes an attempt of the legs 232-234 to move from their insertion position to their natural position such that the implant 215 affixes the bone, bones, or bone pieces through an application of a compressive force thereto.

While the third embodiment of the implant 215 includes either the transition sections 225-227 or the transition section 255 to produce deformation thereof, one of ordinary skill in the art will recognize that the bridge 218 of the implant 215 may include both the transition sections 225-227 and the transition section 255 to produce deformation thereof. Moreover, while the bridge 218 in the third embodiment includes an angular profile in the natural shape of the implant 215, it should be understood by one of ordinary skill in the art that a bridge 218 incorporating the transition sections 225-227 may include a substantially linear profile for the natural shape of the implant 215.

FIGS. 29A-31D illustrate an implant insertion device 400 according to a fifth embodiment that engages an implant 215 and retains the implant 215 in its insertion shape 217 or 257. FIGS. 30A-30B illustrate the implant insertion device 400 in an unloaded position 401 prior to its loading with the implant 215 or after its delivery of the implant 215 whereby the implant 215 releases from the implant insertion device 400 without obstruction. FIGS. 31A-31D illustrate the implant insertion device 400 in a loaded position 402 whereby the implant insertion device 400 may be loaded with the implant 215 such that the implant insertion device 400 constrains the implant 215 in its insertion shape 217 or 257. The implant insertion device 400 allows a surgeon to manipulate the implant 215 and insert the implant 215 into bone, bones, or bone pieces requiring fixation. FIGS. 32A-32D illustrate a body 403 of the implant insertion device 400, whereas FIGS. 33A-35B illustrate an implant grip 404 of the implant insertion device 400 that is coupled with the body 403 and is movable relative to the body 403 between a disengaged position 405 shown in FIGS. 30A-30B and an engaged position 406 shown in FIGS. 31A-31D.

The implant insertion device 400 according to the fourth embodiment, including its body 403 and implant grip 404, is substantially similar in design and operation relative to the implant insertion device 60 according to the first embodiment, including its body 63 and implant grip 64, such that, for the sake of brevity, only differences therebetween will be described herein. Moreover, one of ordinary skill in the art will recognize that like parts of the body 403 and the implant grip 404 for the implant insertion device 400 labeled with like numerals of the body 63 and the implant grip 64 for the implant insertion device 60 incorporate a design and function as previously set forth in the detailed description of the implant insertion device 60 according to the first embodiment.

The implant grip 404 as illustrated in FIGS. 33A-35B is substantially similar to the implant grip 64 with the exception of the following. The implant grip 212, which includes the shell 67 with the interior surface 69 defining the passage 70 therethrough, the grooves 71-74, the retention surfaces 79-82, and the detents 87 and 88, interfaces with the implant 215 and the body 403, whereas the implant grip 64 interfaces with the implant 5 and the body 63. In accordance therewith, the interior surface 69 of the shell 67 and thus the passage 70 include a shape complimentary with the implant 215, substantially triangular in the fifth embodiment, and, in particular, with the first and second sides 181 and 182 and the first and second ends 183 and 184 of the bridge 178 whereby the shell 67 grips the implant 175 and retains therein the implant 175 in its insertion shape 177 or 207. The grooves 71-72 located respectively at the corners 75-76 of the interior surface 69 respectively receive therein the segments 241 and 246 of the legs 232-233 for the implant 215 and frictionally engage the segments 241 and 246 thereby retaining the implant 215 within the shell 67, while the grooves 73-74 located respectively at the corners 77-78 of the interior surface 69 respectively receive therein the segments 251-252 of the leg 234 for the implant 215 and frictionally engage the segments 251-252 thereby retaining the implant 215 within the shell 67. The retention surfaces 79-80 respectively abut an engagement point 242 and 247 of the legs 232-233 for the implant 215 in order to grip and then constrain the legs 232-233 such that the shell 67 retains the implant 215 in its insertion shape 217 or 257, while the retention surfaces 81-82 respectively abut an engagement point 253-254 of the leg 234 for the implant 215 in order to grip and then constrain the leg 234 such that the shell 67 retains the implant 215 in its insertion shape 217 or 257. The detents 87-88 engage the body 403 to assist in coupling the shell 67 with the body 63 and further to limit the motion of the shell 67 relative to the body 403 as the implant grip 404 moves between its disengaged position 405 and its engaged position 406. The shell 67 for the implant grip 404 at its interior surface 69 incorporates the projections 83-84 on the basis the implant 215 includes the two legs 232-233 at the first end 223 of the bridge 218. The shell 67 for the implant grip 404 at its interior surface 69 does not incorporate projections 85-86 on the basis the implant 215 includes only the leg 234 at the second end 224 of the bridge 218.

The body 403 as illustrated in FIGS. 32A-32D is substantially similar to the body 63 with the exception of the following. The body 403, which includes the first end 75 defining the handle 76 and the second end 77 defining the implant grip receiver 78 with the tamp 79 and a stop 84, interfaces with the implant grip 404 and the implant 215, whereas the body 63 interfaces with the implant grip 64 and the implant 5. In accordance therewith, the implant grip receiver 78 and thus the first and second sides 80 and 81 and the first and second ends 82 and 83 thereof include a shape complimentary with the implant grip 404, substantially triangular in the fifth embodiment, and, in particular, with the interior surface 69 of the shell 67 whereby the implant grip receiver 78 receives and then retains the implant grip 404 thereon. The tamp 79 includes a configuration, substantially triangular in the fifth embodiment, for engagement with the bridge 218 when the implant 215 resides in its insertion shape 217 or its insertion shape 257. The notches 91 and 92 aid in retaining the shell 67 on the implant grip receiver 78 and further locate the implant grip 404 in either its disengaged position 405 or its engaged position 406. In the fifth embodiment of the implant insertion device 400, the length of the implant grip receiver 78 for the body 403 substantially equals the length of the implant grip 404.

The implant insertion device 400 according to the fifth embodiment loads with the implant 215, constrains the implant 215 in its insertion position 217 or 257, and transitions from its loaded position 402 to its unloaded position 401 thereby delivering the implant 215 to bone, bones, or bone pieces substantially identical to the implant insertion device 60 according to the first embodiment as previously set forth in the detailed description thereof. During loading of the implant insertion device 400 with the implant 215 and a subsequent retention thereof, the tamp 79 of the implant grip receiver 78 for the body 403 sits atop the bridge 218 of the implant 215, while the grooves 71-74 maintain the implant 215 within the implant grip 404 and the retention surfaces 79-82 in each of the grooves 71-74 defined by the shell 67 constrain the legs 232-234 such that the shell 67 holds the implant 215 in its insertion shape 217 or 257. The projections 83-84 of the interior surface 69 by-pass the bridge 218 at its first end 223 via the concave sections 13a and 14a thereof and then frictionally engage a respective leg 232-233 opposite from the segments 241 and 246, thereby assisting in retaining the implant 5 within the shell 67 in its insertion shape 217 or 257. When delivering the implant 175 to bone, bones, or bone pieces, the projections 83-84 of the interior surface 69 by-pass respectively the bridge 218 at its first end 223 via the concave section 223a and insert into the indentation 93 in the implant grip receiver 78, thereby releasing a respective leg 232-233 opposite from the segments 241 and 246. Likewise, the retention surfaces 79-82 disposed in each of the grooves 71-74 respectively release an engagement point 242, 247, 253, and 254 of the legs 232-234, while the grooves 71-74 of the interior surface 69 for the shell 67 respectively disengage from a segment 241, 246, 251, and 253 of the legs 232-234. Moreover, the interior surface 69 of the shell 67 disengages from the first and second sides 221 and 222 of the bridge 218, whereas the interior surface 69 of the shell 67 further by-passes the bridge 218 of the implant 215 at its first and second sides 221 and 222 and its first and second ends 223 and 224 such that the implant 215 exits the passage 70 of the shell 67, resulting in the discharge of the implant 215 from the implant grip 404 and a subsequent attempted transition of the implant 215 from its insertion shape 217 or 257 to its natural shape 216 whereby the implant 215 delivers the energy stored therein to the bone, bones, or bone pieces.

FIGS. 36A-37D illustrate an implant insertion device 500 according to a sixth embodiment that engages the implant 215 and retains the implant 215 in its insertion shape 217 or 257. FIGS. 36A-36D illustrate the implant insertion device 500 in an unloaded position 501 prior to its loading with the implant 215 or after its delivery of the implant 215 whereby the implant 215 releases from the implant insertion device 500 without obstruction. FIGS. 37A-37D illustrate the implant insertion device 500 in a loaded position 502 whereby the implant insertion device 500 may be loaded with the implant 215 such that the implant insertion device 500 retains the implant 215 in its insertion shape 217 or 257. The implant insertion device 500 allows a surgeon to manipulate the implant 215 and insert the implant 215 into bone, bones, or bone pieces requiring fixation. FIGS. 38A-38B illustrate a body 503 of the implant insertion device 500, whereas FIGS. 39A-39B illustrate an implant grip 504 of the implant insertion device 300 that is coupled with the body 503 and is movable relative to the body 503 between a disengaged position 505 shown in FIGS. 36A-36D and an engaged position 506 shown in FIGS. 37A-37D.

The implant insertion device 500 according to the sixth embodiment, including its body 503 and implant grip 504, is substantially similar in design and operation relative to the implant insertion device 100 according to the second embodiment, including its body 103 and implant grip 104, such that, for the sake of brevity, only differences therebetween will be described herein. Moreover, one of ordinary skill in the art will recognize that like parts of the body 503 and the implant grip 504 for the implant insertion device 500 labeled with like numerals of the body 103 and the implant grip 104 for the implant insertion device 100 incorporate a design and function as previously set forth in the detailed description of the implant insertion device 100 according to the second embodiment.

The implant grip 504 as illustrated in FIGS. 38A-38B is substantially similar to the implant grip 104 with the exception of the following. The implant grip 504, which includes the first and second blades 107 and 108 defining the passage 110 therebetween and the actuator 109, interfaces with the implant 215 and the body 503, whereas the implant grip 104 interfaces with the implant 175 and the body 103. In accordance therewith, the first and second blades 107 and 108 at their first faces 111 include a projection 510 extending therefrom, which, in the sixth embodiment, is substantially triangular. The first faces 111 and their projections 510 define the passage 110 whereby the passage 110 is complimentary in shape with the bridge 218 of the implant 215 in order to receive the implant 215 therein. The actuator 109 in the fourth embodiment and, more particularly, the spacer 122 thereof is dimensioned whereby the spacer 122 locates the first and second blades 107 and 108 such that the passage 110 therebetween receives therein the bridge 218 of the implant 215. The passage 110 in the sixth embodiment therefore is dimensioned to receive therein the bridge 218 of the implant 215 whereby the first and second blades 107 and 108 at their leading edges 117 extend beyond the bridge 218 such that the first blade 107 at its first and second sides 115 and 116 respectively abuts the engagement points 242 and 253 of the legs 232 and 234 for the implant 215 and the second blade 108 at its first and second sides 115 and 116 respectively abut the engagement points 247 and 254 of the legs 233 and 234 for the implant 215, thereby constraining the implant 215 in its insertion shape 217 or 257.

The body 503 as illustrated in FIGS. 38A-38B is substantially similar to the body 103 with the exception of the following. The body 503, which includes the first end 145 defining the handle 146 and the second end 147 defining the tamp 148, interfaces with the implant grip 504 and the implant 215, whereas the body 103 interfaces with the implant grip 104 and the implant 5. In accordance therewith, the body 503 is dimensioned relative to the implant 215 such that the tamp 79 is configured to engage the bridge 218 when the implant 215 resides in its insertion shape 217 or its insertion shape 257. Likewise, the body 503 and, more particularly, the slot 151 is dimensioned relative to the implant grip 504 such that the spacer 122 of the actuator 109 inserts into the slot 151 with the spacer 122 oriented whereby its first side 134 and the opening 138 and the channel 139 communicate exterior to the slot 151 at the first surface 149 of the body 503 and its second side 135 and the opening 138 and the channel 139 communicate exterior to the slot 151 at the second surface 150 of the body 503. Moreover, the second stop 155 and the tamp 148 of the body 503 in the sixth embodiment define a triangular shape similar to the bridge 218 of the implant 215 but are dimensioned smaller than the passage 110 between the first and second blades 107 and 108 in order to allow the first and second blades 107 and 108 to by-pass the second stop 155 and the tamp 148 and extend exterior relative to the body 503.

The implant insertion device 500 according to the sixth embodiment loads with the implant 215, constrains the implant 215 in its insertion position 217 or 257, and transitions from its loaded position 502 to its unloaded position 501 thereby delivering the implant 215 to bone, bones, or bone pieces substantially identical to the implant insertion device 100 according to the second embodiment as previously set forth in the detailed description thereof. During loading of the implant insertion device 500 with the implant 215 and a subsequent retention thereof, the tamp 148 of the body 503 sits atop the bridge 218 of the implant 215, while the actuator 109 progresses along the body 503 towards the second stop 155 of the body 503 until the spacer 122 of the actuator 109 at its second end 133 contacts the second stop 155 whereby the actuator 109 extends the first and second blades 107 and 108 exterior to the body 503 such that the first and second blades 107 and 108 at their first and second sides 115 and 116 respectively abut the engagement points 242, 247, 253, and 254 of the legs 232-234 for the implant 215, thereby constraining the implant 215 in its insertion shape 217 or 257. When delivering the implant 215 to bone, bones, or bone pieces, the actuator 109 progresses along the body 503 to the first stop 154 thereof such that the first and second blades 107 and 108 at their first and second sides 115 and 116 respectively release the engagement points 242, 247, 253, and 254 of the legs 232-234 for the implant 215 while, if engaged, the first and second blades 107 and 108 at their first faces 111 also release the bridge 218, resulting in the discharge of the implant 215 from the implant grip 504 and a subsequent attempted transition of the implant 215 from its insertion shape 217 or 257 to its natural shape 216 whereby the implant 215 delivers the energy stored therein to the bone, bones, or bone pieces.

FIGS. 40A-40F illustrate a drill guide 600 according to a first embodiment employed when an implant 5 according to the first embodiment is delivered to bone, bones, or bone pieces during an orthopedic procedure requiring a drilling of drill holes proximate to fixation devices such as fixation pins or wires (e.g., K-wires). The drill guide 600 in the first embodiment includes a body 601, a template 612, and a grip 614.

The body 601 includes a top 602, a bottom 603, first and second ends 604 and 605, and first and second sides 606 and 607. The body 601 further includes first, second, third, and fourth passages 608-611 extending therethrough from its top 602 to its bottom 603. The first and second passages 608-609 are located adjacent the first end 604 of the body 601, whereas the third and fourth passages 610-611 are located adjacent the second end 605 of the body 601. The first and third passages 608 and 610 are located adjacent the first side 606 of the body 601, whereas the second and fourth passages 609 and 611 are located adjacent the second side 607 of the body 601. The first, second, third, and fourth passages 608-611 accordingly include a configuration complementary in shape with the implant 5 and, in particular, with the legs 23-26 thereof whereby the first, second, third, and fourth passages 608-611 assist in the formation of drill holes that facilitate implantation of the implant 5 into bone, bones, or bone pieces.

The template 612 depends from the bottom 603 of the body 601 between the first and second passages 608-609 adjacent the first end 604 of the body 601 and the third and fourth passages 610-611 adjacent the second end 605 of the body 601. The template 612 includes a slot 613 that receives therein a fixation device holding bone, bones, or bone pieces during an orthopedic procedure. The slot 613 divides the template 612 whereby the first and third passages 608 and 610 reside exterior to the slot 613 at a first side 615 thereof and the second and fourth passages 609 and 611 resides exterior to the slot 613 at a second side 616 thereof. As such, when the slot 613 receives a fixation device therein, the first and third passages 608 and 610 are located proximate of the fixation device on one side thereof, whereas the second and fourth passages 609 and 611 are located proximate of the fixation device on an opposite side thereof. The template 612 accordingly through an engagement thereof with the fixation device via its slot 613 secures the body 601 on bone, bones, or bone pieces with the first, second, third, and fourth passages 608-611 proximate to the fixation device whereby drill holes may be formed without contact of the fixation device.

The grip 614 extends from the body 601 at its second end 605. The grip 614 facilitates the locating and then the holding of the drill guide 600 over bone, bones, or bone pieces. Although the grip 614 facilitates the holding of the drill guide 600 over bone, bones, or bone pieces, a frictional engagement between the template 612 and the fixation device at the slot 613 maintains the body 601 on the bone, bones, or bone pieces such that the grip 614 may be released without altering the location of the body 601 on the bone, bones, or bone pieces.

During an orthopedic procedure, the drill guide 600 via its grip 614 situates on bone, bones, or bone pieces with its bottom 603 adjacent the bone, bones, or bone pieces and its template 612 introduced at a fusion zone of the bone, bones, or bone pieces such that its slot 613 receives therein a fixation device inserted into the bone, bones, or bone pieces. The template 612 via its frictional engagement with the fixation device holds the body 601 on the bone, bones, or bone pieces and positions the first passage 608 on the bone, bones, or bone pieces adjacent a first side of the fusion zone proximate to a first side of the fixation device, the second passage 609 on the bone, bones, or bone pieces adjacent the first side of the fusion zone proximate to a second side of the fixation device, the third passage 610 on the bone, bones, or bone pieces adjacent a second side of the fusion zone proximate to the first side of the fixation device, and the fourth passage 611 on the bone, bones, or bone pieces adjacent the second side of the fusion zone proximate of the second side of the fixation device. With the drill guide 600 thus situated on the bone, bones, or bone pieces, drill holes formed in the bone, bones, or bone pieces are positioned on both sides of the fusion zone proximate of the fixation device.

In the first embodiment of the drill guide 600, the first and second passages 608-609 and the third and fourth passages 610-611 are spaced apart a distance substantially equal to the distance between the legs 23-24 or the legs 25-26 of the implant 5 when the implant 5 resides in its insertion position 7 or 53 such that any drill holes formed using the first and second passages 608-609 or the third and fourth passages 610-611 will receive the legs 23-24 or the legs 25-26 of the implant 5 therein. Nevertheless, the first and third passages 608 and 610 and the second and fourth passages 609 and 611 are spaced apart a distance greater than the distance between the legs 23 and 25 or the legs 24 and 26 of the implant 5 when the implant 5 resides in its insertion position 7 or 53 on the basis the introduction of the template 612 into a fusion zone of bone, bones, or bone pieces separates the bone, bones, or bone pieces a distance equal to a thickness 617 of the template 612. In accordance therewith, the distance between the first and third passages 608 and 610 and the second and fourth passages 609 and 611 in the first embodiment of the drill guide 600 substantially equals the distance between the legs 23 and 25 or the legs 24 and 26 of the implant 5 when the implant 5 resides in its insertion position 7 or 53 plus a distance equal to the thickness 617 of the template 612. As such, any drill holes formed using the first and third passages 608 and 610 and the second and fourth passages 609 and 611 will receive the legs 23 and 25 or the legs 24 and 26 of the implant 5 because, after a removal of the template 612 and a compression of the bone, bones, or bone pieces at their fusion zone that reduces the separation thereof by the distance equal to the thickness 617 of the template 612, the drill holes reside a distance substantially equal to the distance between the legs 23 and 25 or the legs 24 and 26 of the implant 5 when the implant 5 resides in its insertion position 7 or 53.

FIG. 41 illustrates a drill guide 630 according to a second embodiment employed when an implant 175 according to the second embodiment is delivered to bone, bones, or bone pieces during an orthopedic procedure requiring a drilling of drill holes proximate to fixation devices such as fixation pins or wires (e.g., K-wires). The drill guide 630 in the second embodiment includes a body 631, a template 632, and a grip 634. The drill guide 630 according to the second embodiment, including its body 631, template 642, and grip 644, is substantially similar in design and operation relative to the drill guide 600 according to the first embodiment, including its body 601, template 612, and grip 614. Moreover, although the body 631 of the drill guide 630 includes two passages, one of ordinary skill in the art will recognize that any like parts of the drill guide 630 incorporate a design and function as previously set forth in the detailed description of the drill guide 600 according to the first embodiment.

The body 631 includes a top 632, a bottom 633, first and second ends 634 and 635, and first and second sides 636 and 637. The body 631 further includes first and second passages 638-639 extending therethrough from its top 632 to its bottom 633. The first passage 638 is located adjacent the first end 634 of the body 631, whereas the second passage 639 is located adjacent the second end 635 of the body 631. The first passage 638 is located adjacent the second side 637 of the body 631, whereas the second passage 639 is located adjacent the first side 636 of the body 631, although one of ordinary skill in the art will recognize that the locations of the first and second passages 638-639 relative to the first and second sides 636-637 may be reversed. The first and second passages 638-639 accordingly include a configuration complementary in shape with the implant 175 and, in particular, with the legs 187-188 thereof whereby the first and second passages 638-639 assist in the formation of drill holes that facilitate implantation of the implant 175 into bone, bones, or bone pieces.

The template 642 depends from the bottom 633 of the body 631 between the first passage 638 adjacent the first end 634 of the body 631 and the second passage 639 adjacent the second end 635 of the body 631. The template 642 includes a slot 643 that receives therein a fixation device holding bone, bones, or bone pieces during an orthopedic procedure. The slot 643 divides the template 642 whereby the second passage 639 resides exterior to the slot 643 at a first side 645 thereof and the first passage 638 resides exterior to the slot 643 at a second side 646 thereof. As such, when the slot 643 receives a fixation device therein, the second passage 639 is located proximate of the fixation device on one side thereof, whereas the first passage 638 is located proximate of the fixation device on an opposite side thereof. The template 642 accordingly through an engagement thereof with the fixation device via its slot 613 secures the body 631 on bone, bones, or bone pieces with the first and second passages 638-639 proximate to the fixation device whereby drill holes may be formed without contact of the fixation device.

The grip 644 extends from the body 631 at its second end 635. The grip 644 facilitates the locating and then the holding of the drill guide 630 over bone, bones, or bone pieces. Although the grip 644 facilitates the holding of the drill guide 630 over bone, bones, or bone pieces, a frictional engagement between the template 642 and the fixation device at the slot 643 maintains the body 631 on the bone, bones, or bone pieces such that the grip 644 may be released without altering the location of the body 631 on the bone, bones, or bone pieces.

During an orthopedic procedure, the drill guide 630 via its grip 644 situates on bone, bones, or bone pieces with its bottom 633 adjacent the bone, bones, or bone pieces and its template 642 introduced at a fusion zone of the bone, bones, or bone pieces such that its slot 643 receives therein a fixation device inserted into the bone, bones, or bone pieces. The template 642 via its frictional engagement with the fixation device holds the body 631 on the bone, bones, or bone pieces and positions the first passage 638 on the bone, bones, or bone pieces adjacent a first side of the fusion zone proximate to a first side of the fixation device and the second passage 639 on the bone, bones, or bone pieces adjacent a second side of the fusion zone proximate to a second side of the fixation device. With the drill guide 630 thus situated on the bone, bones, or bone pieces, drill holes formed in the bone, bones, or bone pieces are positioned on both sides of the fusion zone proximate of the fixation device.

In the second embodiment of the drill guide 630, the first and second passages 638 and 639 are spaced apart a distance greater than the distance between the legs 187 and of the implant 175 when the implant 175 resides in its insertion position 177 or 207 on the basis the introduction of the template 642 into a fusion zone of bone, bones, or bone pieces separates the bone, bones, or bone pieces a distance equal to a thickness 647 of the template 642. In accordance therewith, the distance between the first and second passages 638 and 639 in the second embodiment of the drill guide 630 substantially equals the distance between the legs 187 and 188 of the implant 175 when the implant 175 resides in its insertion position 177 or 207 plus a distance equal to the thickness 647 of the template 642. As such, any drill holes formed using the first and second passages 638 and 639 will receive the legs 187 and 188 of the implant 175 because, after a removal of the template 642 and a compression of the bone, bones, or bone pieces at their fusion zone that reduces the separation thereof by the distance equal to the thickness 647 of the template 642, the drill holes reside a distance substantially equal to the distance between the legs 187 and 188 of the implant 175 when the implant 175 resides in its insertion position 177 or 207.

FIG. 42 illustrates a drill guide 650 according to a third embodiment employed when an implant 215 according to the third embodiment is delivered to bone, bones, or bone pieces during an orthopedic procedure requiring a drilling of drill holes proximate to fixation devices such as fixation pins or wires (e.g., K-wires). The drill guide 650 in the third embodiment includes a body 651, a template 662, and a grip 664. The drill guide 650 according to the third embodiment, including its body 651, template 662, and grip 664, is substantially similar in design and operation relative to the drill guide 600 according to the first embodiment, including its body 601, template 612, and grip 614. Moreover, although the body 651 of the drill guide 650 includes three passages, one of ordinary skill in the art will recognize that any like parts of the drill guide 650 incorporate a design and function as previously set forth in the detailed description of the drill guide 600 according to the first embodiment.

The body 651 includes a top 652, a bottom 653, first and second ends 654 and 655, and first and second sides 656 and 657. The body 651 further includes first, second, and third passages 658-660 extending therethrough from its top 652 to its bottom 653. The first and second passages 658 and 659 are located adjacent the first end 654 of the body 651, whereas the third passage 660 is located adjacent the second end 655 of the body 651.

The first and third passages 658 and 660 are located adjacent the first side 656 of the body 651, whereas the second passage 659 is located adjacent the second side 657 of the body 651, although one of ordinary skill in the art will recognize that the location of the third passage 660 may be moved to the second side 657. The first, second, and third passages 658-660 accordingly include a configuration complementary in shape with the implant 217 and, in particular, with the legs 232-234 thereof whereby the first, second, and third passages 658-660 assist in the formation of drill holes that facilitate implantation of the implant 217 into bone, bones, or bone pieces.

The template 662 depends from the bottom 653 of the body 651 between the first and second passages 658-659 adjacent the first end 654 of the body 651 and the third passage 660 adjacent the second end 655 of the body 651. The template 662 includes a slot 663 that receives therein a fixation device holding bone, bones, or bone pieces during an orthopedic procedure. The slot 663 divides the template 662 whereby the first and third passages 658 and 660 reside exterior to the slot 663 at a first side 665 thereof and the second passage 659 resides exterior to the slot 663 at a second side 666 thereof. As such, when the slot 663 receives a fixation device therein, the first and third passages 658 and 660 are located proximate of the fixation device on one side thereof, whereas the second passage 659 is located proximate of the fixation device on an opposite side thereof. The template 662 accordingly through an engagement thereof with the fixation device via its slot 663 secures the body 651 on bone, bones, or bone pieces with the first, second, and third passages 658-660 proximate to a fixation device whereby drill holes may be formed without contact of the fixation device.

The grip 664 extends from the body 651 at its second end 655. The grip 664 facilitates the locating and then the holding of the drill guide 650 over bone, bones, or bone pieces. Although the grip 664 facilitates the holding of the drill guide 650 over bone, bones, or bone pieces, a frictional engagement between the template 662 and the fixation device at the slot 663 maintains the body 651 on the bone, bones, or bone pieces such that the grip 664 may be released without altering the location of the body 651 on the bone, bones, or bone pieces.

During an orthopedic procedure, the drill guide 650 via its grip 664 situates on bone, bones, or bone pieces with its bottom 653 adjacent the bone, bones, or bone pieces and its template 662 introduced at a fusion zone of the bone, bones, or bone pieces such that its slot 664 receives therein a fixation device inserted into the bone, bones, or bone pieces. The template 662 via its frictional engagement with the fixation device holds the body 651 on the bone, bones, or bone pieces and positions the first passage 658 on the bone, bones, or bone pieces adjacent a first side of the fusion zone proximate to a first side of the fixation device, the second passage 659 on the bone, bones, or bone pieces adjacent the first side of the fusion zone proximate to a second side of the fixation device, and the third passage 660 on the bone, bones, or bone pieces adjacent a second side of the fusion zone proximate to the first side of the fixation device. With the drill guide 650 thus situated on the bone, bones, or bone pieces, drill holes formed in the bone, bones, or bone pieces are positioned on both sides of the fusion zone proximate of the fixation device.

In the third embodiment of the drill guide 650, the first and second passages 658-659 are spaced apart a distance substantially equal to the distance between the legs 232-233 of the implant 215 when the implant 215 resides in its insertion position 217 or 257 such that any drill holes formed using the first and second passages 658-659 will receive the legs 232-223 of the implant 215 therein. Nevertheless, the first and second passages 658-659 are spaced apart from the third passage 660 a distance greater than the distance between the legs 232-233 and the leg 234 of the implant 215 when the implant 215 resides in its insertion position 217 or 257 on the basis the introduction of the template 662 into a fusion zone of bone, bones, or bone pieces separates the bone, bones, or bone pieces a distance equal to a thickness 667 of the template 662. In accordance therewith, the distance between the first and second passages 658-659 and the third passage 660 in the third embodiment of the drill guide 650 substantially equals the distance between the legs 232-233 and the legs 234 of the implant 215 when the implant 215 resides in its insertion position 217 or 257 plus a distance equal to the thickness 667 of the template 662. As such, any drill holes formed using the first and second passages 658-659 and the third passage 660 will receive the legs 232-233 and the legs 234 of the implant 215 because, after a removal of the template 662 and a compression of the bone, bones, or bone pieces at their fusion zone that reduces the separation thereof by the distance equal to the thickness 667 of the template 662, the drill holes reside a distance substantially equal to the distance between the legs 232-233 and the legs 234 of the implant 215 when the implant 215 resides in its insertion position 217 or 257.

FIGS. 43A-43F illustrate a drill guide 900 according to a fourth embodiment employed when an implant 5 according to the first embodiment is delivered to bone, bones, or bone pieces during an orthopedic procedure requiring a drilling of drill holes proximate to fixation devices such as fixation pins or wires (e.g., K-wires). The drill guide 900 in the fourth embodiment includes a body 901, first and second templates 912 and 922, and first and second grips 914 and 924.

The body 901 includes a top 902, a bottom 903, first and second ends 904 and 905, and first and second sides 906 and 907. The body 901 further includes first, second, third, and fourth passages 908-911 extending therethrough from its top 902 to its bottom 903. The first and second passages 908-909 are located adjacent the first end 904 of the body 901, whereas the third and fourth passages 910-911 are located adjacent the second end 905 of the body 901. The first and third passages 908 and 910 are located adjacent the first side 906 of the body 901, whereas the second and fourth passages 909 and 911 are located adjacent the second side 907 of the body 901. The first, second, third, and fourth passages 908-911 accordingly include a configuration complementary in shape with the implant 5 and, in particular, with the legs 23-26 thereof whereby the first, second, third, and fourth passages 908-911 assist in the formation of drill holes that facilitate implantation of the implant 5 into bone, bones, or bone pieces.

The first grip 914 extends from the body 901 at its first end 904. Similarly, the second grip 924 extends from the body 901 at its second end 905. The first and second grips 914 and 924 facilitate the locating and then the holding of the drill guide 900 over bone, bones, or bone pieces.

The first template 912 depends from the first grip 914 in a position opposite to the first end 904 and beneath the bottom 903 of the body 901. The second template 922 depends from the second grip 924 in a position opposite to the second end 905 and beneath the bottom 903 of the body 901. The first and second templates 912 and 922 respectively include slots 913 and 923 that receive therein a fixation device holding bone, bones, or bone pieces during an orthopedic procedure. The slots 913 and 923 divide respectively the first and second templates 912 and 922 whereby the first and third passages 908 and 910 reside exterior to the slots 913 and 923 at first sides 915 and 925 thereof and the second and fourth passages 909 and 911 resides exterior to the slots 913 and 923 at second sides 916 and 926 thereof. As such, when the slots 913 and 923 receive a fixation device therein, the first and third passages 908 and 910 are located proximate of the fixation device on one side thereof, whereas the second and fourth passages 909 and 911 are located proximate of the fixation device on an opposite side thereof. The first and second templates 912 and 922 accordingly through an engagement thereof with the fixation device via respective slots 913 and 923 secure the body 901 on bone, bones, or bone pieces with the first, second, third, and fourth passages 908-911 proximate to the fixation device whereby drill holes may be formed without contact of the fixation device. While the first and second grips 914 and 922 facilitate the holding of the drill guide 900 over bone, bones, or bone pieces, a frictional engagement between the first and second templates 912 and 922 and the fixation device at the slots 913 and 923 maintains the body 901 on the bone, bones, or bone pieces such that the first and second grips 914 and 922 may be released without altering the location of the body 901 on the bone, bones, or bone pieces.

During an orthopedic procedure, the drill guide 900 via its first and second grips 914 and 924 situates on bone, bones, or bone pieces at a fusion zone thereof with its bottom 903 adjacent the bone, bones, or bone pieces and its first and second templates 912 and 922 located at opposite sides of the bone, bones, or bone pieces such that its slots 913 and 923 receive therein a fixation device inserted into the bone, bones, or bone pieces. The first and second templates 912 and 922 via their frictional engagement with the fixation device holds the body 901 on the bone, bones, or bone pieces and positions the first passage 908 on the bone, bones, or bone pieces adjacent a first side of the fusion zone proximate to a first side of the fixation device, the second passage 909 on the bone, bones, or bone pieces adjacent the first side of the fusion zone proximate to a second side of the fixation device, the third passage 910 on the bone, bones, or bone pieces adjacent a second side of the fusion zone proximate to the first side of the fixation device, and the fourth passage 911 on the bone, bones, or bone pieces adjacent the second side of the fusion zone proximate of the second side of the fixation device. With the drill guide 900 thus situated on the bone, bones, or bone pieces, drill holes formed in the bone, bones, or bone pieces are positioned on both sides of the fusion zone proximate of the fixation device.

In the fourth embodiment of the drill guide 900, the first and second passages 908-909 and the third and fourth passages 910-911 are spaced apart a distance substantially equal to the distance between the legs 23-24 or the legs 25-26 of the implant 5 when the implant 5 resides in its insertion position 7 or 53 such that any drill holes formed using the first and second passages 908-909 or the third and fourth passages 910-911 will receive the legs 23-24 or the legs 25-26 of the implant 5 therein. Likewise, the first and third passages 908 and 910 and the second and fourth passages 909 and 911 are spaced apart a distance substantially equal to the distance between the legs 23 and 25 or the legs 24 and 26 of the implant 5 when the implant 5 resides in its insertion position 7 or 53 such that any drill holes formed using the first and third passages 908 and 910 or the second and fourth passages 909 and 911 will receive the legs 23 and 25 or the legs 24 and 26 of the implant 5 therein.

FIG. 44 illustrates a drill guide 930 according to a fifth embodiment employed when an implant 175 according to the second embodiment is delivered to bone, bones, or bone pieces during an orthopedic procedure requiring a drilling of drill holes proximate to fixation devices such as fixation pins or wires (e.g., K-wires). The drill guide 930 in the fifth embodiment includes a body 931, first and second templates 940 and 942, and first and second grips 944 and 945. The drill guide 930 according to the fifth embodiment, including its body 931, first and second templates 940 and 942, and first and second grips 944 and 945, is substantially similar in design and operation relative to the drill guide 900 according to the fourth embodiment, including its body 901, first and second templates 912 and 922, and first and second grips 914 and 924. Moreover, although the body 931 of the drill guide 930 includes two passages, one of ordinary skill in the art will recognize that any like parts of the drill guide 930 incorporate a design and function as previously set forth in the detailed description of the drill guide 900 according to the fourth embodiment.

The body 931 includes a top 932, a bottom 933, first and second ends 934 and 935, and first and second sides 936 and 937. The body 931 further includes first and second passages 938-939 extending therethrough from its top 932 to its bottom 933. The first passage 938 is located adjacent the first end 934 of the body 931, whereas the second passage 939 is located adjacent the second end 935 of the body 931. The first passage 938 is located adjacent the second side 937 of the body 931, whereas the second passage 939 is located adjacent the first side 936 of the body 931, although one of ordinary skill in the art will recognize that the locations of the first and second passages 938-939 relative to the first and second sides 936-937 may be reversed. The first and second passages 938-939 accordingly include a configuration complementary in shape with the implant 175 and, in particular, with the legs 187-188 thereof whereby the first and second passages 938-939 assist in the formation of drill holes that facilitate implantation of the implant 175 into bone, bones, or bone pieces.

The first grip 944 extends from the body 931 at its first end 934. Similarly, the second grip 945 extends from the body 931 at its second end 935. The first and second grips 944 and 945 facilitate the locating and then the holding of the drill guide 930 over bone, bones, or bone pieces.

The first template 940 depends from the first grip 944 in a position opposite to the first end 934 and beneath the bottom 933 of the body 931. The second template 942 depends from the second grip 945 in a position opposite to the second end 935 and beneath the bottom 933 of the body 931. The first and second templates 940 and 942 respectively include slots 941 and 943 that receive therein a fixation device holding bone, bones, or bone pieces during an orthopedic procedure. The slots 941 and 943 divide respectively the first and second templates 940 and 942 whereby the second passage 639 resides exterior to the slots 941 and 943 at first sides 946 and 948 thereof and the first passage 638 resides exterior to the slots 941 and 943 at second sides 947 and 949 thereof. As such, when the slots 941 and 943 receive a fixation device therein, the second passage 639 is located proximate of the fixation device on one side thereof, whereas the first passage 638 is located proximate of the fixation device on an opposite side thereof. The first and second templates 940 and 942 accordingly through an engagement thereof with the fixation device via respective slots 941 and 943 secure the body 931 on bone, bones, or bone pieces with the first and second passages 638-639 proximate to the fixation device whereby drill holes may be formed without contact of the fixation device. While the first and second grips 944 and 945 facilitate the holding of the drill guide 930 over bone, bones, or bone pieces, a frictional engagement between the first and second templates 940 and 942 and the fixation device at the slots 941 and 943 maintains the body 931 on the bone, bones, or bone pieces such that the first and second grips 944 and 945 may be released without altering the location of the body 931 on the bone, bones, or bone pieces.

During an orthopedic procedure, the drill guide 930 via its first and second grips 944 and 945 situates on bone, bones, or bone pieces at a fusion zone thereof with its bottom 933 adjacent the bone, bones, or bone pieces and its first and second templates 940 and 942 located at opposite sides of the bone, bones, or bone pieces such that its slots 941 and 943 receive therein a fixation device inserted into the bone, bones, or bone pieces. The first and second templates 940 and 942 via their frictional engagement with the fixation device holds the body 931 on the bone, bones, or bone pieces and positions the first passage 938 on the bone, bones, or bone pieces adjacent a first side of the fusion zone proximate to a first side of the fixation device and the second passage 939 on the bone, bones, or bone pieces adjacent a second side of the fusion zone proximate to a second side of the fixation device. With the drill guide 930 thus situated on the bone, bones, or bone pieces, drill holes formed in the bone, bones, or bone pieces are positioned on both sides of the fusion zone proximate of the fixation device. In the fifth embodiment of the drill guide 930, the first and second passages 938 and 939 are spaced apart a distance substantially equal to the distance between the legs 187 and 188 of the implant 175 when the implant 175 resides in its insertion position 177 or 207 such that any drill holes formed using the first and second passages 938 and 939 will receive the legs 187 and 188 of the implant 175 therein.

FIG. 45 illustrates a drill guide 950 according to a sixth embodiment employed when an implant 215 according to the third embodiment is delivered to bone, bones, or bone pieces during an orthopedic procedure requiring a drilling of drill holes proximate to fixation devices such as fixation pins or wires (e.g., K-wires). The drill guide 950 in the fifth embodiment includes a body 951, first and second templates 961 and 963, and first and second grips 965 and 966. The drill guide 950 according to the sixth embodiment, including its body 951, first and second templates 961 and 963, and first and second grips 965 and 966, is substantially similar in design and operation relative to the drill guide 900 according to the fourth embodiment, including its body 901, first and second templates 912 and 922, and first and second grips 914 and 924. Moreover, although the body 931 of the drill guide 930 includes three passages, one of ordinary skill in the art will recognize that any like parts of the drill guide 950 incorporate a design and function as previously set forth in the detailed description of the drill guide 900 according to the fourth embodiment.

The body 951 includes a top 952, a bottom 953, first and second ends 954 and 955, and first and second sides 956 and 957. The body 951 further includes first, second, and third passages 958-960 extending therethrough from its top 952 to its bottom 953. The first and second passages 958 and 959 are located adjacent the first end 954 of the body 951, whereas the third passage 960 is located adjacent the second end 955 of the body 951. The first and third passages 958 and 960 are located adjacent the first side 956 of the body 951, whereas the second passage 959 is located adjacent the second side 957 of the body 951, although one of ordinary skill in the art will recognize that the location of the third passage 960 may be moved to the second side 957. The first, second, and third passages 958-960 accordingly include a configuration complementary in shape with the implant 217 and, in particular, with the legs 232-234 thereof whereby the first, second, and third passages 958-960 assist in the formation of drill holes that facilitate implantation of the implant 217 into bone, bones, or bone pieces.

The first grip 965 extends from the body 951 at its first end 954. Similarly, the second grip 966 extends from the body 951 at its second end 955. The first and second grips 965 and 966 facilitate the locating and then the holding of the drill guide 950 over bone, bones, or bone pieces.

The first template 961 depends from the first grip 965 in a position opposite to the first end 954 and beneath the bottom 953 of the body 951. The second template 963 depends from the second grip 966 in a position opposite to the second end 955 and beneath the bottom 953 of the body 951. The first and second templates 961 and 963 respectively include slots 962 and 964 that receive therein a fixation device holding bone, bones, or bone pieces during an orthopedic procedure. The slots 962 and 964 divide respectively the first and second templates 961 and 963 whereby the first and third passages 958 and 960 reside exterior to the slots 962 and 964 at first sides 967 and 969 thereof and the second passage 959 resides exterior to the slots 962 and 964 at second sides 968 and 970 thereof. As such, when the slots 962 and 964 receive a fixation device therein, the first and third passages 658 and 660 are located proximate of the fixation device on one side thereof, whereas the second passage 659 is located proximate of the fixation device on an opposite side thereof. The first and second templates 961 and 963 accordingly through an engagement thereof with the fixation device via respective slots 962 and 964 secure the body 951 on bone, bones, or bone pieces with the first, second, and third passages 958-660 proximate to a fixation device whereby drill holes may be formed without contact of the fixation device. While the first and second grips 965 and 966 facilitate the holding of the drill guide 950 over bone, bones, or bone pieces, a frictional engagement between the first and second templates 961 and 963 and the fixation device at the slots 961 and 964 maintains the body 951 on the bone, bones, or bone pieces such that the first and second grips 965 and 966 may be released without altering the location of the body 951 on the bone, bones, or bone pieces.

During an orthopedic procedure, the drill guide 950 via its first and second grips 965 and 966 situates on bone, bones, or bone pieces at a fusion zone thereof with its bottom 953 adjacent the bone, bones, or bone pieces and its first and second templates 961 and 963 located at opposite sides of the bone, bones, or bone pieces such that its slots 962 and 964 receive therein a fixation device inserted into the bone, bones, or bone pieces. The first and second templates 961 and 963 via their frictional engagement with the fixation device holds the body 951 on the bone, bones, or bone pieces and positions the first passage 958 on the bone, bones, or bone pieces adjacent a first side of the fusion zone proximate to a first side of the fixation device, the second passage 659 on the bone, bones, or bone pieces adjacent the first side of the fusion zone proximate to a second side of the fixation device, and the third passage 660 on the bone, bones, or bone pieces adjacent a second side of the fusion zone proximate to the first side of the fixation device. With the drill guide 950 thus situated on the bone, bones, or bone pieces, drill holes formed in the bone, bones, or bone pieces are positioned on both sides of the fusion zone proximate of the fixation device.

In the sixth embodiment of the drill guide 950, the first and second passages 658-659 are spaced apart a distance substantially equal to the distance between the legs 232-233 of the implant 215 when the implant 215 resides in its insertion position 217 or 257 such that any drill holes formed using the first and second passages 658-659 will receive the legs 232-223 of the implant 215 therein. Likewise, the first and second passages 958 and 959 are spaced apart from the third passage 960 a distance substantially equal to the distance between the legs 232-233 and the leg 234 of the implant 215 when the implant 215 resides in its insertion position 217 or 257 such that any drill holes formed using the first, second, and third passages 958-960 will receive the legs 232-234 of the implant 215 therein.

Figure 46:
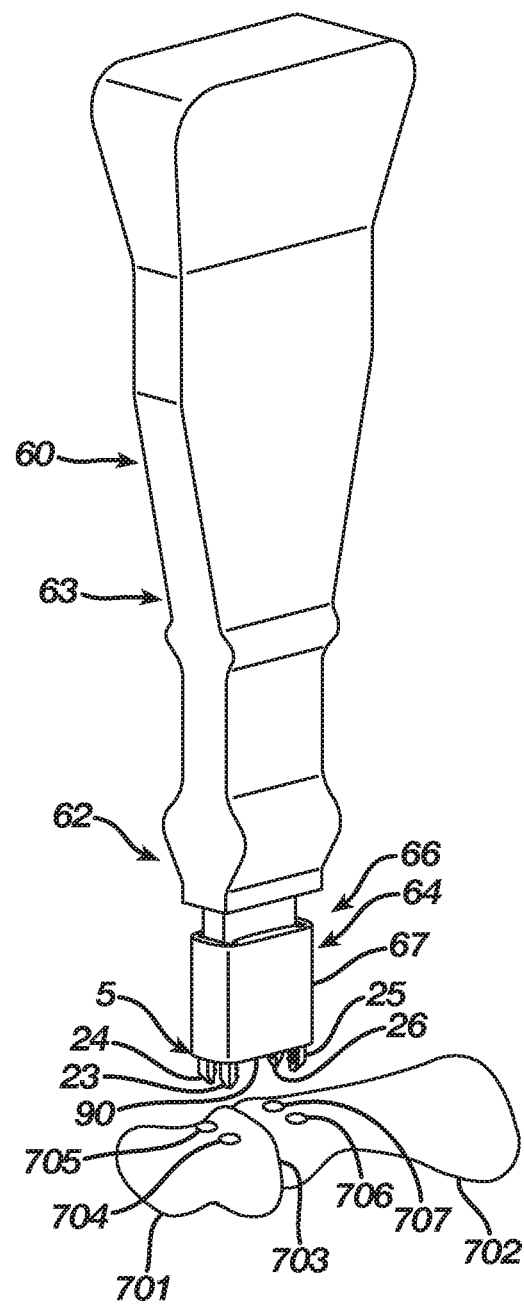

FIG. 46 illustrates the implant insertion device 60 with the implant 5 of the first embodiment loaded thereon in an orthopedic fixation system whereby the implant insertion device 60 retains the implant 5 in its insertion shape 7 or 53 such that the implant 5 is ready for implantation into bone, bones, or bone pieces, and, in particular, into a first bone 701 and a second bone 702, which are presented herein as an example. A surgeon as illustrated in FIG. 46 aligns the first bone 701 with the second bone 702 at a fusion zone 703 in an orientation that promotes fixation of the first bone 701 with the second bone 702 and a proper healing thereof. The surgeon then drills first and second holes 704 and 705 in the first bone 701 and third and fourth holes 706 and 707 in the second bone 702. The first, second, third, and fourth holes 704-707 are drilled at spacings and locations desired for insertion of the legs 23 and 24 into the first bone 701 and the legs 25 and 26 into the second bone 702 with the bridge 8 spanning the fusion zone 703 when the implant 5 resides in its insertion shape 7 or 53. While not required, the surgeon may create grooves in the first and second bones 701 and 702 that facilitate a more flush seating of the bridge 8 for the implant 5 relative to the first and second bones 701 and 702. The surgeon next utilizes the implant insertion device 60 to position the tip 27 of the leg 23 for the implant 5 adjacent the pre-drilled hole 704, the tip 28 of the leg 24 for the implant 5 adjacent the pre-drilled hole 705, the tip 29 of the leg 25 for the implant 5 adjacent the pre-drilled hole 706, and the tip 30 of the leg 26 for the implant 5 adjacent the pre-drilled hole 707.

Figure 47:
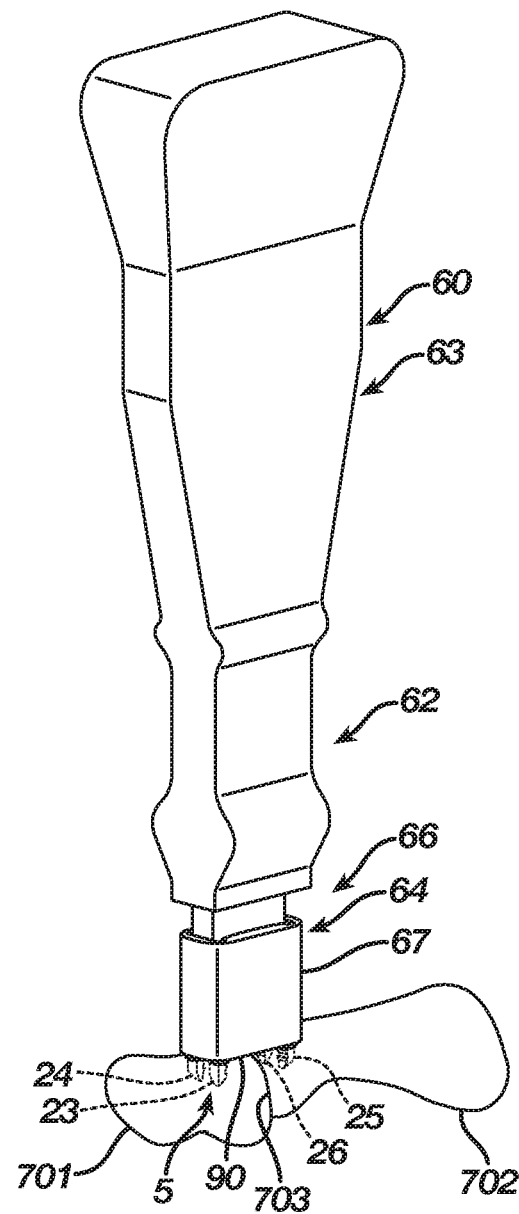

The surgeon as illustrated in FIG. 47 maneuvers the implant insertion device 60 using its body 63 such that the legs 23-26 respectively enter the pre-drilled holes 704-707. The surgeon further manipulates the implant insertion device 60 to insert the legs 23-26 respectively into the pre-drilled holes 704-707 until the implant grip 64 resides on the first and second bones 701 and 702. More particularly, the surgeon pushes on the body 63 resulting in the tamp 79 of the body 63 via its contact with the bridge 8 of the implant 5 pushing on the bridge 8, which, in turn, transfers the pushing force to the legs 23-26 and respectively inserts the legs 23-26 into the pre-drilled holes 704-707 until the lower surface 90 of the shell 67 for the implant grip 64 abuts the first and second bones 701 and 702 exterior of the first, second, third, and fourth holes 704-707.

Figure 48:
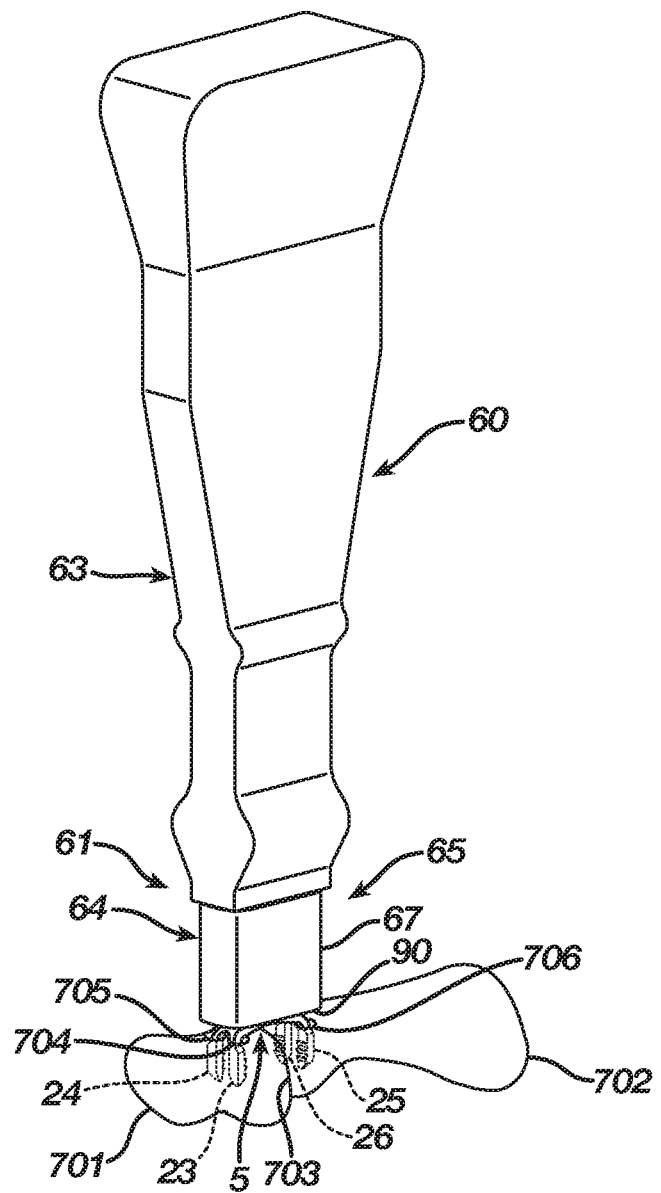

The surgeon as illustrated in FIG. 48 continues manipulating the implant insertion device 60 to insert the legs 23-26, via the tamp 79 and its transfer of the pushing force to the legs 23-26, until the implant 5 at its bridge 8 resides adjacent the first and second bones 701 and 702 across the fusion zone 703 thereof, and, in particular, until the bridge 8 abuts the first and second bones 701 and 702. The surgeon concurrently progresses the implant grip 64 from its engaged position 66 to its disengaged position 65, thereby releasing the implant 5 from the implant insertion device 60. Progression of the implant grip 64 from its engaged position 66 to its disengaged position 65 involves the pushing force also being applied to the implant grip 64 due to the contact thereof with the first and second bones 701 and 702 at the lower surface 90 of its shell 67. The shell 67 accordingly moves along the implant grip receiver 78 of the body 63 until the shell 67 at its upper surface 89 abuts the stop 84 adjacent the implant grip receiver 78, resulting in the detents 88 and 89 disengaging from the notches 92 and respectively sliding into the notches 91 thereby locking the implant grip 64 in its disengaged position 65. If desired, progression of the implant grip 64 from its engaged position 66 to its disengaged position 65 may include the surgeon pulling on the implant grip 64 while inserting the legs 23-26 respectively into the first and second bones 701 and 702.

The tamp 79 of the implant grip receiver 78 for the body 63 remains atop the bridge 8 of the implant 5 to prevent movement of the implant 5 relative to the implant grip 64 during progression of the implant grip 64 from its engaged position 66 to its disengaged position 65. As a consequence, the projections 83-86 of the interior surface 69, when the implant grip 64 moves from its engaged position 66 to its disengaged position 65, by-pass respectively the bridge 8 at its first and second ends 13 and 14 via the concave sections 13a and 14a thereby releasing a respective leg 23-26 opposite from the segments 34, 39, 44, and 49. The projections 83-86 insert into the indentations 93 and 94 in the implant grip receiver 78 to prevent the projections 83-86 from impeding movement of the implant grip 64 relative to the implant grip receiver 78 such that the tamp 79 ultimately reaches a position adjacent the lower surface 90 of the shell 67. Similarly, the retention surfaces 79-82 disposed in each of the grooves 71-74 respectively release an engagement point 35, 40, 44, and 50 of the legs 23-26, while the grooves 71-74 of the interior surface 69 for the shell 67 respectively disengage from a segment 34, 39, 44, and 49 of the legs 23-26. Moreover, the interior surface 69 of the shell 67 disengages from the first and second sides 11 and 12 of the bridge 8 at their concave sections 11a and 12a, whereas the interior surface 69 of the shell 67 further by-passes the bridge 8 of the implant 5 at its first and second sides 11 and 12 and its first and second ends 13 and 14 such that the implant 5 exits the passage 70 of the shell 67, resulting in the discharge of the implant 5 from the implant grip 64. While an insertion of the implant 5 typically includes pre-drilling of the first, second, third, and fourth holes 704-707, the surgeon may use the implant insertion device 60 to impact the legs 23-26 respectively into the first and second bones 701 and 702 at a desired location.

Figure 49:
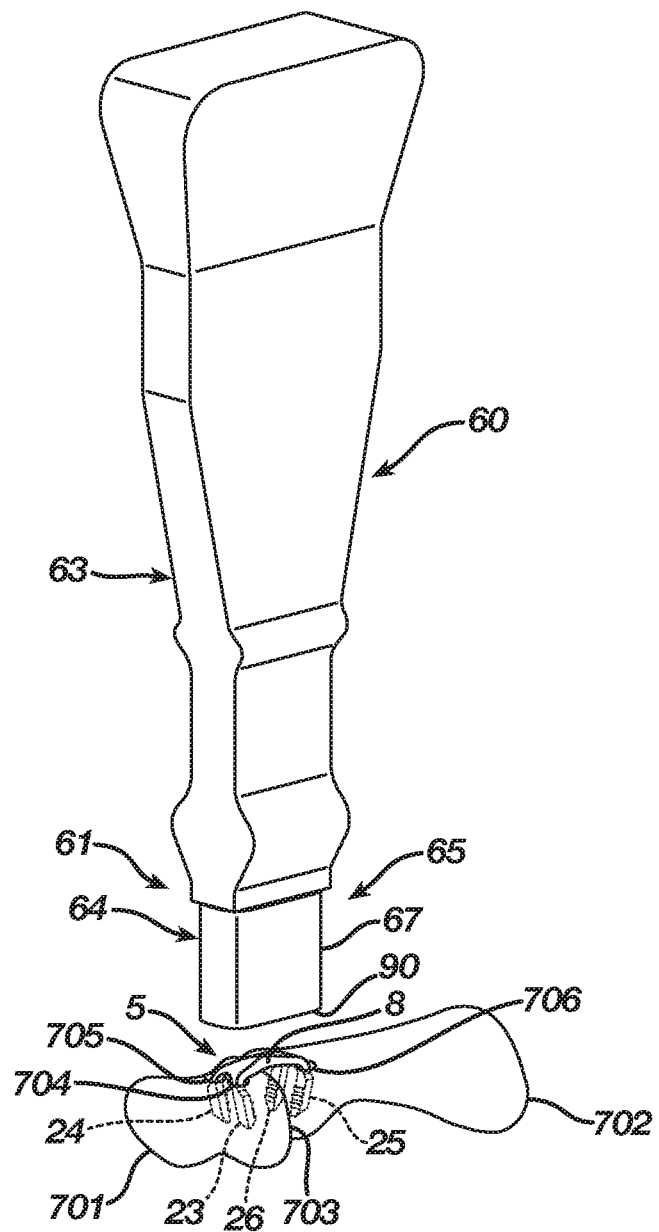

Once the surgeon implants the implant 5 into the first and second bones 701 and 702 with its bridge 8 spanning the fusion zone 703 using the implant insertion device 60, including the implant insertion device 60 traversing to its unloaded position 61, whereby the implant grip 64 in its disengaged position 65 releases the implant 5, the surgeon as illustrated in FIG. 49 removes the implant insertion device 60 from the implant 5, which includes removal of the shell 67 away from the implant 5 and the tamp 79 from atop the bridge 8. The implant 5, due to its superelastic or temperature dependent properties, delivers the energy stored in the transition sections 15-18 and/or the transition section 51 such that the bridge 8 attempts to transition from its insertion form to its natural form, resulting in the legs 23-26 attempting to move from their insertion position to their natural position, whereby the implant 5 affixes the first bone 701 and the second bone 702 through an application of a compressive force to the fixation zone 703.

The implant insertion device 60 accordingly improves insertion of the implant 5 because the implant insertion device 60 does not release its constraint of the implant 5 until the legs 23-26 of the implant 5 fully insert respectively into the first, second, third, and fourth holes 704-707 of the first and second bones 701 and 702 and the bridge 8 of the implant 5 completely seats flush atop the first and second bones 701 and 702. As such, the implant insertion device 60 eliminates an extra tamping step that may not practical or possible, may cause damage to the implant 5, or may cause a failure in the first and second bones 701 and 702. Moreover, the implant insertion device 60 prevents the implant 5 from prematurely delivering the energy stored therein to the first and second bones 701 and 702 at the fixation zone 703 thereof.

When implanting the implant 5 into the first and second bones 701 and 702 utilizing the implant insertion device 100, one of ordinary skill in the art will recognize that the implant insertion device 100 operates substantially similar with respect to the implantation of the implant 5 using the implant insertion device 60 as previously described except that the implant grip 104 for the implant insertion device 100, which includes the actuator 109 and the first and second blades 107 and 108 that contact the first and second bones 701 and 702, facilitates delivery of the implant 5 to first and second bones 701 and 702. Alternatively, when implanting the implant 175 utilizing the implant insertion device 208 or the implant 215 utilizing the implant insertion device 400, one of ordinary skill in the art will recognize that the implant insertion devices 208 or 400 operate substantially similar with respect to the implantation of the implant 5 using the implant insertion device 60 as previously described except that the number of pre-drilled holes will correspond in location, spacing, and number based upon the configuration and number of legs for the implants 175 and 215. Moreover, when implanting the implant 175 utilizing the implant insertion device 300 or the implant 215 utilizing the implant insertion device 500, one of ordinary skill in the art will recognize that the implant insertion devices 300 and 500 operate substantially similar with respect to the implantation of the implant 5 using the implant insertion device 60 as previously described except that the implant grips 304 and 504 for the implant insertion devices 300 and 500, which include respectively the actuators 109 and the first and second blades 107 and 108 that contact the first and second bones 701 and 702, facilitate delivery of the implant 175 or 215 to first and second bones 701 and 702 and that the number of pre-drilled holes will correspond in location, spacing, and number based upon the configuration and number of legs for the implants 175 and 215.

FIGS. 50A-54 illustrate use of the drill guide 600 according to the first embodiment in combination with an orthopedic fixation system that implants an implant into bone, bones, or bone pieces, and, in particular, into a first bone 801 and a second bone 802, which are presented herein as an example. While FIGS. 50A-54 illustrate the drill guide 600 used with an implant insertion device 60 retaining an implant 5 in its insertion shape 7 or 53, one of ordinary skill in the art will recognize that the drill guide 600 may be used with any four-legged implant and alternative techniques or implant insertion devices.

Figure 50A:
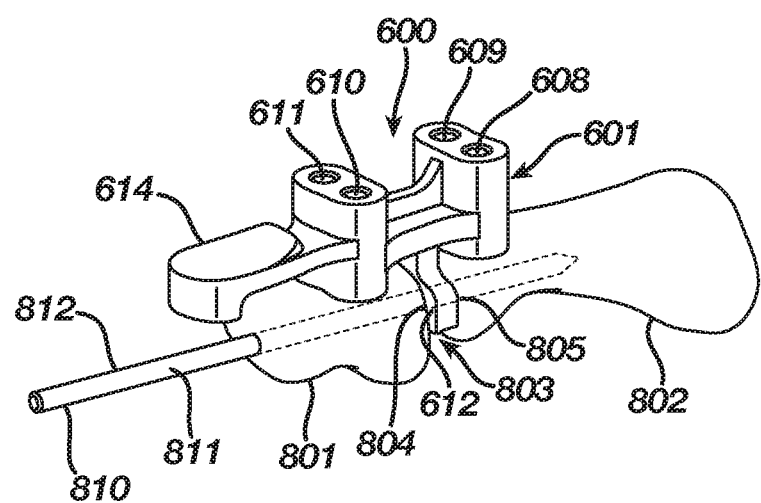
Figure 50B:
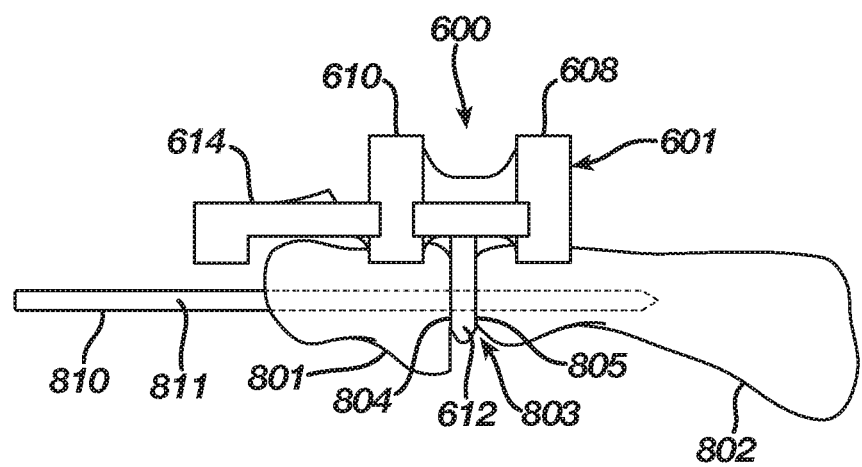

A surgeon as illustrated in FIGS. 50A-50B aligns the first bone 801 with the second bone 802 at a fusion zone 803 in an orientation that promotes fixation of the first bone 801 with the second bone 802 and a proper healing thereof. After aligning the first bone 801 with the second bone 802 at the fusion zone 803 thereof, the surgeon introduces a fixation device into the first bone 801 and the second bone 802. Illustratively, the surgeon inserts a K-wire 810 through the first bone 801 and into the second bone 802 whereby the K-wire 810 spans the fixation zone 803 and secures the first bone 801 with the second bone 802 in the orientation that promotes the proper healing thereof. The surgeon then situates the drill guide 600 on the first bone 801 and the second bone 802 across the fusion zone 803. More particularly, the surgeon using the grip 614 of the drill guide 600 places the body 601 of the drill guide 600 on the first bone 801 and the second bone 802 across the fusion zone 803 with its bottom 603 abutting the first and second bones 801 and 802 and inserts the template 612 of the drill guide 600 into the fusion zone 803 between the first bone 801 and the second bone 802 such that the slot 613 of the template 612 receives therein the K-wire 810. The template 612 via its insertion into the fusion zone 803 and engagement with the K-wire 810 secures the body 601 of the drill guide 600 on the first and second bones 801 and 802 and positions the third passage 610 of the body 601 on the first bone 801 adjacent a first side 804 of the fusion zone 803 proximate to a first side 811 of the K-wire 810, the fourth passage 611 on the first bone 801 adjacent the first side 804 of the fusion zone 803 proximate to a second side 812 of the K-wire 810, the first passage 608 on the second bone 802 adjacent a second side 805 of the fusion zone 803 proximate to the first side 811 of the K-wire 810, and the second passage 609 on the second bone 802 adjacent the second side 805 of the fusion zone 803 proximate to the second side 812 of the K-wire 810.

With the body 601 of the drill guide 600 thus situated on the first and second bones 801 and 802 including the template 612 of the drill guide 600 inserted between the first bone 801 and the second bone 802 and engaged with the K-wire 810, the surgeon drills a first hole 806 in the first bone 801 adjacent the first side 804 of the fusion zone 803 proximate to the first side 811 of the K-wire 810, a second hole 807 in the first bone 801 adjacent the first side 804 of the fusion zone 803 proximate to the second side 812 of the K-wire 810, a third hole 808 in the second bone 802 adjacent the second side 805 of the fusion zone 803 proximate to the first side 811 of the K-wire 810, and a fourth hole 809 in the second bone 802 adjacent the second side 805 of the fusion zone 803 proximate of the second side 812 of the K-wire 810. The drill guide 600 accordingly facilitates the drilling of the first, second, third, and fourth drill holes 806-809 in close proximity to the K-wire 810 while preventing a drill bit of a drill used in forming the first, second, third, and fourth drill holes 806-809 from striking the K-wire 810. Although the insertion of the template 613 into the fusion zone 803 separates the first bone 801 from the second bone 802, the first bone 801 remains aligned with the second bone 802 in the orientation that promotes their fixation and proper healing due to the insertion of the K-wire 810 into the first and second bones 801 and 802 spanning the fusion zone 803 and its engagement with the template 613 via the slot 613 thereof.

Figure 51:
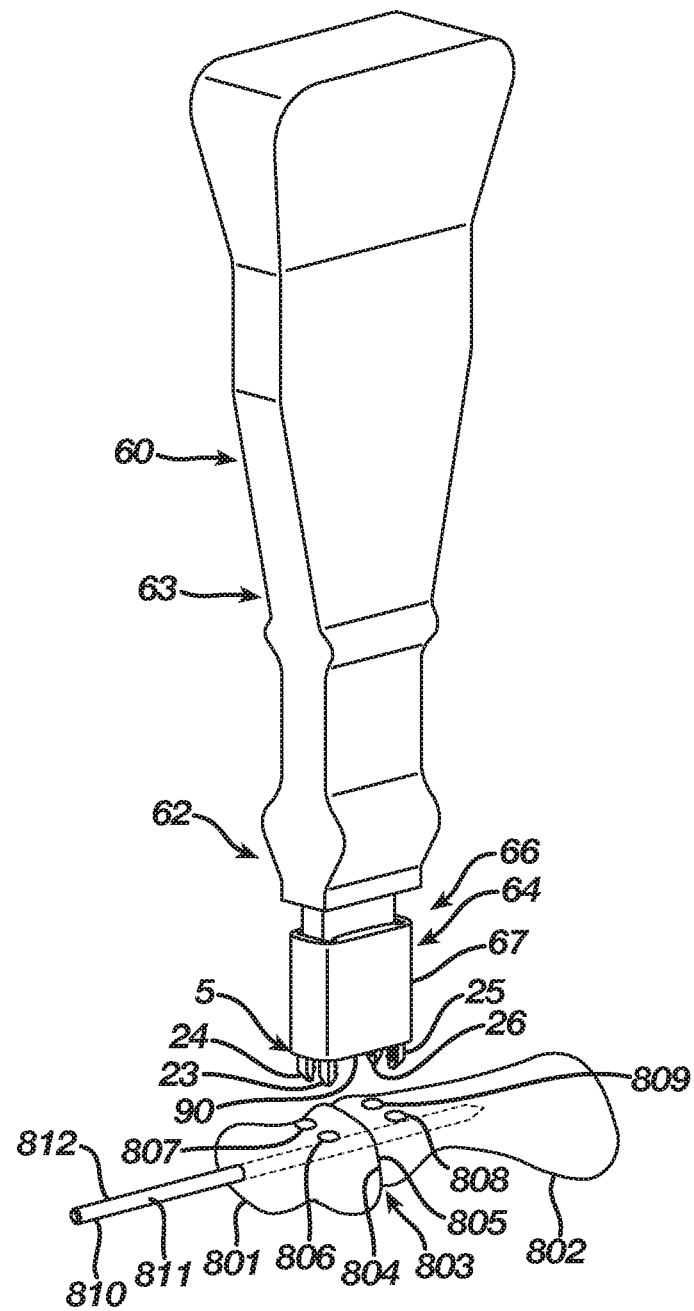

After drilling the first, second, third, and fourth drill holes 806-809, the surgeon as illustrated in FIG. 51 removes the drill guide 600 from the first and second bones 801 and 802 whereby the template 612 disengages from the K-wire 810 and exits the fusion zone 803. The surgeon then compresses the first bone 801 and the second bone 802 until the first and second bones 801 and 802 abut at their fusion zone 803. While the compression of the first and second bones 801 and 802 reduces the distance between the first and third holes 806 and 808 and the second and fourth holes 807 and 809 relative to the distance between the first and third passages 608 and 610 and the second and fourth passages 609 and 611, that reduction in distance does not affect the ability of the first and third holes 806 and 808 and the second and fourth holes 807 and 809 to respectively receive therein the legs 23 and 25 or the legs 24 and 26 of the implant 5 when the implant 5 resides in its insertion position 7 or 53 because the distance between the first and third passages 608 and 610 and the second and fourth passages 609 and 611 in the first embodiment of the drill guide 600 substantially equals the distance between the legs 23 and 25 or the legs 24 and 26 of the implant 5 when the implant 5 resides in its insertion position 7 or 53 plus the distance equal to the thickness 617 of the template 612.

Once any necessary re-orientation of the first and second bones 801 and 802 is performed, the surgeon is ready for implantation of the implant 5 in its insertion shape 7 or 53 into the first and second bones 801 and 802 using the implant insertion device 60. The first, second, third, and fourth holes 806-809 as previously described reside respectively in the first and second bones 801 and 802 at spacings and locations desired for insertion of the legs 23 and 24 into the first bone 801 and the legs 25 and 26 into the second bone 802 with the bridge 8 spanning the fusion zone 803 when the implant 5 resides in its insertion shape 7 or 53. While not required, the surgeon may create grooves in the first and second bones 801 and 802 that facilitate a more flush seating of the bridge 8 for the implant 5 relative to the first and second bones 801 and 802. The surgeon next utilizes the implant insertion device 60 to position the tip 27 of the leg 23 for the implant 5 adjacent the pre-drilled hole 806, the tip 28 of the leg 24 for the implant 5 adjacent the pre-drilled hole 807, the tip 29 of the leg 25 for the implant 5 adjacent the pre-drilled hole 808, and the tip 30 of the leg 26 for the implant 5 adjacent the pre-drilled hole 809.

Figure 52:
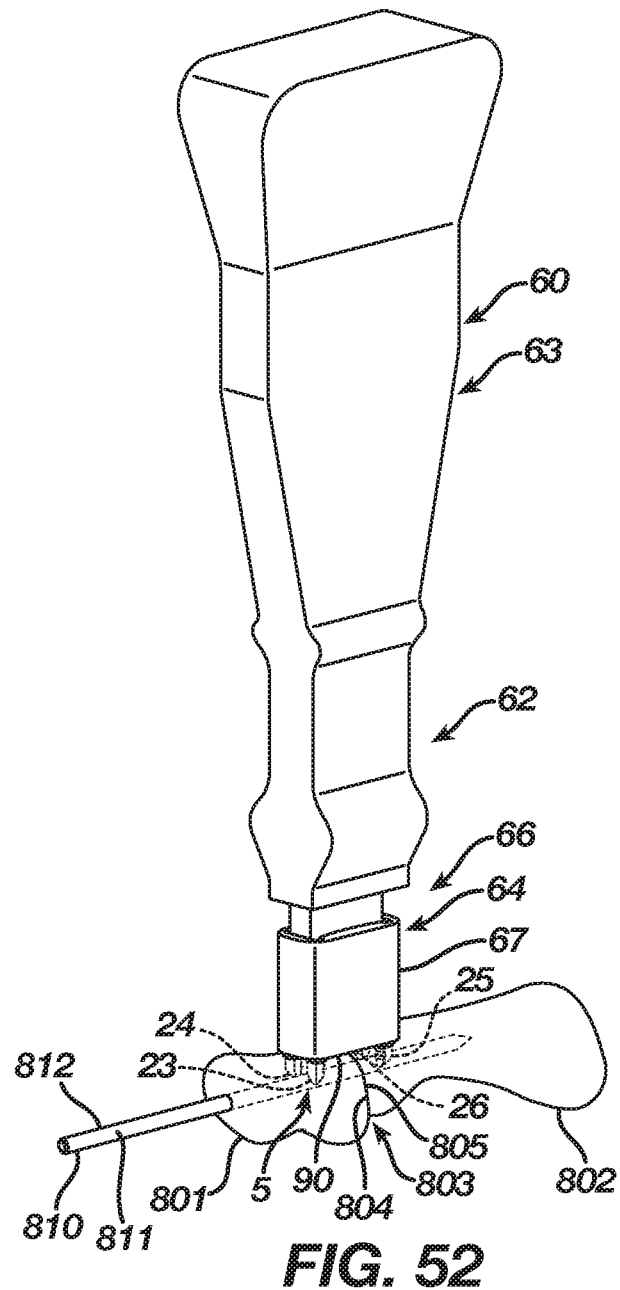

The surgeon as illustrated in FIG. 52 maneuvers the implant insertion device 60 using its body 63 such that the legs 23-26 respectively enter the pre-drilled holes 806-809. The surgeon further manipulates the implant insertion device 60 to insert the legs 23-26 respectively into the pre-drilled holes 806-809 until the implant grip 64 resides on the first and second bones 801 and 802. More particularly, the surgeon pushes on the body 63 resulting in the tamp 79 of the body 63 via its contact with the bridge 8 of the implant 5 pushing on the bridge 8, which, in turn, transfers the pushing force to the legs 23-26 and respectively inserts the legs 23-26 into the pre-drilled holes 806-809 until the lower surface 90 of the shell 67 for the implant grip 64 abuts the first and second bones 801 and 802 exterior of the first, second, third, and fourth holes 806-809.

Figure 53:
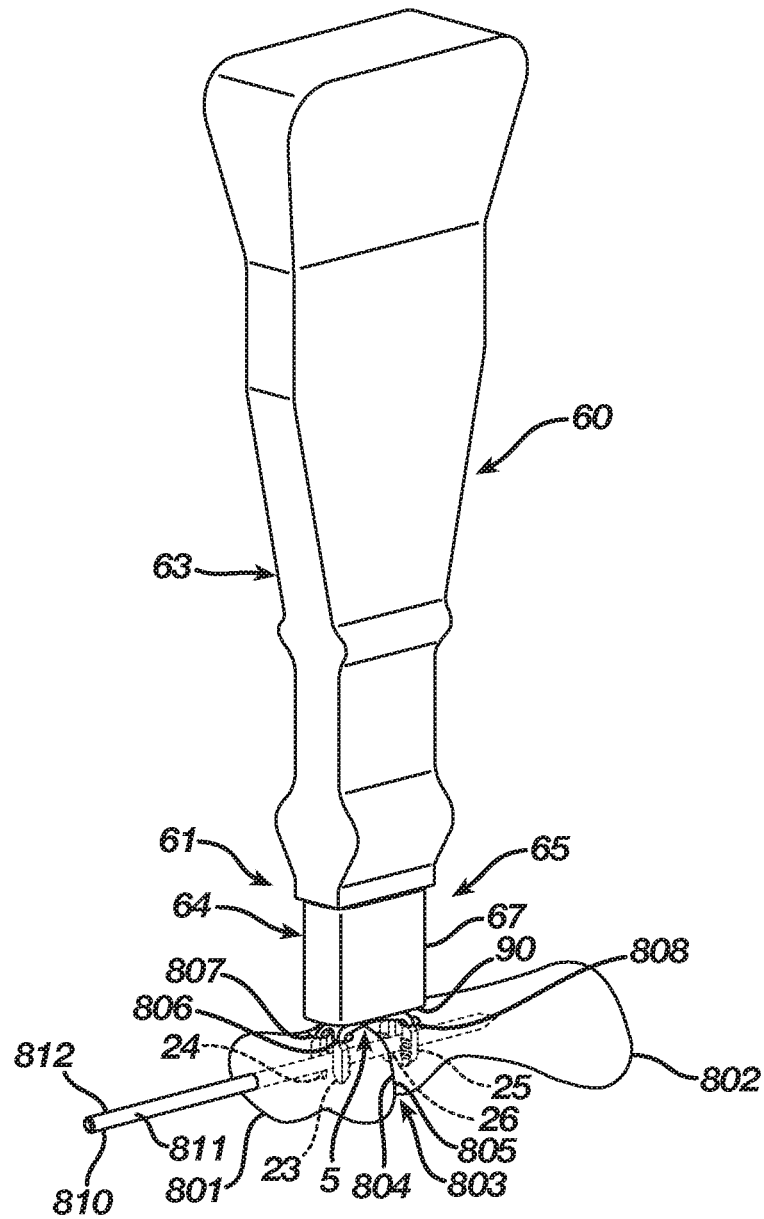

The surgeon as illustrated in FIG. 53 continues manipulating the implant insertion device 60 to insert the legs 23-26, via the tamp 79 and its transfer of the pushing force to the legs 23-26, until the implant 5 at its bridge 8 resides adjacent the first and second bones 801 and 802 across the fusion zone 803 thereof, and, in particular, until the bridge 8 abuts the first and second bones 801 and 802. The surgeon concurrently progresses the implant grip 64 from its engaged position 66 to its disengaged position 65, thereby releasing the implant 5 from the implant insertion device 60. Progression of the implant grip 64 from its engaged position 66 to its disengaged position 65 involves the pushing force also being applied to the implant grip 64 due to the contact thereof with the first and second bones 801 and 802 at the lower surface 90 of its shell 67. The shell 67 accordingly moves along the implant grip receiver 78 of the body 63 until the shell 67 at its upper surface 89 abuts the stop 84 adjacent the implant grip receiver 78, resulting in the detents 88 and 89 disengaging from the notches 92 and respectively sliding into the notches 91 thereby locking the implant grip 64 in its disengaged position 65. If desired, progression of the implant grip 64 from its engaged position 66 to its disengaged position 65 may include the surgeon pulling on the implant grip 64 while inserting the legs 23-26 respectively into the first and second bones 801 and 802.

The tamp 79 of the implant grip receiver 78 for the body 63 remains atop the bridge 8 of the implant 5 to prevent movement of the implant 5 relative to the implant grip 64 during progression of the implant grip 64 from its engaged position 66 to its disengaged position 65. As a consequence, the projections 83-86 of the interior surface 69, when the implant grip 64 moves from its engaged position 66 to its disengaged position 65, by-pass respectively the bridge 8 at its first and second ends 13 and 14 via the concave sections 13*a* and 14*a* thereby releasing a respective leg 23-26 opposite from the segments 34, 39, 44, and 49. The projections 83-86 insert into the indentations 93 and 94 in the implant grip receiver 78 to prevent the projections 83-86 from impeding movement of the implant grip 64 relative to the implant grip receiver 78 such that the tamp 79 ultimately reaches a position adjacent the lower surface 90 of the shell 67. Similarly, the retention surfaces 79-82 disposed in each of the grooves 71-74 respectively release an engagement point 35, 40, 44, and 50 of the legs 23-26, while the grooves 71-74 of the interior surface 69 for the shell 67 respectively disengage from a segment 34, 39, 44, and 49 of the legs 23-26. Moreover, the interior surface 69 of the shell 67 disengages from the first and second sides 11 and 12 of the bridge 8 at their concave sections 11*a* and 12*a*, whereas the interior surface 69 of the shell 67 further by-passes the bridge 8 of the implant 5 at its first and second sides 11 and 12 and its first and second ends 13 and 14 such that the implant 5 exits the passage 70 of the shell 67, resulting in the discharge of the implant 5 from the implant grip 64.

Figure 54:
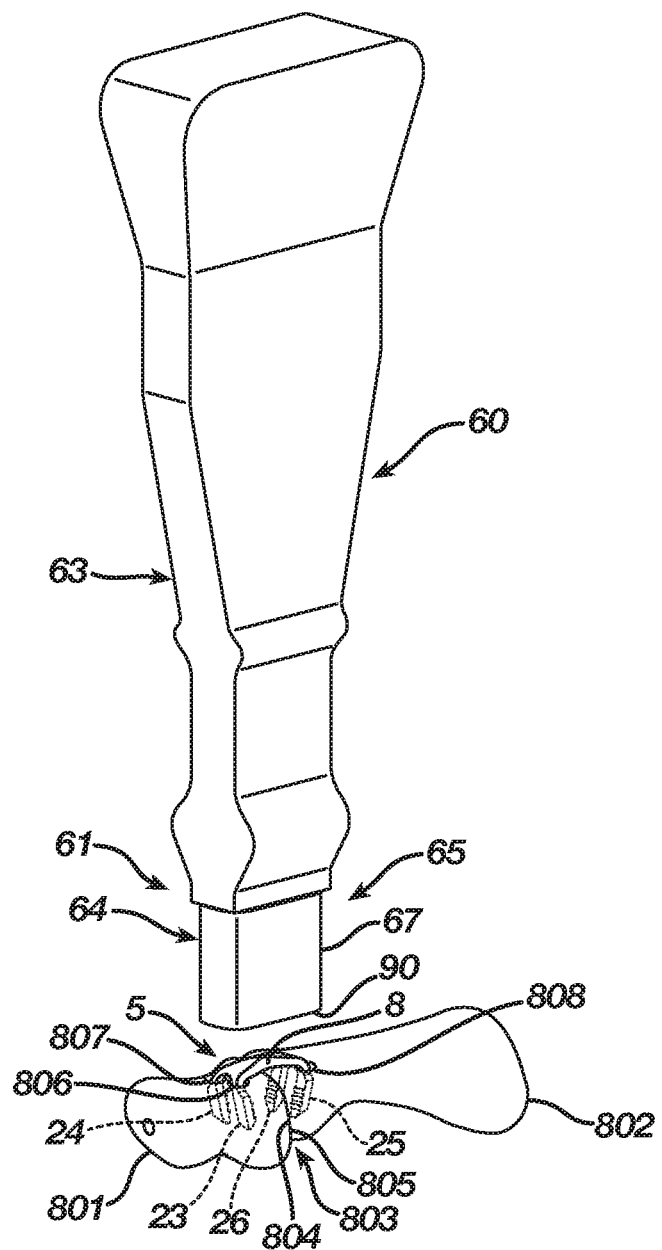

Once the surgeon implants the implant 5 into the first and second bones 801 and 802 with its bridge 8 spanning the fusion zone 803 using the implant insertion device 60, including the implant insertion device 60 traversing to its unloaded position 61, whereby the implant grip 64 in its disengaged position 65 releases the implant 5, the surgeon as illustrated in FIG. 54 removes the implant insertion device 60 from the implant 5, which includes removal of the shell 67 away from the implant 5 and the tamp 79 from atop the bridge 8. The implant 5, due to its superelastic or temperature dependent properties, delivers the energy stored in the transition sections 15-18 and/or the transition section 51 such that the bridge 8 attempts to transition from its insertion form to its natural form, resulting in the legs 23-26 attempting to move from their insertion position to their natural position, whereby the implant 5 affixes the first bone 801 and the second bone 802 through an application of a compressive force to the fixation zone 803. The surgeon finally, if desired, removes the K-wire 810 from the first and second bones 801 and 802.

When implanting a two-legged implant such as the implant 175 utilizing an orthopedic procedure incorporating the drill guide 630 or a three-legged implant such as the implant 215 utilizing an orthopedic procedure incorporating the drill guide 650, one of ordinary skill in the art will recognize that orthopedic procedures incorporating the drill guides 630 and 650 will be substantially similar with respect to the orthopedic procedure incorporating the drill guide 600 as previously described except that the number of pre-drilled holes will correspond in location, spacing, and number based upon the configurations for the drill guides 630 and 650.

FIGS. 55A-59 illustrate use of the drill guide 900 according to the fourth embodiment in combination with an orthopedic fixation system that implants an implant into bone, bones, or bone pieces, and, in particular, into a first bone 851 and a second bone 852, which are presented herein as an example. While FIGS. 55A-59 illustrate the drill guide 900 used with an implant insertion device 60 retaining an implant 5 in its insertion shape 7 or 53, one of ordinary skill in the art will recognize that the drill guide 900 may be used with any four-legged implant and alternative techniques or implant insertion devices.

Figure 55A:
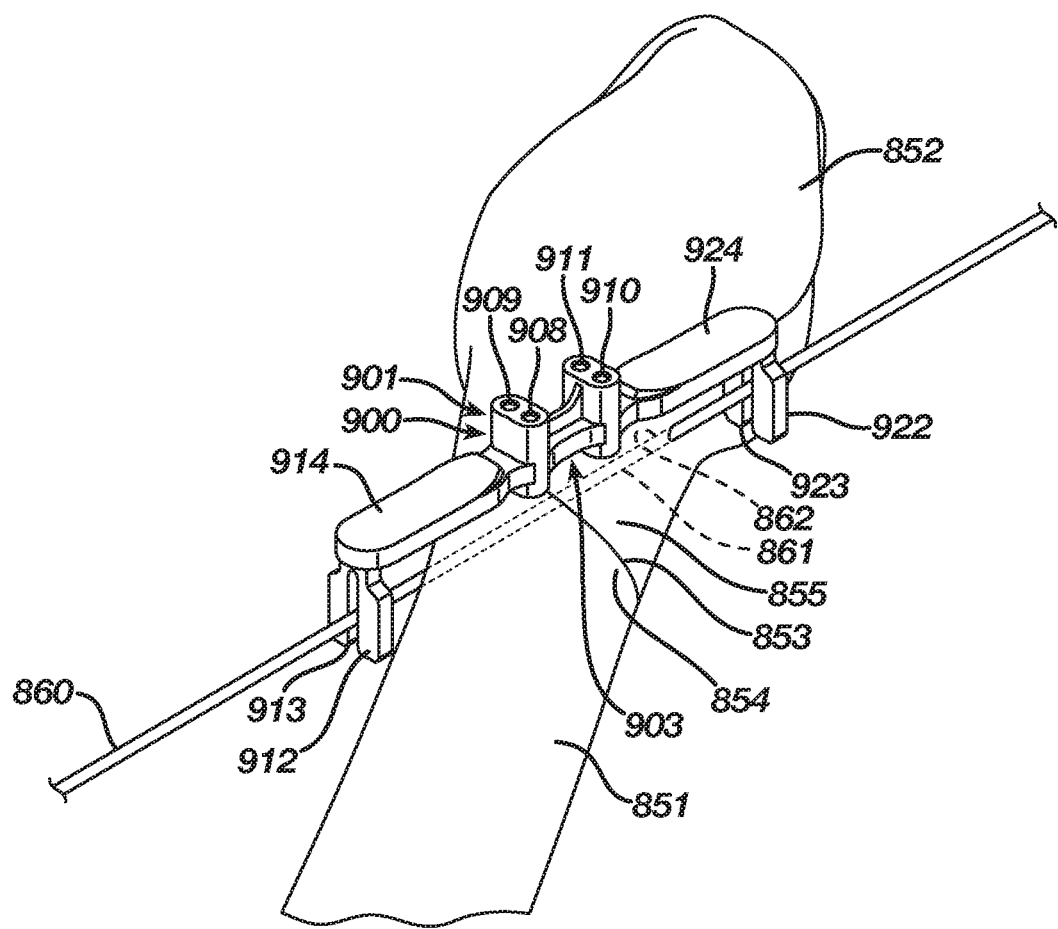
Figure 55B:
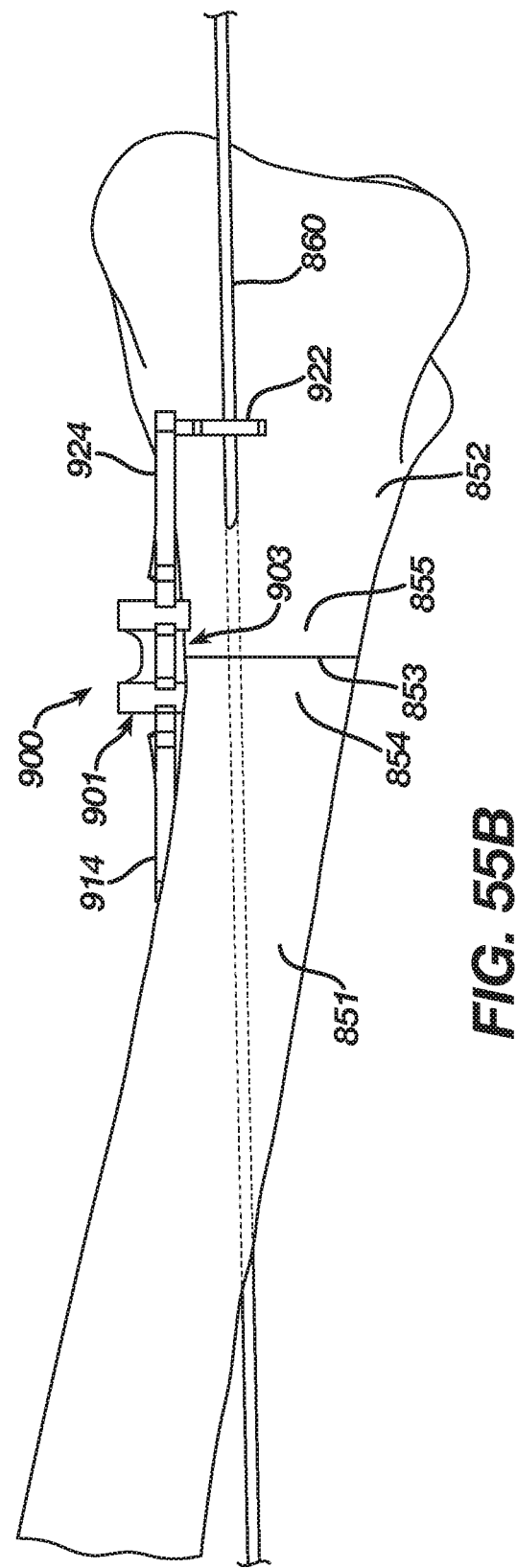

A surgeon as illustrated in FIGS. 55A-55B aligns the first bone 851 with the second bone 852 at a fusion zone 853 in an orientation that promotes fixation of the first bone 851 with the second bone 852 and a proper healing thereof. After aligning the first bone 851 with the second bone 852 at the fusion zone 853 thereof, the surgeon introduces a fixation device into the first bone 851 and the second bone 852. Illustratively, the surgeon inserts a K-wire 860 through the first bone and second bone 851 and 852 whereby the K-wire 860 spans the fixation zone 853 and secures the first bone 851 with the second bone 852 in the orientation that promotes the proper healing thereof. The surgeon then situates the drill guide 900 on the first bone 851 and the second bone 852 across the fusion zone 853. More particularly, the surgeon using the first and/or second grips 914 and 924 of the drill guide 900 places the body 901 of the drill guide 900 on the first bone 851 and the second bone 852 across the fusion zone 853 with its bottom 903 abutting the first and second bones 851 and 852. The surgeon further positions the first template 912 of the drill guide 900 adjacent the first bone 851 such that its slot 913 receives therein the K-wire 860 extending from the first bone 851 and the second template 922 of the drill guide 900 adjacent the second bone 852 such that its slot 923 receives therein the K-wire 860 extending from the second bone 851. The first and second templates 912 and 922 via their positioning respectively adjacent the first and second bones 851 and 852 and engagement with the K-wire 860 secure the body 901 of the drill guide 900 on the first and second bones 851 and 852 and positions the first passage 908 of the body 901 on the first bone 851 adjacent a first side 854 of the fusion zone 853 proximate to a first side 861 of the K-wire 860, the second passage 909 on the first bone 851 adjacent the first side 854 of the fusion zone 853 proximate to a second side 862 of the K-wire 860, the third passage 910 on the second bone 852 adjacent a second side 855 of the fusion zone 853 proximate to the first side 861 of the K-wire 860, and the fourth passage 911 on the second bone 852 adjacent the second side 855 of the fusion zone 853 proximate to the second side 862 of the K-wire 860.

Figure 56:
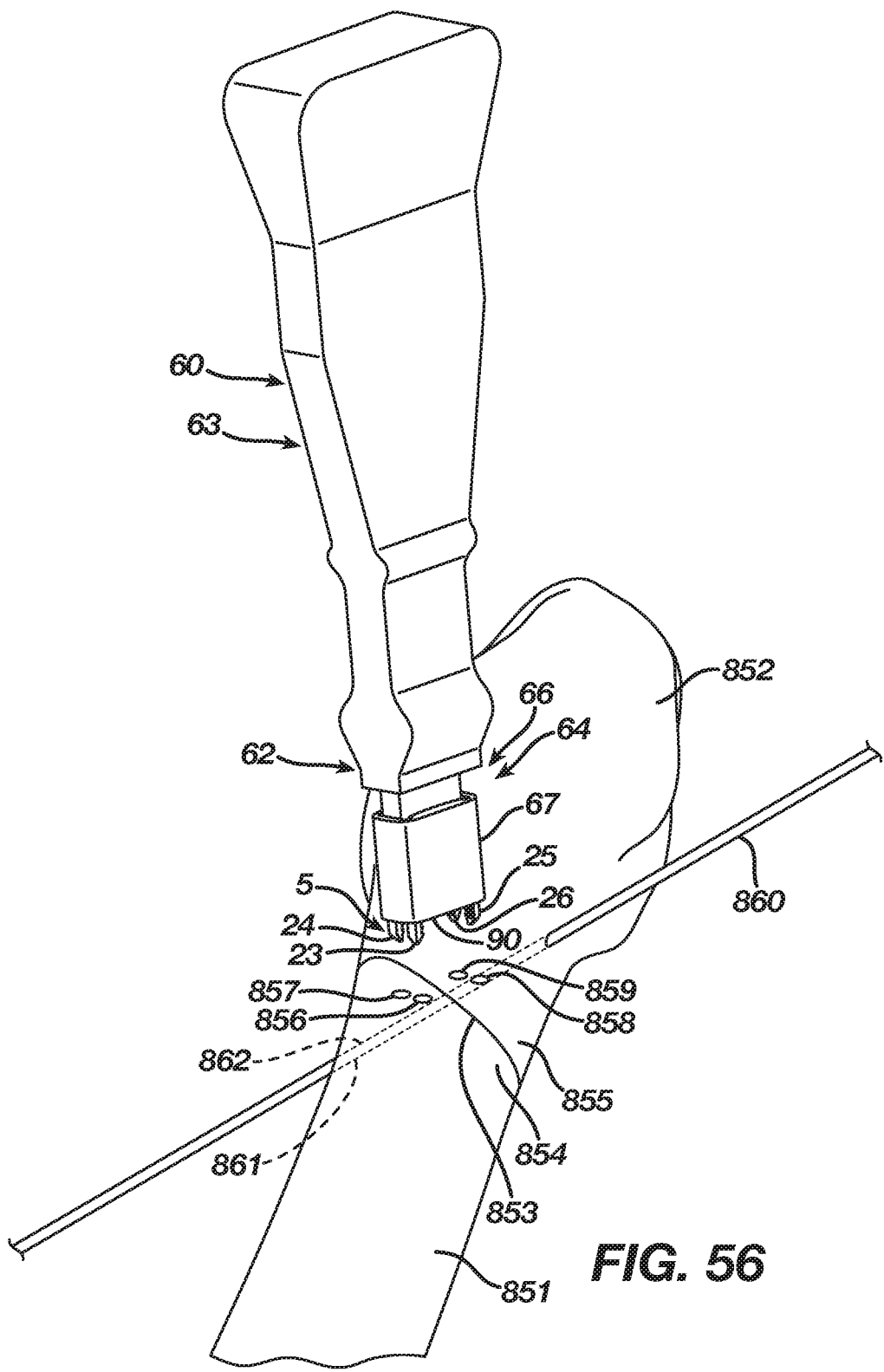

With the body 901 of the drill guide 900 thus situated on the first and second bones 851 and 852 including the first and second templates 912 and 922 of the drill guide 900 positioned respectively adjacent the first and second bones 851 and 852 and engaged with the K-wire 860, the surgeon drills a first hole 856 in the first bone 851 adjacent the first side 854 of the fusion zone 853 proximate to the first side 861 of the K-wire 860, a second hole 857 in the first bone 851 adjacent the first side 854 of the fusion zone 853 proximate to the second side 862 of the K-wire 860, a third hole 858 in the second bone 852 adjacent the second side 855 of the fusion zone 853 proximate to the first side 861 of the K-wire 860, and a fourth hole 859 in the second bone 852 adjacent the second side 855 of the fusion zone 853 proximate to the second side 862 of the K-wire 860. The drill guide 900 accordingly facilitates the drilling of the first, second, third, and fourth drill holes 866-859 in close proximity to the K-wire 860 while preventing a drill bit of a drill used in forming the first, second, third, and fourth drill holes 856-859 from striking the K-wire 860. After drilling the first, second, third, and fourth drill holes 856-859, the surgeon as illustrated in FIG. 56 removes the drill guide 900 from the first and second bones 851 and 852 whereby the first and second templates 912 and 922 disengage from the K-wire 860.

Once any necessary re-orientation of the first and second bones 851 and 852 is performed, the surgeon is ready for implantation of the implant 5 in its insertion shape 7 or 53 into the first and second bones 851 and 852 using the implant insertion device 60. The first, second, third, and fourth holes 856-859, based upon the locations of the first, second, third, and fourth passages 908-911 of the body 901 as previously described, reside respectively in the first and second bones 851 and 852 at spacings and locations desired for insertion of the legs 23 and 24 into the first bone 851 and the legs 25 and 26 into the second bone 852 with the bridge 8 spanning the fusion zone 853 when the implant 5 resides in its insertion shape 7 or 53. While not required, the surgeon may create grooves in the first and second bones 851 and 852 that facilitate a more flush seating of the bridge 8 for the implant 5 relative to the first and second bones 851 and 852. The surgeon next utilizes the implant insertion device 60 to position the tip 27 of the leg 23 for the implant 5 adjacent the pre-drilled hole 856, the tip 28 of the leg 24 for the implant 5 adjacent the pre-drilled hole 857, the tip 29 of the leg 25 for the implant 5 adjacent the pre-drilled hole 858, and the tip 30 of the leg 26 for the implant 5 adjacent the pre-drilled hole 859.

Figure 57:
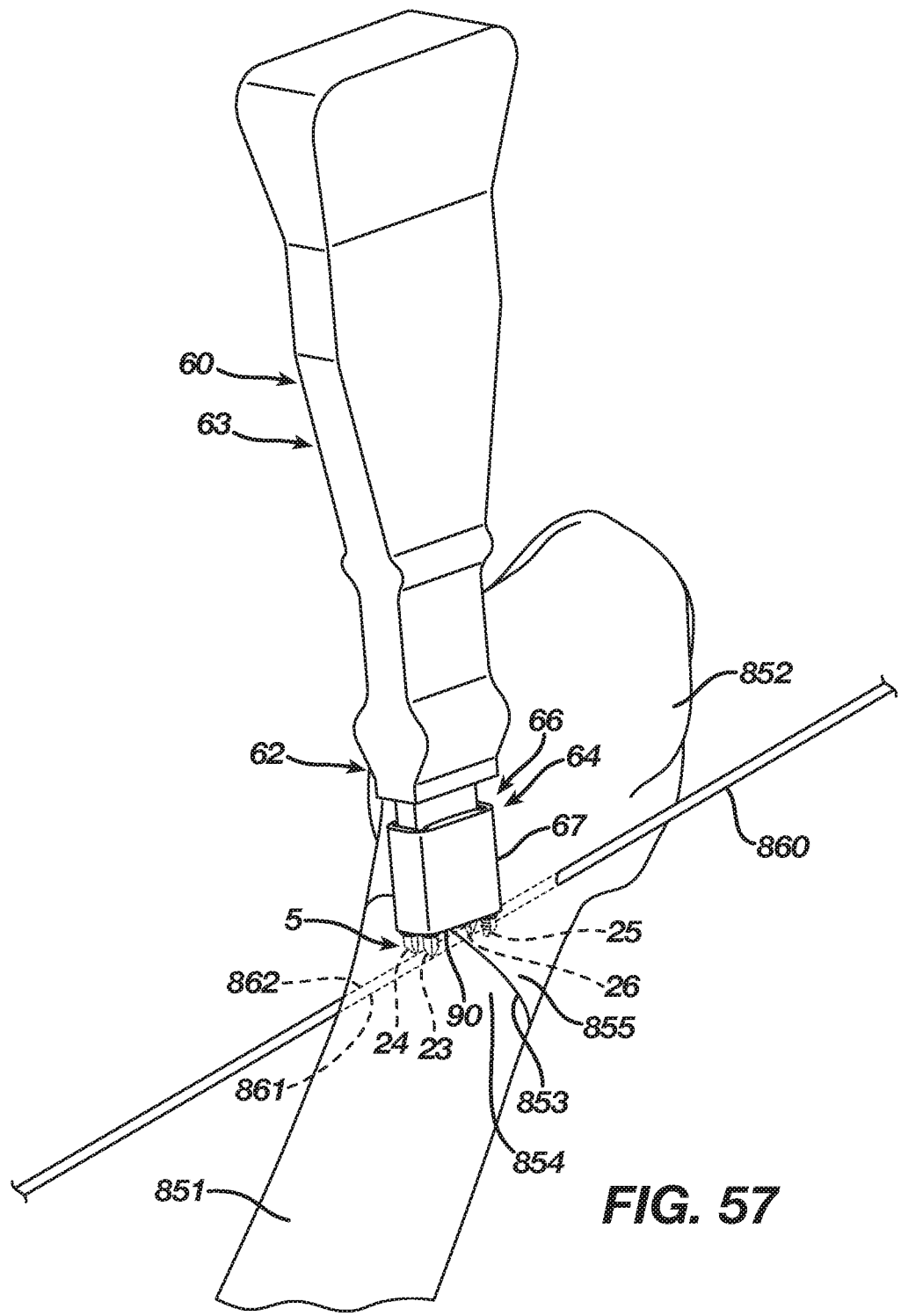

The surgeon as illustrated in FIG. 57 maneuvers the implant insertion device 60 using its body 63 such that the legs 23-26 respectively enter the pre-drilled holes 856-859. The surgeon further manipulates the implant insertion device 60 to insert the legs 23-26 respectively into the pre-drilled holes 856-859 until the implant grip 64 resides on the first and second bones 851 and 852. More particularly, the surgeon pushes on the body 63 resulting in the tamp 79 of the body 63 via its contact with the bridge 8 of the implant 5 pushing on the bridge 8, which, in turn, transfers the pushing force to the legs 23-26 and respectively inserts the legs 23-26 into the pre-drilled holes 856-859 until the lower surface 90 of the shell 67 for the implant grip 64 abuts the first and second bones 851 and 852 exterior of the first, second, third, and fourth holes 856-859.

Figure 58:
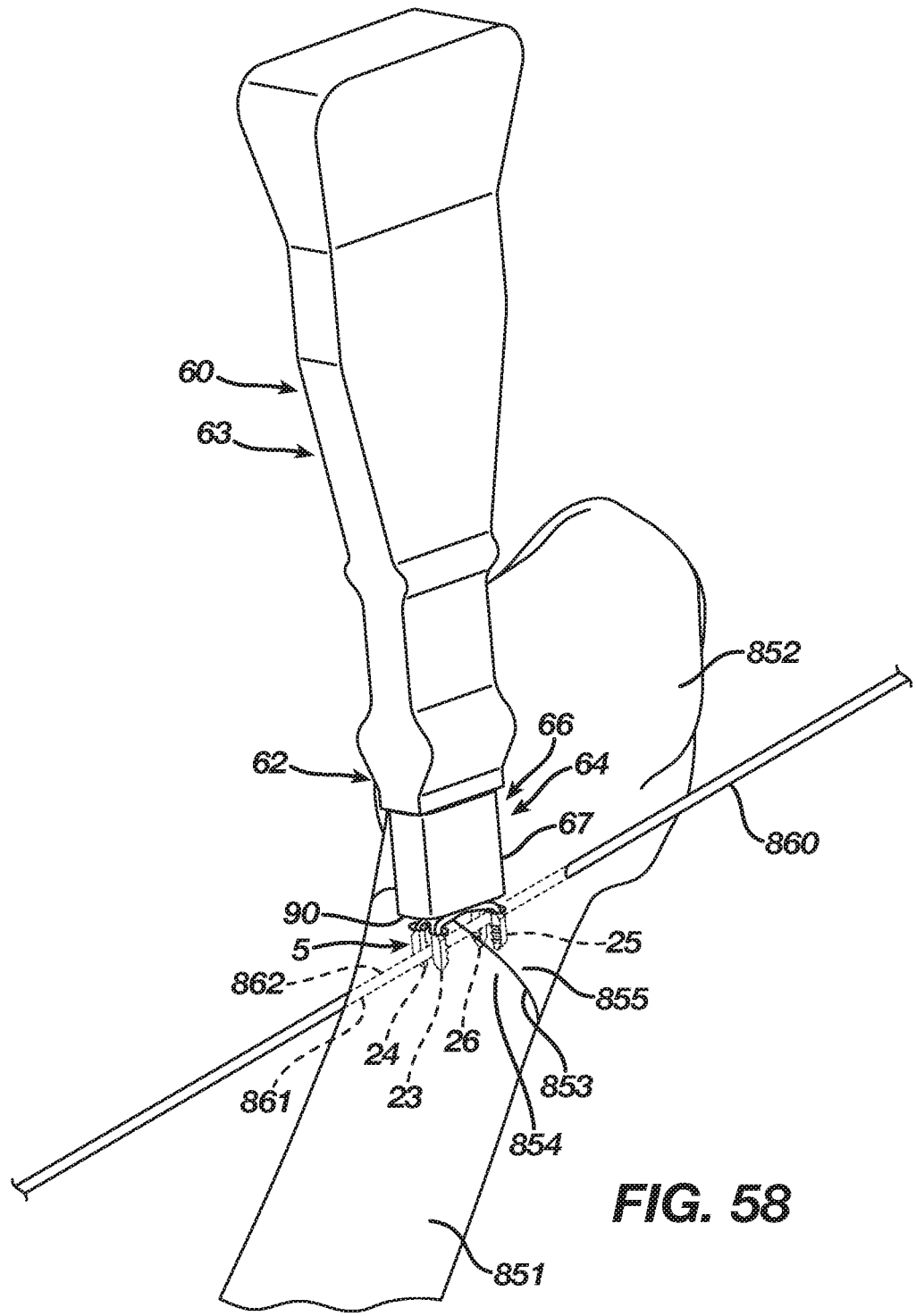

The surgeon as illustrated in FIG. 58 continues manipulating the implant insertion device 60 to insert the legs 23-26, via the tamp 79 and its transfer of the pushing force to the legs 23-26, until the implant 5 at its bridge 8 resides adjacent the first and second bones 851 and 852 across the fusion zone 853 thereof, and, in particular, until the bridge 8 abuts the first and second bones 851 and 852. The surgeon concurrently progresses the implant grip 64 from its engaged position 66 to its disengaged position 65, thereby releasing the implant 5 from the implant insertion device 60. Progression of the implant grip 64 from its engaged position 66 to its disengaged position 65 involves the pushing force also being applied to the implant grip 64 due to the contact thereof with the first and second bones 851 and 852 at the lower surface 90 of its shell 67. The shell 67 accordingly moves along the implant grip receiver 78 of the body 63 until the shell 67 at its upper surface 89 abuts the stop 84 adjacent the implant grip receiver 78, resulting in the detents 88 and 89 disengaging from the notches 92 and respectively sliding into the notches 91 thereby locking the implant grip 64 in its disengaged position 65. If desired, progression of the implant grip 64 from its engaged position 66 to its disengaged position 65 may include the surgeon pulling on the implant grip 64 while inserting the legs 23-26 respectively into the first and second bones 851 and 852.

The tamp 79 of the implant grip receiver 78 for the body 63 remains atop the bridge 8 of the implant 5 to prevent movement of the implant 5 relative to the implant grip 64 during progression of the implant grip 64 from its engaged position 66 to its disengaged position 65. As a consequence, the projections 83-86 of the interior surface 69, when the implant grip 64 moves from its engaged position 66 to its disengaged position 65, by-pass respectively the bridge 8 at its first and second ends 13 and 14 via the concave sections 13a and 14a thereby releasing a respective leg 23-26 opposite from the segments 34, 39, 44, and 49. The projections 83-86 insert into the indentations 93 and 94 in the implant grip receiver 78 to prevent the projections 83-86 from impeding movement of the implant grip 64 relative to the implant grip receiver 78 such that the tamp 79 ultimately reaches a position adjacent the lower surface 90 of the shell 67. Similarly, the retention surfaces 79-82 disposed in each of the grooves 71-74 respectively release an engagement point 35, 40, 44, and 50 of the legs 23-26, while the grooves 71-74 of the interior surface 69 for the shell 67 respectively disengage from a segment 34, 39, 44, and 49 of the legs 23-26. Moreover, the interior surface 69 of the shell 67 disengages from the first and second sides 11 and 12 of the bridge 8 at their concave sections 11a and 12a, whereas the interior surface 69 of the shell 67 further by-passes the bridge 8 of the implant 5 at its first and second sides 11 and 12 and its first and second ends 13 and 14 such that the implant 5 exits the passage 70 of the shell 67, resulting in the discharge of the implant 5 from the implant grip 64.

Figure 59:
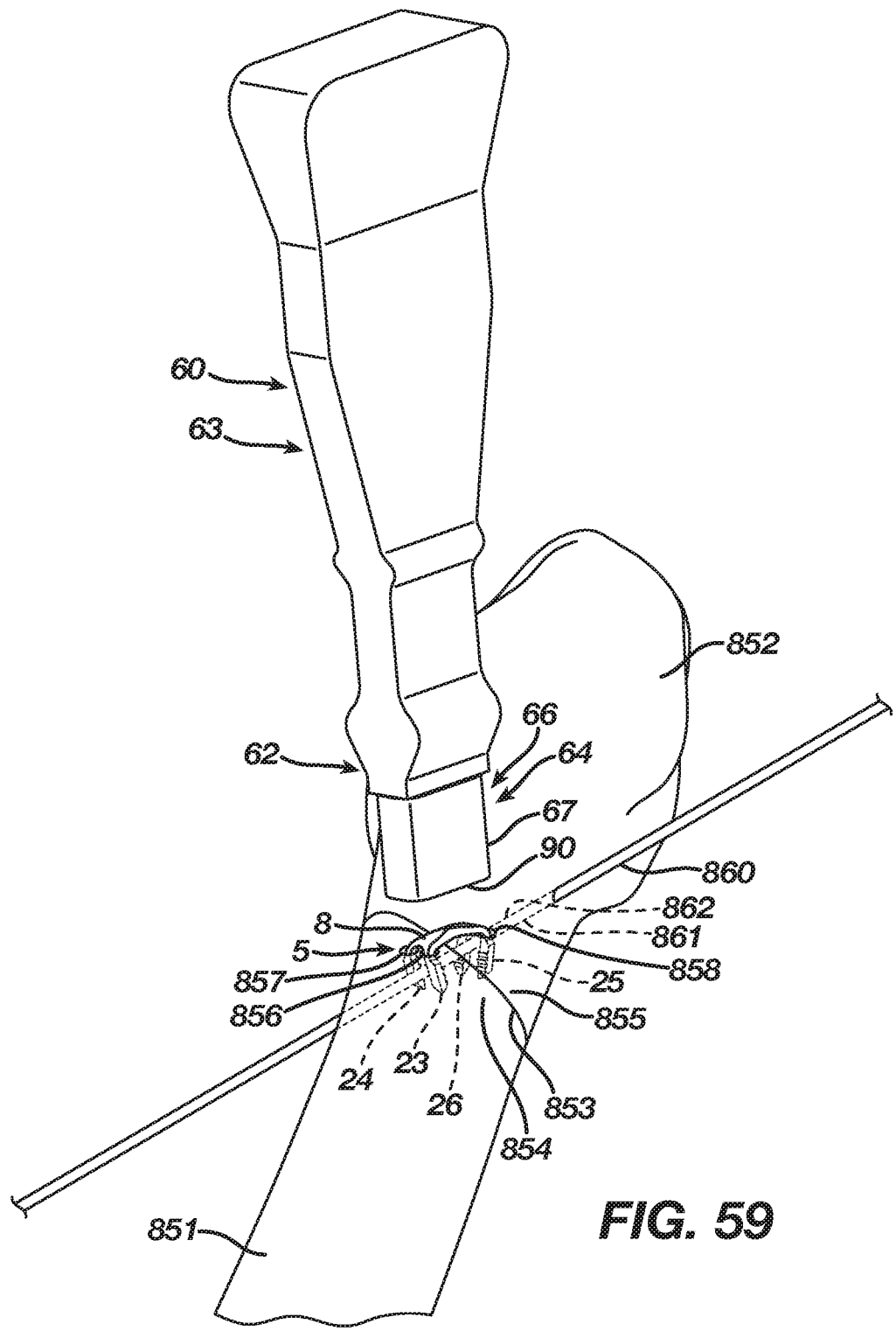

Once the surgeon implants the implant 5 into the first and second bones 851 and 852 with its bridge 8 spanning the fusion zone 853 using the implant insertion device 60, including the implant insertion device 60 traversing to its unloaded position 61, whereby the implant grip 64 in its disengaged position 65 releases the implant 5, the surgeon as illustrated in FIG. 59 removes the implant insertion device 60 from the implant 5, which includes removal of the shell 67 away from the implant 5 and the tamp 79 from atop the bridge 8. The implant 5, due to its superelastic or temperature dependent properties, delivers the energy stored in the transition sections 15-18 and/or the transition section 51 such that the bridge 8 attempts to transition from its insertion form to its natural form, resulting in the legs 23-26 attempting to move from their insertion position to their natural position, whereby the implant 5 affixes the first bone 851 and the second bone 852 through an application of a compressive force to the fixation zone 853. The surgeon finally, if desired, removes the K-wire 860 from the first and second bones 851 and 852.

When implanting a two-legged implant such as the implant 175 utilizing an orthopedic procedure incorporating the drill guide 930 or a three-legged implant such as the implant 215 utilizing an orthopedic procedure incorporating the drill guide 950, one of ordinary skill in the art will recognize that orthopedic procedures incorporating the drill guides 930 and 950 will be substantially similar with respect to the orthopedic procedure incorporating the drill guide 900 as previously described except that the number of pre-drilled holes will correspond in location, spacing, and number based upon the configurations for the drill guides 930 and 950.

In view of the foregoing embodiments illustrating implant insertion devices and orthopedic implants according to the present invention, it should be understood that implant insertion devices and orthopedic implants will fall within the scope of the present invention regardless of the body shape and number of legs for an orthopedic implant. Moreover, although the present invention has been described in terms of the foregoing embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An orthopedic fixation system, comprising:
   an implant transitionable between a natural shape and an insertion shape, the implant, comprising:
      a bridge including upper and lower surfaces, first and second sides, and first and second ends, the first and second sides and the first and second ends defining a perimeter in alignment with a longitudinal axis of the bridge,
      a first anchoring member extending from the lower surface of the bridge interior to the first end of the bridge, the first anchoring member including a width that extends a segment of the first anchoring member laterally away from the perimeter of the bridge at the first side thereof such that the segment provides the first anchoring member with an engagement point located on the first anchoring member interior to the perimeter of the bridge at the first end thereof and exterior to the perimeter of the bridge at the first side thereof, and
      a second anchoring member extending from the lower surface of the bridge interior to the second end of the bridge, the second anchoring member including a width that extends a segment of the second anchoring member laterally away from the perimeter of the bridge at the first side thereof such that the segment provides the second anchoring member with an engagement point located on the second anchoring member interior to the perimeter of the bridge at the second end thereof and exterior to the perimeter of the bridge at the first side thereof; and
   an implant insertion device movable between a loaded position whereby the implant insertion device by-passes the bridge and abuts the segment of the first anchoring member at its engagement point and the segment of the second anchoring member at its engagement point such that the implant insertion device holds the first anchoring member and the second anchoring member at their engagement points thereby constraining the implant in its insertion shape and an unloaded position whereby the implant insertion device disengages from the segment of the first anchoring member at its engagement point and the segment of the second anchoring member at its engagement point thereby releasing the implant.

2. The orthopedic fixation system according to claim 1, the implant insertion device, comprising:
   a body including a first end and a second end; and
   an implant grip coupled with the body and movable relative to the body between an engaged position whereby the implant grip by-passes the bridge and abuts the segment of the first anchoring member at its engagement point and the segment of the second anchoring member at its engagement point such that the implant grip holds the first anchoring member and the second anchoring member at their engagement points thereby constraining the implant in its insertion shape and a disengaged position whereby the implant grip disengages from the segment of the first anchoring member at its engagement point and the segment of the second anchoring member at its engagement point thereby releasing the implant.

3. The orthopedic fixation system according to claim 1, wherein:
   the first anchoring member extends from the bridge at the first end of the bridge adjacent the first side of the bridge, the first anchoring member including the width that extends the segment of the first anchoring member laterally away from the perimeter of the bridge at the first side thereof such that the segment provides the first anchoring member with the engagement point located on the first anchoring member exterior to the perimeter of the bridge at the first side thereof;
   the second anchoring member extends from the bridge at the second end of the bridge adjacent the first side of the bridge, the second anchoring member including the width that extends the segment of the second anchoring member laterally away from the perimeter of the bridge at the first side thereof such that the segment provides the second anchoring member with the engagement point located on the second anchoring member exterior to the perimeter of the bridge at the first side thereof;
   a third anchoring member extends from the bridge at the first end of the bridge adjacent the second side of the bridge, the third anchoring member including a width that extends a segment of the third anchoring member laterally away from the perimeter of the bridge at the second side thereof such that the segment provides the third anchoring member with an engagement point located on the third anchoring member exterior to the perimeter of the bridge at the second side thereof; and
   a fourth anchoring member extends from the bridge at the second end of the bridge adjacent the second side of the bridge, the fourth anchoring member including a width that extends a segment of the fourth anchoring member laterally away from the perimeter of the bridge at the second side thereof such that the segment provides the fourth anchoring member with an engagement point located on the fourth anchoring member exterior to the perimeter of the bridge at the second side thereof.

4. The orthopedic fixation system according to claim 3, the implant insertion device, comprising:
   a body including a first end and a second end; and
   an implant grip coupled with the body at its second end, the implant grip movable relative to the body between an engaged position whereby the implant grip by-passes the bridge and engages abuts the segments of the first, second, third, and fourth anchoring members at their engagement points such that the implant grip holds the first, second, third, and fourth anchoring members at their engagement points thereby constraining the implant in its insertion shape and a disengaged position whereby the implant grip disengages from the segments of the first, second, third, and fourth anchoring members at their engagement points thereby releasing the implant.

5. The orthopedic fixation system according to claim 4, the implant grip, comprising a shell, wherein:
   the shell includes an exterior surface having an upper surface and a lower surface,
   the shell includes an interior surface complimentary in shape with the implant such that the interior surface defines a passage through the shell complimentary in shape with the implant,
   the shell at its upper surface receives into the passage the body at its second end thereby coupling the shell with the body, and
   the shell at its lower surface receives into the passage the implant whereby the shell at its interior surface by-passes the bridge and abuts the segments of the first, second, third, and fourth anchoring members at their engagement points thereby holding the implant in the shell and constraining the implant in its insertion shape.

6. The orthopedic fixation system according to claim 5, wherein the interior surface of the shell defines first, second, third, and fourth grooves, whereby, when the shell at its interior surface by-passes the bridge, each of the first, second, third, and fourth grooves receives therein one of the segments of the first, second, third, and fourth anchoring members, further whereby the interior surface at the first, second, third, and fourth grooves abuts the first, second, third, and fourth anchoring members at their engagement points, thereby retaining the implant within the shell in its insertion shape.

7. The orthopedic fixation system according to claim 6, wherein the interior surface in each of the first, second, third, and fourth grooves defines a retention surface, whereby, when the first, second, third, and fourth grooves receive therein one of the segments of the first, second, third, and fourth anchoring members, each of the retention surfaces abuts one of the engagement points of the segments for the first, second, third, and fourth anchoring members whereby the retention surfaces grip and constrain the first, second, third, and fourth anchoring members at their engagement points such that the shell retains therein the implant in its insertion shape.

8. The orthopedic fixation system according to claim 6, wherein the interior surface of the shell includes projections, whereby, when the shell at its interior surface by-passes the bridge, the projections by-pass the bridge and engage one of the first, second, third, and fourth anchoring members such that the shell retains therein the implant in its insertion shape.

9. The orthopedic fixation system according to claim 8, wherein the projections are resilient, whereby, when the shell at its interior surface by-passes the bridge, the projections by-pass the bridge by moving relative thereto and engage one of the first, second, third, and fourth anchoring members such that the shell retains therein the implant in its insertion shape.

10. The orthopedic fixation system according to claim 5, the body, comprising an implant grip receiver at the second end of the body, the implant grip receiver terminating in a tamp, wherein the implant grip receiver is complimentary in shape with the interior surface of the shell, further wherein the implant grip receiver inserts into the passage of the shell at its upper surface thereby coupling the implant grip receiver with the shell.

11. The orthopedic fixation system according to claim 10, wherein, when the implant grip resides in its engaged position, the tamp sits atop the bridge of the implant, further wherein, the tamp remains atop the bridge of the implant to prevent movement of the implant relative to the implant grip during progression of the implant grip from its engaged position to its disengaged position.

12. The orthopedic fixation system according to claim 10, wherein:
   the implant grip receiver includes a first notch and a second notch; and
   the interior surface of the shell includes a detent engageable with the first and second notches, whereby, when the implant grip moves to its engaged position, the detent engages the first notch thereby locking the implant grip in its engaged position, further whereby, when the implant grip moves to its disengaged position, the detent engages the second notch thereby locking the implant grip in its disengaged position.

13. The orthopedic fixation system according to claim 4, the implant grip, comprising:
   an actuator coupled with the body and movable relative thereto whereby movement of the actuator progresses the implant grip between its engaged and disengaged positions; and
   first and second blades securable with the actuator in an opposed relationship that defines a passage therebetween, whereby the passage receives therein the bridge of the implant, further whereby the first and second blades extend beyond the bridge and engage the segments of the first, second, third, and fourth anchoring members at their engagement points thereby holding the implant and constraining the implant in its insertion shape.

14. The orthopedic fixation system according to claim 13, the actuator, comprising:
   a first slider securable with the first blade;
   a second slider securable with the second blade; and
   a spacer securable between the first and second sliders such that the first and second blades are spaced apart to form the passage therebetween.

15. The orthopedic fixation system according to claim 14, the body, defining:
   a tamp at its second end; and
   a slot therethrough communicating exterior to the body, the slot receiving the spacer therein, wherein the first slider secures with the spacer adjacent a first surface of the body whereby the first blade extends beyond the tamp, further wherein the second slider secures with the spacer adjacent a second surface of the body whereby the second blade extends beyond the tamp such that the passage between the first and second blades is located adjacent the tamp.

16. The orthopedic fixation system according to claim 15, wherein, when the implant grip resides in its engaged position, the tamp sits atop the bridge of the implant, further wherein, the tamp remains atop the bridge of the implant to prevent movement of the implant relative to the implant grip during progression of the implant grip from its engaged position to its disengaged position.

17. The orthopedic fixation system according to claim 1, wherein:
   the first anchoring member extends from the bridge at the first end thereof, the first anchoring member including a width whereby the segment of the first anchoring member is a first segment and the engagement point is a first engagement point such that the first segment extends exterior to the bridge at its first side to provide the first engagement point, further whereby the first anchoring member includes a second segment extending exterior to the bridge at its second side to provide a second engagement point; and the second anchoring member extends from the bridge at the second end thereof, the second anchoring member including a width whereby the segment of the second anchoring member is a first segment and the engagement point is a first engagement point such that the first segment extends exterior to the bridge at its first side to provide the first engagement point, further whereby the second anchoring member includes a second segment extending exterior to the bridge at its second side to provide a second engagement point.

18. The orthopedic fixation system according to claim 17, the implant insertion device, comprising:
  a body including a first end and a second end; and
  an implant grip coupled with the body at its second end, the implant grip movable relative to the body between an engaged position whereby the implant grip by-passes the bridge and engages the first and second segments of the first anchoring member at their first and second engagement points and the first and second segments of the second anchoring member at their first and second engagement points such that the implant grip constrains the implant in its insertion shape and a disengaged position whereby the implant grip releases the implant.

19. The orthopedic fixation system according to claim 18, the implant grip, comprising a shell, wherein:
  the shell includes an exterior surface having an upper surface and a lower surface,
  the shell includes an interior surface complimentary in shape with the implant such that the interior surface defines a passage through the shell complimentary in shape with the implant,
  the shell at its upper surface receives into the passage the body at its second end thereby coupling the shell with the body, and
  the shell at its lower surface receives into the passage the implant whereby the shell at its interior surface by-passes the bridge and engages the first and second segments of the first anchoring member at their first and second engagement points and the first and second segments of the second anchoring member at their first and second engagement points thereby holding the implant in the shell and constraining the implant in its insertion shape.

20. The orthopedic fixation system according to claim 19, wherein the interior surface of the shell defines first, second, third, and fourth grooves, whereby, when the shell at its interior surface by-passes the bridge, each of the first, second, third, and fourth grooves receives therein one of the first and second segments of the first and second anchoring members, further whereby the interior surface at the first, second, third, and fourth grooves engages the first and second anchoring members, thereby retaining the implant within the shell in its insertion shape.

21. The orthopedic fixation system according to claim 20, wherein the interior surface in each of the first, second, third, and fourth grooves defines a retention surface, whereby, when the first, second, third, and fourth grooves receive therein one of the first and second segments of the first and second anchoring members, each of the retention surfaces abuts one of the first and second engagement points of the first and second segments for the first and second anchoring members whereby the retention surfaces grip and constrain the first and second anchoring members such that the shell retains therein the implant in its insertion shape.

22. The orthopedic fixation system according to claim 19, the body, comprising an implant grip receiver at the second end of the body, the implant grip receiver terminating in a tamp, wherein the implant grip receiver is complimentary in shape with the interior surface of the shell, further wherein the implant grip receiver inserts into the passage of the shell at its upper surface thereby coupling the implant grip receiver with the shell.

23. The orthopedic fixation system according to claim 22, wherein, when the implant grip resides in its engaged position, the tamp sits atop the bridge of the implant, further wherein, the tamp remains atop the bridge of the implant to prevent movement of the implant relative to the implant grip during progression of the implant grip from its engaged position to its disengaged position.

24. The orthopedic fixation system according to claim 22, wherein:
  the implant grip receiver includes a first notch and a second notch; and
  the interior surface of the shell includes a detent engageable with the first and second notches, whereby, when the implant grip moves to its engaged position, the detent engages the first notch thereby locking the implant grip in its engaged position, further whereby, when the implant grip moves to its disengaged position, the detent engages the second notch thereby locking the implant grip in its disengaged position.

25. The orthopedic fixation system according to claim 18, the implant grip, comprising:
  an actuator coupled with the body and movable relative thereto whereby movement of the actuator progresses the implant grip between its engaged and disengaged positions; and
  first and second blades securable with the actuator in an opposed relationship that defines a passage therebetween, whereby the passage receives therein the bridge of the implant, further whereby the first and second blades extend beyond the bridge and engage the first and second segments of the first and second anchoring members at their first and second engagement points thereby holding the implant and constraining the implant in its insertion shape.

26. The orthopedic fixation system according to claim 25, the actuator, comprising:
  a first slider securable with the first blade;
  a second slider securable with the second blade; and
  a spacer securable between the first and second sliders such that the first and second blades are spaced apart to form the passage therebetween.

27. The orthopedic fixation system according to claim 26, the body, defining:
  a tamp at its second end; and
  a slot therethrough communicating exterior to the body, the slot receiving the spacer therein, wherein the first slider secures with the spacer adjacent a first surface of the body whereby the first blade extends beyond the tamp, further wherein the second slider secures with the spacer adjacent a second surface of the body whereby the second blade extends beyond the tamp such that the passage between the first and second blades is located adjacent the tamp.

28. The orthopedic fixation system according to claim 27, wherein, when the implant grip resides in its engaged position, the tamp sits atop the bridge of the implant, further wherein, the tamp remains atop the bridge of the implant to prevent movement of the implant relative to the implant grip during progression of the implant grip from its engaged position to its disengaged position.

29. The orthopedic fixation system according to claim 1, wherein:
   the first anchoring member extends from the bridge at the first end of the bridge adjacent the first side of the bridge, the first anchoring member including a width whereby the segment of the first anchoring member extends exterior to the bridge at its first side to provide the engagement point;
   the second anchoring member extends from the bridge at the second end thereof, the second anchoring member including a width whereby the segment of the second anchoring member is a first segment and the engagement point is a first engagement point such that the first segment extends exterior to the bridge at its first side to provide the first engagement point, further whereby the second anchoring member includes a second segment extending exterior to the bridge at its second side to provide a second engagement point; and
   a third anchoring member extends from the bridge at the first end of the bridge adjacent the second side of the bridge, the third anchoring member including a width whereby a segment of the third anchoring member extends exterior to the bridge at its second side to provide an engagement point.

30. The orthopedic fixation system according to claim 29, the implant insertion device, comprising:
   a body including a first end and a second end; and
   an implant grip coupled with the body at its second end, the implant grip movable relative to the body between an engaged position whereby the implant grip by-passes the bridge and engages the segments of the first and third anchoring members at their engagement points and the first and second segments of the second anchoring member at their first and second engagement points such that the implant grip constrains the implant in its insertion shape and a disengaged position whereby the implant grip releases the implant.

31. The orthopedic fixation system according to claim 30, the implant grip, comprising a shell, wherein:
   the shell includes an exterior surface having an upper surface and a lower surface,
   the shell includes an interior surface complimentary in shape with the implant such that the interior surface defines a passage through the shell complimentary in shape with the implant,
   the shell at its upper surface receives into the passage the body at its second end thereby coupling the shell with the body, and
   the shell at its lower surface receives into the passage the implant whereby the shell at its interior surface by-passes the bridge and engages the segments of the first and third anchoring members at their engagement points and the first and second segments of the second anchoring member at their first and second engagement points thereby holding the implant in the shell and constraining the implant in its insertion shape.

32. The orthopedic fixation system according to claim 31, wherein the interior surface of the shell defines first, second, third, and fourth grooves, whereby, when the shell at its interior surface by-passes the bridge, each of the first, second, third, and fourth grooves receives therein one of the segments of the first and third anchoring members and the first and second segments of the second anchoring member, further whereby the interior surface at the first, second, third, and fourth grooves engages the first, second, and third anchoring members, thereby retaining the implant within the shell in its insertion shape.

33. The orthopedic fixation system according to claim 32, wherein the interior surface in each of the first, second, third, and fourth grooves defines a retention surface, whereby, when the first, second, third, and fourth grooves receive therein one of the segments of the first and third anchoring members and the first and second segments of the second anchoring member, each of the retention surfaces abuts one of the engagement points of the segments for the first and third anchoring members and the first and second engagement points of the first and second segments for the second anchoring member whereby the retention surfaces grip and constrain the first, second, and third anchoring members such that the shell retains therein the implant in its insertion shape.

34. The orthopedic fixation system according to claim 32, wherein the interior surface of the shell includes projections, whereby, when the shell at its interior surface by-passes the bridge, the projections by-pass the bridge and engage one of the first and third anchoring members such that the shell retains therein the implant in its insertion shape.

35. The orthopedic fixation system according to claim 34, wherein the projections are resilient, whereby, when the shell at its interior surface by-passes the bridge, the projections by-pass the bridge by moving relative thereto and engage one of the first and third anchoring members such that the shell retains therein the implant in its insertion shape.

36. The orthopedic fixation system according to claim 31, the body, comprising an implant grip receiver at the second end of the body, the implant grip receiver terminating in a tamp, wherein the implant grip receiver is complimentary in shape with the interior surface of the shell, further wherein the implant grip receiver inserts into the passage of the shell at its upper surface thereby coupling the implant grip receiver with the shell.

37. The orthopedic fixation system according to claim 36, wherein, when the implant grip resides in its engaged position, the tamp sits atop the bridge of the implant, further wherein, the tamp remains atop the bridge of the implant to prevent movement of the implant relative to the implant grip during progression of the implant grip from its engaged position to its disengaged position.

38. The orthopedic fixation system according to claim 36, wherein:
   the implant grip receiver includes a first notch and a second notch; and
   the interior surface of the shell includes a detent engageable with the first and second notches, whereby, when the implant grip moves to its engaged position, the detent engages the first notch thereby locking the implant grip in its engaged position, further whereby, when the implant grip moves to its disengaged position, the detent engages the second notch thereby locking the implant grip in its disengaged position.

39. The orthopedic fixation system according to claim 30, the implant grip, comprising:
   an actuator coupled with the body and movable relative thereto whereby movement of the actuator progresses the implant grip between its engaged and disengaged positions; and
   first and second blades securable with the actuator in an opposed relationship that defines a passage therebetween, whereby the passage receives therein the bridge of the implant, further whereby the first and second blades extend beyond the bridge and engage the segments of the first and third anchoring members at their engagement points and the first and second segments of the second anchoring member at their first and second engagement points thereby holding the implant and constraining the implant in its insertion shape.

40. The orthopedic fixation system according to claim 39, the actuator, comprising:
- a first slider securable with the first blade;
- a second slider securable with the second blade; and
- a spacer securable between the first and second sliders such that the first and second blades are spaced apart to form the passage therebetween.

41. The orthopedic fixation system according to claim 40, the body, defining:
- a tamp at its second end; and
- a slot therethrough communicating exterior to the body, the slot receiving the spacer therein, wherein the first slider secures with the spacer adjacent a first surface of the body whereby the first blade extends beyond the tamp, further wherein the second slider secures with the spacer adjacent a second surface of the body whereby the second blade extends beyond the tamp such that the passage between the first and second blades is located adjacent the tamp.

42. The orthopedic fixation system according to claim 41, wherein, when the implant grip resides in its engaged position, the tamp sits atop the bridge of the implant, further wherein, the tamp remains atop the bridge of the implant to prevent movement of the implant relative to the implant grip during progression of the implant grip from its engaged position to its disengaged position.

43. An orthopedic fixation system, comprising:
- an implant transitionable between a natural shape and an insertion shape, the implant, comprising:
  - a bridge,
  - a first anchoring member extending from the bridge, the first anchoring member including a segment extending exterior to the bridge to provide an engagement point, and
  - a second anchoring member extending from the bridge, the second anchoring member including a segment extending exterior to the bridge to provide an engagement point;
- an implant insertion device movable between a loaded position whereby the implant insertion device by-passes the bridge and engages the segment of the first anchoring member at its engagement point and the segment of the second anchoring member at its engagement point such that the implant insertion device constrains the implant in its insertion shape and an unloaded position whereby the implant insertion device releases the implant;
- the implant insertion device, comprising:
  - a body including a first end and a second end, the body comprising an implant grip receiver at the second end thereof including a first notch and a second notch, and
  - an implant grip coupled with the body and movable relative to the body between an engaged position whereby the implant grip by-passes the bridge and engages the segment of the first anchoring member at its engagement point and the segment of the second anchoring member at its engagement point such that the implant grip constrains the implant in its insertion shape and a disengaged position whereby the implant grip releases the implant; and
  - the implant grip, comprising a shell, wherein:
    - the shell includes an exterior surface having an upper surface and a lower surface,
    - the shell includes an interior surface complimentary in shape with the implant such that the interior surface defines a passage through the shell complimentary in shape with the implant,
    - the shell at its upper surface receives into the passage the implant grip receiver of the body whereby the implant grip receiver is complimentary in shape with the interior surface of the shell such that insertion of the implant grip receiver into the passage of the shell at its upper surface couples the implant grip receiver with the shell,
    - the interior surface of the shell includes a detent engageable with the first and second notches, whereby, when the implant grip moves to its engaged position, the detent engages the first notch thereby locking the implant grip in its engaged position, further whereby, when the implant grip moves to its disengaged position, the detent engages the second notch thereby locking the implant grip in its disengaged position, and
    - the shell at its lower surface receives into the passage the implant whereby the shell at its interior surface by-passes the bridge and engages the segments of the first and second anchoring members at their engagement points thereby holding the implant in the shell and constraining the implant in its insertion shape.

44. The orthopedic fixation system according to claim 43, wherein:
- the bridge includes first and second sides and first and second ends;
- the first anchoring member extends from the bridge at the first end of the bridge adjacent the first side of the bridge, the first anchoring member including a width between sides thereof whereby the segment of the first anchoring member extends exterior to the bridge at its first side to provide the engagement point;
- the second anchoring member extends from the bridge at the second end of the bridge adjacent the first side of the bridge, the second anchoring member including a width between sides thereof whereby the segment of the second anchoring member extends exterior to the bridge at its first side to provide the engagement point;
- a third anchoring member extends from the bridge at the first end of the bridge adjacent the second side of the bridge, the third anchoring member including a width between sides thereof whereby a segment of the third anchoring member extends exterior to the bridge at its second side to provide an engagement point; and
- a fourth anchoring member extends from the bridge at the second end of the bridge adjacent the second side of the bridge, the fourth anchoring member including a width between sides thereof whereby a segment of the fourth anchoring member extends exterior to the bridge at its second side to provide an engagement point.

45. The orthopedic fixation system according to claim 44, the implant grip, when moved to the engaged position, by-passes the bridge and engages the segments of the first, second, third, and fourth anchoring members at their engagement points such that the implant grip constrains the implant in its insertion shape, and the implant grip, when moved to disengaged position, releases the implant.

46. The orthopedic fixation system according to claim 45, wherein the shell at its lower surface receives into the passage the implant whereby the shell at its interior surface by-passes the bridge and engages the segments of the first, second, third, and fourth anchoring members at their engagement points thereby holding the implant in the shell and constraining the implant in its insertion shape.

47. The orthopedic fixation system according to claim 46, wherein the interior surface of the shell defines first, second, third, and fourth grooves, whereby, when the shell at its interior surface by-passes the bridge, each of the first, second, third, and fourth grooves receives therein one of the segments of the first, second, third, and fourth anchoring members, further whereby the interior surface at the first, second, third, and fourth grooves engages the first, second, third, and fourth anchoring members, thereby retaining the implant within the shell in its insertion shape.

48. The orthopedic fixation system according to claim 47, wherein the interior surface in each of the first, second, third, and fourth grooves defines a retention surface, whereby, when the first, second, third, and fourth grooves receive therein one of the segments of the first, second, third, and fourth anchoring members, each of the retention surfaces abuts one of the engagement points of the segments for the first, second, third, and fourth anchoring members whereby the retention surfaces grip and constrain the first, second, third, and fourth anchoring members such that the shell retains therein the implant in its insertion shape.

49. The orthopedic fixation system according to claim 47, wherein the interior surface of the shell includes projections, whereby, when the shell at its interior surface by-passes the bridge, the projections by-pass the bridge and engage one of the first, second, third, and fourth anchoring members such that the shell retains therein the implant in its insertion shape.

50. The orthopedic fixation system according to claim 49, wherein the projections are resilient, whereby, when the shell at its interior surface by-passes the bridge, the projections by-pass the bridge by moving relative thereto and engage one of the first, second, third, and fourth anchoring members such that the shell retains therein the implant in its insertion shape.

51. The orthopedic fixation system according to claim 43, wherein the implant grip receiver terminates in a tamp, whereby, when the implant grip resides in its engaged position, the tamp sits atop the bridge of the implant, further whereby, the tamp remains atop the bridge of the implant to prevent movement of the implant relative to the implant grip during progression of the implant grip from its engaged position to its disengaged position.

52. An orthopedic fixation system, comprising:
an implant transitionable between a natural shape and an insertion shape, the implant, comprising:
  a bridge including first and second sides and first and second ends defining a perimeter in alignment with a longitudinal axis of the bridge,
  a first anchoring member extending from the bridge at the first end of the bridge adjacent the first side of the bridge, the first anchoring member including a width between sides thereof that extends a segment of the first anchoring member laterally away from the first side of the bridge such that the segment provides the first anchoring member with an engagement point located on the first anchoring member interior of the sides thereof and outside of the first side of the bridge,
  a second anchoring member extending from the bridge at the second end of the bridge adjacent the first side of the bridge, the second anchoring member including a width between sides thereof that extends a segment of the second anchoring member laterally away from the first side of the bridge such that the segment provides the second anchoring member with an engagement point located on the second anchoring member interior of the sides thereof and outside of the first side of the bridge,
  a third anchoring member extending from the bridge at the first end of the bridge adjacent the second side of the bridge, the third anchoring member including a width between sides thereof that extends a segment of the third anchoring member laterally away from the second side of the bridge such that the segment provides the third anchoring member with an engagement point located on the third anchoring member interior of the sides thereof and outside of the second side of the bridge, and
  a fourth anchoring member extending from the bridge at the second end of the bridge adjacent the second side of the bridge, the fourth anchoring member including a width between sides thereof that extends a segment of the fourth anchoring member laterally away from the second side of the bridge such that the segment provides the fourth anchoring member with an engagement point located on the fourth anchoring member interior of the sides thereof and outside of the second side of the bridge; and
an implant insertion device movable between a loaded position whereby the implant insertion device by-passes the bridge and abuts the segment of the first anchoring member at its engagement point and the segment of the second anchoring member at its engagement point such that the implant insertion device holds the first anchoring member and the second anchoring member at their engagement points thereby constraining the implant in its insertion shape and an unloaded position whereby the implant insertion device disengages from the segment of the first anchoring member at its engagement point and the segment of the second anchoring member at its engagement point thereby releasing the implant.

53. The orthopedic fixation system according to claim 52, the implant insertion device, comprising:
  a body including a first end and a second end; and
  an implant grip coupled with the body at its second end, the implant grip movable relative to the body between an engaged position whereby the implant grip by-passes the bridge and engages abuts the segments of the first, second, third, and fourth anchoring members at their engagement points such that the implant grip holds the first, second, third, and fourth anchoring members at their engagement points thereby constraining the implant in its insertion shape and a disengaged position whereby the implant grip disengages from the segments of the first, second, third, and fourth anchoring members at their engagement points thereby releasing the implant.

54. The orthopedic fixation system according to claim 53, the implant grip, comprising a shell, wherein:
  the shell includes an exterior surface having an upper surface and a lower surface,
  the shell includes an interior surface complimentary in shape with the implant such that the interior surface defines a passage through the shell complimentary in shape with the implant,
  the shell at its upper surface receives into the passage the body at its second end thereby coupling the shell with the body, and the shell at its lower surface receives into the passage the implant whereby the shell at its interior surface by-passes the bridge and abuts the segments of the first, second, third, and fourth anchoring members at their engagement points thereby holding the implant in the shell and constraining the implant in its insertion shape.

55. The orthopedic fixation system according to claim 54, wherein the interior surface of the shell defines first, second, third, and fourth grooves, whereby, when the shell at its interior surface by-passes the bridge, each of the first, second, third, and fourth grooves receives therein one of the segments of the first, second, third, and fourth anchoring members, further whereby the interior surface at the first, second, third, and fourth grooves abuts the first, second, third, and fourth anchoring members at their engagement points, thereby retaining the implant within the shell in its insertion shape.

56. The orthopedic fixation system according to claim 55, wherein the interior surface in each of the first, second, third, and fourth grooves defines a retention surface, whereby, when the first, second, third, and fourth grooves receive therein one of the segments of the first, second, third, and fourth anchoring members, each of the retention surfaces abuts one of the engagement points of the segments for the first, second, third, and fourth anchoring members whereby the retention surfaces grip and constrain the first, second, third, and fourth anchoring members at their engagement points such that the shell retains therein the implant in its insertion shape.

57. The orthopedic fixation system according to claim 55, wherein the interior surface of the shell includes projections, whereby, when the shell at its interior surface by-passes the bridge, the projections by-pass the bridge and engage one of the first, second, third, and fourth anchoring members such that the shell retains therein the implant in its insertion shape.

58. The orthopedic fixation system according to claim 57, wherein the projections are resilient, whereby, when the shell at its interior surface by-passes the bridge, the projections by-pass the bridge by moving relative thereto and engage one of the first, second, third, and fourth anchoring members such that the shell retains therein the implant in its insertion shape.

59. The orthopedic fixation system according to claim 54, the body, comprising an implant grip receiver at the second end of the body, the implant grip receiver terminating in a tamp, wherein the implant grip receiver is complimentary in shape with the interior surface of the shell, further wherein the implant grip receiver inserts into the passage of the shell at its upper surface thereby coupling the implant grip receiver with the shell.

60. The orthopedic fixation system according to claim 59, wherein, when the implant grip resides in its engaged position, the tamp sits atop the bridge of the implant, further wherein, the tamp remains atop the bridge of the implant to prevent movement of the implant relative to the implant grip during progression of the implant grip from its engaged position to its disengaged position.

61. The orthopedic fixation system according to claim 59, wherein:
the implant grip receiver includes a first notch and a second notch; and
the interior surface of the shell includes a detent engageable with the first and second notches, whereby, when the implant grip moves to its engaged position, the detent engages the first notch thereby locking the implant grip in its engaged position, further whereby, when the implant grip moves to its disengaged position, the detent engages the second notch thereby locking the implant grip in its disengaged position.

* * * * *